United States Patent
Barrett et al.

(10) Patent No.: US 7,402,606 B2
(45) Date of Patent: Jul. 22, 2008

(54) DERIVATIVES OF 1-(OXOAMINOACETYL) PENTYLCARBAMATE AS CATHEPSIN K INHIBITORS FOR THE TREATMENT OF BONE LOSS

(75) Inventors: David Gene Barrett, Henstedt-Ulzburg (DE); John G. Catalano, Durham, NC (US); David Norman Deaton, Durham, NC (US); Aaron Bayne Miller, Durham, NC (US); John A. Ray, Durham, NC (US); Vicente Samano, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 651 days.

(21) Appl. No.: 10/510,469

(22) PCT Filed: Apr. 1, 2003

(86) PCT No.: PCT/US03/09893

§ 371 (c)(1),
(2), (4) Date: Oct. 7, 2004

(87) PCT Pub. No.: WO03/086385

PCT Pub. Date: Oct. 23, 2003

(65) Prior Publication Data

US 2005/0245596 A1    Nov. 3, 2005

Related U.S. Application Data

(60) Provisional application No. 60/371,524, filed on Apr. 10, 2002.

(51) Int. Cl.
| | |
|---|---|
| *A61K 31/341* | (2006.01) |
| *A61K 31/4015* | (2006.01) |
| *A61K 31/4025* | (2006.01) |
| *A61K 31/404* | (2006.01) |
| *A61K 31/4155* | (2006.01) |
| *A61K 31/416* | (2006.01) |
| *A61K 31/4192* | (2006.01) |
| *A61K 31/4196* | (2006.01) |
| *A61K 31/4245* | (2006.01) |
| *A61K 31/42* | (2006.01) |
| *A61K 31/433* | (2006.01) |
| *A61K 31/4439* | (2006.01) |
| *A61K 31/4709* | (2006.01) |
| *A61K 31/497* | (2006.01) |
| *A61K 31/5377* | (2006.01) |

(52) U.S. Cl. .................. 514/424; 514/423; 514/414; 514/406; 514/378; 514/367; 514/365; 514/361; 514/364; 514/363; 514/314; 514/343; 514/255.05; 514/235.5; 544/141; 544/405; 546/278.4; 546/168; 546/270.4; 548/544; 548/556; 548/525; 548/127; 548/236; 548/255; 548/261; 548/468; 548/248; 548/266.8; 548/362.5; 548/247; 548/203; 548/131; 548/162; 549/475

(58) Field of Classification Search .............. 514/235.5, 514/255.05, 343, 314, 363, 364, 361, 365, 514/367, 378, 406, 414, 423, 424; 544/141, 544/405; 546/278.4, 168, 270.4; 548/544, 548/556, 525, 127, 236, 255, 261, 468, 248, 548/266.8, 362.5, 247, 203, 131, 162; 549/475
See application file for complete search history.

(56) References Cited

FOREIGN PATENT DOCUMENTS

| EP | 1 008 592 | 6/2000 |
|---|---|---|
| WO | 96/16079 | 5/1996 |
| WO | 03/013518 | 2/2003 |
| WO | 03/062192 | 7/2003 |

OTHER PUBLICATIONS

Morissette et al. Advanced Drug Delivery Reviews 2004, 56, 275-300.*

* cited by examiner

*Primary Examiner*—Joseph K. McKane
*Assistant Examiner*—Jason M Nolan
(74) *Attorney, Agent, or Firm*—John L. Lemanowicz; Kathryn L. Coulter

(57) ABSTRACT

Heterocycle substituted ketoamide derivatives of Formula (I), wherein the substitutes A, D, A and R are defined as in claim in, which are useful as cathepsin K inhibitors are described herein. The described invention also includes methods of making such heterocycle substituted ketoamide derivatives as well as method of using the same in the manufacture of medicaments for the treatment of disorders, including osteoporosis, associated with an imbalance between bone resorption and formation which can ultimately lead to fracture.

46 Claims, No Drawings

DERIVATIVES OF 1-(OXOAMINOACETYL) PENTYLCARBAMATE AS CATHEPSIN K INHIBITORS FOR THE TREATMENT OF BONE LOSS

This application is filed pursuant to 35 U.S.C. § 371 as a United States National Phase Application of International Application No. PCT/US03/09893 filed Apr. 1, 2003, which claims priority from U.S. Pat. No. 60/371,524 filed Apr. 10, 2002.

FIELD OF THE INVENTION

The present invention relates to heterocycle substituted ketoamide derivatives, compositions and medicaments containing the same, as well as processes for the preparation and use of such compounds, compositions and medicaments. Such ketoamide derivatives are inhibitors of serine and cysteine proteases. In particular, such ketoamide derivatives are inhibitors of cysteine proteases of the papain superfamily. More particularly, the ketoamides of the present invention are inhibitors of cathepsin family cysteine proteases such as cathepsin K. Further, such ketoamide derivatives are useful in the treatment of diseases associated with serine and cysteine protease activity, more particularly, in the treatment of diseases associated with cathepsin family cysteine proteases, for instance in the treatment of diseases associated with cathepsin K activity.

BACKGROUND OF THE INVENTION

Osteoclasts are multinuclear cells of hematopoietic lineage, which function in the process of bone resorption. Typically, osteoclasts adhere to a bone surface and form a tight sealing zone. This activity is followed by extensive membrane ruffling on the surface of the osteoclasts. Such action creates an enclosed extracellular compartment on the bone surface that is acidified by proton pumps in the ruffled membrane and into which the osteoclast secretes proteolytic enzymes. The low pH of the compartment dissolves hydroxyapatite crystals at the bone surface, while the proteolytic enzymes digest the protein matrix. In this way a resorption pit is formed, after which the osteoclast releases from the surface of the bone. At the completion of this cycle, osteoblasts remodel the bone; that is, the osteoblasts deposit a new protein matrix, which is subsequently mineralized, at this zone.

Normally, a balance exists between the processes of bone resorption and new bone formation during remodeling. This normal balance of bone resorption and bone formation may be disrupted, resulting in a net loss of bone in each cycle of remodeling. Such net bone loss may lead to osteoporosis. Osteoporosis is characterized by reduced bone mass and disruptions in the microarchitecture of the bone. These characteristics may lead to fractures, which can result from a minimal amount of trauma. Typical sites of fractures include vertebral bodies, distal radius, and the proximal femur. However, because those suffering from osteoporosis have general skeletal weakness, fractures may occur at other sites.

Since osteoporosis is characterized by an increase in bone resorption with respect to bone formation, therapeutic agents that suppress bone resorption would be expected to provide a suitable treatment for osteoporosis. Administration of estrogens or calcitonin has been the bone resorption suppression treatment typically employed. However, these treatments do not always achieve the desired effect. Consequently, there is a continuing need for therapeutic agents that attenuate bone resorption in a subject in need of such attenuation.

Cathepsin K, which has also been called cathepsin O, cathepsin O2, and cathepsin X, is a member of the cysteine cathepsin family of enzymes, which are part of the papain superfamily of cysteine proteases. Other distinct cysteine protease cathepsins, designated cathepsin B, cathepsin C, cathepsin F, cathepsin H, cathepsin L, cathepsin O, cathepsin S. cathepsin V (also called L2), cathepsin W. &cathepsin Z (also called cathepsin X), have also been described in the literature. Cathepsin K polypeptide and the cDNA encoding such polypeptide have been disclosed in U.S. Pat. No. 5,501,969. A crystal structure for cathepsin K has also been disclosed in PCT Patent Application WO 97/16177, published May 9, 1997. It has been reported that cathepsin K is abundantly expressed in osteoclasts under normal conditions and may be the major cysteine protease present in these cells. (See Tezuka, et al., J. Biol. Chem., 1994, 269, 1106; Inaoka, et al, Biochem. Biophys. Res. Commun., 1995, 206, 89; and Shi, et al., FEBS Lett., 1995, 357,129.) This abundant selective expression of cathepsin K in osteoclasts suggests that this enzyme is essential for bone resorption. Thus, selective inhibition of cathepsin K may provide an effective treatment for diseases of excessive bone loss, such as osteoporosis.

The selective inhibition of cathepsin K may also be useful in treating other diseases. Such disorders include autoimmune diseases such as rheumatoid arthritis, osteoarthritis, neoplastic diseases, parasitic diseases, and atherosclerosis. For instance, cathepsin K is expressed in the synovium and synovial bone destruction sites of patients with rheumatoid arthritis (see Votta, B. J. et al.; *J. Bone Miner. Res.* 1997, 12, 1396; Hummel, K. M. et al., *J. Rheumatol.* 1998, 25, 1887; Nakagawa, T. Y. et al., *Immunity* 1999, 10, 207; Otsuka, T. et al., S. *J. Antibiot.* 1999, 52, 542; Li, Z. et al, *Biochemistry* 2000, 39, 529; Diaz, A. et al, *Mol. Med.* 2000, 6, 648; Moran, M. T. et al., *Blood* 2000, 96, 1969). Cathepsin K levels are elevated in chondroclasts of osteoarthritic synovium (See Dodds, R. A. et al., *Arthritis Rheum.* 1999, 42, 1588; Lang, A. et al., *J. Rheumatol.* 2000, 27, 1970). Neoplastic cells also have been shown to express cathepsin K (see Littlewood-Evans, A. J. et al, J. A. *Cancer Res.* 1997, 57, 5386; Komarova, E. A., et al., *Oncogene* 1998, 17, 1089; Santamaria, I., et al., *Cancer Res.* 1998, 58, 1624; Blagosklonny, M. V. et al., *Oncogene* 1999, 18, 6460; Kirschke, H. et al., *Eur. J. Cancer* 2000, 36, 787; Zhu, D.-M. et al., *Clin. Cancer Res.* 2000, 6, 2064). Cysteine protease inhibitors have been suggested as chemotherapy for parasitic diseases (see McKerrow, J. H. *Int. J. Parasitol.* 1999, 29, 833; Selzer, P. M. et al., *Proc. Natl. Acad. Sci. U.S.A.* 1999, 96, 11015; Caffrey, C. R. et al, *Curr. Drug Targets* 2000, 1, 155; Du, X. et al., *Chem. Biol.* 2000, 7, 733; Hanspal, M. *Biochim. Biophys. Acta* 2000, 1493, 242; Werbovetz, K. A. *Curr. Med. Chem.* 2000, 7, 835). Elastolytic cathepsins S and K are shown to be expressed in human atheroma (see Sukhova, G. K. et al., *J. Clin. Invest.* 1998, 102, 576-583; Parks, W. C. *J. Clin. Invest.* 1999, 104, 1167; Shi, G.-P. et al., *J. Clin. Invest.* 1999, 104, 1191; Cao, H. et al., *J. Hum. Genet.* 2000, 45, 94).

The present inventors have now discovered novel heterocycle substituted ketoamide derivative compounds that are inhibitors of serine and cysteine protease activities, more particularly, cathepsin family cysteine protease activities, and most particularly, cathepsin K activity. Such ketoamide derivatives are useful in the treatment of disorders associated with serine and cysteine protease activity, including osteoporosis, Paget's disease, hypercalcemia of malignancy, metabolic bone disease, osteoarthritis, rheumatoid arthritis, periodontitis, gingivitis, atherosclerosis, and neoplastic diseases associated with cathepsin K activity.

BRIEF SUMMARY OF THE INVENTION

In a first aspect of the present invention, there is provided a compound of Formula (I):

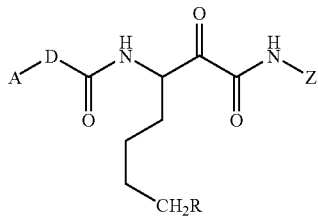

(I)

or a salt, solvate, or physiologically functional derivative thereof wherein

A is the group defined by $(Q^4)_p\text{-}(Q^3)_n\text{-}(Q^2)_m\text{-}(Q^1)\text{-}$, wherein
  $Q^1$ is heterocyclyl or heterocyclylene,
  $Q^2$ is OC(O), C(O), N(H)C(O), C(O)N(H)C(O), $S(O)_2N(H)C(O)$, $S(O)_2$, or $N(H)S(O)_2$, and m is 0 or 1,
  $Q^3$ is $C_1$-$C_6$ alkyl, $C_1$-$C_6$ haloalkyl, $C_3$-$C_7$ cycloalkyl, aralkyl, aralkylene, aryl, arylene, heteroaryl, heteroarylene, heterocyclyl, or heterocyclylene, and n is 0 or 1, and
  $Q^4$ is $C_1$-$C_6$ alkyl, $C_1$-$C_6$ haloalkyl, aryl, aryloxy, heteroaryl, halo, or cyano, and p is 0, 1, or 2;
D is O or S;
R is hydrogen or —N($R^1$)—$R^2$—$R^3$;
$R^1$ is hydrogen or $C_1$-$C_6$ alkyl;
$R^2$ is C(O), C(O)O, C(O)N(H), $S(O)_2$, or $S(O)_2N(H)$;
$R^3$ is hydrogen or $C_1$-$C_6$ alkyl;
Z is the group defined by —(X)$_m$—(X$^1$), wherein
  X is C(R')(R"), wherein R' is hydrogen or $C_1$-$C_6$ alkyl, R" is hydrogen or $C_1$-$C_6$ alkyl, and m is 0, 1, or 2; and
  X$^1$ is aryl, heteroaryl, or heterocyclyl.

In a second aspect of the present invention, there is provided a compound of formula II:

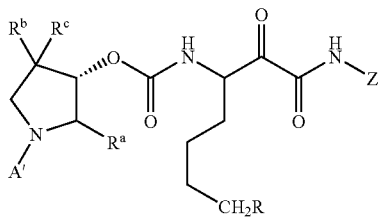

II or a salt, solvate, or physiologically functional derivative thereof wherein

A' is the group defined by $(Q^4)_p\text{-}(Q^3)_n\text{-}(Q^2)_m\text{-}$, wherein
  $Q^2$ is OC(O), C(O), N(H)C(O), C(O)N(H)C(O), $S(O)_2N(H)C(O)$, $S(O)_2$, or $N(H)S(O)_2$, and m is 0 or 1,
  $Q^3$ is $C_1$-$C_6$ alkyl, $C_1$-$C_6$ haloalkyl, $C_3$-$C_7$ cycloalkyl, aralkyl, aralkylene, aryl, arylene, heteroaryl, heteroarylene, heterocyclyl, or heterocyclylene, and n is 0 or 1, and
  $Q^4$ is $C_1$-$C_6$ alkyl, $C_1$-$C_6$ haloalkyl, aryl, aryloxy, heteroaryl, halo, or cyano, and p is 0, 1, or 2;

$R^a$ is hydrogen or oxo;
$R^b$ is hydrogen or $C_1$-$C_6$ alkyl;
$R^c$ is hydrogen or $C_1$-$C_6$ alkyl;
R is hydrogen or —N($R^1$)—$R^2$—$R^3$;
$R^1$ is hydrogen or $C_1$-$C_6$ alkyl;
$R^2$ is C(O), C(O)O, C(O)N(H), $S(O)_2$, or $S(O)_2N(H)$;
$R^3$ is hydrogen or $C_1$-$C_6$ alkyl;
Z is the group defined by —(X)$_m$—(X$^1$), wherein
  X is C(R')(R"), wherein R' is hydrogen or $C_1$-$C_6$ alkyl, R" is hydrogen or $C_1$-$C_6$ alkyl, and m is 0, 1, or 2; and
  X$^1$ is aryl, heteroaryl, or heterocyclyl.

In a third aspect of the present invention, there is provided a pharmaceutical composition, comprising: a therapeutically effective amount of a compound of formula (I), or a salt, solvate, or a physiologically functional derivative thereof and one or more of pharmaceutically acceptable carriers, diluents and excipients.

In a fourth aspect of the present invention, there is provided a method of treating a disorder in a mammal, said disorder being characterized by bone loss, comprising: administering to said mammal a therapeutically effective amount of a compound of formula (I) or a salt, solvate or a physiologically functional derivative thereof.

In a fifth aspect of the present invention, there is provided a compound of formula (I), or a salt, solvate, or a physiologically functional derivative thereof for use in therapy.

In a sixth aspect of the present invention, there is provided the use of a compound of formula (I), or a salt, solvate, or a physiologically functional derivative thereof in the preparation of a medicament for use in the treatment of a disorder characterized by bone loss.

In a seventh aspect of the present invention, there is provided a method of treating osteoporosis, comprising: administering to said mammal a therapeutically effective amount of a compound of formula (I), or a salt, solvate or physiologically functional derivative thereof.

In an eighth aspect of the present invention, there is provided a method of treating osteoporosis, comprising: administering to said mammal therapeutically effective amounts of (i) a compound of formula (I), or a salt, solvate or physiologically functional derivative thereof and (ii) at least one bone building agent such as parathyroid hormone (PTH).

DETAILED DESCRIPTION OF THE INVENTION

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount that, as compared to a corresponding subject who has not received said amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "lower" refers to a group having between one and six carbons.

As used herein, the term "alkyl" refers to a straight or branched chain hydrocarbon having from one to twelve carbon atoms, optionally substituted with substituents selected from the group consisting of lower alkyl, lower alkoxy, lower alkylsulfanyl, lower alkylsulfenyl, lower alkylsulfonyl, oxo, mercapto, amino optionally substituted by alkyl, carboxy, carbamoyl optionally substituted by alkyl, aminosulfonyl optionally substituted by alkyl, nitro, or lower perfluoroalkyl, multiple degrees of substitution being allowed. Examples of "alkyl" as used herein include, but are not limited to, n-butyl, n-pentyl, isobutyl, isopropyl, and the like.

As used herein, the term "$C_1$-$C_6$ alkyl" refers to an alkyl group, as defined above, which contains at least 1, and at most 6, carbon atoms. Examples of "$C_1$-$C_6$ alkyl" groups useful in the present invention include, but are not limited to, methyl, ethyl, propyl, isopropyl, isobutyl, n-butyl, tert-butyl, and isopentyl.

As used herein, the term "alkylene" refers to a straight or branched chain divalent hydrocarbon radical having from one to ten carbon atoms, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen and lower perfluoroalkyl, multiple degrees of substitution being allowed. Examples of "alkylene" as used herein include, but are not limited to, methylene, ethylene, n-propylene, n-butylene, and the like.

As used herein, the terms "$C_1$-$C_3$ alkylene" and "$C_1$-$C_4$ alkylene" refer to an alkylene group, as defined above, which contains at least 1, and at most 3 or 4, carbon atoms respectively. Examples of "$C_1$-$C_3$ alkylene" groups useful in the present invention include, but are not limited to, methylene, ethylene, and n-propylene.

As used herein, the term "halogen" refers to fluorine, chlorine, bromine, or iodine and the term "halo" refers to fluoro (—F), chloro (—Cl), bromo (—Br), or iodo (—I).

As used herein, the term "haloalkyl" refers to an alkyl group, as defined herein, substituted with at least one halo, halo being as defined herein. Examples of branched or straight chained "haloalkyl" groups useful in the present invention include, but are not limited to, methyl, ethyl, propyl, isopropyl, n-butyl, and t-butyl substituted independently with one or more halo groups, e.g., fluoro, chloro, bromo and iodo.

As used herein, the term "$C_1$-$C_6$ haloalkyl" refers to haloalkyl as defined above containing at least 1, and at most 6 carbon atoms substituted with at least one halo group, halo being as defined herein. Examples of branched or straight chained "$C_1$-$C_6$ haloalkyl" groups useful in the present invention include, but are not limited to methyl, ethyl, propyl, and isopropyl, substituted independently with one or more halogens, e.g., fluoro, chloro, bromo, and iodo.

As used herein, the term "$C_3$-$C_7$ cycloalkyl" refers to a non-aromatic cyclic hydrocarbon ring having from three to seven carbon atoms, which optionally includes a $C_1$-$C_4$ alkylene linker through which it may be attached. Exemplary "$C_3$-$C_7$ cycloalkyl" groups include, but are not limited to cyclopropyl, cyclobutyl, cyclopentyl, cyclohexyl, and cycloheptyl.

As used herein, the term "$C_3$-$C_7$ cycloalkylene" refers to a non-aromatic alicyclic divalent hydrocarbon radical having from three to seven carbon atoms, optionally substituted with substituents selected from the group which includes $C_1$-$C_6$ alkyl, $C_1$-$C_6$ alkoxy, $C_1$-$C_6$ alkylsulfanyl, $C_1$-$C_6$ alkylsulfenyl, $C_1$-$C_6$ alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, $C_1$-$C_6$ perfluoroalkyl, multiple degrees of substitution being allowed. Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,4-diyl, cycloheptyl-1,4-diyl, or cyclooctyl-1,5-diyl, and the like.

As used herein, the term "aryl" refers to an optionally substituted benzene ring or to an optionally substituted benzene ring system fused to one or more optionally substituted benzene rings to form, for example, anthracene, phenanthrene, or napthalene ring systems. Exemplary optional substituents include lower alkyl, $C_3$-$C_7$ cycloalkyl, lower haloakyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl, or aryl, multiple degrees of substitution being allowed. Examples of "aryl" groups include, but are not limited to, phenyl, 2-naphthyl, 1-naphthyl, and biphenyl, as well as substituted derivatives thereof.

As used herein, the term "arylene" refers to a benzene ring diradical or to a benzene ring system diradical fused to one or more optionally substituted benzene rings, optionally substituted with substituents selected from the group which includes $C_1$-$C_6$alkyl, $C_1$-$C_6$ alkoxy, $C_1$-$C_6$ alkylsulfanyl, $C_1$-$C_6$ alkylsulfenyl, $C_1$-$C_6$ alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, $C_1$-$C_6$ perfluoroalkyl, heteroaryl and aryl, multiple degrees of substitution being allowed. Examples of "arylene" include, but are not limited to, benzene-1,4-diyl, naphthalene-1,8-diyl, anthracene-1,4-diyl, and the like.

As used herein, the term "aralkyl" refers to an aryl or heteroaryl group, as defined herein, attached through a lower alkylene linker, wherein the lower alkylene linker is as defined herein. Examples of "aralkyl" include, but are not limited to benzyl, phenylpropyl, 2-pyridylmethyl, 3-isoxazolylmethyl, 5-methyl-3-isoxazolylmethyl, and 2-imidazoyly ethyl.

As used herein, the term "aralkylene" refers to an arylene or heteroarylene group, as defined herein, having one attachment through a lower alkylene linker, wherein the lower alkylene linker is as defined herein. Examples of "aralkylene" include, but are not limited to benzylene, phenylpropylene, 2-pyridylmethylene, 3-isoxazolylmethylene, 5-methyl-3-isoxazolylmethylene, and 2-imidazolyl ethylene.

As used herein, the term "heteroaryl" refers to a monocyclic five to seven membered aromatic ring, or to a fused bicyclic aromatic ring system comprising two of such monocyclic five to seven membered aromatic rings. These heteroaryl rings contain one or more nitrogen, sulfur, and/or oxygen atoms, where N-oxides and sulfur oxides and dioxides are permissible heteroatom substitutions and may be optionally substituted with up to three members selected from a group consisting of lower alkyl, lower haloalkyl, $C_3C_7$ cycloalkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl, or aryl, multiple degrees of substitution being allowed. Examples of "heteroaryl" groups used herein include furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, indazole, and substituted versions thereof.

As used herein, the term "heteroarylene" refers to a five- to seven-membered aromatic ring diradical, or to a polycyclic heterocyclic aromatic ring diradical, containing one or more nitrogen, oxygen, or sulfur heteroatoms, where N-oxides and sulfur monoxides and sulfur dioxides are permissible heteroaromatic substitutions, optionally substituted with substituents selected from the group consisting of: $C_1$-$C_6$ alkyl $C_1$-$C_6$ alkoxy, $C_1$-$C_6$ alkylsulfanyl, $C_1$-$C_6$ alkylsulfenyl, $C_1$-$C_6$ alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, $C_1$-$C_6$ perfluoroalkyl, heteroaryl, or aryl, multiple degrees of substitution being allowed. For polycyclic aromatic ring system diradicals, one or more of the rings may contain one or more heteroatoms. Examples of "heteroarylene" used herein are furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, and the like.

As used herein, the term "heterocyclic" or the term "heterocyclyl" refers to a three to twelve-membered non-aromatic heterocyclic ring being saturated or having one or more degrees of unsaturation containing one or more heteroatomic substitutions selected from S, S(O), S(O)$_2$, O, or N, optionally substituted with substituents selected from the group consisting of lower alkyl, lower haloalkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more of another "heterocyclic" ring(s) or cycloalkyl ring(s). Furthermore, such heterocyclyl group optionally includes a $C_1$-$C_4$ alkylene linker through which it may be attached. Examples of "heterocyclic" include, but are not limited to, tetrahydrofuran, pyran, 1,4-dioxane, 1,3-dioxane, piperidine, pyrrolidine, morpholine, tetrahydrothiopyran, tetrahydrothiophene, and the like.

As used herein, the term "heterocyclylene" refers to a three to twelve-membered non-aromatic heterocyclic ring diradical being unsaturated or having one or more degrees of unsaturation containing one or more heteroatoms selected from S, SO, SO$_2$, O, or N, optionally substituted with substituents selected from the group which includes $C_1$-$C_6$ alkyl, $C_1$-$C_6$ alkoxy, $C_1$-$C_6$ alkylsulfanyl, $C_1$-$C_6$ alkylsulfenyl, $C_1$-$C_6$ alkylsulfonyl, oxo, hydroxy, mercapto, amino optionally substituted by alkyl, carboxy, carbamoyl optionally substituted by alkyl, aminosulfonyl optionally substituted by alky, nitro, cyano, halogen and $C_1$-$C_6$ perfluoroalkyl, multiple degrees of substitution being allowed. Such a ring may be optionally fused to one or more benzene rings or to one or more of another "heterocyclic" rings or cycloalkyl rings. Examples of "heterocyclylene" include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, morpholine-2,4-diyl, and the like.

As used herein, the term "alkoxy" refers to the group $R_aO$—, where $R_a$ is alkyl as defined above.

As used herein the term "aralkoxy" refers to the group $R_bR_aO$—, where $R_a$ is alkylene and $R_b$ is aryl, both as defined above.

As used herein, the term "alkylsulfanyl" refers to the group $R_aS$—, where $R_a$ is alkyl as defined above.

As used herein, the term "alkylsulfenyl" refers to the group $R_aS(O)$—, where $R_a$ is alkyl as defined above.

As used herein, the term "alkylsulfonyl" refers to the group $R_aS(O)_2$—, where $R_a$ is alkyl as defined above.

As used herein, the term "oxo" refers to the group =O.

As used herein, the term "mercapto" refers to the group —SH.

As used herein, the term "carboxy" refers to the group —COO—.

As used herein, the term "cyano" refers to the group —CN.

As used herein the term "cyanoalkyl" refers to the group —$R_a$CN wherein $R_a$ is $C_1$-$C_3$ alkylene as defined above. Exemplary "cyanoalkyl" groups useful in the present invention include, but are not limited to cyanomethyl, cyanoethyl, and cyanopropyl.

As used herein, the term "aminosulfonyl" refers to the group —S(O)$_2$NH$_2$.

As used herein, the term "carbamoyl" refers to the group —C(O)N($R_a$)—, wherein $R_a$ is any suitable substituent.

As used herein, the term "sulfanyl" shall refer to the group —S—.

As used herein, the term "sulfenyl" shall refer to the group —S(O)—.

As used herein, the term "sulfonyl" shall refer to the group —S(O)$_2$—.

As used herein, the term "acyl" refers to the group $R_aC(O)$—, where $R_a$ is alkyl, cycloalkyl, or heterocyclyl as defined herein.

As used herein, the term "aroyl" refers to the group $R_aC(O)$—, where $R_a$ is aryl as defined herein.

As used herein, the term "heteroaroyl" refers to the group $R_aC(O)$—, where $R_a$ is heteroaryl as defined herein.

As used herein, the term "alkoxycarbonyl" refers to the group $R_aOC(O)$—, where $R_a$ is alkyl as defined herein.

As used herein, the term "acyloxy" refers to the group $R_aC(O)O$— where $R_a$ is alkyl, cycloalkyl, or heterocyclyl as defined herein.

As used herein, the term "aroyloxy" refers to the group $R_aC(O)O$—, where $R_a$ is aryl as defined herein.

As used herein, the term "heteroaroyloxy" refers to the group $R_aC(O)O$—, where $R_a$ is heteroaryl as defined herein.

As used herein, the term "optionally" means that the subsequently described event(s) may or may not occur, and includes both event(s) that occur, and events that do not occur.

As used herein, the term "physiologically functional derivative" refers to any pharmaceutically acceptable derivative of a compound of the present invention; for example, an ester or an amide, which upon administration to a mammal is capable of providing (directly or indirectly) a compound of the present invention or an active metabolite thereof. Such derivatives are clear to those skilled in the art, without undue experimentation, and with reference to the teaching of Burger's Medicinal Chemistry And Drug Discovery, 5$^{th}$ Edition, Vol 1: Principles and Practice, which is incorporated herein by reference to the extent that it teaches physiologically functional derivatives.

As used herein, the term "solvate" refers to a complex of variable stoichiometry formed by a solute (in this invention, a compound of formula (I)), or a salt or physiologically functional derivative thereof) and a solvent. Such solvents for the purpose of the invention may not interfere with the biological activity of the solute. Examples of suitable solvents include, but are not limited to water, methanol, ethanol, and acetic acid. Preferably the solvent used is a pharmaceutically acceptable solvent. Examples of suitable pharmaceutically acceptable solvents include water, ethanol, and acetic acid. Most preferably the solvent used is water.

The compounds of formula (I) have the ability to crystallize in more than one form, a characteristic known as polymorphism, and it is understood that such polymorphic forms ("polymorphs") are within the scope of formula (I). Polymorphism generally can occur as a response to changes in temperature or pressure or both and can also result from variations in the crystallization process. Polymorphs can be distinguished by various physical characteristics known in the art such as x-ray diffraction patterns, solubility, and melting point.

As used herein, the term "substituted" refers to substitution with the named substituent or substituents, multiple degrees of substitution being allowed unless otherwise stated.

Certain of the compounds described herein contain one or more chiral centers, or may otherwise be capable of existing as multiple stereoisomers. The compounds of this invention include mixtures of stereoisomers as well as purified enantiomers or enantiomerically or diastereomerically enriched mixtures. Also included within the scope of the invention are the individual isomers of the compounds represented by formula (I) above as well as any wholly or partially equilibrated mixtures thereof. The present invention also covers the individual isomers of the compounds represented by the formulas above as mixtures with isomers thereof in which one or more chiral centers are inverted.

It is to be understood that the following embodiments refer to compounds within the scope of both formula (I) and formula (II) as defined above unless specifically limited by the definition of each formula or specifically limited otherwise. It is also understood that the embodiments of the present invention described herein, including uses and compositions, although described with reference to formula (I) are applicable to both formula (I) and formula (II).

As recited above A is the group defined by $(Q^4)_p$-$(Q^3)_n$-$(Q^2)_m$-$(Q^1)$-. In one embodiment, m is 0, n is 0, p is 0, and A is $(Q^1)$-. In another embodiment, n is 0, p is 0, and A is $(Q^2)_m$-$(Q^1)$-. In a further embodiment, p is 0 and A is $(Q^3)_n$-$(Q^2)_m$-$(Q^1)$-. In another embodiment, m is 0, n is 1, p is 0,1, or 2, and A is $(Q^4)_p$-$(Q^3)$-$(Q^1)$-.

In one embodiment, the compound of formula (I) is a compound of formula (II):

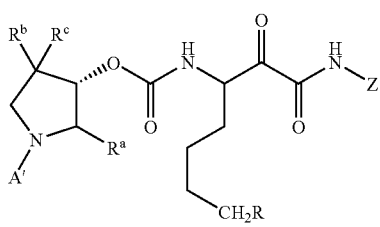

(II)

wherein $R^a$ is hydrogen or oxo, $R^b$ is hydrogen or $C_1$-$C_6$ alkyl, and $R^c$ is hydrogen or $C_1$-$C_6$ alkyl.

In one embodiment, $Q^1$ is heterocyclyl. In another embodiment, $Q^1$ is heterocyclylene.

In one embodiment, $Q^1$ is selected from the group:

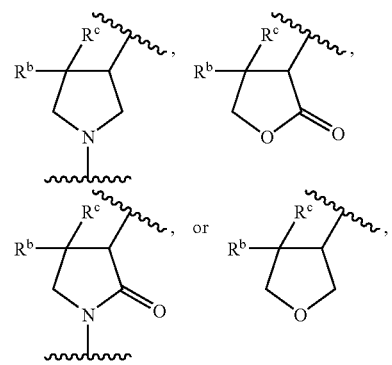

wherein $R^b$ is hydrogen or $C_1$-$C_6$ alkyl and $R^c$ is hydrogen or $C_1$-$C_6$ alkyl.

In another embodiment, $Q^1$ is selected from the group:

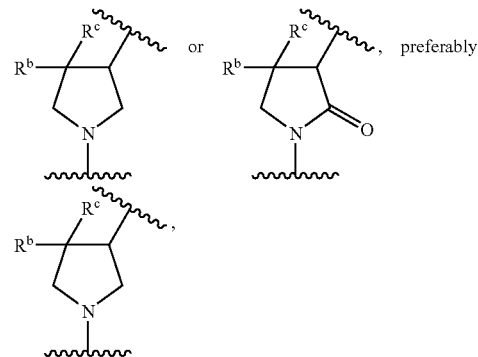

wherein $R^b$ is hydrogen or $C_1$-$C_6$ alkyl and $R^c$ is hydrogen or $C_1$-$C_6$ alkyl.

In another embodiment, $Q^1$ is selected from the group:

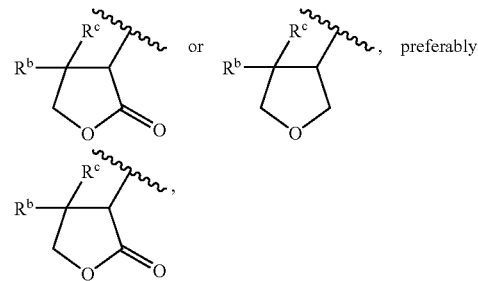

wherein $R^b$ is hydrogen or $C_1$-$C_6$ alkyl and $R^c$ is hydrogen or $C_1$-$C_6$ alkyl.

In one embodiment, m is 1 and $Q^2$ is OC(O), C(O), N(H)C(O), S(O)$_2$, or N(H)S(O)$_2$. In another embodiment, m is 1 and $Q^2$ is OC(O) or C(O), preferably OC(O). In an alternative embodiment, m is 1 and $Q^2$ is N(H)C(O). In another alternative embodiment, m is 1 and $Q^2$ is S(O)$_2$.

In one embodiment, n is 1 and $Q^3$ is aryl or arylene, heteroaryl or heterarylene, heterocyclyl or heterocyclylene, or aralkyl or aralkylene.

In one embodiment, $Q^3$ is aryl or arylene, preferably selected from the group:
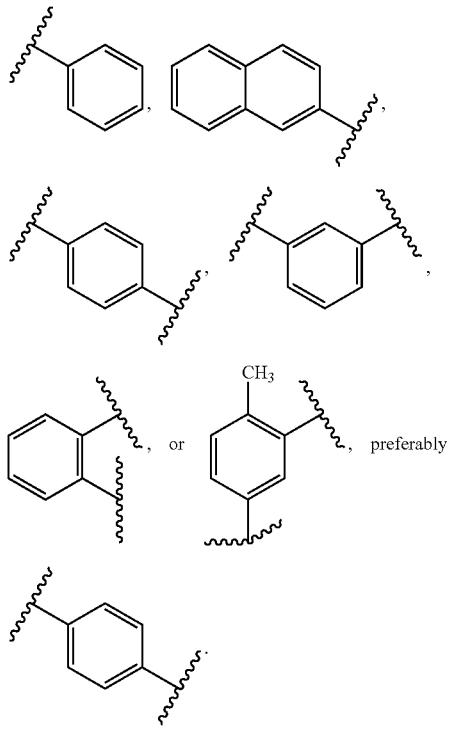
In one embodiment, $Q^3$ is aralkyl or aralkylene, preferably selected from the group:
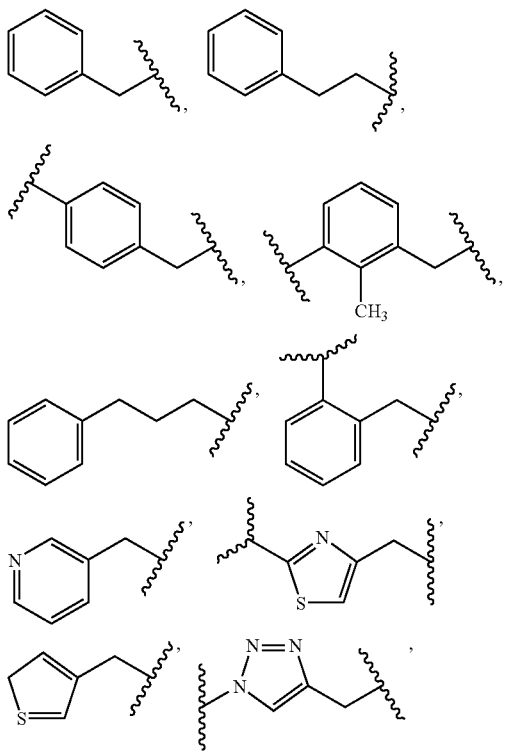
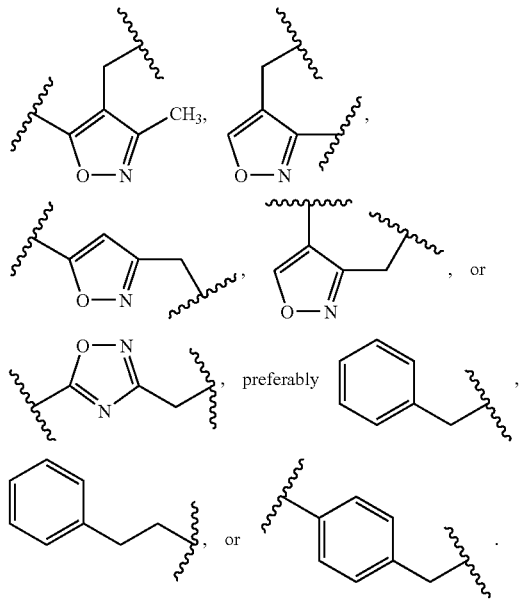
In another embodiment, $Q^3$ is heteroaryl or heteroarylene, preferably selected from the group:
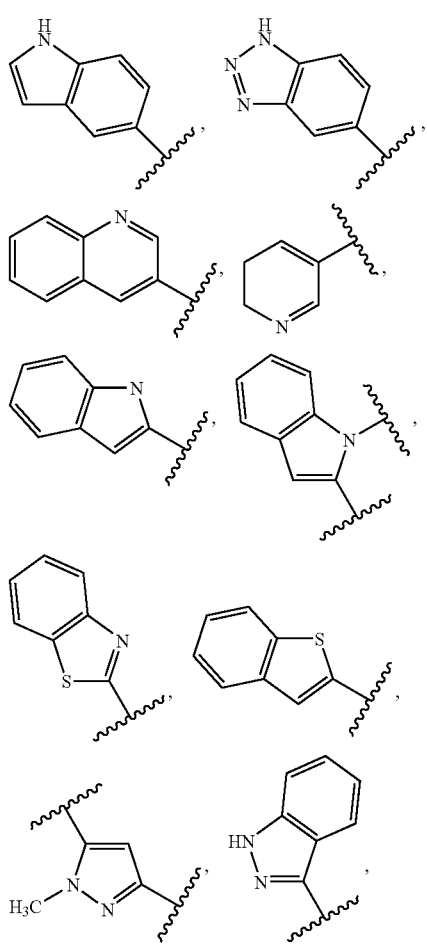

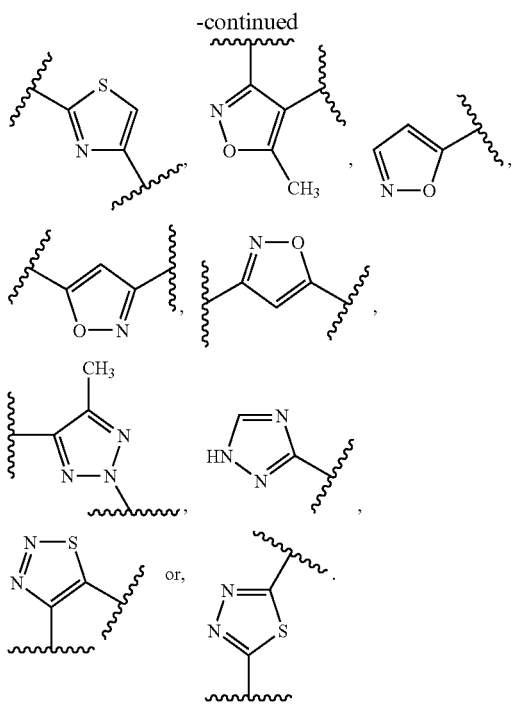

In a further embodiment, Q³ is heterocyclyl or heterocyclylene, preferably selected from the group:

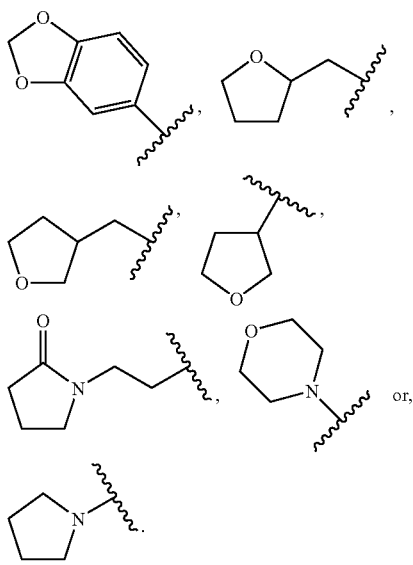

In one embodiment, Q⁴ is methyl, tert-butyl, —CF₃, phenyl, phenoxy, isoxazolyl, thiadiazolyl, thienyl, pyrazinyl, fluoro, chloro, cyano, and p is 1 or 2. In a preferred embodiment, Q⁴ is methyl, tert-butyl, —CF3, phenyl, phenoxy, and fluoro and p is 1 or 2. In a more preferred embodiment, Q⁴ is methyl, and p is 1.

It is understood that Q¹, Q², Q³, and Q⁴ as well as X¹ below are attached to the indicated linking group of Formula (I) or (II) through the bond or bonds of Q¹, Q², Q³, and Q⁴, and X¹ having an unfilled valence and being indicated by

The appropriate attachments are further illustrated in the working examples recited below.

As recited above D is O or S. In one embodiment D is S. In a preferred embodiment D is O.

In a preferred embodiment, R is hydrogen.

As recited above Z is the group defined by —(X)$_m$—(X¹). In one embodiment, m is 0 and Z is —(X¹). In another embodiment, m is 1 and Z is the group defined by —(X)—(X¹).

In one embodiment, X is C(R")(R'"), wherein R" is hydrogen or $C_1$-$C_6$ alkyl, R'" is hydrogen and $C_1$-$C_6$ alkyl, and m is 0, 1, or 2. In another embodiment, X is C(H)(R") where R" is hydrogen and m is 0, 1, or 2, preferably m is 0 or 1, more preferably m is 0. In another embodiment, X is C(H)(R") where R" is —CH₃ and m is 1.

In one embodiment X¹ is aryl. In a preferred embodiment X¹ is

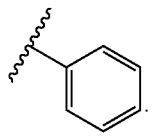

In one embodiment X¹ is heteroaryl or heterocyclyl. In a preferred embodiment X¹ is selected from the group

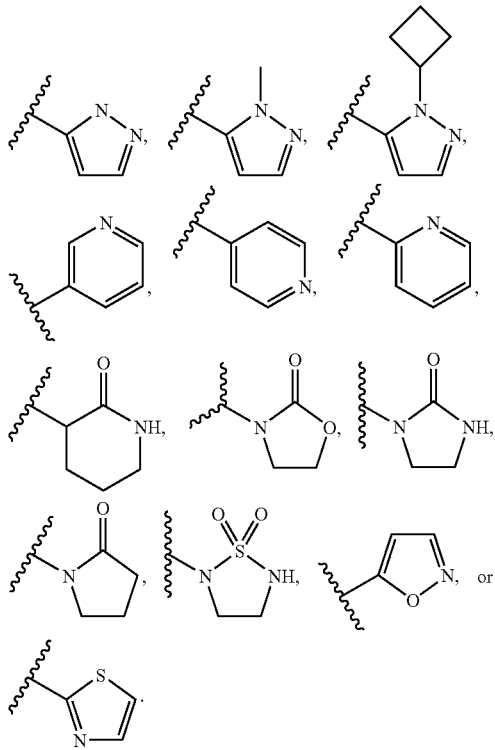

Specific examples of compounds of the present invention include the following:

(3S)-4,4-dimethyl-2-oxotetrahydro-3-furanyl (1S)-1-(oxo{[(1R)-1-phenylethyl]amino}acetyl)pentylcarbamate;

(3S)-4,4-dimethyl-2-oxotetrahydro-3-furanyl (1S)-5-{[(methylamino) carbonyl]amino}-1-(oxo{[(1R)-1-phenylethyl]amino}acetyl)pentylcarbamate;

(4S)-4-ethyl-4-methyl-2-oxotetrahydro-3-furanyl (1S)-1-(oxo{[(1R)-1-phenylethyl]amino}acetyl)pentylcarbamate;

1-Benzyl-4,4-dimethyl-2-oxo-3-pyrrolidinyl (1S)-1-(oxo{[(1R)-1-phenylethyl]amino}acetyl)pentylcarbamate;

Benzyl 4,4-dimethyl-2-oxo-3-[({[(1S)-1-(oxo{[(1R)-1-phenylethyl]amino}acetyl)pentyl]amino}carbonyl)oxy]-1-pyrrolidinecarboxylate;

3S)-4,4-dimethyl-2-oxopyrrolidinyl (1S)-1-(1-hydroxy-2-oxo-2-{[(1R)-1-phenylethyl]amino}ethyl)pentylcarbamate;

(3R)-4,4-dimethyl-2-oxopyrrolidinyl (1S)-1-(1-hydroxy-2-oxo-2-{[(1R)-1-phenylethyl]amino}ethyl)pentylcarbamate;

1,4,4-trimethyl-2-oxo-3-pyrrolidinyl (1S)-1-(oxo{[(1R)-1-phenylethyl]amino}acetyl)pentylcarbamate;

(3S)-1-Benzyl-4,4-dimethylpyrrolidinyl 1-(oxo{[(1R)-1-phenylethyl]amino}acetyl)pentylcarbamate;

(3S)-1-Benzoyl-4,4-dimethylpyrrolidinyl (1S)-1-(oxo{[(1R)-1-phenylethyl]amino}acetyl)pentylcarbamate;

(3S)-1-Acetyl-4,4-dimethylpyrrolidinyl (1S)-1-(oxo{[(1R)-1-phenylethyl]amino}acetyl)pentylcarbamate;

(3S)-4,4-Dimethyl-1-(phenylacetyl)pyrrolidinyl (1S)-1-(oxo{[(1R)-1-phenylethyl]amino}acetyl)pentylcarbamate;

(3S)-1-(5-Isoxazolylcarbonyl)-4,4-dimethylpyrrolidinyl (1S)-1-(oxo{[(1R)-1-phenylethyl]amino}acetyl)pentylcarbamate;

(3S)-4,4-Dimethyl-1-[(4-methyl-1,2,3-thiadiazol-5-yl)carbonyl]pyrrolidinyl (1S)-1-(oxo{[(1R)-1-phenylethyl]amino}acetyl)pentylcarbamate;

(3S)-1-[(3-tert-Butyl-1-methyl-1H-pyrazol-5-yl)carbonyl]-4,4-dimethylpyrrolidinyl (3S)-1-(oxo{[(1R)-1-phenylethyl]amino}acetyl)pentylcarbamate;

(3S)-4,4-Dimethyl-1-[(5-methyl-2-phenyl-2H-1,2,3-triazol-4-yl)carbonyl]pyrrolidinyl (1S)-1-(oxo{[(1R)-1-phenylethyl]amino}acetyl)pentylcarbamate;

(3S)-1-(1,3-Benzodioxol-5-ylcarbonyl)-4,4-dimethylpyrrolidinyl (1S)-1-(oxo{[(1R)-1-phenylethyl]amino}acetyl)pentylcarbamate;

(3S)-1-(1-Benzothien-2-ylcarbonyl)-4,4-dimethylpyrrolidinyl (1S)-1-(oxo{[(1R)-1-phenylethyl]amino}acetyl)pentylcarbamate;

(3S)-4,4-Dimethyl-1-(2-naphthoyl)pyrrolidinyl (1S)-1-(oxo{[(1R)-1-phenylethyl]amino}acetyl)pentylcarbamate;

(3S)-4,4-Dimethyl-1-[(5-methyl-3-isoxazolyl)carbonyl]pyrrolidinyl (1S)-1-(oxo{[(1R)-1-phenylethyl]amino}acetyl)pentylcarbamate;

(3S)-1-([1,1'-Biphenyl]-4-ylcarbonyl)-4,4-dimethylpyrrolidinyl (1S)-1-(oxo{[(1R)-1-phenylethyl]amino}acetyl)pentylcarbamate;

(3S)-1-(1H-Indol-5-ylcarbonyl)-4,4-dimethylpyrrolidinyl (1S)-1-(oxo{[(1R)-1-phenylethyl]amino}acetyl)pentylcarbamate;

(3S)-1-(1H-1,2,3-Benzotriazol-5-ylcarbonyl)-4,4-dimethylpyrrolidinyl (1S)-1-(oxo{[(1R)-1-phenylethyl]amino}acetyl)pentylcarbamate;

(3S)-4,4-Dimethyl-1-{[(3-phenoxyphenyl)acetyl]pyrrolidinyl (1S)-1-(oxo{[(1R)-1-phenylethyl]amino}acetyl)pentylcarbamate;

(3S)-4,4-Dimethyl-1-(4-phenylbutanoyl)pyrrolidinyl (1S)-1-(oxo{[(1R)-1-phenylethyl]amino}acetyl)pentylcarbamate;

(3S)-1-[(4-tert-Butylphenyl)acetyl]-4,4-dimethylpyrrolidinyl (1S)-1-(oxo{[(1R)-1-phenylethyl]amino}acetyl)pentylcarbamate;

(3S)-4,4-Dimethyl-1-{[2-(4-pyridinyl)-1,3-thiazol-4-yl]carbonyl}pyrrolidinyl (1S)-1-(oxo{[(1R)-1-phenylethyl]amino}acetyl)pentylcarbamate;

(3S)-4,4-Dimethyl-1-[(5-methyl-3-phenyl-4-isoxazolyl)carbonyl]pyrrolidinyl (1S)-1-(oxo{[(1R)-1-phenylethyl]amino}acetyl)pentylcarbamate;

(3S)-4,4-Dimethyl-1-[(1-methyl-1H-indol-2-yl)carbonyl]pyrrolidinyl (1S)-1-(oxo{[(1R)-1-phenylethyl]amino}acetyl)pentylcarbamate;

(3S)-4,4-Dimethyl-1-(3-quinolinylcarbonyl)pyrrolidinyl 1-(oxo{[(1R)-1-phenylethyl]amino}acetyl)pentylcarbamate;

(3S)-1-([1,1'-Biphenyl]-4-ylacetyl)-4,4-dimethylpyrrolidinyl (1S)-1-(oxo{[(1R)-1-phenylethyl]amino}acetyl)pentylcarbamate;

(3S)-4,4-Dimethyl-1-[(2-phenoxyphenyl)acetyl]pyrrolidinyl (1S)-1-(oxo{[(1R)-1-phenylethyl]amino}acetyl)pentylcarbamate;

(3S)-1-(1H-Indol-2-ylcarbonyl)-4,4-dimethylpyrrolidinyl (1S)-1-(oxo{[(1R)-1-phenylethyl]amino}acetyl)pentylcarbamate;

(3S)-4,4-Dimethyl-1-(3-pyridinylacetyl)pyrrolidinyl 1-(oxo{[(1R)-1-phenylethyl]amino}acetyl)pentylcarbamate;

(3S)-4,4-Dimethyl-1-(1H-1,2,4-triazol-3-ylcarbonyl)pyrrolidinyl (1S)-1-(oxo{[(1R)-1-phenylethyl]amino}acetyl)pentylcarbamate;

(3S)-4,4-Dimethyl-1-[(3-methyl-5-isoxazolyl)acetyl]pyrrolidinyl (1S)-1-(oxo{[(1R)-1-phenylethyl]amino}acetyl)pentylcarbamate;

(3S)-1-(1H-Indazol-3-ylcarbonyl)-4,4-dimethylpyrrolidinyl (1S)-1-(oxo{[(1R)-1-phenylethyl]amino}acetyl)pentylcarbamate;

(3S)-4,4-Dimethyl-1-{[2-(4-methyl-1,2,3-thiadiazol-5-yl)-1,3-thiazol-4-yl]carbonyl}pyrrolidinyl (1S)-1-(oxo{[(1R)-1-phenylethyl]amino}acetyl)pentylcarbamate;

(3S)-4,4-Dimethyl-1-{[2-(2-pyrazinyl)-1,3-thiazol-4-yl]acetyl}pyrrolidinyl (1S)-1-(oxo{[(1R)-1-phenylethyl]amino}acetyl)pentylcarbamate;

(3S)-1-[(4-Fluorophenyl)acetyl]-4,4-dimethylpyrrolidinyl (1S)-1-(oxo{[(1R)-1-phenylethyl]amino}aminocarbonyl)oxy]-1-pyrrolidinecarboxylate;

[1,1'-biphenyl]-4-ylmethyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

Tetrahydro-2-furanyl methyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

3-Thienylmethyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

(3S)-Tetrahydro-3-furanyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

Benzyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

2-Phenylethyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

(1-Phenyl-1H-1,2,3-triazol-4-yl)methyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

2-(2-Oxo-1-pyrrolidinyl)ethyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

Tetrahydro-2H-pyran-2-ylmethyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

Tetrahydro-3-furanylmethyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

[3-Methyl-5-(5-methyl-isoxazol-3-yl)-4-isoxazolyl]methyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

2-(4Methyl-1,3-thiazol-5-yl)ethyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

(5-methyl-3-isoxazolyl)methyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

[3-(2,6-Dichlorophenyl)-5-methyl-4-isoxazolyl]methyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

(2-Methyl[1,1'-biphenyl]-3-yl)methyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

[5-(2-Thienyl)-1,2,4-oxadiazol-3-yl]methyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

(3R)-Tetrahydro-3-furanyl (4S)-3,3-dimethyl-4-[({[(5)-1-(oxo{[(1R)-1-phenylethyl]amino}acetyl)pentyl]amino}carbonyl)oxy]-1-pyrrolidinecarboxylate;

[1,1'-Biphenyl]-4-yl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

4-Phenoxyphenyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

3-Phenoxyphenyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

2-Naphthyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

4-(1,2,3-Thiadiazol-4-yl)phenyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

Phenyl 3,3-dimethyl-4-[({[(1S)-1-(oxo{[(1R)-1-phenylethyl]amino}acetyl)pentyl]amino}carbonyl)oxy]-1-pyrrolidinecarboxylate;

(3S)-1-(Anilinocarbonyl)-4,4-dimethylpyrrolidinyl (1S)-1-(oxo{[(1R)-1-phenylethyl]amino}acetyl)pentylcarbamate;

(3S)-1-[(Benzylamino)carbonyl]-4,4-dimethylpyrrolidinyl (1S)-1-(oxo{[(1R)-1-phenylethyl]amino}acetyl)pentylcarbamate;)

(3S)-4,4-Dimethyl-1-{[(2-phenylethyl)amino]carbonyl}pyrrolidinyl (1S)-1-(oxo{[(1R)-1-phenylethyl]amino}acetyl)pentylcarbamate;

(3S)-4,4-Dimethyl-1-(3-pyridinylcarbonyl)pyrrolidinyl (1S)-1-(oxo{[(1R)-1-phenylethyl]amino}acetyl)pentylcarbamate;

(3S)-1-{[(3,5-Dimethyl-4-isoxazolyl)amino]carbonyl}-4,4-dimethylpyrrolidinyl (1S)-1-(oxo{[(1R)-1-phenylethyl]amino}acetyl)pentylcarbamate;

(3S)-1-[(Cyclohexylamino)carbonyl]-4,4-dimethylpyrrolidinyl (1S)-1-(oxo{[(1R)-1-phenylethyl]amino}acetyl)pentylcarbamate;

(3S)-1-[(4-Cyanoanilino)carbonyl]-4,4-dimethylpyrrolidinyl (1S)-1-(oxo{[(1R)—1-phenylethyl]amino}acetyl)pentylcarbamate;

(3S)-4,4-Dimethyl-1-{[4-(trifluoromethyl)anilino]carbonyl}pyrrolidinyl (1S)-1-(oxo{[(1R)-1-phenylethyl]amino}acetyl)pentylcarbamate;

(3S)-4,4-dimethyl-1-{[4-(trifluoromethyl)anilino]carbonyl}pyrrolidinyl (1S)-1-(oxo{[(1H-pyrazol-5-ylamino)acetyl]pentylcarbamate;

(3S)-1-[(5-Fluoro-2-methylanilino)carbonyl]-4,4-dimethylpyrrolidinyl (1S)-1-(oxo{[(1R)-1-phenylethyl]amino}acetyl)pentylcarbamate;

(3S)-4,4-Dimethyl-1-(4-morpholinylcarbonyl)pyrrolidinyl (1S)-1-(oxo{[(1R)-1-phenylethyl]amino}acetyl)pentylcarbamate;

(3S)-4,4-Dimethyl-1-(1-pyrrolidinylcarbonyl)pyrrolidinyl (1S)-1-(oxo{[(1R)-1-phenylethyl]amino}acetyl)pentylcarbamate;

(3S)-1-[(Benzoylamino)carbonyl]-4,4-dimethylpyrrolidinyl (1S)-1-(oxo{[(1R)-1-phenylethyl]amino}acetyl)pentylcarbamate;

(3S)-4,4-Dimethyl-1-({[(4-methylphenyl)sulfonyl]amino}carbonyl)pyrrolidinyl (1S)-1-(oxo{[(1R)-1-phenylethyl]amino}acetyl)pentylcarbamate;

(3S)-4,4-Dimethyl-1-(phenylsulfonyl)pyrrolidinyl (1S)-1-(oxo{[(1R)-1-phenylethyl]amino}acetyl)pentylcarbamate;

(3S)-1-(Benzylsulfonyl)-4,4-dimethylpyrrolidinyl (1S)-1-(oxo{[(1R)-1-phenylethyl]amino}acetyl)pentylcarbamate;

(3S)-1-(1,3-Benzodioxol-5-ylsulfonyl)-4,4-dimethylpyrrolidinyl (1S)-1-(oxo{[(1R)-1-phenylethyl]amino}acetyl)pentylcarbamate;

(3S)-1-(2,3-Dihydro-1,4-benzodioxin-6-ylsulfonyl)-4,4-dimethylpyrrolidinyl (1S)-1-(oxo{[(1R)-1-phenylethyl]amino}acetyl)pentylcarbamate;

(3S)-1-(1,3-Benzothiazol-2-yl)-4,4-dimethylpyrrolidinyl (1S)-1-[oxo(1H-pyrazol-5-ylamino)acetyl]pentylcarbamate;

(3S)-4,4-Dimethyl-1-[5-(trifluoromethyl)-1,3,4-thiadiazol-2-yl]pyrrolidinyl (1S)-1-[oxo(1H-pyrazol-5-ylamino)acetyl]pentylcarbamate; and (3S)-4,4-Dimethyltetrahydro-3-furanyl 1-(oxo{[(1R)-1-phenylethyl]amino}acetyl)pentylcarbamate;

or a salt, solvate, or physiologically functional derivative thereof.

Typically, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts derived from a nitrogen on a substituent in the compound of formula (I) or formula (II). Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium, and valerate. Other salts, which are not pharmaceutically acceptable, may be useful in the preparation of compounds of this invention and these form a further aspect of the invention.

While it is possible that, for use in therapy, therapeutically effective amounts of a compound of formula (I) or formula (II), as well as salts, solvates and physiological functional derivatives thereof, may be administered as the raw chemical, it is possible to present the active ingredient as a pharmaceutical composition. Accordingly, the invention further provides pharmaceutical compositions which include therapeutically effective amounts of compounds of the formula (I) or (II) and salts, solvates and physiological functional derivatives thereof, and one or more pharmaceutically acceptable carriers, diluents, or excipients. The compounds of the formula (I) or (II) and salts, solvates and physiologically functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula (I) or (II), or salts, solvates and physiological functional derivatives thereof, with one or more pharmaceutically acceptable carriers, diluents or excipients.

Pharmaceutical formulations may be presented in unit dose forms containing a predetermined amount of active ingredient per unit dose. Such a unit may contain, for example, 0.5 mg to 1 g, preferably 1 mg to 700 mg, of a compound of the formula (I) or (II) depending on the condition being treated, the route of administration and the age, weight and condition of the patient. Preferred unit dosage formulations are those containing a daily dose or sub-dose, as herein above recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are prepared by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride, and the like. Disintegrators include, without limitation, starch, methylcellulose, agar, bentonite, xanthan gum and the like. Tablets are formulated, for example, by preparing a powder mixture, granulating or slugging, adding a lubricant and disintegrant, and pressing into tablets. A powder mixture is prepared as described above by mixing the compound, suitably comminuted, with a diluent or base and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials, and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives; flavor additives such as peppermint oil, or natural sweeteners, saccharin, or other artificial sweeteners; and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula (I) or (II) and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula (I) or (II) and salts, solvates and physiologically functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropyl-methacrylamide-phenol, polyhydroxyethylasparta-midephenol, or polyethyleneoxidepolylysine substituted with palmitoyl residues. Furthermore, the compounds may be coupled to a class of biodegradable polymers useful in achieving controlled release of a drug; for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouthwashes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns, which is administered in the manner in which snuff is taken, i.e., by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurised aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of formula (I) or (II) for the treatment of osteoporosis will generally be in the range of 0.1 to 100 mg/kg body weight of recipient (mammal) per day and more usually in the range of 1 to 10 mg/kg body weight per day. Thus, for a 70 kg adult mammal, the actual amount per day would usually be from 70 to 700 mg. This amount may be given in a single dose per day or more usually in a number (such as two, three, four, five or six) of sub-doses per day such that the total daily dose is the same. An effective amount of a salt or solvate, or physiologically functional derivative thereof, may be determined as a proportion of the effective amount of the compound of formula (I) or (II) per se. It is envisaged that similar dosages would be appropriate for treatment of the other conditions referred to above.

The compounds of the present invention and their salts and solvates, and physiologically functional derivatives thereof, may be employed alone or in combination with other therapeutic agents for the treatment of the above-mentioned conditions. In particular, in osteoporosis therapy, combination with other osteoporosis therapeutic agents is envisaged. Combination therapies according to the present invention thus comprise the administration of at least one compound of formula (I) or (II) or a pharmaceutically acceptable salt or solvate thereof, or a physiologically functional derivative thereof, and the use of at least one other osteoporosis treatment method. Preferably, combination therapies according to the present invention comprise the administration of at least one compound of formula (I) or (II) or a pharmaceutically acceptable salt or solvate thereof, or a physiologically functional derivative thereof, and at least one other osteoporosis treatment agent, preferably a bone building agent. The compound(s) of formula (I) or (II) and the other pharmaceutically active agent(s) may be administered together or separately and, when administered separately, this may occur simultaneously or sequentially in any order. The amounts of the compound(s) of formula (I) or (II) and the other pharmaceutically active agent(s) and the relative timings of administration will be selected in order to achieve the desired combined therapeutic effect. The administration in combination of a compound of formula (I) or (II) or salts, solvates, or physiologically functional derivatives thereof with other osteoporosis treatment agents may be in combination in accordance with the invention by administration concomitantly in (1) a unitary pharmaceutical composition including both compounds or (2) separate pharmaceutical compositions each including one of the compounds. Alternatively, the combination may be administered separately in a sequential manner wherein one osteoporosis treatment agent is administered first and the other second or vice versa. Such sequential administration may be close in time or remote in time.

A preferred additional osteoporosis treatment agent is a bone building (anabolic) agent. Bone building agents can lead to increases in parameters such as bone mineral density greater than those than can be achieved with anti-resorptive agents. In some cases, such anabolic agents can increase trabecular connectivity leading to greater structural integrity of the bone. A combination therapy composed of a bone forming agent with an anti-resorptive drug such as a cathepsin K inhibitor could provide even greater efficacy than treatment with either agent alone.

The present invention is directed to methods of regulating, modulating, or inhibiting cathepsin K for the prevention and/or treatment of disorders related to an imbalance between bone resorption and formation, which can ultimately lead to fracture. In particular, the compounds of the present invention can also be used in the treatment of osteoporosis. Furthermore, the compounds of the present invention can be used to provide additive or synergistic effects with existing osteoporosis therapies.

The present invention thus also provides compounds of formula (I) or (II) and pharmaceutically acceptable salts or solvates thereof, or physiologically functional derivatives thereof, for use in medical therapy, and particularly in the treatment of disorders mediated by an imbalance between bone resorption and formation which can ultimately leading to fracture.

The present invention also provides compounds of formula (I) or (II) and pharmaceutically acceptable salts or solvates thereof, or physiologically functional derivatives thereof, for use in medical therapy, and particularly in the treatment of disorders characterized by bone loss or characterized by excessive cartilage or matrix degradation.

The compounds of the present invention are also useful in the treatment of one or more diseases afflicting mammals that are characterized by potential involvement of cathepsin K in autoimmune diseases such as rheumatoid arthritis, osteoathritis, neoplastic diseases, parasitic diseases, and atherosclerosisis.

A further aspect of the invention provides a method of treatment of a mammal suffering from a disorder mediated by an imbalance between bone resorption and formation that can ultimately lead to fracture, which includes administering to said subject an effective amount of a compound of formula (I) or (II) or a pharmaceutically acceptable salt, solvate, or a physiologically functional derivative thereof.

A further aspect of the invention provides a method of treatment of a mammal suffering from a disorder characterized by bone loss, which includes administering to said subject an effective amount of a compound of formula (I) or (II) or a pharmaceutically acceptable salt, solvate, or a physiologically functional derivative thereof. In a preferred embodiment, the disorder is osteoporosis.

A further aspect of the invention provides a method of treatment of a mammal suffering from osteoporosis, which includes administering to said subject an effective amount of a compound of formula (I) or (II) or a pharmaceutically acceptable salt or solvate thereof, or a physiologically functional derivative thereof.

A further aspect of the present invention provides the use of a compound of formula (I) or (II), or a pharmaceutically acceptable salt or solvate thereof, or a physiologically functional derivative thereof, in the preparation of a medicament for the treatment of a disorder characterized by an imbalance between bone resorption and formation that can ultimately lead to fracture. In a preferred embodiment, the disorder is osteoporosis.

A further aspect of the present invention provides the use of a compound of formula (I) or (II), or a pharmaceutically acceptable salt or solvate thereof, or a physiologically functional derivative thereof, in the preparation of a medicament for the treatment of a disorder characterized by bone loss. In a preferred embodiment, the disorder is osteoporosis.

A further aspect of the present invention provides the use of a compound of formula (I) or (II), or a pharmaceutically acceptable salt or solvate thereof, or a physiologically functional derivative thereof, in the preparation of a medicament for the treatment of osteoporosis.

The mammal requiring treatment with a compound of the present invention is typically a human being.

In another embodiment, therapeutically effective amounts of the compounds of formula (I) or (II) or salts, solvates or physiologically derived derivatives thereof and at least one bone building agent may be administered in combination to a mammal for treatment of osteoporosis.

The compounds of this invention may be made by a variety of methods, including standard synthetic methods. Any previously defined variable will continue to have the previously defined meaning unless otherwise indicated. Illustrative general synthetic methods are set out below and then specific compounds of the invention are prepared in the working Examples.

Compounds of general formula (I) or formula (II) may be prepared by methods known in the art of organic synthesis as set forth in part by the following synthetic schemes. Generally, the following schemes are illustrated using compounds of formula (II), but it is recognized that such schemes are easily adaptable by the skilled artisan to prepare other compounds of formula (I). It is also recognized that in all of the schemes described below, it is well understood that protecting groups for sensitive or reactive groups are employed where necessary in accordance with general principles of synthetic chemistry. Protecting groups are manipulated according to standard methods of organic synthesis (T. W. Green and P. G. M. Wuts (1991) *Protecting Groups in Organic Synthesis*, John Wiley &Sons). These groups are removed at a convenient stage of the compound synthesis using methods that are readily apparent to those skilled in the art The selection of processes as well as the reaction conditions and order of their execution shall be consistent with the preparation of compounds of formula (I) or (II). Those skilled in the art will recognize if a stereocenter exists in compounds of formula (I) or (II). Accordingly, the present invention includes all possible stereoisomers and includes not only racemic compounds but the individual enantiomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, *Stereochemistry of Organic Compounds* by E. L. Eliel, S. H. Wilen, and L. N. Mander (Wiley-Interscience, 1994).

Compounds of formula (I) and (II), can be prepared according to the synthetic sequences shown in Schemes I, II, and II, which are further detailed in the Examples section following.

Scheme I

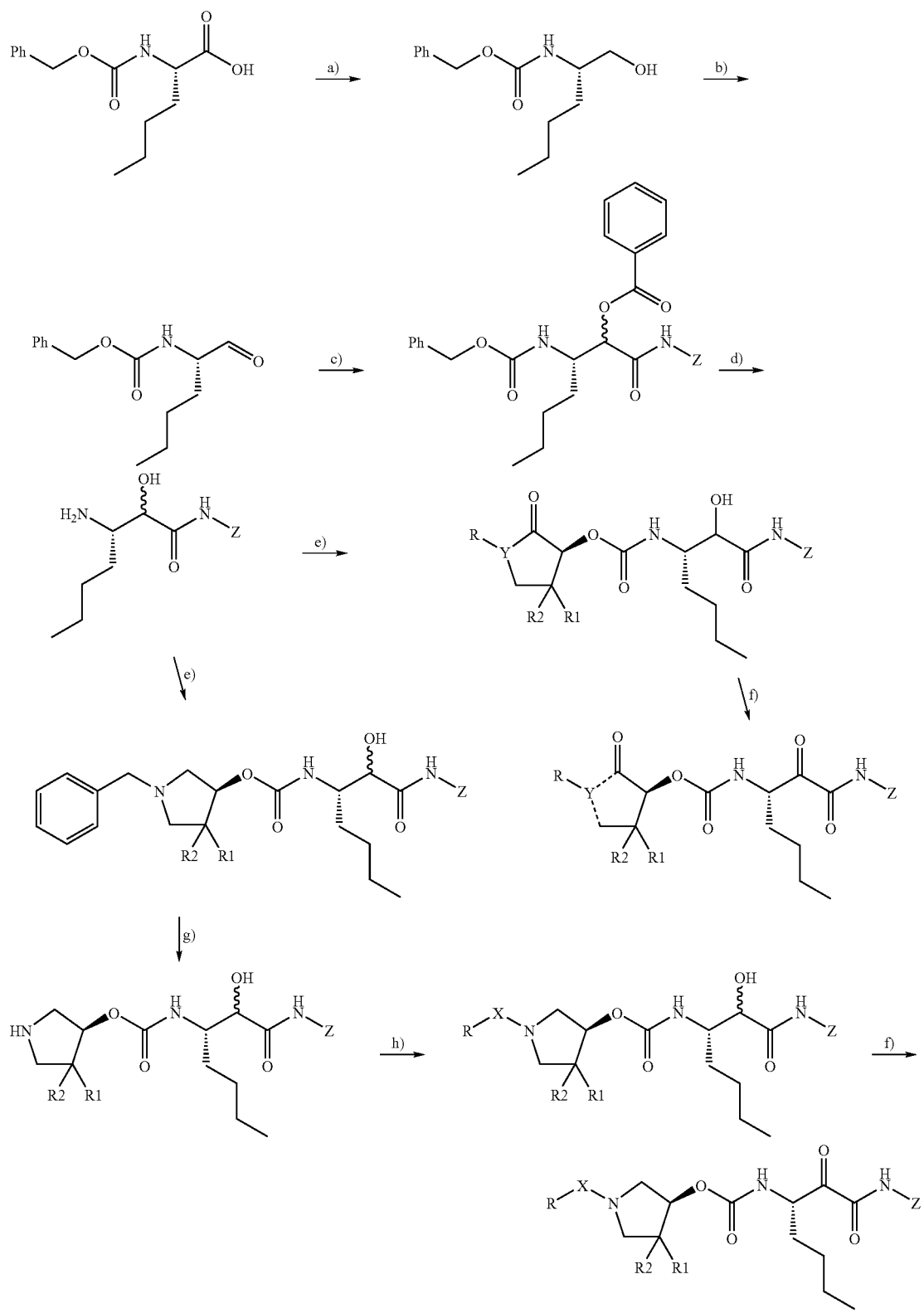

a) iPrOCOCl, NEt₃, THF, 0° C.; NaBH₄, THF, H₂O, 0° C. to rt; b) pyridine•SO₃, NEt₃, DMSO, CH₂Cl₂, -10° C. to rt; c) isonitrile, PhCOOH, CH₂Cl₂; d) NaOH, dioxane, H₂O, 100° C.; e) chloroformate, DMF; iPr₂NEt; f) TEMPO, sodium hypochlorite, water, dichloromethane; or Dess-Martin Periodinane, CH₂Cl₂; g) H₂, Pd/C, ethanol; h) chloroformate, acid chloride, sulfonyl chloride, or carbamoyl chloride; iPr₂NEt, CH₂Cl₂.

27

Scheme II

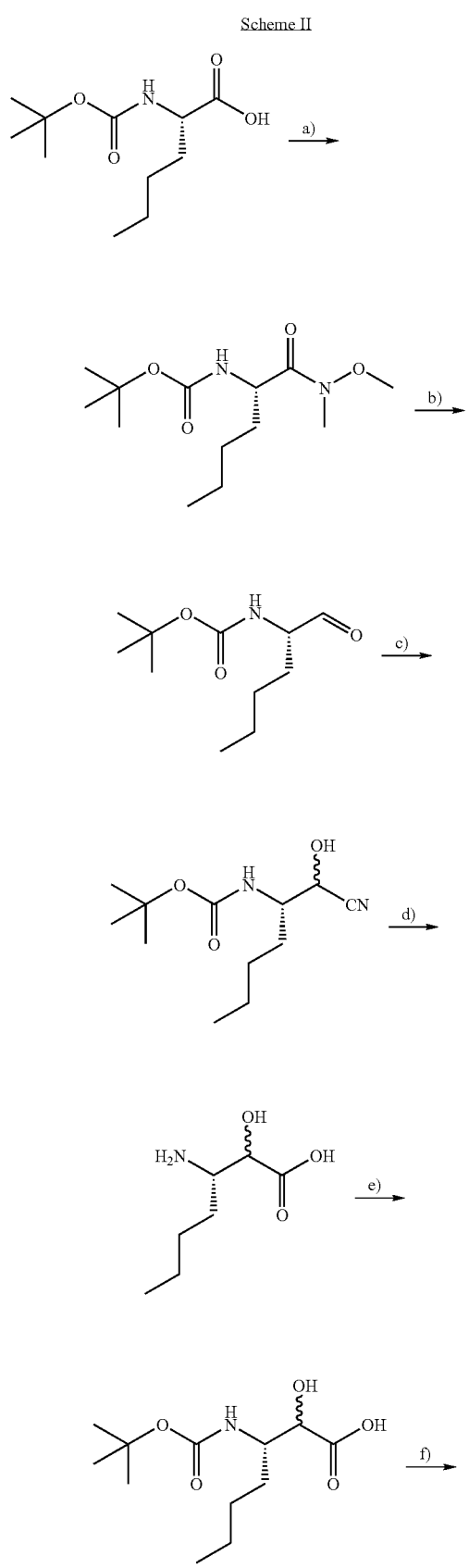

28
-continued

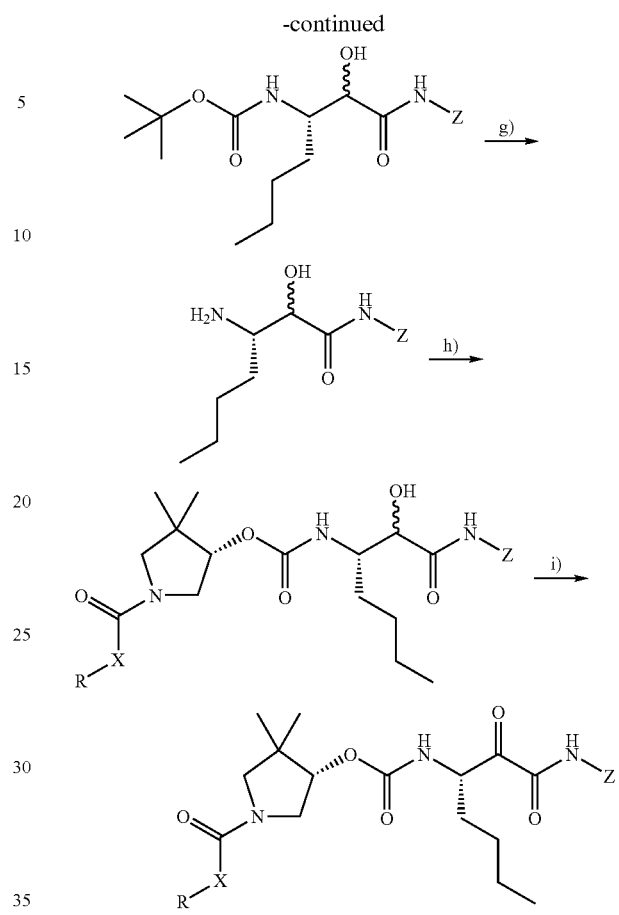

a) 1-methylpiperidine, CH$_2$Cl$_2$, -40° C.; EtOCOCl, CH$_2$Cl$_2$, -40° C.; MeONHMe•HCL, 1-methyl piperidine, CH$_2$Cl$_2$, -40° C. to rt; b) [(MeOCH$_2$CH$_2$O)$_2$AlH$_2$]Na, MePh, -20° C.; c) acetone cyanohydrin, KCN, nBu$_4$NI, MePh, H$_2$O; d) conc. HCl, 110° C.; e) 1N NaOH; Boc$_2$O, THF; f) 1-methylpiperidine, CH$_2$Cl$_2$, -40° C.; EtOCOCl, CH$_2$Cl$_2$, -40° C.; N,N'-carbonyldiimidazole; amine; K$_2$CO$_3$, MeOH, H$_2$O; g) 4N HCl in dioxane, dioxane; h) carbonate or chloroformate, DMF; iPr$_2$NEt; i) Dess-Martin Periodinane, CH$_2$Cl$_2$.

Scheme III

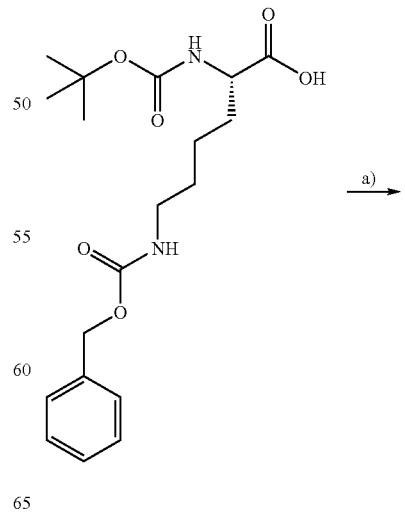

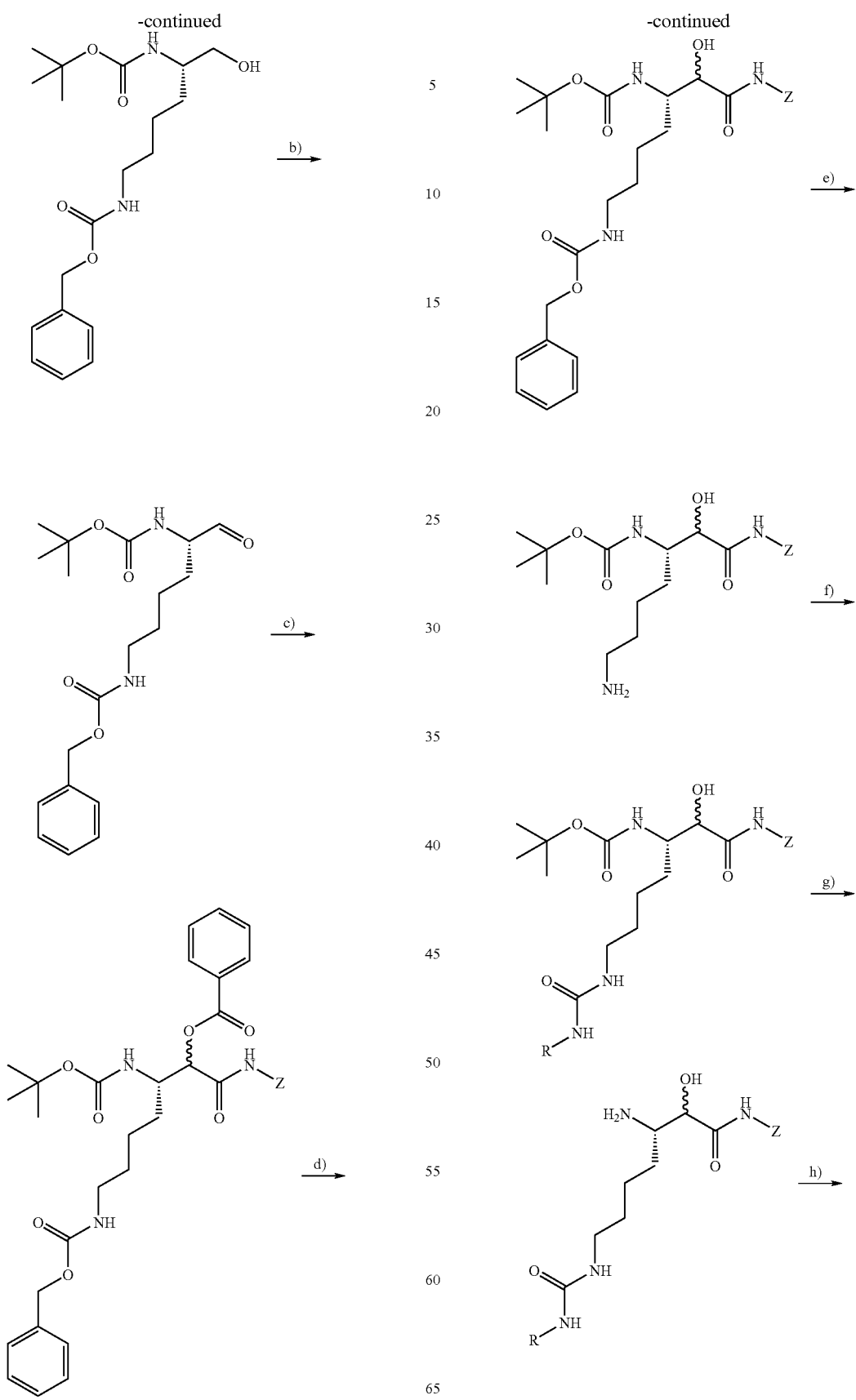

-continued

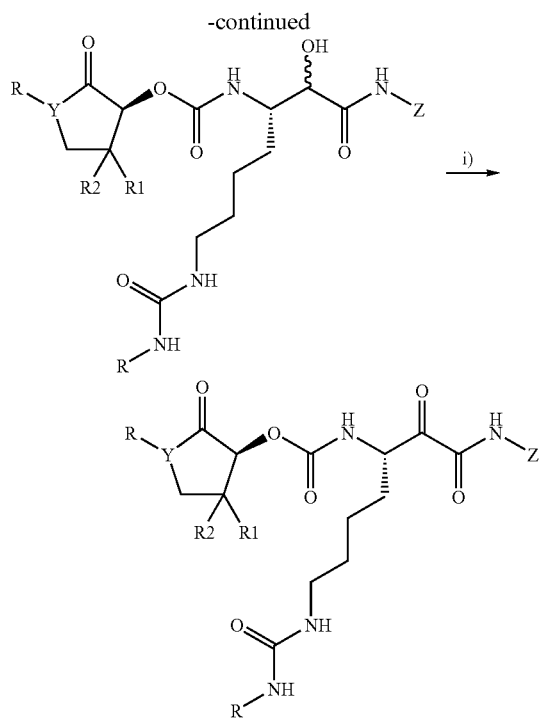

a) iPrOCOCl, NEt₃, THF, 0° C.; NaBH₄, THF, H₂O, 0° C. to rt; b) pyridine•SO₃, NEt₃, DMSO, CH₂Cl₂, -10° C. to rt; c) isonitrile, PhCOOH, CH₂Cl₂; d) LiOH, dioxane, H₂O; e) H₂, Pd/C, ethanol; f) isocyanate; g) 4N hydrogen chloride in dioxane; h) chloroformate, DMF; iPrNEt; i) Swern Oxidation Certain embodiments of the present invention will now be illustrated by way of example only. The physical data given for the compounds exemplified is consistent with the assigned structure of those compounds.

EXAMPLES

As used herein the symbols and conventions used in these processes, schemes and examples are consistent with those used in the contemporary scientific literature, for example, the *Journal of the American Chemical Society* or the *Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

g (grams); mg (milligrams);
L (liters); ml (milliliters);
μL (microliters); psi (pounds per square inch);
M (molar); mM (millimolar);
h (hour(s)); Hz (Hertz);
MHz (megahertz); mol (moles);
mmol (millimoles); RT (room temperature);
mm (minutes);
mp (melting point); TLC (thin layer chromatography);
$T_r$ (retention time); RP (reverse phase);
MeOH (methanol); i-PrOH (isopropanol);
TEA (triethylamine); TFA (trifluoroacetic acid);
TFAA (trifluoroacetic anhydride); THF (tetrahydrofuran);

-continued

DMSO (dimethylsulfoxide); EtOAc (ethyl acetate);
DME (1,2-dimethoxyethane); DCM (dichloromethane);
DCE (dichloroethane); DMF (N,N-dimethylformamide);
DMPU (N,N'-dimethylpropyleneurea); CDI (1,1-carbonyldiimidazole);
IBCF (isobutyl chloroformate); HOAc (acetic acid);
HOSu (N-hydroxysuccinimide); HOBT (1-hydroxybenzotriazole);
mCPBA (meta-chloroperbenzoic acid); EDC (ethylcarbodiimide hydrochloride);
BOC (tert-butyloxycarbonyl); FMOC (9-fluorenylmethoxycarbonyl);
DCC (dicyclohexylcarbodiimide); CBZ (benzyloxycarbonyl);
Ac (acetyl); atm (atmosphere);
TMSE (2-(trimethylsilyl)ethyl); TMS (trimethylsilyl);
TIPS (triisopropylsilyl); TBS (t-butyldimethylsilyl);
DMAP (4-dimethylaminopyridine); Me (methyl);
HPLC (high pressure liquid chromatography);
BOP (bis(2-oxo-3-oxazolidinyl)phosphinic chloride);
TBAF (tetra-n-butylammonium fluoride);
Et (ethyl); tBu (tert-butyl).

All references to ether are to diethyl ether; brine refers to a saturated aqueous solution of NaCl. Unless otherwise indicated, all temperatures are expressed in ° C. (degrees Centigrade). All reactions were conducted under an inert atmosphere at room temperature unless otherwise noted.

¹H NMR spectra were recorded on a Varian VXR-300, a Varian Unity-300, a Varian Unity-400 instrument, or a General Electric QE-300. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), m (multiplet), br (broad).

Low-resolution mass spectra (MS) were recorded on a JOEL JMS-AX505HA, JOEL SX-102, or a SCIEX-APIiii spectrometer; high resolution MS were obtained using a JOEL SX-102A spectrometer. All mass spectra were taken under electrospray ionization (ESI), chemical ionization (CI), electron impact (EI) or by fast atom bombardment (FAB) methods. Infrared (IR) spectra were obtained on a Nicolet 510 Fr-IR spectrometer using a 1-mm NaCl cell. All reactions were monitored by thin-layer chromatography on 0.25 mm E. Merck silica gel plates (60F-254), visualized with UV light, 5% ethanolic phosphomolybdic acid, iodine, iodoplatinate (potassium), permanganate(potassium), or p-anisaldehyde solution. Flash column chromatography was performed on silica gel (230-400 mesh, Merck). Melting points were determined using a Mel-Temp II apparatus and are uncorrected.

The following examples describe the syntheses of compounds of Formula (I) and (II) as well as intermediates particularly useful in the synthesis of compounds of Formula (I) and (II):

Example 1

(3S)-4,4-dimethyl-2-oxotetrahydro-3-furanyl (1S)-1-(oxo{[(1R)-1-phenylethyl]amino}acetyl)pentylcarbamate

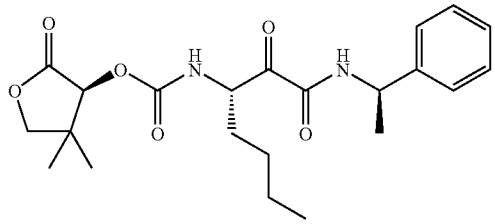

Example 1a

Preparation of benzyl (1S)-1-(hydroxymethyl)pentylcarbamate

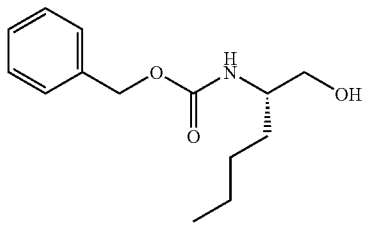

A solution of 95.0 mL (95.0 mmol) of 1 M isopropylchloroformate in toluene was added dropwise to a solution of 13.2 mL (95.0 mmol) of triethylamine and 25.16 g (95.0 mmol) of (2S)-2-{[(benzyloxy)carbonyl]amino}hexanoic acid in 200 mL of anhydrous tetrahydrofuran at 0° C. under nitrogen. After 2 h, the resulting mixture was filtered directly into a solution of 7.2 g (190 mmol) of sodium borohydride in 200 mL water. The resulting mixture was stirred for 18 h, and then extracted with ethyl acetate. The extract was washed with saturated aqueous sodium bicarbonate, dried over magnesium sulfate, and concentrated under vacuum. The oily solid was further purified by column chromatography on silica gel, eluting with 4:6 ethyl acetate:hexane to afford 9.63 g (40%) of (1S)-1-(hydroxymethyl)pentylcarbamate. $^1$H NMR (300 MHz, DMSO-$d_6$) δ 7.37 (m, 5H), 6.97 (d, J=9 Hz, 1H), 5.03 (s, 2H), 4.62 (br s, 1H), 3.46-3.23 (m under water peak, 3H), 1.53 (m, 1H), 1.26 (m, 5H), 0.87 (t, J=6 Hz, 3H). ES-LCMS m/z 274 (M+Na).

Example 1b

Preparation of benzyl (1S)-1-formylpentylcarbamate

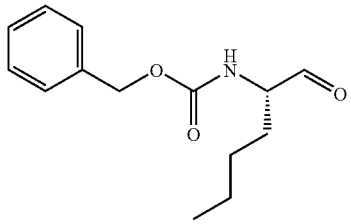

A solution of 16.38 g (103 mmol) of sulfur trioxide pyridine complex in 130 mL of dimethylsulfoxide was added to a solution of 8.64 g (34.4 mmol) of (1S)-1-(hydroxymethyl)pentylcarbamate) and 14.4 mL (103 mmol) of triethylamine in 130 mL of dichloromethane at –10° C. After 1 h, the cold bath was removed, and the reaction mixture was stirred for 18 h. It was then poured slowly into a mixture of ice and saturated aqueous sodium chloride. The resulting mixture was extracted with ether. The ether extracts were then washed with 5% aqueous citric acid, and saturated aqueous sodium chloride. After drying over magnesium sulfate, volatiles were removed under vacuum to afford 7.27 g (85%) of benzyl (1S)-1-formylpentylcarbamate. $^1$H NMR (400 MHz, DMSO-$d_6$) δ 9.41 (s, 1H), 7.66 (d, J=8 Hz, 1H), 7.33-7.28 (m, 5H), 5.00 (s, 2H), 3.85 (m, 1H), 1.65 (m, 1H), 1.40 (m, 1H), 1.27-1.18 (m 4H), 0.79 (m, 3H). ES-LCMS m/z 248 (M–H).

Example 1c

Preparation of (1R)-α-methylbenzylisonitrile

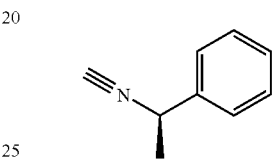

50 mL of 50% (w/w) aqueous sodium hydroxide was added to a solution of 17.5 mL (136 mmol) of (1R)-1-phenylethanamine, 10.8 mL (136 mmol) of chloroform, and 0.5 g (2.2 mmol) of benzyltriethylammonium chloride in 50 mL of dichloromethane. The resulting mixture was stirred for 3 h, and was then diluted with 100 mL of water and extracted with three 150 mL portions of dichloromethane. The combined extracts were washed with 50 mL portions of water and saturated aqueous sodium chloride, dried over magnesium sulfate, and concentrated under vacuum to afford a dark liquid, which was further purified by column chromatography on silica gel. Elution with dichloromethane afforded 9.86 g (55%) of (1R)-α-methylbenzylisonitrile. $^1$H NMR (400 MHz, DMSO-$d_6$) δ 7.38-7.36 (m, 4H), 7.32 (m, 1H), 5.08 (m, 1H), 1.53 (m, 3H).

Example 1d

Preparation of (2S)-2-{[(benzyloxy)carbonyl]amino}-1-({[(1R)-1-phenylethyl]amino}carbonyl)hexyl benzoate

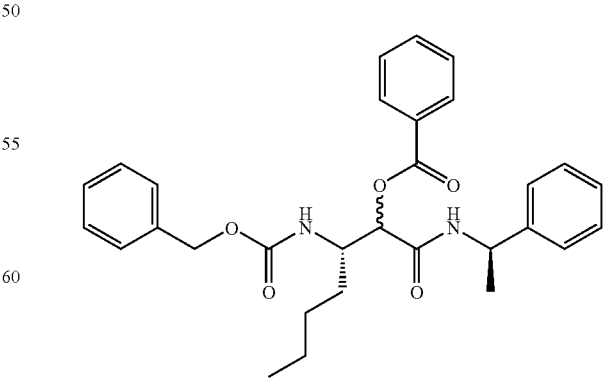

To a solution of 7.27 g (29.0 mmol) of benzyl (1S)-1-formylpentylcarbamate in 300 mL of dichloromethane was added 3.8 g (29 mmol) of (1R)-α-methylbenzylisonitrile and 3.54 g (29.0 mmol) of benzoic acid. The reaction mixture was stirred at room temperature for 48 h and diluted with a copious amount of hexanes. The precipitate was collected by filtration and the filtrate was passed through a silica plug with 1:9 ethyl ether:dichloromethane. The eluent was concentrated and the residue combined with the collected precipitate to afford 8.7 g (60%) of (2S)-2-{[(benzyloxy)carbonyl]amino}-1-({[(1R)-1-phenylethyl]amino}carbonyl)hexyl benzoate. $^1$H NMR (400 MHz, DMSO-$d_6$) δ 8.60 (d, J=8 Hz, 1H), 8.05 (d, J=7 Hz, 2H), 7.62 (t, J=8 Hz, 1H), 7.47 (t, J=8 Hz, 2H), 7.31-7.07 (m, 11H), 4.96 (m, 3H), 4.85 (qnt, J=7 Hz, 1H), 4.06 (m, 1H), 1.45-1.05 (m, 9H), 0.73 (t, J=7 Hz, 3H). ES-LCMS m/z 525 (M+Na).

Example 1e

Preparation of (3S)-3-amino-2-hydroxy-N-[(1R)-1-phenylethyl]heptanamide

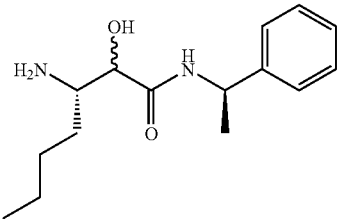

A mixture of 8.75 g (17.4 mmol) of (2S)-2-{[(benzyloxy)carbonyl]amino}-1-({[(1R)-1-phenylethyl]amino}carbonyl)hexyl benzoate and 6.97 g (174 mmol) of sodium hydroxide in 175 mL of dioxane and 75 mL of water was heated at reflux for 3 h. Upon cooling to room temperature, the reaction mixture was diluted with 100 mL of water and extracted with ethyl acetate. The combined ethyl acetate layers were dried over potassium carbonate and concentrated to afford 4.38 g (95%) of (3S)-3-amino-2-hydroxy-N-[(1R)-1-phenylethyl]heptanamide as a white solid. $^1$H NMR (300 MHz, DMSO-$d_6$) δ 8.08 (d, J=8 Hz, 1H), 7.39-7.20 (m, 5H), 4.99 (m, 1H), 4.51 (br s, 1H), 3.71 (d, J=3 Hz, 1H), 2.81 (m, 1H), 1.50-1.05 (m, 9H), 0.87 (t, 3H). ES-LCMS m/z 265 (M+H).

Example 1f

Preparation of (3S)-4,4-dimethyl-2-oxotetrahydro-3-furanyl (1S)-1-(oxo{[(1R)-1-phenylethyl]amino}acetyl)pentylcarbamate

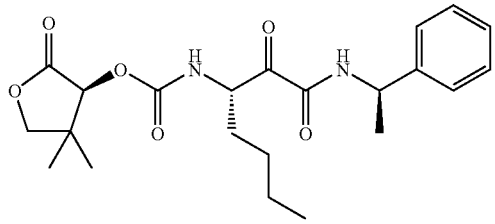

Phosgene (1.04 mL, 1.93 M, 2.00 mmol) was added dropwise to a solution of (S)-(+)-pantolactone (130 mg, 1.00 mmol) and quinoline (0.241 mL, 2.00 mmol) in anhydrous tetrahydrofuran (3 mL) at 0° C. under nitrogen. The cold bath was removed, and the mixture was stirred for 18 h at room temperature. Volatiles were then removed under vacuum, and the resulting solid was slurried in anhydrous tetrahydrofuran (4 mL) under nitrogen. A solution of triethylamine (0.153 mL, 1.10 mmol) and (3S)-3-amino-2-hydroxy-N-[(1R)-1-phenylethyl]heptanamide (264 mg, 1.00 mmol) in anhydrous tetrahydrofuran was added. The resulting mixture was stirred for 18 h, and was then partitioned between ethyl acetate (70 mL) and 1 N hydrochloric acid (35 mL). The ethyl acetate layer was washed further with two 35 mL portions of 1 N hydrochloric acid, followed by saturated aqueous sodium chloride (35 mL). After drying over magnesium sulfate, volatiles were removed to afford (3S)-4,4-dimethyl-2-oxotetrahydro-3-furanyl (1S)-1-(1-hydroxy-2-oxo-2-{[(1R)-1-phenylethyl]amino}ethyl)pentylcarbamate as a tan oil (358 mg, 85%).

The tan oil from above (358 mg, 0.850 mmol) was dissolved in dichloromethane (15 mL). TEMPO (3 mg, 0.02 mmol), potassium bromide (10.0 mg, 0.085 mmol), and water (0.1 mL) were added, and the resulting mixture was cooled to 0° C. A solution of 5.25% aqueous sodium hypochlorite (5 mL) containing sodium bicarbonate (60 mg) was then added dropwise. After 1.3 h, the reaction mixture was diluted with ethyl acetate (70 mL), and washed with two 30 mL portions of 1 N hydrochloric acid, followed by saturated sodium chloride (30 mL). The ethyl acetate layer was then dried over magnesium sulfate, and concentrated under vacuum to a yellow oil, which was further purified by column chromatography on silica gel. Elution with 25% ethyl acetate in hexanes afforded a colorless oil, from which three 5 mL portions of ether were distilled. Drying under vacuum afforded (3S)-4,4-dimethyl-2-oxotetrahydro-3-furanyl (1S)-1-(oxo{[(1R)-1-phenylethyl]amino}acetyl)pentylcarbamate as a colorless gum (150 mg, 42%). $^1$H NMR (300 MHz, DMSO-$d_6$) δ 9.24 (d, J=8 Hz, 1H), 7.97 (d, J=8 Hz, 1H), 7.35-7.22 (m, 5H), 5.00 (m, 1H), 4.83 (m, 1H), 4.14 (1/2Abq, J=8 Hz, 1H), 4.05 (1/2Abq, J=8 Hz, 1H), 1.45 (d, J=7 Hz, 3H), 1.11 (s, 31H), 1.04 (s, 3H). ES-LCMS m/z 419 (M+H) HRMS $C_{22}H_{30}N_2O_6$ m/z 441.2002 (M+Na)$_{Cal.}$ 441.2013 (M+Na)$_{Obs}$.

Example 2

(3S)-4,4-dimethyl-2-oxotetrahydro-3-furanyl (1S)-5-{[(methylamino)carbonyl]amino}-1-(oxo{[(1R)-1-phenylethyl]amino}acetyl)pentylcarbamate

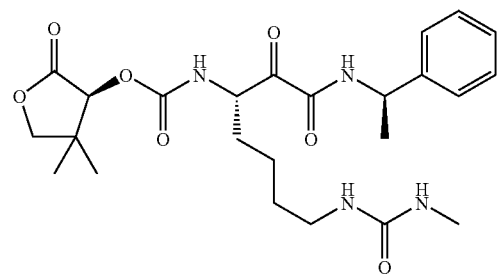

Example 2a

Preparation of benzyl (5S)-5-{[t-butyloxycarbonyl]amino}-6-hydroxyhexylcarbamate A solution of 150.0 mL (150.0 mmol) of 1 M isopropylchloroformate in toluene was added dropwise to a solution of 20.9 mL (150.0 mmol) of triethylamine and 57.06 g (150.0 mmol) of (2S)-6-{[(benzyloxy)carbonyl]amino}-2-[(tert-butoxy)carbonyl]amino]hexanoic acid in 500 mL of anhydrous tetrahydrofuran at 0° C. under nitrogen. After 2 h, the resulting mixture was filtered to remove solids, rinsing with anhydrous tetrahydrofuran (100 mL). The filtrate was then added dropwise to a stirred solution of 11.35 g (300.0 mmol) of sodium borohydride in 500 mL water, cooled in an ice bath. The cold bath was removed, and the resulting mixture was stirred for 18 h. It was then diluted with ethyl acetate (800 mL) and saturated aqueous sodium bicarbonate (300 mL). The two layers were separated, the aqueous layer was extracted with two 250 mL aliquots of ethyl acetate, and the extracts were combined with the original ethyl acetate layer. The combined ethyl acetate phase was washed with three 100 ml portions of saturated aqueous sodium bicarbonate, dried over magnesium sulfate, and concentrated under vacuum. The yellow oil was further purified by column chromatography on silica gel, eluting with 4:1 ethyl acetate:hexane to afford 37.70 g (68%) of benzyl (5S)-5-{[t-butyloxycarbonyl]amino}-6-hydroxyhexylcarbamate. $^1$H NMR (300 MHz, DMSO-$d_6$) δ 7.43-7.30 (m, 5H), 7.25 (t, J=5 Hz, 1H), 6.45 (d, J=8 Hz, 1H), 5.02 (s, 2H), 4.57 (br s, 1H), 3.35-3.29 (m overlapping water peak, 2H), 3.26-3.16 (m, 1H), 3.04-2.93 (m, 2H), 1.39 (s, 9H), 1.57-1.16 (m, 6H). ES-LCMS m/z 389 (M+Na).

Example 2b

Preparation of (2S)-6-{[(benzyloxy)carbonyl]amino}-2-[(tert-butoxycarbonyl)amino]hexanal

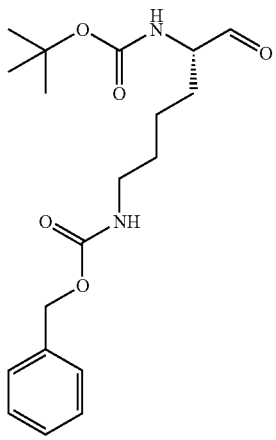

A solution of sulfur trioxide pyridine complex (53.0 g, 333 mmol) in dimethylsulfoxide (300 mL) was added to a solution of benzyl (5S)-5-{[t-butyloxycarbonyl]amino}-6-hydroxyhexylcarbamate (8.64 g, 34.4 mmol) and triethylamine (14.4 mL, 103 mmol) in dichloromethane (130 mL) at 0° C. The cold bath was removed, and the reaction mixture was stirred for 23 h. It was then poured slowly into a mixture of ice and saturated aqueous sodium chloride (1000 mL). The resulting mixture was extracted with three 600 mL portions of ether. The ether extracts were then combined, washed with three 150 mL portions of saturated aqueous sodium chloride, and concentrated to 1200 mL. The concentrated ether phase was further washed with three 200 mL aliquots of 5% aqueous citric acid, and a 200 mL portion of saturated aqueous sodium chloride. After drying over magnesium sulfate, volatiles were removed under vacuum to afford (2S)-6-{[(benzyloxy)carbonyl]amino}-2-[(tert-butoxycarbonyl)amino]hexanal (37.58 g, 93%). $^1$H NMR (300 MHz, DMSO-$d_6$) δ 9.44 (s, 1H), 7.46-7.23 (m, 6H), 5.02 (s, 2H), 3.85-3.75 (m, 1H), 3.07-2.93 (m, 2H), 1.77-1.60 (m, 1H), 1.56-1.23 (m, 5H), 1.41 (s, 9H).

Example 2c

Preparation of (2S)-6-{[(benzyloxy)carbonyl]amino}-2-[(tert-butoxycarbonyl)amino]-1-({[(1R)-1-phenylethyl]amino}carbonyl)hexyl benzoate

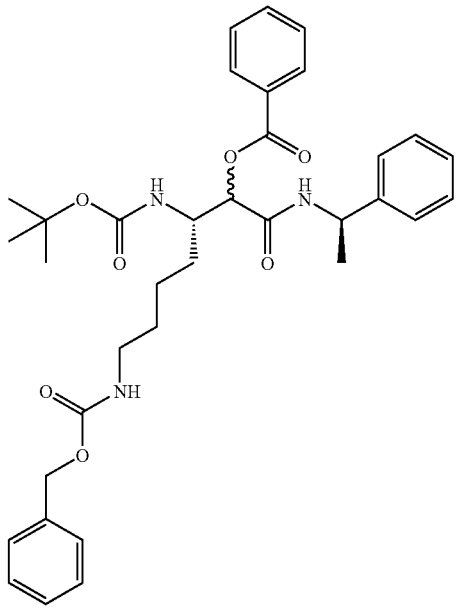

A solution of (1R)-α-methylbenzylisonitrile (9.6 g, 73 mmol) in dichloromethane (200 mL) was added to a solution of (2S)-6-{[(benzyloxy)carbonyl]amino}-2-[(tert-butoxycarbonyl)amino]hexanal in dichloromethane (355 mL, 0.206 M, 73.0 mmol). Benzoic acid (8.9 g, 73 mL) was then added, and the resulting solution was stirred at room temperature for 18 h. Volatiles were then removed under vacuum, and the resulting yellow solid was further purified by column chromatography on silica gel. Elution with a gradient of 5-15% ether in dichloromethane afforded an oil, which was precipitated from hot ether with hexane to provide (2S)-6-{[(benzyloxy)carbonyl]amino}-2-[(tert-butoxycarbonyl)amino]-1-({[(1R)-1-phenylethyl]amino}carbonyl)hexyl benzoate as a white solid (28.03 g, 62%), after drying under vacuum. $^1$H NMR (300 MHz, DMSO-$d_6$) δ 8.67 (d, J=8 Hz) and 8.58 (d, J=8 Hz) total 1H, 8.15 (d, J=7 Hz), 8.09 (d, J=8 Hz), and 7.97 (d, J=7 Hz) total 2H, 7.72-7.67 (m, 1H); 7.68-7.60 (m, 2H); 7.44-7.18 (m, 10H); 6.86 (d, J=10 Hz, 1H); 5.08-4.89 (m, 3H); 4.11-3.98 (m, 1H); 3.04-2.89 (m, 2H); 1.50-1.13 (m, 18H). ES-LCMS m/z 618 (M+H).

Example 2d tert-butyl (1S)-5-{[(benzyloxy)carbonyl]amino}-1-(1-hydroxy-2-oxo-2-{[(1R)-1-phenylethyl]amino}ethyl)pentylcarbamate

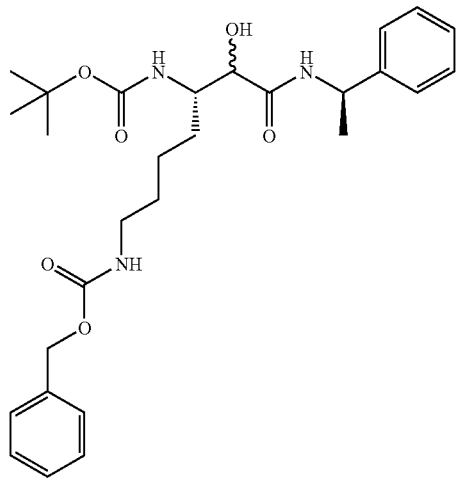

(2S)-6-{[(benzyloxy)carbonyl]amino}-2-[(tert-butoxycarbonyl)amino]-1-({[(1R)-1-phenylethyl]amino}carbonyl)hexyl benzoate (28.0 g, 45.0 mmol) was dissolved in dioxane (200 mL), and a solution of lithium hydroxide (2.47 g, 174 mmol) in water (100 mL) was added. The resulting mixture was stirred for 24 h at room temperature. It was then diluted with ethyl acetate (500 mL), and washed with 1N hydrochloric acid (300 mL). The aqueous layer was back-extracted with two 100 mL portions of ethyl acetate. The extracts were then combined with the original ethyl acetate layer, washed with three 200 mL aliqouts of saturated aqueous sodium bicarbonate, followed by saturated aqueous sodium chloride (100 mL), and dried over magnesium sulfate. Volatiles were then removed under vacuum to afford tert-butyl (1S)-5-{[(benzyloxy)carbonyl]amino}-1-(1-hydroxy-2-oxo-2-{[(1R)-1-phenylethyl]amino}ethyl)pentylcarbamate as a waxy light yellow solid (25.61 g, quantitative crude yield). $^1$H NMR (300 MHz, DMSO-d$_6$) δ 7.98-7.88 (m, 1H); 7.68-7.63 (m) and 7.49-7.42 (m) total 1H, 7.35-7.10 (m, 10H); 6.31 (d, J=9 Hz) and 6.02 (d, J=9 Hz) total 1H, 5.62-5.53 (br s) and 5.53-5.42 (br s) total 1H, 4.94 (s, 2H), 4.91-4.83 (m, 1H); 3.87 (br s) and 3.79 (br s) total 1H, 3.72-3.58 (m, 1H); 2.99-2.76 (m, 2H); 1.47-1.10 (m, 18H). ES-LCMS m/z 514 (M+H).

Example 2e

Preparation of tert-butyl (1S)-5-amino-1-(1-hydroxy-2-oxo-2-{[(1R)-1-phenylethyl]amino}ethyl)pentylcarbamate

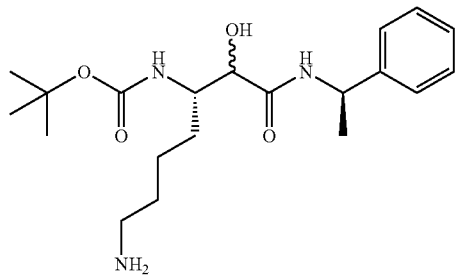

A slurry of palladium on carbon (1.5 g, 10% w/w) in water (3 mL) was added to a solution of tert-butyl (1S)-5-{[(benzyloxy)carbonyl]amino}-1-(1-hydroxy-2-oxo-2-{[(1R)-1-phenylethyl]amino}ethyl)pentylcarbamate (15.28 g, 29.70 mmol) in ethanol (200 mL). The resulting slurry was stirred vigorously under a hydrogen atmosphere (45 psi) at 50° C. for 18 h. Catalyst was then filtered off, rinsing with ethanol (400 mL). Concentration of the filtrate under vacuum afforded tert-butyl (1S)-5-amino-1-(1-hydroxy-2-oxo-2-{[(1R)-1-phenylethyl]amino}ethyl)pentylcarbamate as a colorless oil that crystallized upon standing under vacuum (10.52 g, 93%). $^1$H NMR (300 MHz, DMSO-d$_6$) δ 8.15 (d, J=8 Hz) and 8.08 (d, J=8 Hz) total 1H, 7.90-7.87 (m, ca 1H); 7.87-7.28 (m, 4H); 7.25-7.20 (m, 1H); 6.51 (d, J=9 Hz) and 6.17 (d, J=9 Hz) total 1H; 4.99-4.92 (m, 1H); 3.96 (d, J=4 Hz) and 3.90 (d, J=3 Hz) total 1H, 3.80-3.69 (m, 1H); 2.68-2.64 (m) and 2.53-2.57 (m) total 1H, 1.53-1.23 (m, 18H). ES-LCMS m/z 380 (M+H).

Example 2f

Preparation of tert-butyl (1S)-1-(1-hydroxy-2-oxo-2-{[(1R)-1-phenylethyl]amino}ethyl)-5-{[(methylamino)carbonyl]amino}pentylcarbamate

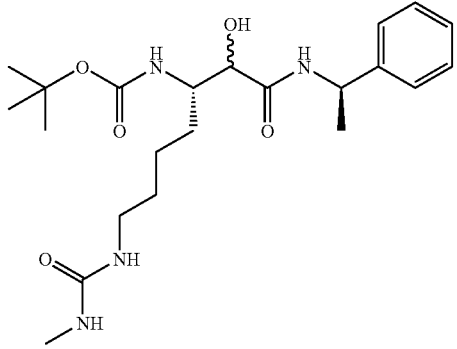

Methylisocyanate (0.472 mL, 8.00 mmol) was added to a slurry of tert-butyl (1S)-5-amino-1-(1-hydroxy-2-oxo-2-{[(1R)-1-phenylethyl]amino}ethyl)pentylcarbamate (3.03 g, 8.00 mmol) at 0° C. in anhydrous tetrahydrofuran (60 mL) under nitrogen. The mixture was stirred at 0° C. for 1 h, during which time all solids dissolved. The cold bath was then removed, and the solution was stirred overnight. Volatiles were removed under vacuum, and the resulting foam was further purified by column chromatography on silica gel. Elution with a gradient from 50% to 75% acetone in hexane afforded tert-butyl (1S)-1-(1-hydroxy-2-oxo-2-{[(1R)-1-phenylethyl]amino}ethyl)-5-{[(methylamino)carbonyl]amino}pentylcarbamate as a white solid after drying under vacuum (3.00 g, 86%). $^1$H NMR (300 MHz, DMSO-d$_6$) δ 8.06-8.01 (m, 1H); 7.38-7.18 (m, 5H); 6.40 (d, J=10 Hz) and 6.08 (d, J=9 Hz) total 1H, 5.86-5.75 (m, 1H); 5.71-5.51 (m, 2H); 5.01-4.91 (m, 1H); 3.94 (br s) and 3.87 (br s) total 1H, 3.79-3.64 (m, 1H); 3.01-2.81 (m, 2H); 2.54 (d, J=5 Hz, 3H); 1.52-1.16 (m, 18H). ES-LCMS m/z 437 (M+H).

Example 2g

Preparation of (3S)-3-amino-2-hydroxy-7-{[(methylamino)carbonyl]amino}-N-[(1R)-1-phenylethyl]heptanamide hydrochloride

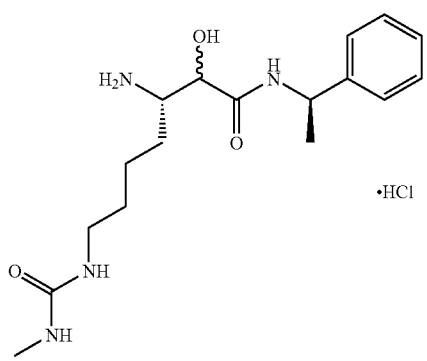

A solution of tert-butyl (1S)-1-(1-hydroxy-2-oxo-2-{[(1R)-1-phenylethyl]amino}ethyl)-5-{[(methylamino)carbonyl]amino}pentylcarbamate (2.86 g, 6.55 mmol) in ethyl acetate (200 mL) and methanol (50 mL) was cooled to 0° C., and saturated with hydrogen chloride by bubbling anhydrous hydrogen chloride through it for 7 min. The resulting solution was stirred for 1.5 h. Volatiles were then removed, and the resulting oil was dried further under vacuum to afford (3S)-3-amino-2-hydroxy-7-{[(methylamino)carbonyl]amino}-N-[(1R)-1-phenylethyl]heptanamide hydrochloride as a solid foam (2.74 g, quantitative yield) containing ethanol (0.53 eq based on integration of signals in the $^1$H NMR spectrum). $^1$H NMR (300 MHz, DMSO-$d_6$) δ 8.56 (d, J=8 Hz) and 8.45 (d, J=8 Hz) total 1H, 8.14 (br s) and 7.95 (br s) total 3H; 7.39-7.18 (m, 5H); 7.16-6.50 (br s, ca 3H); 5.02-4.91 (m, 1H); 4.30 (br s) and 4.09 (d, J=5 Hz) total 1H, 3.38-3.17 (m, 1H); 3.02-2.82 (m, 2H); 2.55 (s, 3H); 1.63-1.15 (m, 6H); 1.44 (s, 3H). ES-LCMS m/z 337 (M+H).

Example 2h

Preparation of (3S)-4,4-dimethyl-2-oxotetrahydro-3-furanyl chloridocarbonate

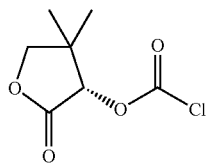

A solution of (S)-(+)-pantolactone (651 mg, 5.00 mmol) and 2,6-lutidine (0.641 mL, 5.50 mmol) in ether (15 mL) was stirred in the presence of powdered 4 A molecular sieves in a heat dried flask under nitrogen. After 30 min, the mixture was allowed to settle, and the supernatant was cannulated onto a solution of phosgene in toluene (15.5 mL, 1.93 M, 30.0 mmol) under nitrogen at 0° C. The resulting mixture was stirred for 2 h and was then filtered through celite under nitrogen. Volatiles were removed under vacuum, and two 15 mL portions of anhydrous ether were distilled from the residue under vacuum to afford (3S)-4,4-dimethyl-2-oxotetrahydro-3-furanyl chloridocarbonate as a yellow oil, a small portion of which was characterized by NMR. The rest was dissolved in dichloromethane (5 mL) to make a 1 M solution. $^1$H NMR (400 MHz, CDCl$_3$) δ 5.21 (s, 1H), 4.03 (1/2Abq, J=9 Hz, 1H), 3.97 (1/2Abq, J=9 Hz, 1H), 1.22 (s, 3H), 1.12 (s, 3H). $^{13}$C NMR (100 MHz, CDCl$_3$) δ 169.90 (C), 150.70 (C), 81.23 (CH), 76.04 (CH$_2$), 40.35 (C), 22.91 (CH$_3$), 19.72 (CH$_3$).

Example 2i

Preparation of (3S)-4,4-dimethyl-2-oxotetrahydro-3-furanyl (1S)-1-(1-hydroxy-2-oxo-2-{[(1R)-1-phenylethyl]amino}ethyl)-5-{[(methylamino)carbonyl]amino}pentylcarbamate

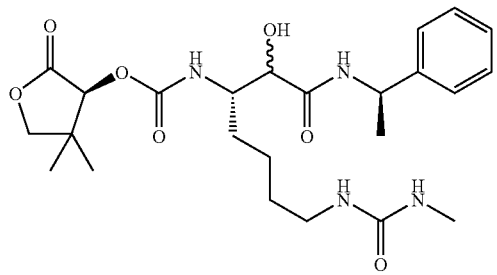

A solution of (3S)-3-amino-2-hydroxy-7-{[(methylamino)carbonyl]amino}-N-[(1R)-1-phenylethyl]heptanamide hydrochloride (198 mg, 0.500 mmol) in methanol (5 mL) was cooled to 0° C. under nitrogen. Triethylamine (0.153 mL, 1.10 mmol) was then added, followed by a solution of (3S)-4,4-dimethyl-2-oxotetrahydro-3-furanyl chloridocarbonate in dichloromethane (0.60 mL, 1 M, 0.60 mmol). The reaction mixture was allowed to warm slowly to room temperature, and was stirred for 15 h. Volatiles were removed under vacuum, and the resulting oil was dissolved in ethyl acetate (50 mL). This solution was washed with three 15 mL portions of 1 N hydrochloric acid, and the washes were back-extracted with three 35 mL aliquots of ethyl acetate. The extracts were combined with the original ethyl acetate solution, and the resulting solution was dried over magnesium sulfate. Concentration under vacuum afforded a gummy solid, which was further purified by column chromatography on silica gel. Elution with 7% methanol in chloroform afforded (3S)-4,4-dimethyl-2-oxotetrahydro-3-furanyl (1S)-1-(1-hydroxy-2-oxo-2-{[(1R)-1-phenylethyl]amino}ethyl)-5-{[(methylamino)carbonyl]amino}pentylcarbamate as a colorless glass (180 mg, 73%). $^1$H NMR (300 MHz, DMSO-$d_6$) δ 8.07 (d, J=9 Hz, 1H); 7.41-7.22 (m, 5H); 6.95 (d, J=9 Hz, 1H); 5.89-5.74 (m, 1H); 5.39 (s) and 5.36 (s) total 1H, 4.99-4.90 (m, 1H); 4.14 (1/2Abq, J=9 Hz, 1H); 4.03 (1/2Abq, J=9 Hz, 1H); 3.95-3.90 (m, 1H); 3.86-3.73 (m, 1H); 3.01-2.85 (m, 2H); 2.55 (part of d overlapping DMSO, 3H); 1.52-1.17 (m, 9H); 1.12 (s) and 1.09 (s) total 1H, 1.01 (s) and 0.99 (s) total 1H. ES-LCMS m/z 493 (M+H).

Example 2j

Preparation of (3S)-4,4-dimethyl-2-oxotetrahydro-3-furanyl (1S)-5-{[(methylamino)carbonyl]amino}-1-(oxo{[(1R)-1-phenylethyl]amino}acetyl)pentylcarbamate

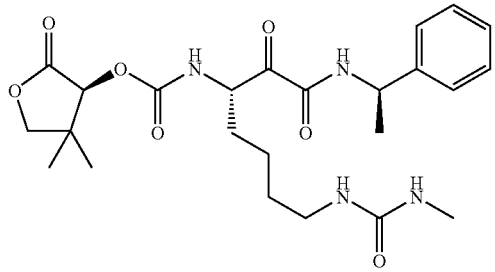

A solution of oxalylchloride (0.058 mL, 0.67 mmol) in anhydrous dichloromethane (2 mL) was cooled to −60° C. under nitrogen. Anhydrous dimethylsulfoxide (0.095 mL, 1.34 mmol) was then added dropwise, and the resulting solution was stirred for 10 min. A solution of (3S)-4,4-dimethyl-2-oxotetrahydro-3-furanyl (1S)-1-(1-hydroxy-2-oxo-2-{[(1R)-1-phenylethyl]amino}ethyl)-5-{[(methylamino)carbonyl]amino}pentylcarbamate (150 mg, 0.30 mmol) in dichloromethane (3 mL) was then added. After 15 min, triethylamine (0.212 mL, 1.52 mmol) was added to the reaction mixture, which was kept cold for 2 min. and then allowed to warm to room temperature. After 40 min, the reaction mixture was subjected directly to column chromatography on silica gel. Elution with 10% acetone in ethyl acetate afforded (3S)-4,4-dimethyl-2-oxotetrahydro-3-furanyl (1S)-5-{[(methylamino)carbonyl]amino}-1-(oxo{[(1R)-1-phenylethyl]amino}acetyl)pentylcarbamate as a colorless gum after drying under vacuum (82 mg, 56%). $^1$H NMR (300 MHz, DMSO-$d_6$) δ 9.26 (d, J=8 Hz, 1H); 7.99 (d, J=8 Hz, 1H); 7.40-7.33 (m, 4H); 7.31-7.23 (m, 1H); 5.92-5.84 (m, 1H); 5.71-5.63 (m, 1H); 5.40 (s, 1H); 5.08-4.96 (m, 1H); 4.85-4.78 (m, 1H); 4.16 (1/2Abq, J=8 Hz, 1H); 4.06 (1/2Abq, J=8 Hz, 1H); 3.04-2.91 (m, 2H); 2.55 (part of d overlapping DMSO, 3H); 1.74-1.61 (m, 1H); 1.46 (d, J=7 Hz, 1H); 1.45-1.29 (m, 5H); 1.12 (s, 1H); 1.05 (s, 1H). ES-LCMS m/493 (M+H) HRMS $C_{24}H_{34}N_4O_7$ m/491.2505 (M+H)$_{cal.}$ 491.2490 (M+H)$_{Obs}$.

Example 3

(4S)-4-ethyl-4-methyl-2-oxotetrahydro-3-furanyl (1S)-1-(oxo{[(1R)-1-phenylethyl]amino}acetyl)pentylcarbamate

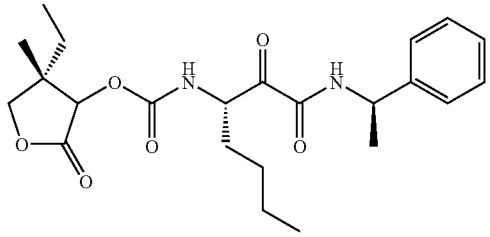

Example 3a

Preparation of dimethyl (2R,3S)-2-ethyl-3-hydroxy methylbutanedioate

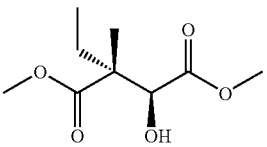

To a −78° C. solution of 9.09 mL (65 mmol) of diisopropylamine in 100 mL of tetrahydrofuran was added dropwise 40.5 mL (65 mmol) of 1.6 M n-butyl lithium in hexanes. The solution was allowed to warm to 0° C. briefly before being cooled to −78° C. To the solution was added 4.09 mL (30.9 mmol) of dimethyl (S)-(−)-malate dropwise and the resulting solution was allowed to warm to room temperature. After 30 min at room temperature, it was cooled to −78° C. before 2.3 mL (37.1 mmol) of methyl iodide was added dropwise. The solution was allowed to warm to room temperature, and was stirred for 18 h. It was then poured onto a mixture of ether, ice water, and 9.27 mL of acetic acid. The resulting mixture was extracted with ether, and the extracts were combined, washed with saturated sodium bicarbonate and brine, dried over magnesium sulfate, and concentrated under reduced pressure. The residue was purified by silica gel chromatography eluting with 3:7 ethyl acetate:hexanes to afford 1.04 g (5.9 mmol) of dimethyl (2S,3S)-2-hydroxy-3-methylbutanedioate.

A solution of 1.74 mL (12.4 mmol) of diisopropylamine in 20 mL of tetrahydrofuran was cooled to −78° C. before 7.75 mL (12.4 mmol) of 1.6 M n-butyl lithium in hexanes was added dropwise. The solution was allowed to warm to 0° C. briefly before being cooled to −78° C. A solution of dimethyl (2S,3S)-2-hydroxy-3-methylbutanedioate in 1 mL of tetrahydrofuran was then added dropwise. The reaction mixture was allowed to warm to −10° C., and was stirred for 45 min before being cooled to −78° C. To the reaction mixture was added 0.52 mL (6.5 mmol) of ethyl iodide dropwise. The reaction mixture was then stirred for 1 h before being allowed to warm to room temperature. After 18 h, the reaction mixture was poured onto a mixture of ether, ice water, and 1.8 mL of acetic acid. The mixture was extracted with ether, and the combined extracts were washed with saturated sodium bicarbonate and brine, dried over magnesium sulfate, and concentrated under reduced pressure. The residue was purified by silica chromatography eluting with 3:7 ethyl acetate:hexanes to afford 430 mg (6.8%) of dimethyl (2R,3S)-2-ethyl-3-hydroxy-2-methylbutanedioate. $^1$H NMR (300 MHz, DMSO-$d_6$) δ 5.73 (s, 1H), 4.28 (s, 1H), 3.66 (s, 3H), 3.62 (s, 3H), 1.66 (m, 1H), 1.38 (m, 1H), 0.76 (t, J=7 Hz, 3H).

Example 3b

Preparation of (3S,4S)-4-ethyl-3-hydroxy-4-methyldihydro-2(3H)-furanone

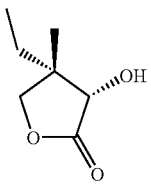

To a solution of 430 mg (2.1 mmol) of dimethyl (2R,3S)-2-ethyl-3-hydroxy-2-methylbutanedioate in 5 mL of methanol was added a solution of 0.29 g (4.4 mmol) of potassium hydroxide (>85%) in 0.5 mL of water and 1 mL of methanol. The reaction mixture was stirred for 96 h and diluted with ether. The ether layer was removed and the aqueous phase was washed with ether. The aqueous phase was then acidified to pH=2 with 1N HCl before being extracted with ether. The combined ether extracts were dried over magnesium sulfate and concentrated under reduced pressure to leave 310 mg (1.6 mmol) of an oil. The oil was dissolved in 15 mL of tetrahydrofuran and the solution was cooled to −40° C. before 8.8 mL (8.8 mmol) of 1M lithium triethylborohydride in tetrahydrofuran was added dropwise. The reaction mixture was allowed to warm to room temperature and was stirred for 18 h. It was then cooled to −10° C. and 5 drops of water were added. The mixture was diluted with ether, and 1N HCl was added until the pH of the aqueous layer reached a value of 2. The mixture was extracted with ether. The combined ether layers were diluted with toluene before being concentrated under reduced pressure. The residue was subjected to silica gel chromatography eluting with 4:6 ethyl acetate:hexanes. Appropriate fractions were concentrated under reduced pressure and the residue was passed through a silica plug with ether. The filtrate was concentrated under reduced pressure to afford 120 mg (40%) of (3S,4S)-4-ethyl-3-hydroxy-4-methyldihydro-2(3H)-furanone. $^1$H NMR (300 MHz, DMSO-$d_6$) δ 5.99 (s, 1H), 4.12 (s, 1H), 4.10 (d, J=9 Hz, 1H), 3.88 (d, J=9 Hz, 1H), 1.33 (m, 2H), 1.05 (s, 3H), 0.84 (t, J=7 Hz, 3H). ES-LCMS m/z 145 (M+H).

Example 3c

Preparation of (3S,4S)-4-ethyl-4-methyl-2-oxotetrahydro-3-furanyl (1S)-1-(1-hydroxy-2-oxo-2-{[(1R)-0.1-phenylethyl]amino}ethyl)pentylcarbamate

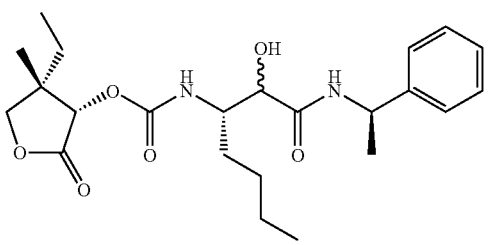

To a solution of 120 mg (0.83 mmol) of (3S,4S)-4-ethyl-3-hydroxy-4-methyldihydro-2(3H)-furanone and 0.11 mL (0.92 mmol) of 2,6-lutidine in 3 mL of ether was added 180 mg of 4 Å molecular sieves. The mixture was stirred for 45 min and let settle for 30 min. The supernatant was transferred via cannula to a solution of phosgene (2.6 mL, 1.93 M in toluene, 5.0 mmol) in 10 mL of ether at 0° C. After 30 min, the reaction mixture was allowed to warm to room temperature. It was stirred for 2 h, and then filtered through a celite plug with ether. The filtrate was concentrated to 1 mL, and added to a solution of 220 mg (0.83 mmol) of (3S)-3-amino-2-hydroxy-N-[(1R)-1-phenylethyl]heptanamide and 0.13 mL (0.91 mmol) of triethylamine in 2 mL of tetrahydrofuran. The reaction mixture was stirred for 18 h at room temperature. It was then diluted with ethyl acetate, washed with 1N HCl, and dried over magnesium sulfate before being concentrated. The residue was purified by silica gel chromatography, eluting with 1:1 ethyl acetate:hexanes to afford 170 mg (47%) of (3S,4S)-4-ethyl-4-methyl-2-oxotetrahydro-3-furanyl (1S)-1-(1-hydroxy-2-oxo-2-{[(1R)-1-phenylethyl]amino}ethyl)pentylcarbamate. $^1$H NMR (300 MHz, DMSO-$d_6$) δ 7.99 (d, J=8 Hz, 1H), 7.23-7.29 (m, 5H), 7.16 (m, 1H), 6.85 (d, J=9 Hz, 1H), 5.53 (s, 1H), 4.87 (m, 1H), 4.10 (d, J=9 Hz, 1H), 3.98 (d, J=9 Hz, 1H), 3.83 (s, 1H), 3.73 (m, 1H), 1.15-1.55 (m, 11H), 0.97 (s, 3H), 0.76-0.81 (m, 6H). ES-LCMS m/z 435 (M+H).

Example 3d

Preparation of (4S)-4-ethyl-4-methyl-2-oxotetrahydro-3-furanyl (1S)-1-(oxo{[(1R)-1-phenylethyl]amino}acetyl)pentylcarbamate

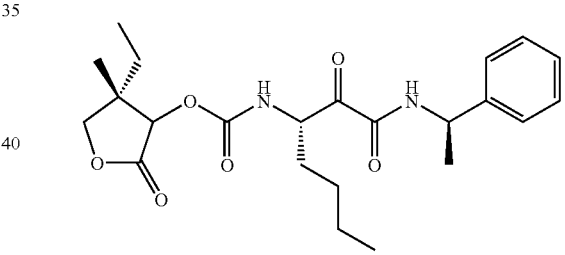

To a −60° C. solution of 0.062 mL (0.71 mmol) of oxalyl chloride in 1 mL of dichloromethane was added 0.10 mL (1.4 mmol) of dimethylsulfoxide dropwise. After 2 min, a solution of 140 mg (0.32 mmol) of (3S,4S)-4-ethyl-4-methyl-2-oxotetrahydro-3-furanyl (1S)-1-(1-hydroxy-2-oxo-2-{[(1R)-1-phenylethyl]amino}ethyl)pentylcarbamate in 1 mL of dichloromethane was added. The mixture was stirred for 10 min before 0.22 mL (1.6 mmol) of triethylamine was added. The reaction mixture was allowed to warm to room temperature and was stirred for 15 min before being poured directly onto a silica gel column. The column was eluted with 2:3 ethyl acetate:hexanes to afford 111 mg (80%) of (3S)-1-benzyl-4,4-dimethylpyrrolidinyl 1-(oxo{[(1R)-1-phenylethyl]amino}acetyl)pentylcarbamate. $^1$H NMR (300 MHz, 80° C., DMSO-$d_6$) δ 8.95 (m, 1H), 7.77 (m, 1H), 7.21-7.40 (m, 1H), 5.36 (d, J=6 Hz, 1H), 5.03 (m, 1H), 4.85 (m, 1H), 4.18 (m, 1H), 4.05 (m, 1H), 1.23-1.88 (m, 11H), 1.10 (s, 1H), 0.89 (m, 6H). ES-LCMS m/z 433 (M+H); HRMS $C_{23}H_{32}N_2O_6$ m/z 487.2420 (M+Na+MeOH)$^+_{Cal}$; 487.2411 (M+Na+MeOH)$^+_{Obs.}$.

Example 4

1-Benzyl-4,4-dimethyl-2-oxo-3-pyrrolidinyl (1S)-1-(oxo{[(1R)-1-phenylethyl]amino}acetyl)pentylcarbamate

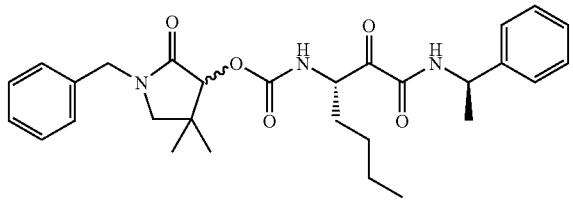

Example 4a

Preparation of 1-benzyl-3-hydroxy-4,4-dimethyl-2-pyrrolidinone

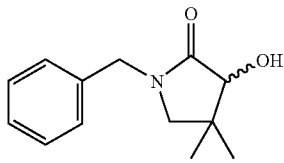

A solution of (S)-(+)-pantolactone (2.60 g, 20.0 mmol) and benzylamine hydrochloride (10 g, 70 mmol) in benzylamine (60.0 mL, 550 mmol) was stirred at 180° C. for 3 d. After cooling, the mixture was poured into dichloromethane (200 mL). The resulting mixture was filtered, and the filtrate was washed with three 150 mL portions of 1 N hydrochloric acid, followed by 100 mL of saturated aqueous sodium chloride. After drying over magnesium sulfate, the solution was concentrated to a tan crystalline solid, which was further purified by column chromatography on silica gel. Elution with a gradient of 3-5% methanol in chloroform separated the desired product from the intermediate, N-benzyl-2,4dihydroxy-3,3-dimethylbutanamide, which was isolated as a colorless oil (1.28 g, 27%). The desired product was further purified by column chromatography on silica gel, eluting with 2:1 to 1:1 hexane:ethyl acetate to afford 1-benzyl-3-hydroxy-4,4-dimethyl-2-pyrrolidinone as a white crystalline solid (1.501 g, 34%). $^1$H NMR (300 MHz, DMSO-d$_6$) δ 7.43-7.12 (m, 5H), 5.52 (br s, 1H), 4.39 (1/2Abq, J=15 Hz, 1H), 4.25 (1/2Abq, J=15 Hz, 1H), 3.78 (br s, 1H), 2.89 (1/2Abq, J=10 Hz, 1H), 2.80 (1/2Abq, J=9 Hz, 1H), 1.01 (s, 3H), 0.79 (s, 3H). ES-LCMS m/z 220 (M+H).

Example 4b

Preparation of 1-benzyl-4,4-dimethyl-2-oxo-3-pyrrolidinyl chloridocarbonate

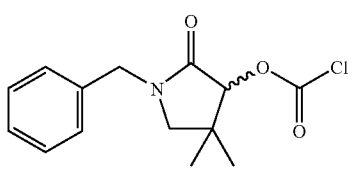

1-benzyl-4,4-dimethyl-2-oxo-3-pyrrolidinyl chloridocarbonate (281 mg, quantitative yield) was obtained as an oil from 1-benzyl-3-hydroxy-4,4-dimethyl-2-pyrrolidinone (219 mg, 1.00 mmol) following the procedure outlined in example 2h. $^1$H NMR (400 MHz, CDCl$_3$) δ 7.32-7.15 (m, 5H), 5.12 (s, 1H), 4.46 (1/2Abq, J=14 Hz, 1H), 4.34 (1/2Abq, J=15 Hz, 1H), 2.95 (1/2Abq, J=10 Hz, 1H), 2.89 (1/2Abq, J=10 Hz, 1H), 1.13 (s, 3H), 0.97 (s, 3H). $^{13}$C NMR (100 MHz, CDCl$_3$) δ 167.58 (C), 151.05 (C), 135.39 (C), 129.08 (CH), 128.24 (CH), 84.92 (CH), 56.48 (CH$_2$), 47.22 (CH$_2$), 37.88 (C), 25.24 (CH$_3$), 21.12 (CH$_3$).

Example 4c

Preparation of 1-benzyl-4,4-dimethyl-2-oxo-3-pyrrolidinyl (1S)-1-(1-hydroxy-2-oxo-2-{[(1R)-1-phenylethyl]amino}ethyl)pentylcarbamate

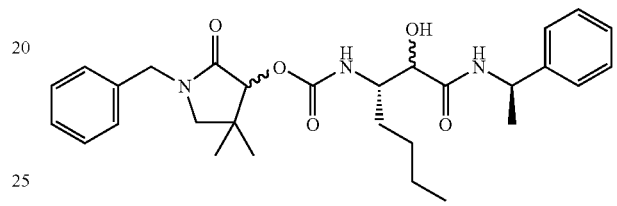

1-benzyl-4,4-dimethyl-2-oxo-3-pyrrolidinyl (1S)-1-(1-hydroxy-2-oxo-2-{[(1R)-1-phenylethyl]amino}ethyl)pentylcarbamate was obtained as a colorless film (146 mg, 92%) from 1-benzyl-4,4-dimethyl-2-oxo-3-pyrrolidinyl chloridocarbonate (98 mg, 0.40 mmol) and (3S)-3-amino-2-hydroxy-N-[(1R)-1-phenylethyl]heptanamide (82 mg, 0.31 mmol) following the procedure outlined in example 2i, except that the reaction mixture was not cooled to 0° C. The title compound was purified by column chromatography on silica gel, eluting with 3% methanol in chloroform. $^1$H NMR (300 MHz, DMSO-d$_6$) δ 8.06 (m, 1H); 7.41-7.24 (m, 10H); 6.80 (m, 1H); 5.58 (m, 1H); 5.07 (s), 5.05 (s), and 5.04 (s) total 1H, 4.97 (m, 1H); 4.45 (m, 1H); 4.30 (m, 1H); 3.91 (m, 1H); 3.80 (m, 1H); 3.12-3.06 (m, 1H); 2.92-2.85 (m, 1H); 1.60-1.20 (m, 12H); 1.08 (s) and 1.06 (s) total 3H, 0.90-0.73 (m, 6H). ES-LCMS m/z 510 (M+H).

Example 4d

Preparation of 1-benzyl-4,4-dimethyl-2-oxo-3-pyrrolidinyl (1S)-1-(oxo{[(1R)-1-phenylethyl]amino}acetyl)pentylcarbamate

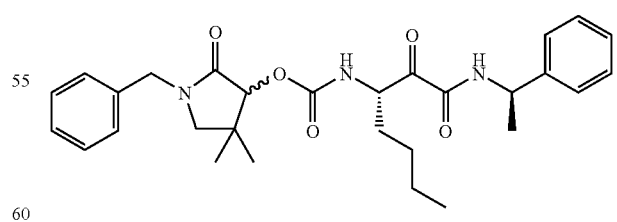

1-benzyl-4,4-dimethyl-2-oxo-3-pyrrolidinyl (1S)-1-(oxo{[(1R)-1-phenylethyl]amino}acetyl)pentylcarbamate was obtained as a cloudy gum (105 mg, 71%) containing ethyl acetate (0.67 eq based on integration of signals in the $^1$H NMR spectrum) from 1-benzyl-4,4-dimethyl-2-oxo-3-pyrrolidinyl (1S)-1-(1-hydroxy-2-oxo-2-{[(1R)-1-phenylethyl]

amino}ethyl)pentylcarbamate (133 mg, 0.260 mmol) following the procedure outlined in example 2j. The title compound was purified by column chromatography on silica gel, eluting with a gradient of 33-40% ethyl acetate in hexane. $^1$H NMR (300 MHz, DMSO-$d_6$) δ 9.16 (m, 1H); 7.86 (d, J=8 Hz) and 7.76 (d, J=7 Hz) total 1H, 7.32-7.15 (m, 10H); 4.98 (s) and 4.96 (s) total 1H, 4.95-4.88 (m, 1H); 4.82-4.71 (m, 1H); 4.42 (m, 1H); 4.22 (m, 1H); 3.01 (m, 1H); 2.83 (m, 1H); 1.64-1.52 (m, 1H); 1.40-1.09 (m, 8H); 1.03 (s), 1.01 (s), and 0.99 (s) total 3H, 0.84-0.72 (m, 6H). ES-LCMS m/z 508 (M+H) HRMS $C_{29}H_{37}N_3O_5$ m/z 508.2811 (M+H)$_{Cal.}$ 508.2827 (M+H)$_{Obs.}$.

Example 5

Benzyl 4,4-dimethyl-2-oxo-3-[({[(1S)-1-(oxo{[(1R)-1-phenylethyl]amino}acetyl)pentyl]amino}carbonyl)oxy]-1-pyrrolidinecarboxylate

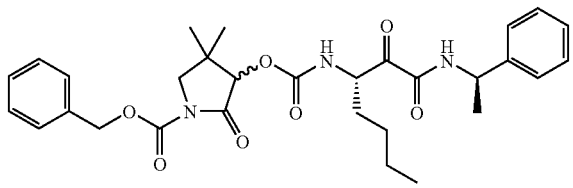

Example 5a

Preparation of 3-hydroxy-4,4-dimethyl-2-pyrrolidinone

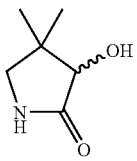

A solution of (S)-(+)-pantolactone (1.30 g, 10.0 mmol) in ammonium hydroxide (50 mL, 28%) and ethanol (40 mL) was stirred in a sealed pressure reactor at 230° C. for 23 h. After cooling to room temperature, the reaction mixture was diluted with dichloromethane (60 mL) and water (30 mL). 1 N hydrochloric acid was added until the pH of the aqueous layer reached a value of 2, and the two phases were separated. The aqueous layer was extracted with three 30 mL portions of dichloromethane, and the dichlormethane layers were combined. They were then washed with aqueous saturated sodium chloride (30 mL), dried over magnesium sulfate, and concentrated to afford impure product (152 mg). The aqueous layer was then made neutral by the addition of 5 N aqueous sodium hydroxide, and volatiles were removed under vacuum. The residue was slurried in 10% methanol in chloroform, and passed over a short silica gel column, eluting with the same system. The filtrate was concentrated, and the residue was combined with the impure product obtained from extraction of the aqueous layer. This impure product was further purified by column chromatography on silica gel. Elution with 10% methanol in chloroform afforded 3-hydroxy-4,4-dimethyl-2-pyrrolidinone as a white crystalline solid (0.670 g, 52%) after drying under vacuum. $^1$H NMR (300 MHz, DMSO-$d_6$) δ 7.56 (br s, 1H), 5.33 (d, J=6 Hz, 1H), 3.66 (d, J=6 Hz, 1H), 2.93-2.83 (m, 2H), 1.09 (s, 3H), 0.90 (s, 3H). ES-LCMS m/z 130 (M+H).

Example 5b

Preparation of 3-{[tert-butyl(dimethyl)silyl]oxy}-4,4-dimethyl-2-pyrrolidinone

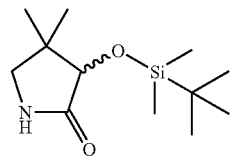

tert-Butyldimethylsilyl trifluoromethanesulfonate (0.810 ml, 3.45 mmol) was added to a mixture of 3-hydroxy-4,4-dimethyl-2-pyrrolidinone (405 mg, 3.1 mmol) and triethylamine (0.481 mmol, 3.45 mmol) in anhydrous dichloromethane (20 mL) at 0° C. under nitrogen. The reaction mixture was allowed to warm to room temperature, and was stirred for 18 h. A catalytic portion of 4-(dimethylamino)pyridine was added, and the mixture was stirred for 5 h. 1,8-Diazabicyclo[5.4.0]undec-7-ene (0.470 mL, 3.13 mmol) and tert-butyldimethylsilyl trifluoromethanesulfonate (0.360 ml, 1.61 mmol) were then added. After an additional 16 h, a third portion of tert-butyldimethylsilyl trifluoromethanesulfonate was added (0.360 ml, 1.61 mmol). The reaction mixture was then stirred for a further 7.5 h, before being diluted with dichloromethane (75 mL). It was then washed with two 30 mL portions of 1N hydrochloric acid. The washes were combined and back-extracted with dichloromethane (30 mL). The dichloromethane layers were then combined, washed with saturated aqueous sodium chloride (20 mL), dried over magnesium sulfate, and concentrated to a tan oil. Further purification of this oil by column chromatography on silica gel, eluting with a gradient of 20-50% ethyl acetate in hexane afforded 3-{[tert-butyl(dimethyl)silyl]oxy}-4,4-dimethyl-2-pyrrolidinone as a colorless oil that crystallized upon standing (362 mg, 48%). $^1$H NMR (300 MHz, DMSO-$d_6$) δ 7.63 (br s, 1H), 3.85 (s, 1H), 2.96-2.84 (m, 2H), 1.08 (s, 3H), 0.92 (s, 3H), 0.91 (s, 9H), 0.13 (s, 3H), 0.10 (s, 3H). ES-LCMS m/z 244 (M+H).

Example 5c

Preparation of benzyl 3-{[tert-butyl(dimethyl)silyl]oxy}-4,4-dimethyl-2-oxo-1-pyrrolidinecarboxylate

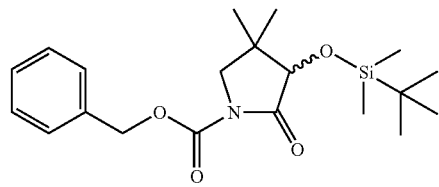

Sodium hydride (39 mg, 0.97 mmol) was added to a solution of 3-{[tert-butyl(dimethyl)silyl]oxy}-4,4-dimethyl-2-pyrrolidinone (214 mg, 0.880 mmol) in anhydrous tetrahydrofuran (6 mL) under nitrogen at 0° C. After 10 min, benzyl chloroformate (0.200 mL, 1.32 mmol) was added, and the mixture was allowed to warm to room temperature. After 24 h, the mixture was diluted with saturated aqueous sodium chloride (30 mL) and dichloromethane (30 mL). Hydrochloric acid (10 mL, 1 N) was then added, and the two phases were separated. The aqueous layer was extracted with dichloromethane (35 mL), and the dichloromethane layers were combined. After washing with saturated aqueous sodium chloride, they were dried over magnesium sulfate and concentrated to a tan oil, which was further purified by column chromatography on silica gel. Elution with 10:1 hexane:ethyl acetate afforded benzyl 3-{[tert-butyl(dimethyl)silyl]oxy}-4,4-dimethyl-2-oxo-1-pyrrolidinecarboxylate as a colorless oil (312 mg, 94%). $^1$H NMR (300 MHz, DMSO-$d_6$) δ 7.47-7.34 (m, 5H), 5.27 (1/2Abq, J=13 Hz, 1H), 5.21 (1/2Abq, J=13 Hz, 1H), 4.24 (s, 1H), 3.50 (1/2Abq, J=11 Hz, 1H), 3.38 (1/2Abq, J=11 Hz, 1H), 1.12 (s, 3H), 0.92 (s, 9H), 0.90 (s, 3H), 0.13 (s, 3H), 0.10 (s, 3H). ES-LCMS m/z 378 (M+H).

Example 5d

Preparation of benzyl 3-hydroxy-4,4-dimethyl-2-oxo-1-pyrrolidinecarboxylate

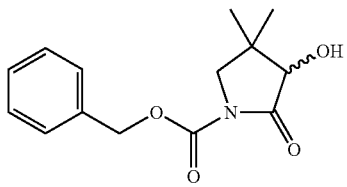

A solution of tetrabutylammonium fluoride in anhydrous tetrahydrofuran (1.1 mL, 1M, 1.1 mmol) was added to a solution of 3-{[tert-butyl(dimethyl)silyl]oxy}-4,4-dimethyl-2-oxo-1-pyrrolidinecarboxylate (202 mg, 0.54 mmol) in anhydrous tetrahydrofuran (2 mL) under nitrogen. After 45 min, the reaction mixture was subjected directly to column chromatography. Elution with 50% ethyl acetate in hexane afforded benzyl 3-hydroxy-4,4-dimethyl-2-oxo-1-pyrrolidinecarboxylate as an oil that solidified upon standing (133 mg, 94%). $^1$H NMR (300 MHz, DMSO-$d_6$) δ 7.47-7.36 (m, 1H), 5.88 (d, J=6 Hz, 1H), 5.24 (s, 2H), 3.99 (d, J=6 Hz, 1H), 3.48 (1/2Abq, J=10 Hz, 1H), 3.35 (1/2Abq, J=10 Hz, 1H), 1.11 (s, 3H), 0.89 (s, 3H). ES-LCMS m/z 378 (M+H).

Example 5e

Preparation of benzyl 3-[({[(1S)-1-(1-hydroxy-2-oxo-2-{[(1R)-1-phenylethyl]amino}ethyl)pentyl]amino}carbonyl)oxy]-4,4-dimethyl-2-oxo-1-pyrrolidinecarboxylate

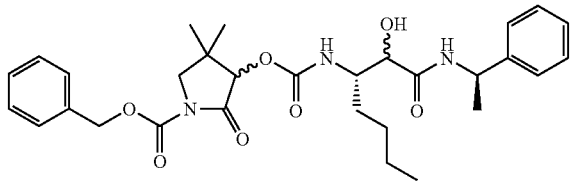

Benzyl 3-[({[(1S)-1-(1-hydroxy-2-oxo-2-{[(1R)-1-phenylethyl]amino}ethyl)pentyl]amino}carbonyl)oxy]-4,4-dimethyl-2-oxo-1-pyrrolidinecarboxylate was prepared from benzyl 3-hydroxy-4,4-dimethyl-2-oxo-1-pyrrolidinecarboxylate and (3S)-3-amino-2-hydroxy-N-[(1R)-1-phenylethyl]heptanamide following the procedure outlined in example 3c (56% yield). $^1$H NMR (400 MHz, DMSO-$d_6$) δ 8.15 (m, 1H), 7.07-7.40 (m, 10H), 5.17 (m, 1H), 5.80 (m, 1H), 5.53 (m, 1H), 5.17 (m, 2H), 4.89 (m, 1H), 3.83 (m, 1H), 3.71 (m, 1H), 3.54 (m, 1H), 3.44 (s, 1H), 0.75-1.45 (m, 18H). ES-LCMS m/z 554 (M+H).

Example 5f

Preparation of benzyl 4,4-dimethyl-2-oxo-3-[({[(1S)-1-(oxo{[(1R)-1-phenylethyl]amino}acetyl)pentyl]amino}carbonyl)oxy]-1-pyrrolidinecarboxylate

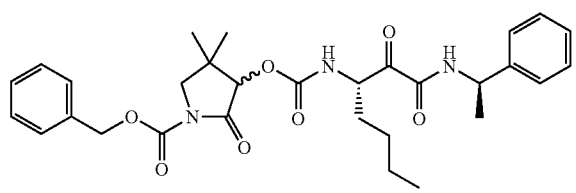

Benzyl 4,4-dimethyl-2-oxo-3-[({[(1S)-1-(oxo{[(1R)-1-phenylethyl]amino}acetyl)pentyl]amino}carbonyl)oxy]-1-pyrrolidinecarboxylate was prepared from benzyl 3-[({[(1S)-1-(1-hydroxy-2-oxo-2-{[(1R)-1-phenylethyl]amino}ethyl)pentyl]amino}carbonyl)oxy]-4,4-dimethyl-2-oxo-1-pyrrolidinecarboxylate following the procedure outlined in example 3d (45% yield). $^1$H NMR (300 MHz, DMSO-$d_6$) δ 9.20 (m, 1H), 7.90 (m, 1H), 7.15-7.43 (m, 10H), 5.21 (s, 1H), 4.96 (m, 1H), 4.80(m, 1H), 3.54 (s, 2H), 3.25 under water peak (m, 1H), 0.75-1.80 (m, 18H). ES-LCMS m/z 574 (M+Na); HRMS $C_{30}H_{37}N_3O_7$ m/z 574.2529 (M+Na)$^+_{Cal}$; 574.2516 (M+Na)$^+_{Obs.}$.

Example 6

(3S)-4,4-dimethyl-2-oxopyrrolidinyl (1S)-1-(1-hydroxy-2-oxo-2-{[(1R)-1-phenylethyl]amino}ethyl)pentylcarbamate and (3R)-4,4-dimethyl-2-oxopyrrolidinyl (1S)-1-(1-hydroxy-2-oxo-2-{[(1R)-1-phenylethyl]amino}ethyl)pentylcarbamate

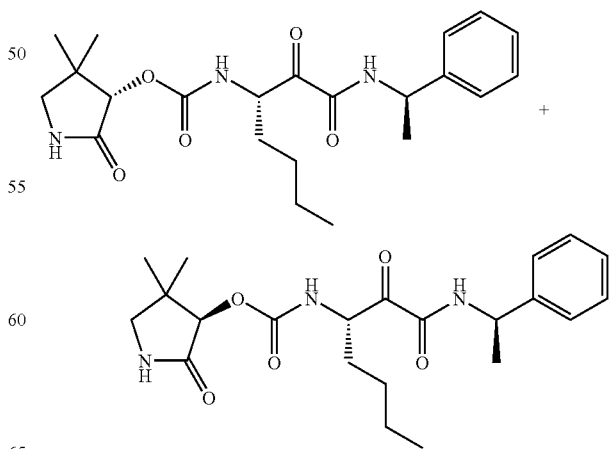

Example 6a

Preparation of 4,4-dimethyl-2-oxo-3-pyrrolidinyl (1S)-1-(1-hydroxy-2-oxo-2-{[(1R)-1-phenylethyl]amino}ethyl)pentylcarbamate

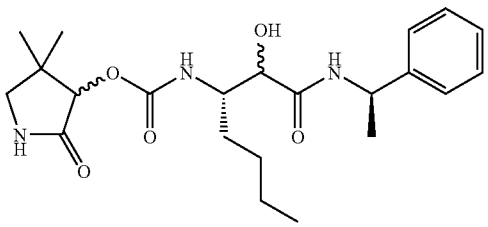

A solution of 120 mg (0.22 mmol) of benzyl 3-[({[(1S)-1-(1-hydroxy-2-oxo-2-{[(1R)-1-phenylethyl]amino}ethyl)pentyl]amino}carbonyl)oxy]-4,4-dimethyl-2-oxo-1-pyrrolidinecarboxylate in 5 mL of tetrahydrofuran was stirred in the presence of 15 mg of 10% Pd/C under a hydrogen atmosphere (50 psi) for 18 h. The catalyst was filtered off over celite and the filtrate was concentrated under reduced pressure. The residue was purified by silica gel chromatography eluting with 3:2 acetone:dichloromethane to afford 60 mg (66%) of 4,4-dimethyl-2-oxo-3-pyrrolidinyl (1S)-1-(1-hydroxy-2-oxo-2-{[(1R)-1-phenylethyl]amino}ethyl)pentylcarbamate. ES-LCMS m/z 420 (M+H).

Example 6b

Preparation and Separation of (3S)-4,4-dimethyl-2-oxopyrrolidinyl (1S)-1-(1-hydroxy-2-oxo-2-{[(1R)-1-phenylethyl]amino}ethyl)pentylcarbamate and (3R)-4,4-dimethyl-2-oxopyrrolidinyl (1S)-1-(1-hydroxy-2-oxo-2-{[(1R)-1-phenylethyl]amino}ethyl)pentylcarbamate

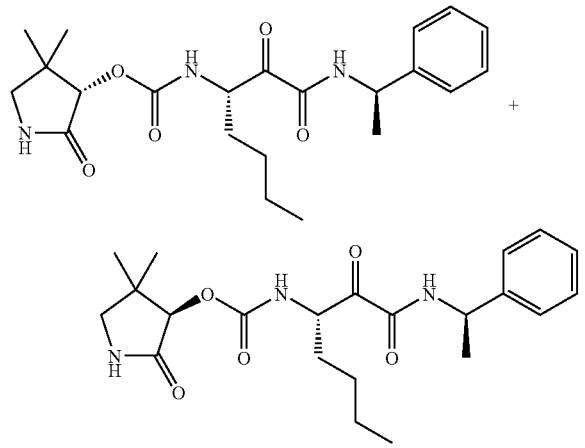

(3S)-4,4-dimethyl-2-oxopyrrolidinyl (1S)-1-(1-hydroxy-2-oxo-2-{[(1R)-1-phenylethyl]amino}ethyl)pentylcarbamate and (3R)-4,4-dimethyl-2-oxopyrrolidinyl (1S)-1-(1-hydroxy-2-oxo-2-{[(1R)-1-phenylethyl]amino}ethyl)pentylcarbamate were prepared from 4,4-dimethyl-2-oxo-3-pyrrolidinyl (1S)-1-(1-hydroxy-2-oxo-2-{[(1R)-1-phenylethyl]amino}ethyl)pentylcarbamate following the procedure outlined in example 3d. The diastereomers were separated by silica gel chromatography eluting with a gradient of 15-25% acetone in dichloromethane. The configuration of the chiral center at the 3 position of the 2-pyrrolidinone ring of the diastereomers was not determined. The diastereomers are labeled diastereomer one and two, based on the order of elution on silica gel. Diastereomer one: $R_f$=0.51 for silica gel TLC eluting with 25% acetone in dichloromethane; $^1$H NMR (300 MHz, 80° C., DMSO-$d_6$) δ 8.88 (d, J=7 Hz, 1H), 7.70 (m, 1H), 7.45 (m, 1H), 7.22-7.39 (m, 5H), 5.01 (qnt, J=7 Hz, 1H), 4.87 (s, 1H), 4.79 (m, 1H), 3.01 (dd, J=10 Hz, J=32 Hz, 2H), 1.70 (m, 1H), 1.56 (m, 1H), 1.48 (d, J=7 Hz, 3H), 1.33 (m, 4H), 1.12 (s, 3H), 1.02 (s, 3H), 0.86 (t, J=7 Hz, 3H). ES-LCMS m/z 418 (M+H) HRMS $C_{22}H_{31}N_3O_5$ m/z 440.2161 (M+Na)$^+_{Cal.}$ 440.2180 (M+Na)$^+_{Obs.}$. Diastereomer two: $R_f$=0.49 for silica gel TLC eluting with 25% acetone in dichloromethane. $^1$H NMR (300 MHz, 80° C., DMSO-$d_6$) δ 8.93 (m, 1H), 7.71 (m, 1H), 7.58 (m, 1H), 7.22-7.39 (m, 5H), 5.01 (qnt, J=7 Hz, 1H), 4.87 (m, 2H), 3.00 (dd, J=10 Hz, J=33 Hz, 2H), 1.69 (m, 1H), 1.56 (m, 1H), 1.47 (d, J=7 Hz, 3H), 1.31 (m, 4H), 1.12 (s, 3H), 0.99 (s, 3H), 0.85 (t, J=7 Hz, 3H). ES-LCMS m/z 418 (M+H) HRMS $C_{22}H_{31}N_3O_5$ m/z 472.2424 (M+Na+MeOH)$^+_{Cal.}$ 472.2430 (M+Na$^+$ MeOH)$^+_{Obs.}$.

Example 7

1,4,4-trimethyl-2-oxo-3-pyrrolidinyl (1S)-1-(oxo{[(1R)-1-phenylethyl]amino}acetyl)pentylcarbamate

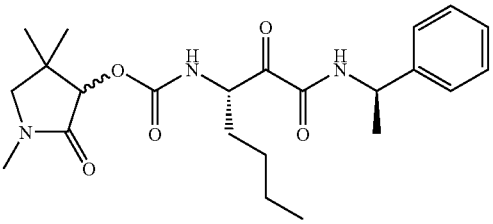

Example 7a

Preparation of 3-hydroxy-1,4,4-trimethyl-2-pyrrolidinone

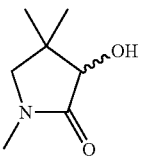

To a 0° C. solution of 700 mg (2.9 mmol) of 3-{[tert-butyl(dimethyl)silyl]oxy}-1,4,4-trimethyl-2-pyrrolidinone in 10 mL of tetrahydrofuran was added 130 mg (3.2 mmol) of sodium hydride (60% in mineral oil), and the reaction mixture was stirred for 10 min before 0.27 mL (4.4 mmol) of methyl iodide was added dropwise. The reaction mixture was stirred for 30 min and let warm to room temperature. After 4 h, the reaction mixture was diluted with ethyl acetate and then water. The mixture was extracted with ethyl acetate, washed with brine, dried over magnesium sulfate, and concentrated under reduced pressure to afford 550 mg of a dark oil. The oil was dissolved in 15 mL of tetrahydrofuran and cooled to 0° C. A solution of tetrabutylammonium fluoride in tetrahydrofuran (4.3 mL, 1M, 4.3 mmol) was added, and the reaction mixture was stirred for 30 min. It was then concentrated under reduced pressure, and the residue was purified by silica gel chromatography eluting with 1:9 methanol:ethyl acetate to afford 250 mg (82%) of 3-hydroxy-1,4,4-trimethyl-2-pyrrolidinone. $^1$H NMR (300 MHz, DMSO-$d_6$) δ 5.44 (m, 1H), 3.71 (s, 1H), 3.03 (d, J=9 Hz, 1H), 2.94 (d, J=9 Hz, 1H), 2.72 (s, 3H), 1.08 (s, 3H), 0.89 (s, 3H). ES-LCMS m/z 144 (M+H).

Example 7b

Preparation of 1,4,4-trimethyl-2-oxo-3-pyrrolidinyl (1S)-1-(1-hydroxy-2-oxo-2-{[(1R)-1-phenylethyl]amino}ethyl)pentylcarbamate

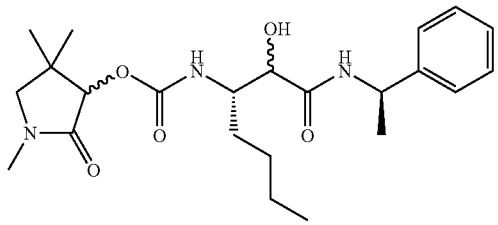

1,4,4-trimethyl-2-oxo-3-pyrrolidinyl (1S)-1-(1-hydroxy-2-oxo-2-{[(1R)-1-phenylethyl]amino}ethyl)pentylcarbamate was prepared from 3-hydroxy-1,4,4-trimethyl-2-pyrrolidinone and (3S)-3-amino-2-hydroxy-N-[(1R)-1-phenylethyl]heptanamide following the procedure outlined in example 3c (57% yield). $^1$H NMR (300 MHz, CDCl$_3$) δ 7.25-7.41 (m, 6H), 5.52 (m, 1H), 5.17 (m, 1H), 5.05 (m, 1H), 4.91 and 4.21 (m, 1H), 4.21 (m, 1H), 3.90 (m, 1H), 3.18 (m, 1H), 3.04 (m, 1H), 2.89 (s, 3H), 1.77 (s, 2H), 1.52 (m, 3H), 1.35 (m, 3H), 1.24 (m, 3H), 1.05 (m, 3H), 0.91 (m, 3H). ES-LCMS m/z 434 (M+H).

Example 7c

Preparation of 1,4,4-trimethyl-2-oxo-3-pyrrolidinyl (1S)-1-(oxo {[(1R)-1-phenylethyl]amino}acetyl) pentylcarbamate

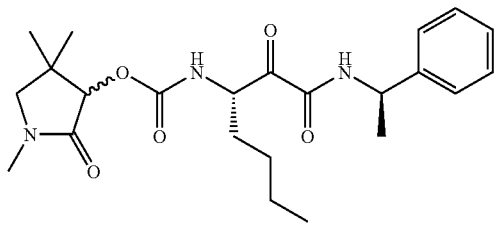

1,4,4-trimethyl-2-oxo-3-pyrrolidinyl (1S)-1-(oxo {[(1R)-1-phenylethyl]amino}acetyl)pentylcarbamate was prepared from 1,4,4-trimethyl-2-oxo-3-pyrrolidinyl (1S)-1-(1-hydroxy-2-oxo-2-{[(1R)-1-phenylethyl]amino}ethyl)pentylcarbamate following the procedure outlined in example 3d (77% yield). $^1$H NMR (300 MHz, DMSO-$d_6$) δ 9.23 (m, 1H), 7.25 and 7.35 (m, 1H), 7.20-7.38 (m, 5H), 4.89-5.05 (m, 2H), 4.80 (m, 1H), 3.15 (m, 1H), 3.02 (d, J=9 Hz, 1H), 2.76 (s, 3H), 1.76 (m, 1H), 1.64 (m, 1H), 1.21-1.55 (m, 7H), 0.80-1.12 (m, 9H). ES-LCMS m/z 432 (M+H) HRMS C$_{23}$H$_{33}$N$_3$O$_5$ m/z 454.2318 (M+Na)$^+_{Cal.}$ 454.2311 (M+Na)$^+_{Obs.}$.

Example 8

(3S)-1-Benzyl-4,4-dimethylpyrrolidinyl 1-(oxo{[(1R)-1-phenylethyl]amino}acetyl)pentylcarbamate

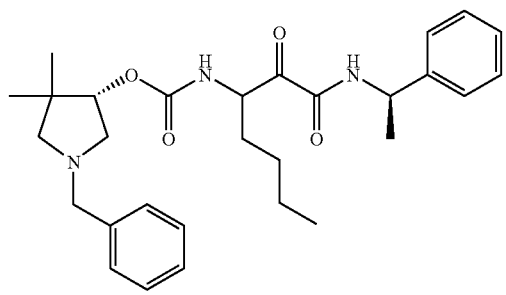

Example 8a

Preparation of (2S)-3,3-dimethyl-1,2,4-butanetriol

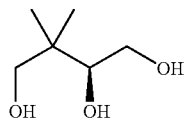

To a 0° C. solution of 5.01 g (38.5 mmol) of (S)-(+)-pantolactone in 150 mL of methanol was carefully added 3.72 g (98.5 mmol) of sodium borohydride. After gas evolution had subsided, the ice-bath was removed and the reaction closely monitored, cooling to 0° C. with an ice-water bath as needed when gas evolution became vigorous. The ice-water bath was removed and the reaction mixture was stirred at room temperature for 4 h. Dowex 50W×4-400 (H$^+$) resin was added to the solution until a pH of 7 was achieved, as indicated by wet pH paper. The resin was filtered off, and the filtrate was evaporated under reduced pressure. Portions of methanol and toluene were distilled from the resulting oil, which was further dried under high vacuum to afford 5.16 g (quantitative yield) of (2S)-3,3-dimethyl-1,2,4-butanetriol. $^1$H NMR (300 MHz, CDCl$_3$) δ 3.49-3.82 (m, 5H), 3.11 (d, J=4 Hz, 1H), 2.62 (m, 1H), 2.42 (m, 1H), 0.98 (d, J=6 Hz, 6H).

Example 8b

Preparation of (2S)-2-hydroxy-3,3-dimethyl-4-[(methylsulfonyl)oxy]butyl methanesulfonate

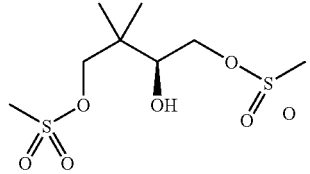

To a 0° C. solution of 25.3 g (189 mmol) of (2S)-3,3-dimethyl-1,2,4butanetriol in 170 mL of pyridine was added dropwise 29.1 mL (378 mmol) of methanesulfonyl chloride. The reaction mixture was allowed to slowly warm to room temperature, stirred for 18 h, and then diluted with dichloromethane. To the mixture was added 200 mL of 1N hydrochloric acid followed by concentrated hydrochloric acid until the pH of the aqueous phase was brought to a value of 2. The mixture was extracted with dichloromethane, and the combined extracts were washed with brine and concentrated under reduced pressure. The residue was purified by silica gel chromatography eluting with 10% acetone in dichloromethane to afford 21.75 g (52.10%) of (2S)-2-hydroxy-3,3-dimethyl-4-[(methylsulfonyl)oxy]butyl methanesulfonate. $^1$H NMR (300 MHz, DMSO-$d_6$) δ 5.48 (d, J=6 Hz, 1H), 4.30 (dd, J=2 Hz, J=10 Hz, 1H), 3.91-4.05 (m, 3H), 3.16 (d, J=4 Hz, 6H), 0.90 (d, J=13 Hz, 6H).

Example 8c

Preparation of (3S)-1-benzyl-4,4-dimethyl-3-pyrrolidinol

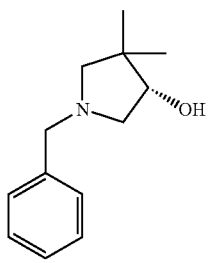

A solution of 21.7 g (75 mmol) of (2S)-2-hydroxy-3,3-dimethyl-4-[(methylsulfonyl)oxy]butyl methanesulfonate and 24.4 mL (228 mmol) of benzylamine in 200 mL of ethanol was heated at 120° C. for 18 h in a 400 mL capacity bomb. The reaction mixture was allowed to cool to room temperature, the bomb was vented, and the reaction mixture was concentrated under reduced pressure to 100 mL. The reaction was diluted with 50 mL of water and made acidic with concentrated hydrochloric acid. The aqueous phase was then washed with ether, made basic with 5M aqueous sodium hydroxide, and extracted with ether. The ether extract was concentrated under reduced pressure and the residue was purified by silica gel chromatography eluting with 0.25:9.75 2M ammonia in methanol:ethyl acetate to afford 13.8 g (90%) of (3S)-1-benzyl-4,4-dimethyl-3-pyrrolidinol. $^1$H NMR (300 MHz, CDCl$_3$) δ 7.30-7.36 (m, 5H), 3.77 (br s, 1H), 3.65 (s, 2H), 2.93-2.99 (m, 1H), 2.55-2.64 (m, 2H), 2.31 (d, J=9 Hz, 1H), 1.76 (d, J=7 Hz, 1H), 1.09 (d, J=1 Hz, 6H).

Example 8d

Preparation of (3S)-1-benzyl-4,4-dimethylpyrrolidinyl (1S)-1-(1-hydroxy-2-oxo-2-{[(1R)-1-phenylethyl]amino}ethyl)pentylcarbamate

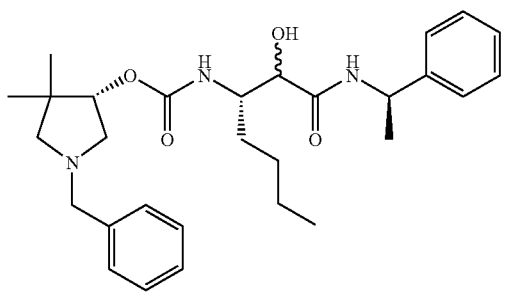

To a −20° C. solution of 110 mg (0.54 mmol) of (3S)-1-benzyl-4,4-dimethyl-3-pyrrolidinol in 3 mL of dichloromethane was added 0.58 mL (1.1 mmol) of 1.93 M phosgene in toluene. The mixture was stirred for 3 min before 0.05 mL (0.59 mmol) of pyridine was added dropwise. The reaction mixture was allowed to warm to room temperature and was stirred overnight. A stream of nitrogen was then blown through the solution for 15 min and the residue was dissolved in 1 mL of tetrahydrofuran. To this solution was added a solution of 140 mg (0.54 mmol) of (3S)-3-amino-2-hydroxy-N-[(1R)-1-phenylethyl]heptanamide and 0.15 mL (1.1 mmol) of triethylamine in tetrahydrofuran. The reaction mixture was stirred at room temperature overnight. It was then concentrated under reduced pressure and the residue was purified by silica gel chromatography eluting with 25% acetone in hexanes to afford 110 mg (41%) of (3S)-1-benzyl-4,4-dimethylpyrrolidinyl (1S)-1-(1-hydroxy-2-oxo-2-{[(1R)-1-phenylethyl]amino}ethyl)pentylcarbamate. $^1$H NMR (300 MHz, DMSO-$d_6$) δ 8.05 (d, J=8 Hz, 1H), 7.40-7.19 (m, 10H), 6.47 (d, J=9 Hz, 1H), 5.58 (d, J=7 Hz, 1H), 4.92 (qnt, J=7 Hz, 1H), 4.55 (dd, J=7 Hz, J=4 Hz, 1H), 4.37 (d, J=4 Hz, 1H), 3.92-3.72 (m, 3H), 3.57 (m, 2H), 3.01 (dd, J=10 Hz, J=7 Hz, 1H), 2.41 (m, 1H), 1.58-0.81 (m, 18H). ES-LCMS m/z 496 (M+H).

Example 8e

Preparation of (3S)-1-benzyl-4,4-dimethylpyrrolidinyl 1-(oxo {[(1R)-1-phenylethyl]amino}acetyl)pentylcarbamate

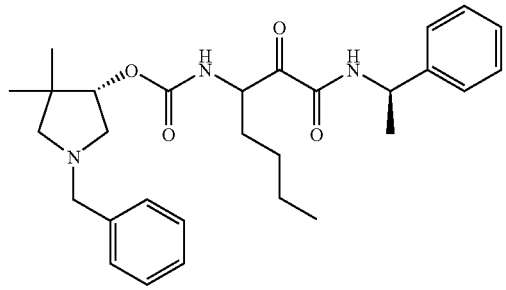

To a solution of 0.029 mL (0.33 mmol) of oxalyl chloride in 2 mL of dichloromethane at −60° C. was added 0.047 mL (0.67 mmol) of dimethylsulfoxide dropwise. After 3 min, a solution of 75 mg (0.15 mmol) of (3S)-1-benzyl-4,4-dimethylpyrrolidinyl (1S)-1-(1-hydroxy-2-oxo-2-{[(1R)-1-phenylethyl]amino}ethyl)pentylcarbamate in 2 mL of dichloromethane was added, and the mixture was stirred for 10 min before 0.11 mL (0.76 mmol) of triethylamine was added. The reaction mixture was then allowed to warm to room temperature and was stirred for 15 min before being subjected directly to column chromatography on silica gel. Elution with 10% acetone in dichloromethane afforded 50 mg (66%) of (3S)-1-benzyl-4,4-dimethylpyrrolidinyl 1-(oxo{[(1R)-1-phenylethyl]amino}acetyl)pentylcarbamate. $^1$H NMR (300 MHz, Temp=80° C., DMSO-$d_6$) δ 8.90 (m, 1H), 7.20-7.39 (m, 10H), 5.00 (m, 1H), 4.80 (m, 1H), 4.55 (m, 1H), 3.60 (s, 2H), 3.25-3.00 under water peak (m, 4H), 2.42 (m, 1H), 1.85-0.65 (m, 18). ES-LCMS m/z 494 (M+H); HRMS C$_{29}$H$_{39}$N$_3$O$_4$ m/z 494.3019 (M+Na)$^+_{Cal}$ 494.3032 (M+Na)$^+_{Obs}$.

Example 9

(3S)-1-Benzoyl-4,4-dimethylpyrrolidinyl (1S)-1-(oxo{[(1R)-1-phenylethyl]amino}acetyl)pentylcarbamate

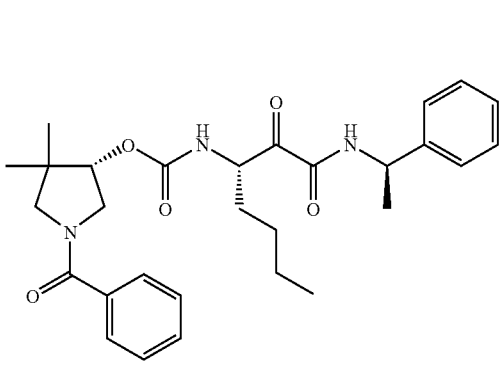

Example 9a

Preparation of (3S)-4,4-dimethylpyrrolidinyl (1S)-1-(1-hydroxy-2-oxo-2-{[(1R)-1-phenylethyl]amino}ethyl)pentylcarbamate

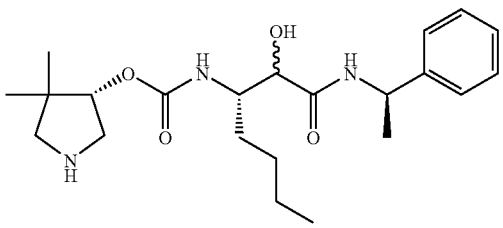

A solution of 8.0 g (16 mmol) of (3S)-1-benzyl-4,4-dimethylpyrrolidinyl (1S)-1-(1-hydroxy-2-oxo-2-{[(1R)-1-phenylethyl]amino}ethyl)pentylcarbamate in 100 mL of ethanol was stirred under hydrogen (50 psi) in the presence of 0.70 g of 10% Pd/C. After 72 h, 100 mg of fresh catalyst was added, and the mixture was stirred under hydrogen (50 psi) for an additional 4 h. At that time, 800 mg of fresh catalyst was added, and the mixture was stirred for an additional 18 h under hydrogen (50 psi). The catalyst was filtered off over celite and the filtrate was concentrated. The residue was purified by silica gel chromatography eluting with 1:5 2M ammonia in methanol: dichloromethane to afford 4.87 g (75%) of (3S)-4,4-dimethylpyrrolidinyl (1S)-1-(1-hydroxy-2-oxo-2-{[(1R)-1-phenylethyl]amino}ethyl)pentylcarbamate as a pale yellow glass. $^1$H NMR (300 MHz, DMSO-$d_6$) δ 8.05 (d, J=8 Hz, 1H); 7.19-7.40 (m, 5H); 6.56 (d, J=9 Hz) and 6.39 (d, J=9 Hz) total 1H, 5.73 (m, 1H); 4.95 (qnt, J=8 Hz, 1H); 4.51 (m, 1H); 3.89 (m) and 3.96 (m) total 1H); 3.76 (m, 1H); 3.27 (m, 4H); 2.61 (dd, J=12 Hz, J=3 Hz, 1H); 1.60-0.71 (m, 18H). ES-LCMS m/z 406 (M+H).

Example 9b

Preparation of (3S)-1-benzoyl-4,4-dimethylpyrrolidinyl (1S)-1-(oxo{[(1R)-1-phenylethyl]amino}acetyl)pentylcarbamate

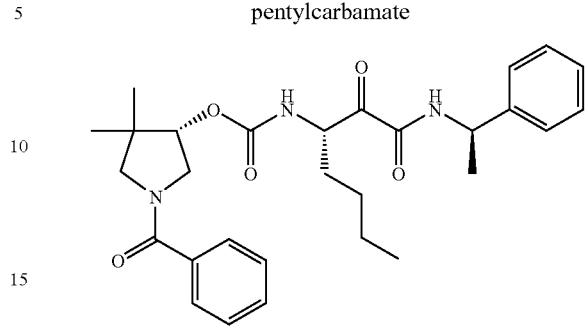

Benzoyl chloride (0.032 mL, 0.28 mmol) was added to a solution of (3S)-4,4-dimethylpyrrolidinyl (1S)-1-(1-hydroxy-2-oxo-2-{[(1R)-1-phenylethyl]amino}ethyl)pentylcarbamate (101 mg, 0.25 mmol) in dichloromethane (4 mL) in the presence of 3-(morpholino)propylpolystyrenesulfonamide (280 mg, 1.8 mmol/g, 0.50 mmol). The resulting mixture was shaken at 800 Hz for 1.5 h. Tris-(2-aminoethyl)amine polystyrene (103 mg, 2.43 mmol/g, 0.25 mmol) was then added, and the mixture was shaken for an additional 4 h. Solids were then removed by filtration, rinsing with five 2 mL portions of dichloromethane. The filtrate and rinses were combined and concentrated to afford a white film (138 mg, quantitative yield). The film was dissolved in dichloromethane (2.5 mL), and Dess-Martin periodinane (118 mg, 0.310 mmol) was added. The resulting mixture was stirred for 3 h, and then the reaction mixture was subjected directly to column chromatography on silica gel. Elution with 5% acetone in dichloromethane afforded (3S)-1-benzoyl-4,4-dimethylpyrrolidinyl (1S)-1-(oxo{[(1R)-1-phenylethyl]amino}acetyl)pentylcarbamate as a gum (112 mg, 79%), after drying under vacuum. $^1$H NMR (300 MHz, DMSO-$d_6$) δ 9.26 (d, J=8 Hz, 1H), 7.99 (d, J=8 Hz, 1H), 7.40-7.33 (m, 4H), 7.31-7.23 (m, 1H), 5.92-5.84 (m, 1H), 5.71-5.63 (m, 1H), 5.40 (s, 1H), 5.08-4.96 (m, 1H), 4.85-4.78 (m, 1H), 4.16 (1/2Abq, J=8 Hz, 1H), 4.06 (1/2Abq, J=8 Hz, 1H), 3.04-2.91 (m, 2H), 2.55 (part of d overlapping DMSO, 3H), 1.74-1.61 (m, 1H), 1.46 (d, J=7 Hz, 1H), 1.45-1.29 (m, 5H), 1.12 (s, 1H), 1.05 (s, 1H). ES-LCMS m/z 493 (M+H) HRMS $C_{24}H_{34}N_4O_7$ m/z 491.2505 $(M+H)_{Cal.}$ 491.2490 $(M+H)_{Obs.}$

Example 10

(3S)-1-Acetyl-4,4-dimethylpyrrolidinyl (1S)-1-(oxo{[(1R)-1-phenylethyl]amino}acetyl)pentylcarbamate

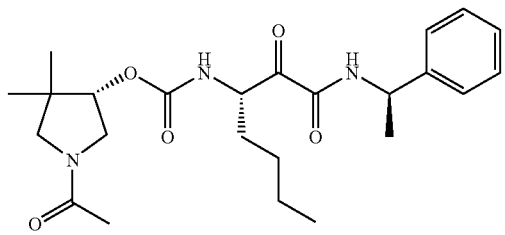

Acetyl chloride (0.0094 mL, 0.13 mmol) was added to a solution of (3S)-4,4-dimethylpyrrolidinyl (1S)-1-(1-hydroxy-2-oxo-2-{[(1R)-1-phenylethyl]amino}ethyl)pentylcarbamate (49 mg, 0.12 mmol) in dichloromethane (2 mL) in the presence of 3-(morpholino)propylpolystyrenesulfonamide (133 mg, 1.8 mmol/g, 0.24 mmol). The resulting mixture was shaken at 800 Hz for 1 h. Additional acetylchloride (0.004 mL, 0.08 mmol) was added, and the mixture was shaken for 1 h. Tris-(2-aminoethyl)amine polystyrene (52 mg, 2.43 mmol/g, 0.12 mmol) was then added, and the mixture was shaken for an additional 5 h. Solids were then removed by filtration, rinsing with four 1 mL portions of dichloromethane. The filtrate and rinses were combined and concentrated to a volume of 4 mL. Sodium bicarbonate (15 mg, 0.18 mmol) and Dess-Martin periodinane (66 mg, 0.18 mmol) were added. The resulting mixture was shaken at 800 Hz for 30 min. More Dess Martin periodinane (30 mg, 0.08 mmol) was added, and the reaction mixture was shaken for 15 min. It was then subjected directly to column chromatography on silica gel. Elution with a gradient of 5-20% acetone in dichloromethane afforded impure product, which was purified further by column chromatography on silica gel. Elution with 10% acetone in dichloromethane afforded (3S)-1-acetyl-4,4-dimethylpyrrolidinyl (1S)-1-(oxo{[(1R)-1-phenylethyl]amino}acetyl)pentylcarbamate as a solid white foam (26 mg, 46%) that contained dichloromethane and acetone (0.16 eq. and 0.11 eq. respectively, based on integration of signals in the $^1$H NMR spectrum), after drying under vacuum. $^1$H NMR (300 MHz, DMSO-$d_6$, Temp=100° C.) δ 8.82-8.72 (m, 1H); 7.40-7.20 (m, 6H); 5.06-4.96 (m, 1H); 4.86-4.78 (m, 1H); 4.78-4.66 (m, 1H); 3.88-3.82 (m, 1H); 3.76-3.63 (m, 1H); 3.40-3.25 (m, 1H); 1.95 (s) and 1.94 (s) total 3H, 1.78-1.64 (m, 1H); 1.62-1.51 (m, 1H); 1.49 (d, J=7 Hz, 1H); 1.40-1.20 (m, 4H); 1.05 (br s, 6H); 0.85 (m, 3H). ES-LCMS m/z 446 (M+H) HRMS $C_{24}H_{35}N_3O_5$ m/z 446.2644 (M+H)$_{Cal.}$ 446.2632 (M+H)$_{Obs.}$.

Example 11

(3S)-4,4-Dimethyl-1-(phenylacetyl)pyrrolidinyl (1S)-1-(oxo{[(1R)-1-phenylethyl]amino}acetyl)pentylcarbamate

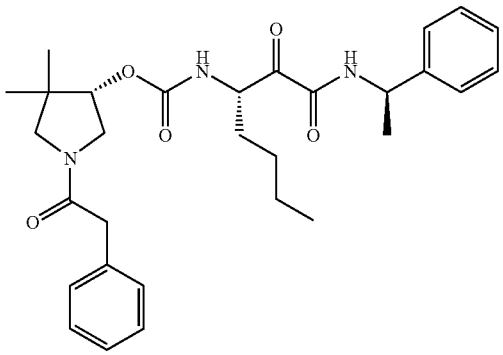

Phenylacetyl chloride (0.0178 mL, 0.132 mmol) was added to a solution of (3S)-4,4-dimethylpyrrolidinyl (1S)-1-(1-hydroxy-2-oxo-2-{[(1R)-1-phenylethyl]amino}ethyl)pentylcarbamate (49 mg, 0.12 mmol) in dichloromethane (2 mL) in the presence of 3-(morpholino)propylpolystyrenesulfonamide (133 mg, 1.8 mmol/g, 0.24 mmol). The resulting mixture was shaken at 800 Hz for 1 h. Tris-(2-aminoethyl)amine polystyrene (52 mg, 2.43 mmol/g, 0.12 mmol) was then added, and the mixture was shaken for an additional 6 h. Solids were then removed by filtration, rinsing with four 1 mL portions of dichloromethane. The filtrate and rinses were combined and concentrated to a volume of 4 mL. Sodium bicarbonate (15 mg, 0.18 mmol) and Dess-Martin periodinane (66 mg, 0.18 mmol) were added. The resulting mixture was shaken at 800 Hz for 30 min. It was then subjected directly to column chromatography on silica gel. Elution with 10% acetone in dichloromethane afforded impure product, which was further purified by column chromatography on silica gel under the same conditions. In this manner, (3S)-4,4-dimethyl-1-(phenylacetyl)pyrrolidinyl (1S)-1-(oxo{[(1R)-1-phenylethyl]amino}acetyl)pentylcarbamate as a solid white foam (23 mg, 37%), after drying under vacuum. $^1$H NMR (300 MHz, DMSO-$d_6$, Temp=100° C.) δ 8.78 (m, 1H), 7.40-7.20 (m, 11H), 5.06-4.98 (m, 1H), 4.86-4.78 (m, 1H), 4.84-4.68 (m, 2H), 4.00-3.86 (m, 1H), 3.80-3.65 (m, 1H), 3.63 (br s, 2H), 3.50-3.20 (m, 2H), 1.74-1.64 (m, 1H), 1.60-1.50 (m, 1H), 1.48 (d, J=7 Hz, 1H), 1.38-1.22 (m, 4H), 1.03 (s, 3H), 1.01 (s, 3H), 0.87 (m, 3H). ES-LCMS m/z 522 (M+H) HRMS $C_{30}H_{39}N_3O_5$ m/z 522.2968 (M+H)$_{Cal.}$ 522.2971 (M+H)$_{Obs.}$.

Example 12

(3S)-1-(5-Isoxazolylcarbonyl)-4,4-dimethylpyrrolidinyl (1S)-1-(oxo{[(1R)-1-phenylethyl]amino}acetyl)pentylcarbamate

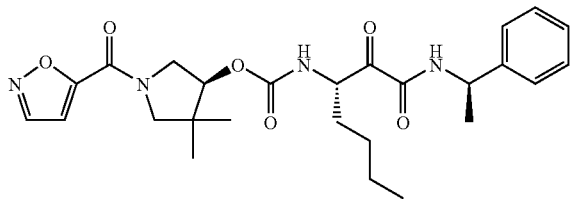

A solution of 5-isoxazolecarbonyl chloride in dichloromethane (0.264 mL, 0.500 M, 0.132 mmol) was added to a solution of (3S)-4,4-dimethylpyrrolidinyl (1S)-1-(1-hydroxy-2-oxo-2-{[(1R)-1-phenylethyl]amino}ethyl)pentylcarbamate (49 mg, 0.12 mmol) in dichloromethane (2 mL) in the presence of 3-(morpholino)propylpolystyrenesulfonamide (118 mg, 2.03 mmol/g, 0.24 mmol). The resulting mixture was shaken at 800 Hz for 2 h. A second portion of 5-isoxazolecarbonyl chloride in dichloromethane (0.132 mL, 0.500 M, 0.064 mmol) was added, and the mixture was shaken for another 2 h. Tris-(2-aminoethyl)amine polystyrene (29 mg, 4.08 mmol/g, 0.12 mmol) was then added, and the mixture was shaken for an additional 18 h. Solids were then removed by filtration, rinsing with five 1 mL portions of dichloromethane. The filtrate and rinses were combined and concentrated. The residue was then redissolved in dichloromethane (2 mL). Sodium bicarbonate (13 mg, 0.16 mmol) and a solution of Dess-Martin periodinane in dichloromethane (0.75 mL, 0.20 M, 0.15 mmol) were added, and the resulting mixture was shaken at 800 Hz for 1 h. It was then subjected directly to column chromatography on silica gel. Elution with a gradient of 5-10% acetone in dichloromethane afforded impure product, which was further purified by column chromatography on silica gel. Elution with 5% acetone in dichloromethane afforded (3S)-1-(5-isoxazolylcarbonyl)-4,4-dimethylpyrrolidinyl (1S)-1-(oxo{[(1R)-1-phenylethyl]amino}acetyl)pentylcarbamate as a solid white foam (33 mg, 55%) after drying under vacuum. $^1$H NMR (300 MHz, DMSO-$d_6$) δ 9.16 (m) and 9.01 (m) total 1H; 8.77 (d, J=2 Hz) and 8.76 (d, J=2 Hz) total 1H, 7.68 (m, 1H); 7.35-7.17 (m, 5H); 7.07-7.00 (m, 1H); 5.01-4.63 (m, 3H); 4.25-4.19 (m)

3.95-3.89 (m) total 1H, 3.70-3.43 (m, 3H); 1.67-1.53 (m, 1H); 1.48-1.35 (m, 4H); 1.31-1.11 (m, 4H); 1.05 (s), 1.04 (s), and 1.01 (s) total 6H, 0.82-0.73 (m, 3H). ES-LCMS m/z 499 (M+H) HRMS $C_{26}H_{34}N_4O_6$ m/z 499.2557 (M+H)cal. 499.2530 (M+H)$_{Obs.}$.

Example 13

(3S)-4,4-Dimethyl-1-[(4-methyl-1,2,3-thiadiazol-5-yl)carbonyl]pyrrolidinyl (1S)-1-(oxo {[(1R)-1-phenylethyl]amino}acetyl)pentylcarbamate

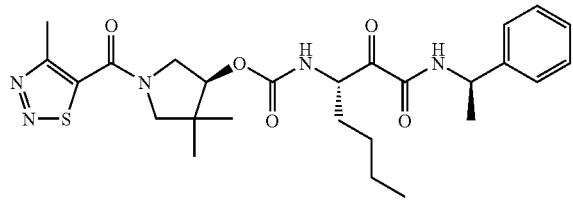

A solution of 4-methyl-1,2,3-thiadiazole-5-carbonyl chloride in dichloromethane (0.264 mL, 0.500 M, 0.132 mmol) was added to a solution of (3S)-4,4-dimethylpyrrolidinyl (1S)-1-(1-hydroxy-2-oxo-2-{[(1R)-1-phenylethyl]amino}ethyl)pentylcarbamate (49 mg, 0.12 mmol) in dichloromethane (2 mL) in the presence of 3-(morpholino)propylpolystyrenesulfonamide (118 mg, 2.03 mmol/g, 0.24 mmol). The resulting mixture was shaken at 800 Hz. A second portion of 4-methyl-1,2,3-thiadiazole-5-carbonyl chloride in dichloromethane (0.132 mL, 0.500 M, 0.064 mmol) was added after 2h, and a third (0.264 mL, 0.500 M, 0.132 mmol) after 4h. The mixture was shaken for another 18 h. Tris-(2-aminoethyl)amine polystyrene (29 mg, 4.08 mmol/g, 0.12 mmol) was then added, and the mixture was shaken for an additional 6 h. Solids were then removed by filtration, rinsing with five 1 mL portions of dichloromethane. The filtrate and rinses were combined and concentrated. The residue was then redissolved in dichloromethane (2 mL). Sodium bicarbonate (13 mg, 0.16 mmol) and a solution of Dess-Martin periodinane in dichloromethane (0.75 mL, 0.20 M, 0.15 mmol) were added, and the resulting mixture was shaken at 800 Hz for 1 h. It was then subjected directly to column chromatography on silica gel. Elution with a gradient of 5-10% acetone in dichloromethane afforded impure product, which was further purified by column chromatography on silica gel. Elution with 5% acetone in dichloromethane afforded the title compound as a gum, from which three 2 mL portions of ether were distilled. In this manner, (3S)-4,4-dimethyl-1-[(4-methyl-1,2,3-thiadiazol-5-yl)carbonyl]pyrrolidinyl (1S)-1-(oxo{[(1R)-1-phenylethyl]amino}acetyl)pentylcarbamate was obtained as a colorless-gum (32 mg, 48%) that contained ether (0.4 eq. based on integration of signals in the $^1$H NMR spectrum), after drying under vacuum. $^1$H NMR (300 MHz, DMSO-d$_6$) δ 9.29-9.07 (m, 1H); 7.71-7.67 (m, 1H), 7.34-7.18 (m, 5H); 5.01-4.57 (m, 3H); 3.98-3.69 (m, 1H); 3.46 (m, 1H); 3.18-3.05 (m, 2H); 2.67 (s) and 2.65 (s) total 3H, 1.67-1.55 (m, 1H); 1.44-1.34 (m, 4H); 1.32-1.12 (m, 4H); 1.08-0.91 (m, 6H); 0.85-0.73 (m, 3H). ES-LCMS m/z 530 (M+H) HRMS $C_{26}H_{35}N_5O_5S$ m/z 530.2437 (M+H)$_{Cal.}$ 530.2462 (M+H)$_{Obs.}$.

Example 14

(3S)-1-[(3-tert-Butyl-1-methyl-1H-pyrazol-5-yl)carbonyl]-4,4-dimethylpyrrolidinyl (1S)-1-(oxo{[(1R)-1-phenylethyl]amino}acetyl)pentylcarbamate

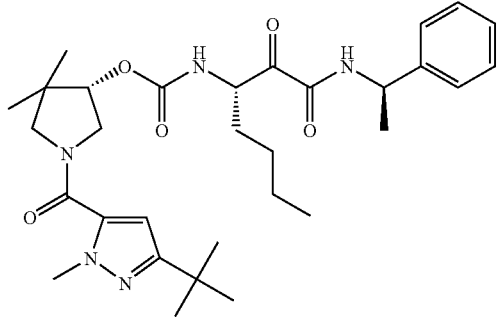

A solution of 3-tert-butyl-1-methyl-1H-pyrazole-5-carbonyl chloride in dichloromethane (0.264 mL, 0.500 M, 0.132 mmol) was added to a solution of (3S)-4,4-dimethylpyrrolidinyl (1S)-1-(1-hydroxy-2-oxo-2-{[(1R)-1-phenylethyl]amino}ethyl)pentylcarbamate (49 mg, 0.12 mmol) in dichloromethane (2 mL) in the presence of 3-(morpholino)propylpolystyrenesulfonamide (118 mg, 2.03 mmol/g, 0.24 mmol). The resulting mixture was shaken at 800 Hz for 2 h. A second portion of 3-tert-butyl-1-methyl-1H-pyrazole-5-carbonyl chloride in dichloromethane (0.132 mL, 0.500 M, 0.064 mmol) was then added, and the mixture was shaken for another 2 h. Tris-(2-aminoethyl)amine polystyrene (29 mg, 4.08 mmol/g, 0.12 mmol) was then added, and the mixture was shaken for an additional 18 h. Solids were then removed by filtration, rinsing with five 1 mL portions of dichloromethane. The filtrate and rinses were combined and concentrated. The residue was then redissolved in dichloromethane (2 mL). Sodium bicarbonate (13 mg, 0.16 mmol) and a solution of Dess-Martin periodinane in dichloromethane (0.75 mL, 0.20 M, 0.15 mmol) were added, and the resulting mixture was shaken at 800 Hz for 1 h. A second portion of Dess-Martin periodinane (21 mg, 0.06 mmol) was added, and the mixture was shaken for 15 min. It was then subjected directly to column chromatography on silica gel. Elution with a gradient of 5-10% acetone in dichloromethane afforded impure product, which was further purified by column chromatography on silica gel. Elution with 5% acetone in dichloromethane afforded the title compound as a solid, from which three 2 mL portions of ether were distilled. In this manner, (3S)-1-[(3-tert-butyl-1-methyl-1H-pyrazol-5-yl)carbonyl]-4,4-dimethylpyrrolidinyl (1S)-1-(oxo{[(1R)-1-phenylethyl]amino}acetyl)pentylcarbamate was obtained as a white solid (36 mg, 53%), after drying under vacuum. $^1$H NMR (300 MHz, DMSO-d$_6$, Temp=100° C.) δ 8.80-8.73 (m, 1H), 7.38-7.21 (m, 6H), 6.44 (br s, 1H), 5.05-4.95 (m, 1H), 4.87-4.73 (m, 2H), 4.05-3.94 (m, 1H), 3.88 (s, 3H), 3.49-3.39 (m, 3H), 1.75-1.63 (m, 1H), 1.56-1.45 (m, 1H), 1.47 (d, J=7 Hz, 3H), 1.30 (s, 9H), 1.36-1.24 (m, 4H), 1.08 (br s, 6H), 0.84 (t, J=7 Hz, 3H). ES-LCMS m/z 568 (M+H) HRMS $C_{31}H_{45}N_5O_5$ m/z 568.3499 (M+H)$_{Cal.}$ 568.3503(M+H)$_{Obs.}$.

Example 15

(3S)-4,4-Dimethyl-1-[(5-methyl-2-phenyl-2H-1,2,3-triazol-4-yl)carbonyl]pyrrolidinyl (1S)-1-(oxo{[(1R)-1-phenylethyl]amino}acetyl)pentylcarbamate

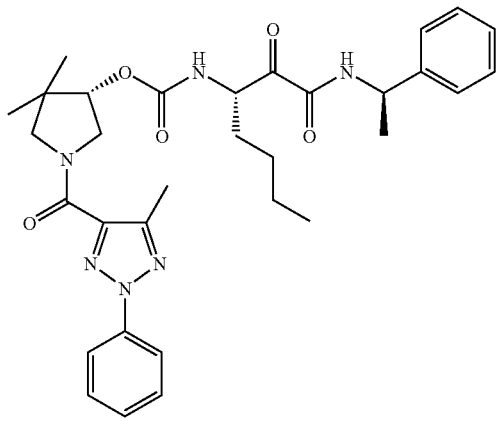

A solution of 5-methyl-2-phenyl-2H-1,2,3-triazole-4-carbonyl chloride in dichloromethane (0.264 mL, 0.500 M, 0.132 mmol) was added to a solution of (3S)-4,4-dimethylpyrrolidinyl (1S)-1-(1-hydroxy-2-oxo-2-{[(1R)-1-phenylethyl]amino}ethyl)pentylcarbamate (49 mg, 0.12 mmol) in dichloromethane (2 mL) in the presence of 3-(morpholino)propylpolystyrenesulfonamide (118 mg, 2.03 mmol/g, 0.24 mmol). The resulting mixture was shaken at 800 Hz for 2 h. A second portion of 5-methyl-2-phenyl-2H-1,2,3-triazole-4-carbonyl chloride in dichloromethane (0.264 mL, 0.500 M, 0.132 mmol) was then added, and the mixture was shaken for another 2 h. A third portion of 5-methyl-2-phenyl-2H-1,2,3-triazole-4-carbonyl chloride in dichloromethane (0.132 mL, 0.500 M, 0.064 mmol) was then added, and the mixture was shaken for 18 h. Tris-(2-aminoethyl)amine polystyrene (29 mg, 4.08 mmol/g, 0.12 mmol) was added, and the mixture was shaken for an additional 6 h. Solids were then removed by filtration, rinsing with five 1 mL portions of dichloromethane. The filtrate and rinses were combined and concentrated. The residue was then redissolved in dichloromethane (2 mL). Sodium bicarbonate (13 mg, 0.16 mmol) and a solution of Dess-Martin periodinane in dichloromethane (0.75 mL, 0.20 M, 0.15 mmol) were added, and the resulting mixture was shaken at 800 Hz for 1 h. It was then subjected directly to column chromatography on silica gel. Elution with a gradient of 5-10% acetone in dichloromethane afforded impure product, which was further purified by column chromatography on silica gel. Elution with 5% acetone in dichloromethane afforded the title compound as a gum, from which three 2 mL portions of ether were distilled. In this manner, (3S)-4,4-dimethyl-1-[(5-methyl-2-phenyl-2H-1,2,3-triazol-4-yl)carbonyl]pyrrolidinyl (1S)-1-(oxo{[(1R)-1-phenylethyl]amino}acetyl)pentylcarbamate was obtained as a colorless gum (25 mg, 33%) that contained ether (0.65 eq. based on integration of signals in the $^1$H NMR spectrum), after drying under vacuum. $^1$H NMR (300 MHz, DMSO-$d_6$) δ 9.18-9.14 (m); 9.10 (d, J=8 Hz) and 8.94 (d, J=9 Hz) total 1H, 8.00 (d, J=8 Hz, 2H); 7.69-7.66 (m, 1H); 7.61-7.54 (m, 2H); 7.48-7.41 (m, 1H); 7.35-7.06 (m, 5H); 5.01-4.64 (m, 3H); 4.36-4.28 (m) and 3.97-3.92 (m) total 1H, 3.93-3.89 (m, 1H); 3.80-3.64 (m, 1H); 3.60-3.43 (m, 1H); 1.66-1.52 (m, 1H); 1.46-1.35 (m, 1H); 1.31-1.12 (m, 4H); 1.10 (s), 1.07 (s), 1.05 (s), and 1.02 (s) total 6H; 0.89-0.68 (m, 3H). ES-LCMS m/z 589 (M+H) HRMS $C_{32}H_{40}N_6O_5$ m/z 589.3138 (M+H)$_{Cal.}$ 589.3137(M+H)$_{Obs.}$.

Example 16

(3S)-1-(1,3-Benzodioxol-5-ylcarbonyl)-4,4-dimethylpyrrolidinyl (1S)-1-(oxo{[(1R)-1-phenylethyl]amino}acetyl)pentylcarbamate

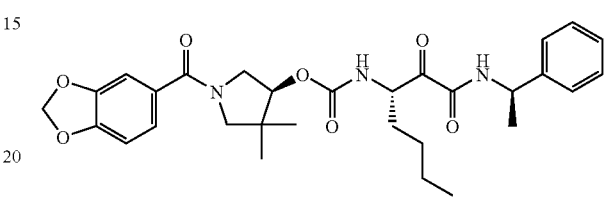

A solution of 1,3-benzodioxole-5-carbonyl chloride in 1:1 acetonitrile:dichloromethane (0.528 mL, 0.250 M, 0.132 mmol) was added to a solution of (3S)-4,4-dimethylpyrrolidinyl (1S)-1-(1-hydroxy-2-oxo-2-{[(1R)-1-phenylethyl]amino}ethyl)pentylcarbamate (49 mg, 0.12 mmol) in dichloromethane (2 mL) in the presence of 3-(morpholino)propylpolystyrenesulfonamide (118 mg, 2.03 mmol/g, 0.24 mmol). The resulting mixture was shaken at 800 Hz for 2 h. A second portion of 3-benzodioxole-5-carbonyl chloride in 1:1 acetonitrile:dichloromethane (0.264 mL, 0.250 M, 0.064 mmol) was added, and the mixture was shaken for another 2 h. Tris-(2-aminoethyl)amine polystyrene (29 mg, 4.08 mmol/g, 0.12 mmol) was then added, and the mixture was shaken for an additional 18 h. Solids were then removed by filtration, rinsing with five 1 mL portions of dichloromethane. The filtrate and rinses were combined and concentrated. The residue was then redissolved in dichloromethane (2 mL). Sodium bicarbonate (13 mg, 0.16 mmol) and a solution of Dess-Martin periodinane in dichloromethane (1.00 mL, 0.15 M, 0.15 mmol) were added, and the resulting mixture was shaken at 800 Hz for 1 h. A second portion of Dess-Martin periodinane (15 mg, 0.04 mmol) was added, and the mixture was shaken for 15 min. Sodium bicarbonate (15 mg, 0.18 mmol) was then added, the mixture was filtered, and the filtrate was subjected directly to column chromatography on silica gel. Elution with a gradient of 5-10% acetone in dichloromethane afforded impure product, which was further purified by column chromatography on silica gel. Elution with 5% acetone in dichloromethane afforded (3S)-1-(1,3-benzodioxol-5-ylcarbonyl)-4,4-dimethylpyrrolidinyl (1S)-1-(oxo{[(1R)-1-phenylethyl]amino}acetyl)pentylcarbamate as a solid white foam (42 mg, 63%), after drying under vacuum. $^1$H NMR (300 MHz, DMSO-$d_6$, Temp=100° C.) δ 8.82-8.74 (m, 1H), 7.38-7.22 (m, 6H), 7.07 (m, 1H), 7.05 (br s, 1H), 6.95 (m, 1H), 6.08 (s, 2H), 5.05-4.95 (m, 1H), 4.86-4.76 (m, 1H), 4.71 (br s, 1H), 3.94 (dd, J=13 Hz, 5 Hz, 1H), 3.41-3.29 (m, 3H), 1.77-1.62 (m, 1H), 1.60-1.45 (m, 1H), 1.47 (d, J=7 Hz, 3H), 1.38-1.20 (m, 4H), 1.05 (br s, 6H), 0.84 (t, J=7 Hz, 3H). ES-LCMS m/z 552 (M+H) HRMS $C_{30}H_{37}N_3O_7$ m/z 552.2710 (M+H)$_{Cal.}$ 552.2714 (M+H)$_{Obs.}$.

Example 17

(3S)-1-(1-Benzothien-2-ylcarbonyl)-4,4-dimethylpyrrolidinyl (1S)-1-(oxo{[(1R)-1-phenylethyl]amino}acetyl)pentylcarbamate

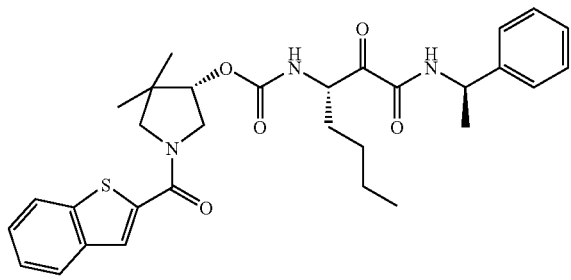

A solution of 1-benzothiophene-2-carbonyl chloride in 1:1 acetonitrile:dichloromethane (0.528 mL, 0.250 M, 0.132 mmol) was added to a solution of (3S)-4,4-dimethylpyrrolidinyl (1S)-1-(1-hydroxy-2-oxo-2-{[(1R)-1-phenylethyl]amino}ethyl)pentylcarbamate (49 mg, 0.12 mmol) in dichloromethane (2 mL) in the presence of 3-(morpholino)propylpolystyrenesulfonamide (118 mg, 2.03 mmol/g, 0.24 mmol). The resulting mixture was shaken at 800 Hz for 2 h. A second portion of 1-benzothiophene-2-carbonyl chloride in 1:1 acetonitrile:dichloromethane (0.264 mL, 0.250 M, 0.064 mmol) was then added, and the mixture was shaken for another 2 h. Tris-(2-aminoethyl)amine polystyrene (29 mg, 4.08 mmol/g, 0.12 mmol) was then added, and the mixture was shaken for an additional 18 h. Solids were then removed by filtration, rinsing with five 1 mL portions of dichloromethane. The filtrate and rinses were combined and concentrated. The residue was then redissolved in dichloromethane (2 mL). Sodium bicarbonate (13 mg, 0.16 mmol) and a solution of Dess-Martin periodinane in dichloromethane (1.00 mL, 0.15 M, 0.15 mmol) were added, and the resulting mixture was shaken at 800 Hz for 1 h. A second portion of Dess-Martin periodinane (15 mg, 0.04 mmol) was added, and the mixture was shaken for 15 min. Sodium bicarbonate (15 mg, 0.18 mmol) was then added, the mixture was filtered, and the filtrate was subjected directly to column chromatography on silica gel. Elution with a gradient of 5-10% acetone in dichloromethane afforded impure product, which was further purified by column chromatography on silica gel. Elution with 5% acetone in dichloromethane afforded the title compound as a solid, from which three 2 mL portions of ether were distilled. In this manner, (3S)-1-(1-benzothien-2-ylcarbonyl)-4,4-dimethylpyrrolidinyl (1S)-1-(oxo{[(1R)-1-phenylethyl]amino}acetyl)pentylcarbamate was obtained as a white solid (45 mg, 64%) that contained ether (0.36 eq. based on integration of signals in the $^1$H NMR spectrum), after drying under vacuum. $^1$H NMR (300 MHz, DMSO-$d_6$) δ 9.18-9.13 (m, 1H); 8.04-7.88 (m, 3H); 7.70 (d, J=8 Hz, 1H); 7.49-7.38 (m, 2H); 7.37-7.11 (m, 5H); 5.01-4.87 (m, 1H); 4.85-4.66 (m, 2H); 4.36 (dd, J=12 Hz, 6 Hz) and 3.96 (dd, J=13 Hz, 5 Hz) total 1H, 3.86-3.62 (m, 2H); 3.53-3.38 (m, 1H); 1.67-1.51 (m, 1H); 1.48-1.34 (m, 4H); 1.32-1.13 (m, 4H); 1.10 (s), 1.09 (s), 1.07 (s), 1.05 (s), 1.02 (S), and 1.00 (s) total 6H; 0.86-0.68 (m, 3H). ES-LCMS m/z 564 (M+H) HRMS $C_{31}H_{37}N_3O_5$ m/z 564.2532 (M+H)$_{Cal.}$ 564.2522 (M+H)$_{Obs.}$.

Example 18

(3S)-4,4-Dimethyl-1-(2-naphthoyl)pyrrolidinyl (1S)-1-(oxo{[(1R)-1-phenylethyl]amino}acetyl)pentylcarbamate

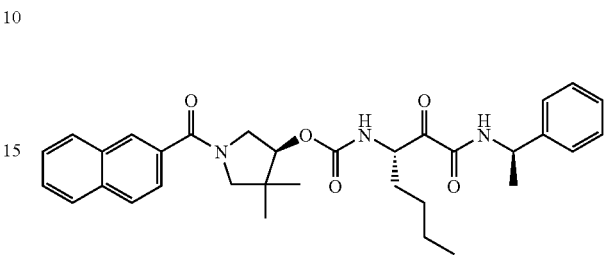

A solution of 2-naphthoyl chloride in 1:1 acetonitrile:dichloromethane (0.528 mL, 0.250 M, 0.132 mmol) was added to a solution of (3S)-4,4-dimethylpyrrolidinyl (1S)-1-(1-hydroxy-2-oxo-2-{[(1R)-1-phenylethyl]amino}ethyl)pentylcarbamate (49 mg, 0.12 mmol) in dichloromethane (2 mL) in the presence of 3-(morpholino)propylpolystyrenesulfonamide (118 mg, 2.03 mmol/g, 0.24 mmol). The resulting mixture was shaken at 800 Hz for 2 h. A second portion of 2-naphthoyl chloride in 1:1 acetonitrile:dichloromethane (0.264 mL, 0.250 M, 0.064 mmol) was then added, and the mixture was shaken for another 2 h. A third portion of 2-naphthoyl chloride (0.528 mL, 0.250 M, 0.132 mmol) was added, and the mixture was shaken for 18 h. Tris-(2-aminoethyl)amine polystyrene (29 mg, 4.08 mmol/g, 0.12 mmol) was then added, and the mixture was shaken for an additional 6 h. Solids were then removed by filtration, rinsing with five 1 mL portions of dichloromethane. The filtrate and rinses were combined and concentrated. The residue was then redissolved in dichloromethane (2 mL). Sodium bicarbonate (13 mg, 0.16 mmol) and a solution of Dess-Martin periodinane in dichloromethane (1.00 mL, 0.15 M, 0.15 mmol) were added, and the resulting mixture was shaken at 800 Hz for 1 h. A second portion of Dess-Martin periodinane (15 mg, 0.04 mmol) was added, and the mixture was shaken for 15 min. Sodium bicarbonate (15 mg, 0.18 mmol) was then added, the mixture was filtered, and the filtrate was subjected directly to column chromatography on silica gel. Elution with a gradient of 5-10% acetone in dichloromethane afforded impure product, which was further purified by column chromatography on silica gel. Elution with 5% acetone in dichloromethane afforded the title compound as a gum, from which three 2 mL portions of ether were distilled. In this manner, (3S)-4,4-dimethyl-1-(2-naphthoyl)pyrrolidinyl (1S)-1-(oxo{[(1R)-1-phenylethyl]amino}acetyl)pentylcarbamate was obtained as a white solid (45 mg, 62%) that contained ether (0.6 eq. based on integration of signals in the $^1$H NMR spectrum), after drying under vacuum. $^1$H NMR (300 MHz, DMSO-$d_6$) δ 9.34 (d, J=8 Hz, 1H); 9.17 (d, J=8 Hz), 9.10 (d, J=8 Hz) and 9.02 (d, J=9 Hz) total 1H, 8.15-7.92 (m, 4H); 7.72-7.54 (m, 4H); 7.44-7.15 (m, 5H); 5.02-4.51 (m, 3H); 4.12-3.89 (m, 1H); 3.48-3.35 (m, 3H); 1.70-1.04 (m, 12H); 0.95 (s), 0.93 (s), and 0.91 (s) total 3H, 0.82-0.67 (m, 3H). ES-LCMS m/z 558 (M+H) HRMS $C_{33}H_{39}N_3O_5$ m/z 558.2968 $(M+H)_{Cal.}$ 558.2967 $(M+H)_{Obs.}$.

Example 19

(3S)-4,4-Dimethyl-1-[(5-methyl-3-isoxazolyl)carbonyl]pyrrolidinyl (1S)-1-(oxo{[(1R)-1-phenylethyl]amino}acetyl)pentylcarbamate

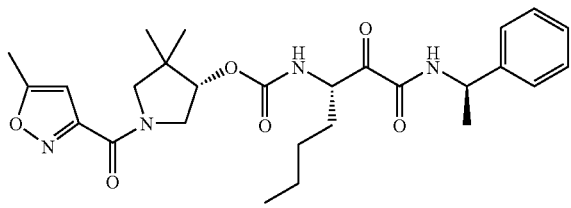

A solution of presumed 5-methyl-3-isoxazolecarbonyl chloride in 1:1 acetonitrile:dichloromethane (0.528 mL, 0.250 M, 0.132 mmol) was added to a solution of (3S)-4,4-dimethylpyrrolidinyl (1S)-1-(1-hydroxy-2-oxo-2-{[(1R)-1-phenylethyl]amino}ethyl)pentylcarbamate (49 mg, 0.12 mmol) in dichloromethane (2 mL) in the presence of 3-(morpholino)propylpolystyrenesulfonamide (118 mg, 2.03 mmol/g, 0.24 mmol). The resulting mixture was shaken at 800 Hz for 2 h. A second portion of presumed 5-methyl-3-isoxazolecarbonyl chloride in 1:1 acetonitrile:dichloromethane (0.264 mL, 0.250 M, 0.064 mmol) was added then, and the mixture was shaken for another 18 h. Tris-(2-aminoethyl)amine polystyrene (29 mg, 4.08 mmol/g, 0.12 mmol) was then added, and the mixture was shaken for an additional 6 h. Solids were removed by filtration, rinsing with five 1 mL portions of dichloromethane. The filtrate and rinses were combined and concentrated. Analysis of the filtrate by LC-MS showed the presence of unreacted (3S)-4,4-dimethylpyrrolidinyl (1S)-1-(1-hydroxy-2-oxo-2-{[(1R)-1-phenylethyl]amino}ethyl) pentylcarbamate and 5-methyl-3-isoxazolecarboxylic acid. The residue was then redissolved in dichloromethane (2 mL). N-Cyclohexylcarbodiimide-N'-propyloxymethyl polystyrene (350 mg, 1-1.5 mmol/g, 0.35-0.52 mmol) was added, followed by a solution of 1-hydroxybenzotriazole in 20% N,N-dimethylformamide in dichloromethane (1.2 mL, 120 mM, 0.14 mmol). The resulting mixture was shaken for 4.5 h at 800 Hz. Tris-(2-aminoethyl)amine polystyrene (29 mg, 4.08 mmol/g, 0.12 mmol) was then added, and the mixture was shaken for an additional 18 h. Solids were removed by filtration, rinsing with five 1 mL portions of dichloromethane. The filtrate and rinses were combined and concentrated to a volume of 2 mL. Sodium bicarbonate (13 mg, 0.16 mmol) and Dess-Martin periodinane (55 mg, 0.15 mmol) were added, and the resulting mixture was shaken at 800 Hz for 1 h. The mixture was washed with saturated aqueous sodium thiosulfate (2 mL), and the aqueous wash was back-extracted twice with 1 mL portions of dichloromethane. The dichloromethane layers were combined, and subjected to column chromatography on silica gel. Elution with 5% acetone in dichloromethane afforded impure product, which was further purified by column chromatography on silica gel. Elution with 40% ethyl acetate in hexane afforded the title compound as a gum, from which three 2 mL portions of ether were distilled. In this manner, (3S)-4,4-dimethyl-1-[(5-methyl-3-isoxazolyl)carbonyl]pyrrolidinyl (1S)-1-(oxo{[(1R)-1-phenylethyl]amino}acetyl)pentylcarbamate was obtained as a colorless gum (35 mg, 54%) that contained ether (0.32 eq. based on integration of signals in the $^1H$ NMR spectrum), after drying under vacuum. $^1H$ NMR (300 MHz, DMSO-$d_6$, Temp=100° C.) δ 8.76 (m, 1H); 7.38-7.22 (m, 6H); 6.47 (s, 1H); 5.05-4.94 (m, 1H); 4.88-4.74 (m, 2H); 4.16-4.07 (m) and 3.98-3.90 (m) total 1H, 3.72-3.38 (m, 3H); 2.48 (s, 3H); 1.76-1.63 (m, 1H); 1.60-1.45 (m, 1H); 1.47 (d, J=7 Hz, 3H); 1.38-1.22 (m, 4H); 1.10 (s) and 1.09 (s) total 3H, 1.06 (s) and 1.06 (s) total 3H, 0.89-0.80 (m, 3H). ES-LCMS m/z 513 (M+H) HRMS $C_{27}H_{36}N_4O_6$ m/z 535.2533 $(M+Na)_{Cal.}$ 535.2537 $(M+Na)_{Obs.}$.

Example 20

(3S)-1-([1,1'-Biphenyl]-4-ylcarbonyl)-4,4-dimethylpyrrolidinyl (1S)-1-(oxo{[(1R)-1-phenylethyl]amino}acetyl)pentylcarbamate

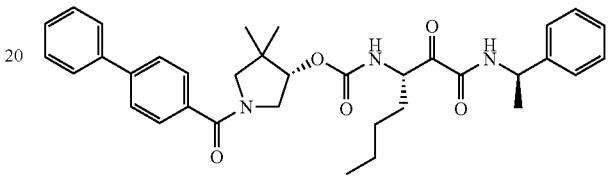

A solution of presumed [1,1'-biphenyl]-4-carbonyl chloride in 1:1:0.5 acetonitrile:dichloromethane:N,N-dimethylformamide (0.660 mL, 0.200 M, 0.132 mmol) was added to a solution of (3S)-4,4-dimethylpyrrolidinyl (1S)-1-(1-hydroxy-2-oxo-2-{[(1R)-1-phenylethyl]amino}ethyl)pentylcarbamate (49 mg, 0.12 mmol) in dichloromethane (2 mL) in the presence of 3-(morpholino)propylpolystyrenesulfonamide (118 mg, 2.03 mmol/g, 0.24 mmol). The resulting mixture was shaken at 800 Hz for 2 h. A second portion of presumed [1,1'-biphenyl]-4-carbonyl chloride in 1:1:0.5 acetonitrile:dichloromethane:N,N-dimethyl formamide (0.330 mL, 0.200 M, 0.064 mmol) was added, and the mixture was shaken for another 18 h. Tris-(2-aminoethyl)amine polystyrene (29 mg, 4.08 mmol/g, 0.12 mmol) was then added, and the mixture was shaken for an additional 6 h. Solids were then removed by filtration, rinsing with five 1 mL portions of dichloromethane. The filtrate and rinses were combined and concentrated. Analysis of the filtrate by LC-MS showed the presence of unreacted (3S)-4,4-dimethylpyrrolidinyl (1S)-1-(1-hydroxy-2-oxo-2-{[(1R)-1-phenylethyl]amino}ethyl) pentylcarbamate and [1,1'-biphenyl]-4-carboxylic acid. The residue was then redissolved in dichloromethane (2 mL). N-Cyclohexylcarbodiimide-N'-propyloxymethyl polystyrene (350 mg, 1-1.5 mmol/g, 0.35-0.52 mmol) was added, followed by a solution of 1-hydroxybenzotriazole in 20% N,N-dimethylformamide in dichloromethane (1.2 mL, 120 mM, 0.14 mmol). The resulting mixture was shaken for 4.5 h at 800 Hz. Tris-(2-aminoethyl)amine polystyrene (29 mg, 4.08 mmol/g, 0.12 mmol) was then added, and the mixture was shaken for an additional 18 h. Solids were removed by filtration, rinsing with five 1 mL portions of dichloromethane. The filtrate and rinses were combined and concentrated to a volume of 2 mL. Sodium bicarbonate (13 mg, 0.16 mmol) and Dess-Martin periodinane (55 mg, 0.15 mmol) were added, and the resulting mixture was shaken at 800 Hz for 1 h. The mixture was washed with saturated aqueous sodium thiosulfate (2 mL). The aqueous wash was back-extracted twice with 1 mL portions of dichloromethane. The dichloromethane layers were combined, and subjected to column chromatography on silica gel. Elution with 5% acetone in dichloromethane afforded impure product, which was further purified by column chromatography on silica gel. Elution with 40% ethyl acetate in hexane afforded the title compound as a foam, from which three 2 mL portions of ether were distilled. In this manner, (3S)-1-([1,1'-biphenyl]-4-ylcarbonyl)-4,4-dimethylpyrrolidinyl (1S)-1-(oxo{[(1R)-1-phenylethyl]amino}acetyl)pentylcarbamate was obtained as a white foam (27 mg, 38%) that contained ether (0.17 eq. based on integration of signals in the $^1$H NMR spectrum), after drying under vacuum. $^1$H NMR (300 MHz, DMSO-$d_6$, Temp=100° C.) δ 8.80-8.72 (m, 1H), 7.73 (m, 4H), 7.63 (m, 2H), 7.64-7.49 (m, 2H), 7.45-7.22 (m, 7H), 6.47 (s, 1H), 5.05-4.95 (m, 1H), 4.87-4.71 (m, 2H), 3.98 (dd, J=13 Hz, 6 Hz, 1H), 3.45-3.36 (m, 3H), 1.76-1.64 (m, 1H), 1.61-1.49 (m, 1H), 1.48 (d, J=7 Hz, 3H), 1.38-1.21 (m, 4H), 1.07 (br s, 6H), 0.86-0.82 (m, 3H). ES-LCMS m/z 584 (M+H) HRMS $C_{35}H_{41}N_3O_5$ m/z 584.3124 (M+H)$_{Cal.}$ 584.3104 (M+H)$_{Obs.}$.

in dichloromethane afforded impure product, which was further purified by column chromatography on silica gel. Elution with 50% ethyl acetate in hexane afforded (3S)-1-(1H-indol-5-ylcarbonyl)-4,4-dimethylpyrrolidinyl (1S)-1-(oxo{[(1R)-1-phenylethyl]amino}acetyl)pentylcarbamate as a colorless glass (23 mg, 34%) that contained ethyl acetate (0.28 eq. based on integration of signals in the $^1$H NMR spectrum), after drying under vacuum. $^1$H NMR (300 MHz, DMSO-$d_6$, Temp=100° C.) δ 11.03 (br s, 1H), 8.72 (m, 1H), 7.72 (s, 1H), 7.42-7.18 (m, 9H), 6.49 (br s, 1H), 5.02-4.92 (m, 1H), 4.84-4.72 (m, 1H), 4.69 (br s, 1H), 3.95 (dd, J=13 Hz, 6 Hz, 1H), 3.42-3.30 (m, 3H), 1.73-1.59 (m, 1H), 1.54-1.43 (m, 1H), 1.42 (d, J=7 Hz, 3H), 1.35-1.17 (m, 4H), 1.01 (br s, 6H), 0.79 (t, J=6 Hz, 3H). ES-LCMS m/z 547 (M+H) HRMS $C_{31}H_{38}N_4O_5$ m/z 547.2920 (M+H)$_{Cal.}$ 547.2920 (M+H)$_{Obs.}$.

Example 21

(3S)-1-(1H-Indol-5-ylcarbonyl)-4,4-dimethylpyrrolidinyl (1S)-1-(oxo{[(1R)-1-phenylethyl]amino}acetyl)pentylcarbamate

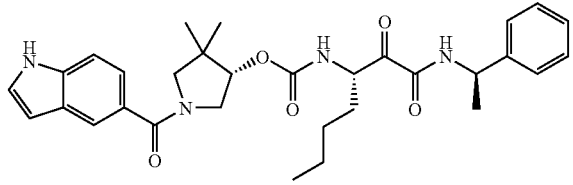

A solution of 1-hydroxybenzotriazole in 20% N,N-dimethylformamide in dichloromethane (1.2 mL, 120 mM, 0.14 mmol) was added to a slurry of 1H-indole-5-carboxylic acid (21 mg, 0.13 mmol) in dichloromethane (1.0 mL) in the presence of N-cyclohexylcarbodiimide-N'-propyloxymethyl polystyrene (350 mg, 1-1.5 mmol/g, 0.35-0.52 mmol). The resulting mixture was shaken at 800 Hz for 20 min. A solution of (3S)-4,4-dimethylpyrrolidinyl (1S)-1-(1-hydroxy-2-oxo-2-{[(1R)-1-phenylethyl]amino}ethyl)pentylcarbamate in dichloromethane (1.0 mL, 120 mM, 0.12 mmol) was added, and the reaction mixture was shaken at 800 Hz for 16 h. Tris-(2-aminoethyl)amine polystyrene (50 mg, 4.08 mmol/g, 0.20 mmol) was then added, and the mixture was shaken for an additional 24 h. Solids were then removed by filtration, rinsing with five 1 mL portions of dichloromethane. The filtrate and rinses were combined and concentrated. The residue was then redissolved in dichloromethane (2 mL). Sodium bicarbonate (13 mg, 0.16 mmol) and a solution of Dess-Martin periodinane (1.0 mL, 180 mM, 0.18 mmol) were added, and the resulting mixture was shaken at 800 Hz for 1.5 h. Saturated aqueous sodium thiosulfate (2 mL) was then added, and the mixture was shaken at 800 Hz for 30 min. The layers were separated, and the aqueous wash was back-extracted with dichloromethane (1 mL). The dichloromethane layers were combined, and subjected to column chromatography on silica gel. Elution with a gradient of 5-50% acetone

Example 22

(3S)-1-(1H-1,2,3-Benzotriazol-5-ylcarbonyl)-4,4-dimethylpyrrolidinyl (1S)-1-(oxo{[(1R)-1-phenylethyl]amino}acetyl)pentylcarbamate

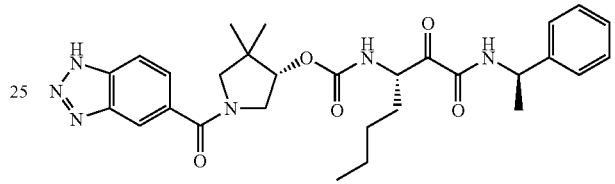

(3S)-1-(1H-1,2,3-Benzotriazol-5-ylcarbonyl)-4,4-dimethylpyrrolidinyl (1S)-1-(oxo{[(1R)-1-phenylethyl]amino}acetyl)pentylcarbamate (5 mg, 6%) was obtained as a white solid that contained ethyl acetate (0.18 eq. based on integration of signals in the $^1$H NMR spectrum) in two steps from (3S)-4,4-dimethylpyrrolidinyl (1S)-1-(1-hydroxy-2-oxo-2-{[(1R)-1-phenylethyl]amino}ethyl)pentylcarbamate (1.0 mL, 120 mM in dichloromethane, 0.12 mmol) and 1H-1,2,3-benzotriazole-5-carboxylic acid (22 mg, 0.13 mmol) following the procedure outlined in example 21. $^1$H NMR (300 MHz, DMSO-$d_6$, Temp=100° C.) δ 8.76-8.68 (m, 1H), 8.07-7.99 (m, 1H), 7.96-7.87 (m, 1H), 7.68-7.52 (m, 1H), 7.35-7.18 (m, 6H), 5.02-4.92 (m, 1H), 4.85-4.67 (m, 2H), 3.95 (dd, J=13 Hz, 6 Hz, 1H), 3.43-3.30 (m, 3H), 1.72-1.58 (m, 1H), 1.56-1.43 (m, 1H), 1.42 (d, J=7 Hz, 3H), 1.35-1.17 (m, 4H), 1.02 (br s, 6H), 0.87-0.74 (m, 3H). ES-LCMS m/z 549 (M+H) HRMS $C_{29}H_{36}N_6O_5$ m/z 549.2825 (M+H)$_{Cal.}$ 549.2819 (M+H)$_{Obs.}$.

Example 23

(3S)-4,4-Dimethyl-1-[(3-phenoxyphenyl)acetyl]pyrrolidinyl (1S)-1-(oxo{[(1R)-1-phenylethyl]amino}acetyl)pentylcarbamate

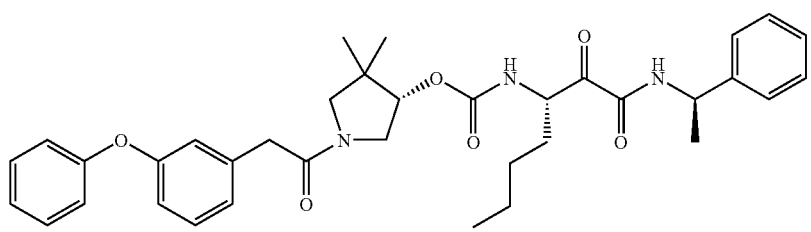

(3S)-4,4-Dimethyl-1-[(3-phenoxyphenyl)acetyl]pyrrolidinyl (1S)-1-(oxo{[(1R)-1-phenylethyl]amino}acetyl)pentylcarbamate (41 mg, 53%) was obtained as a colorless gum that contained ethyl acetate (0.4 eq. based on integration of signals in the $^1$H NMR spectrum) in two steps from (3S)-4,4-dimethylpyrrolidinyl (1S)-1-(1-hydroxy-2-oxo-2-{[(1R)-1-phenylethyl]amino}ethyl)pentylcarbamate (1.0 mL, 120 mM in dichloromethane, 0.12 mmol) and (3-phenoxyphenyl)acetic acid (30 mg, 0.13 mmol) following the procedure outlined in example 21. $^1$H NMR (300 MHz, DMSO-d$_6$, Temp=100° C.) δ 8.78-8.68 (m, 1H); 8.07-7.99 (m, 1H); 7.39-7.21 (m, 9H); 7.11 (m, 1H); 7.03-6.97 (m, 3H); 6.90 (br s, 1H); 6.86 (d, J=9 Hz, 1H); 5.01-4.91 (m, 1H); 4.81-4.63 (m, 2H); 3.91-3.83 (m) and 3.72-3.64 (m) total 1H, 3.59 (br s, 2H); 3.39-3.10 (m, 3H); 1.71-1.59 (m, 1H); 1.55-1.43 (m, 1H); 1.44 (d, J=7 Hz, 3H); 1.34-1.17 (m, 4H); 0.99 (br s, 3H); 0.96 (s, 3H); 0.82-0.78 (m, 3H). ES-LCMS m/z 614 (M+H) HRMS C$_{36}$H$_{43}$N$_3$O$_6$ m/z 614.3230 (M+)$_{Cal.}$ 614.3239 (M+H)$_{Obs.}$.

Example 24

(3S)-4,4-Dimethyl-1-(4-phenylbutanoyl)pyrrolidinyl (1S)-1-(oxo {[(1R)-1-phenylethyl]amino}acetyl)pentylcarbamate

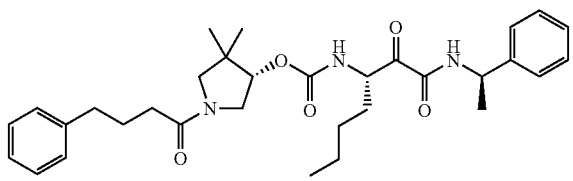

(3S)-4,4-Dimethyl-1-(4-phenylbutanoyl)pyrrolidinyl (1S)-1-(oxo{[(1R)-1-phenylethyl]amino}acetyl)pentylcarbamate (46 mg, 67%) was obtained as a colorless gum that contained ethyl acetate (0.26 eq. based on integration of signals in the $^1$H NMR spectrum) in two steps from (3S)-4,4-dimethylpyrrolidinyl (1S)-1-(1-hydroxy-2-oxo-2-{[(1R)-1-phenylethyl]amino}ethyl)pentylcarbamate (1.0 mL, 120 mM in dichloromethane, 0.12 mmol) and 4-phenylbutanoic acid (22 mg, 0.13 mmol) following the procedure outlined in example 21. $^1$H NMR (300 MHz, DMSO-d$_6$, Temp=100° C.) δ 88.76-8.67 (m, 1H); 7.34-7.13 (m, 11H); 5.01-4.91 (m, 1H); 4.82-4.72 (m, 1H); 4.72-4.62 (m, 1H); 3.84-3.75 (m) and 3.71-3.60 (m) total 1H, 3.31-3.10 (m, 3H); 2.64-2.58 (m, 2H); 2.26-2.16 (m, 2H); 1.88-1.78 (m, 2H); 1.73-1.59 (m, 1H); 1.57-1.44 (m, 1H); 1.44 (d, J=7 Hz, 3H); 1.35-1.17 (m, 4H); 1.00 (br s, 36H); 0.99 (s, 3H); 0.83-0.78 (m, 3H). ES-LCMS m/z 550 (M+H) HRMS C$_{32}$H$_{43}$N$_3$O$_5$ m/z 550.3281 (M+H)$_{Cal.}$ 550.3274 (M+H)$_{Obs.}$.

Example 25

(3S)-1-[(4-tert-Butylphenyl)acetyl]-4,4-dimethylpyrrolidinyl (1S)-1-(oxo{[(1R)-1-phenylethyl]amino}acetyl)pentylcarbamate

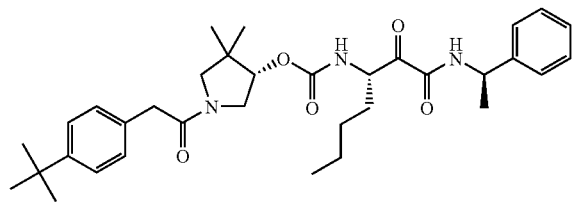

(3S)-1-[(4-tert-Butylphenyl)acetyl]-4,4-dimethylpyrrolidinyl (1S)-1-(oxo{[(1R)-1-phenylethyl]amino}acetyl)pentylcarbamate (34 mg, 46%) was obtained as a colorless gum that contained ethyl acetate (0.4 eq. based on integration of signals in the $^1$H NMR spectrum) in two steps from (3S)-4,4-dimethylpyrrolidinyl (1S)-1-(1-hydroxy-2-oxo-2-{[(1R)-1-phenylethyl]amino}ethyl)pentylcarbamate (1.0 mL, 120 mM in dichloromethane, 0.12 mmol) and (4-tert-butylphenyl)acetic acid (25 mg, 0.13 mmol) following the procedure outlined in example 21. $^1$H NMR (300 MHz, DMSO-d$_6$, Temp=100° C.) δ 8.75-8.67 (m, 1H); 7.35-7.103 (m, 10H); 5.01-4.91 (m, 1H); 4.81-4.64 (m, 2H); 3.99-3.87 (m) and 3.77-3.65 (m) total 1H, 3.54 (m, 2H); 3.45-3.12 (m, 3H); 1.73-1.60 (m, 1H); 1.55-1.44 (m, 1H); 1.44 (d, J=7 Hz, 3H); 1.35-1.18 (m, 4H); 1.27 (s, 9H); 1.00 (br s, 36H); 0.97 (s, 3H); 0.85-0.78 (m, 3H). ES-LCMS m/z 578 (M+H) HRMS C$_{34}$H$_{47}$N$_3$O$_5$ m/z 578.3594 (M+H)$_{Cal.}$ 578.3580 (M+H)$_{Obs.}$.

Example 26

(3S)-4,4-Dimethyl-1-{[2-(4-pyridinyl)-1,3-thiazol-4-yl]carbonyl}pyrrolidinyl (1S)-1-(oxo{[(1R)-1-phenylethyl]amino}acetyl)pentylcarbamate

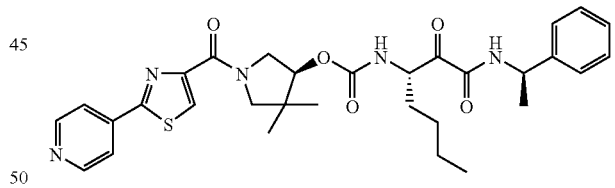

(3S)-4,4-Dimethyl-1-{[2-(4-pyridinyl)-1,3-thiazole-4-yl]carbonyl}pyrrolidinyl (1S)-1-(oxo{[(1R)-1-phenylethyl]amino}acetyl)pentylcarbamate (9 mg, 10%) was obtained as a colorless gum that contained ethyl acetate (0.43 eq. based on integration of signals in the $^1$H NMR spectrum) in two steps from (3S)-4,4-dimethylpyrrolidinyl (1S)-1-(1-hydroxy-2-oxo-2-{[(1R)-1-phenylethyl]amino}ethyl)pentylcarbamate (1.0 mL, 120 mM in dichloromethane, 0.12 mmol) and 2-(4-pyridinyl)-1,3-thiazole-4-carboxylic acid (27 mg, 0.13 mmol) following the procedure outlined in example 21, except that the eluent used for the final chromatographic purification was 15% acetone in dichloromethane. $^1$H NMR (300 MHz, DMSO-d$_6$, Temp=100° C.) δ 8.72 (d, J=6 Hz, 1H), 8.72-8.62 (m, 1H), 8.36 (s, 1H), 7.88 (d, J=6 Hz, 2H), 7.37-7.15 (m, 6H), 5.00-4.90 (m, 1H), 4.84-4.71 (m, 2H), 4.42-4.21 (m, 1H), 4.05-3.32 (m, 3H); 1.71-1.59 (m, 1H), 1.56-

1.42 (m, 1H), 1.41 (d, J=7 Hz, 3H), 1.35-1.16 (m, 4H), 1.07 (br s, 6H), 0.89-0.73 (m, 3H). ES-LCMS m/z 592 (M+H) HRMS $C_{31}H_{37}N_5O_5S$ m/z 592.2593 (M+H)$_{Cal.}$ 592.2607 (M+H)$_{Obs.}$.

Example 27

(3S)-4,4-Dimethyl-1-[(5-methyl-3-phenyl-4-isoxazolyl)carbonyl]pyrrolidinyl (1S)-1-(oxo{[(1R)-1-phenylethyl]amino}acetyl)pentylcarbamate

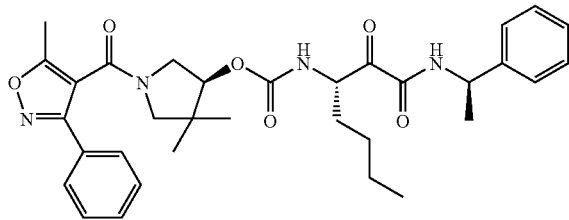

(3S)-4,4-Dimethyl-1-[(5-methyl-3-phenyl-4-isoxazolyl)carbonyl]pyrrolidinyl (1S)-1-(oxo{[(1R)-1-phenylethyl]amino}acetyl)pentylcarbamate (17 mg, 23%) was obtained as a colorless gum that contained ethyl acetate (0.3 eq. based on integration of signals in the $^1$H NMR spectrum) in two steps from (3S)-4,4-dimethylpyrrolidinyl (1S)-1-(1-hydroxy-2-oxo-2-{[(1R)-1-phenylethyl]amino}ethyl)pentylcarbamate (1.0 mL, 120 mM in dichloromethane, 0.12 mmol) and 5-methyl-3-phenyl-4-isoxazolecarboxylic acid (27 mg, 0.13 mmol) following the procedure outlined in example 21. $^1$H NMR (300 MHz, DMSO-d$_6$, Temp=100° C.) δ 8.76-8.64 (m, 1H), 7.65-7.58 (m, 2H), 7.61-7.46 (m, 3H), 7.71-7.35 (m, 6H), 5.01-4.92 (m, 1H), 4.82-4.52 (m, 2H), 4.00-3.80 (m, 1H), 3.56-3.20 (m, 3H), 2.45 (s, 3H), 1.70-1.57 (m, 1H), 1.54-1.40 (m, 1H), 1.43 (d, J=7 Hz, 3H), 1.34-1.14 (m, 4H), 1.06-0.75 (m, 9H). ES-LCMS m/z 589(M+H) HRMS $C_{33}H_{40}N_4O_6$ m/z 589.3026 (M+H)$_{Cal.}$ 589.3036 (M+H)$_{Obs.}$.

Example 28

(3S)-4,4-Dimethyl-1-[(1-methyl-1H-indol-2-yl)carbonyl]pyrrolidinyl (1S)-1-(oxo{[(1R)-1-phenylethyl]amino}acetyl)pentylcarbamate

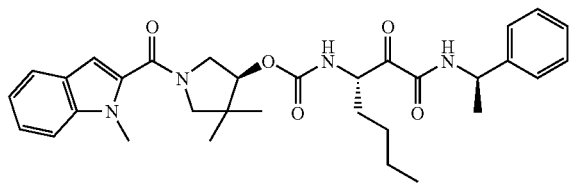

(3S)-4,4-Dimethyl-1-[(1-methyl-1H-indol-2-yl)carbonyl]pyrrolidinyl (1S)-1-(oxo{[(1R)-1-phenylethyl]amino}acetyl)pentylcarbamate (34 mg, 47%) was obtained as a yellow gum that contained ethyl acetate (0.5 eq. based on integration of signals in the $^1$H NMR spectrum) in two steps from (3S)-4,4-dimethylpyrrolidinyl (1S)-1-(1-hydroxy-2-oxo-2-{[(1R)-1-phenylethyl]amino}ethyl)pentylcarbamate (1.0 mL, 120 mM in dichloromethane, 0.12 mmol) and 1-methyl-1H-indole-2-carboxylic acid (23 mg, 0.13 mmol) following the procedure outlined in example 21. $^1$H NMR (300 MHz, DMSO-d$_6$, Temp=100° C.) δ 8.71 (d, J=8 Hz, 1H), 7.62 (m, 1H), 7.47 (dd, J=8 Hz, 1 Hz, 1H), 7.34-7.18 (m, 7H), 7.11-7.06 (m, 1H), 6.78 (s, 1H), 5.01-4.91 (m, 1H), 4.82-4.71 (m, 2H), 4.05-3.99 (m, 1H), 3.82 (s, 3H), 3.02-2.86 (m, 3H), 1.72-1.60 (m, 1H), 1.57-1.45 (m, 1H), 1.42 (d, J=7 Hz, 3H), 1.35-1.17 (m, 4H), 1.05 (s, 6H), 0.82-0.77 (m, 3H). ES-LCMS m/z 561 (M+H) HRMS $C_{32}H_{40}N_4O_5$ m/z 561.3077 (M+H)$_{Cal.}$ 561.3096 (M+H)$_{Obs.}$.

Example 29

(3S)-4,4-Dimethyl-(3-quinolinylcarbonyl)pyrrolidinyl 1-(oxo{[(1R)-1-phenylethyl]amino}acetyl)pentylcarbamate

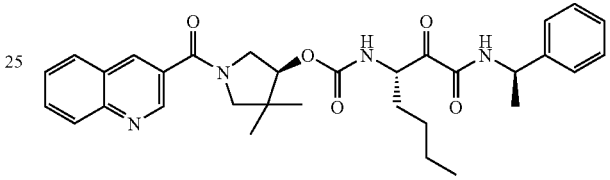

(3S)-4,4-Dimethyl-1-(3-quinolinylcarbonyl)pyrrolidinyl 1-(oxo{[(1R)-1-phenylethyl]amino}acetyl)pentylcarbamate (36 mg, 54%) was obtained as a colorless gum in two steps from (3S)-4,4-dimethylpyrrolidinyl (1S)-1-(1-hydroxy-2-oxo-2-{[(1R)-1-phenylethyl]amino}ethyl)pentylcarbamate (1.0 mL, 120 mM in dichloromethane, 0.12 mmol) and 3-quinolinecarboxylic acid (23 mg, 0.13 mmol) following the procedure outlined in example 21, except that the eluent used for the final chromatographic purification was 15% acetone in dichloromethane. $^1$H NMR (300 MHz, DMSO-d$_6$, Temp=100° C.) δ 8.98 (d, J=2 Hz, 1H), 8.76-8.66 (m, 1H), 8.51 (s, 1H), 8.08-8.03 (m, 2H), 7.86-7.80 (m, 1H), 7.69-7.64 (m, 1H), 7.34-7.18 (m, 6H), 5.01-4.90 (m, 1H), 4.83-4.70 (m, 2H), 4.02 (dd, J=13 Hz, 5 Hz, 1H), 3.60-3.38 (m, 3H), 1.73-1.58 (m, 1H), 1.55-1.47 (m, 1H), 1.42 (d, J=7 Hz, 3H), 1.35-1.17 (m, 4H), 1.13-0.99 (m, 6H), 0.84-0.74 (m, 3H). ES-LCMS m/z 559 (M+H) HRMS $C_{32}H_{38}N_4O_5$ m/z 559.2920 (M+H)$_{Cal.}$ 559.2931 (M+H)$_{Obs.}$.

Example 30

(3S)-1-([1,1'-Biphenyl]-4-ylacetyl)-4,4-dimethylpyrrolidinyl (1S)-1-(oxo {[(1R)-1-phenylethyl]amino}acetyl)pentylcarbamate

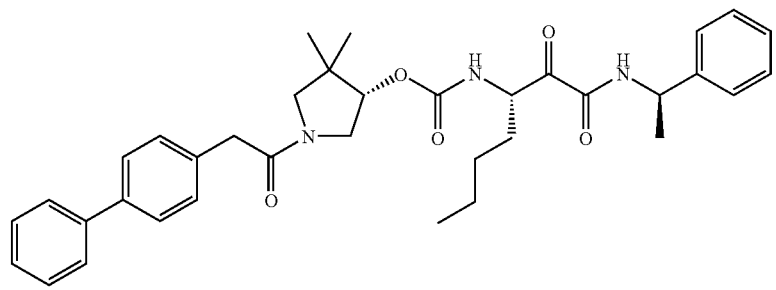

(3S)-1-([1,1'-Biphenyl]-4-ylacetyl)-4,4-dimethylpyrrolidinyl (1S)-1-(oxo{[(1R)-1-phenylethyl]amino}acetyl)pentylcarbamate (46 mg, 60%) was obtained as a colorless gum that contained ethyl acetate and acetic acid (0.36 eq. and 0.16 eq. respectively, based on integration of signals in the $^1$H NMR spectrum) in two steps from (3S)-4,4-dimethylpyrrolidinyl (1S)-1-(1-hydroxy-2-oxo-2-{[(1R)-1-phenylethyl]amino}ethyl)pentylcarbamate (1.0 mL, 120 mM in dichloromethane, 0.12 mmol) and [1,1'-biphenyl]-4-ylacetic acid (28 mg, 0.13 mmol) following the procedure outlined in example 21. $^1$H NMR (300 MHz, DMSO-d$_6$, Temp=100° C.) δ 8.76-8.67 (m, 1H); 7.63-7.56 (m, 2H); 7.43 (m, 2H); 7.36-7.17 (m, 9H); 5.02-4.92 (m, 1H); 4.82-4.65 (m, 2H); 3.99-3.90 (m) and 3.76-3.69 (m) total 1H, 3.64 (br s, 2H); 3.50-3.18 (m, 3H); 1.73-1.58 (m, 1H); 1.56-1.44 (m, 1H); 1.44 (d, J=7 Hz, 3H); 1.33-1.17 (m, 4H); 1.01 (s, 3H); 0.99 (s, 3H); 0.82-0.78 (m, 3H). ES-LCMS m/z 598 (M+H) HRMS C$_{36}$H$_{43}$N$_3$O$_5$ m/z 598.3281 (M+H)$_{Cal.}$ 598.3281 (M+H)$_{Obs.}$.

Example 31

(3S)-4,4-Dimethyl-1-[(2-phenoxyphenyl)acetyl]pyrrolidinyl (1S)-1-(oxo{[(1R)-1-phenylethyl]amino}acetyl)pentylcarbamate

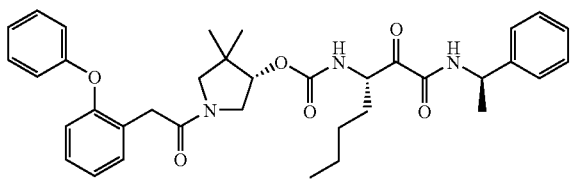

(3S)-4,4-Dimethyl-1-[(2-phenoxyphenyl)acetyl]pyrrolidinyl (1S)-1-(oxo{[(1R)-1-phenylethyl]amino}acetyl)pentylcarbamate (25 mg, 32%) was obtained as a colorless gum that contained ethyl acetate and acetic acid (0.2 eq. of each, based on integration of signals in the $^1$H NMR spectrum) in two steps from (3S)-4,4-dimethylpyrrolidinyl (1S)-1-(1-hydroxy-2-oxo-2-{[(1R)-1-phenylethyl]amino}ethyl)pentylcarbamate (1.0 mL, 120 mM in dichloromethane, 0.12 mmol) and (2-phenoxyphenyl)acetic acid (0.030 g, 0.13 mmol) following the procedure outlined in example 21. $^1$H NMR (300 MHz, DMSO-d$_6$, Temp=100° C.) δ 8.76-8.66 (m, H); 7.37-7.05 (m, 12H); 6.92 (d, J=8 Hz, 2H); 6.84 (d, J=6 Hz, 1H); 5.02-4.92 (m, 1H); 4.81-4.71 (m, 1H); 4.70-4.59 (m, 1H); 3.88-3.77 (m) and 3.70-3.48 (m) total 3H, 3.39-3.08 (m, 3H); 1.71-1.59 (m, 1H); 1.56-1.44 (m, 1H); 1.44 (d, J=7 Hz, 3H); 1.33-1.17 (m, 4H); 0.96 (s, 3H); 0.92 (s, 3H); 0.83-0.78 (m, 3H). ES-LCMS m/z 614 (M+H) HRMS C$_{36}$H$_{43}$N$_3$O$_6$ m/z 614.3230 (M+H)$_{Cal.}$ 614.3231 (M+H)$_{Obs.}$.

Example 32

(3S)-1-(1H-Indol-2-ylcarbonyl)-4,4-dimethylpyrrolidinyl (1S)-1-(oxo {[(1R)-1-phenylethyl]amino}acetyl)pentylcarbamate

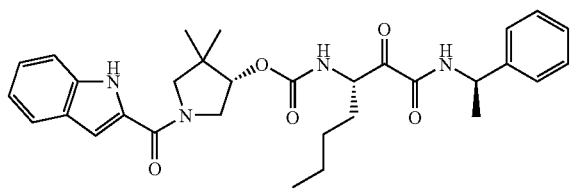

(3S)-1-(1H-Indol-2-ylcarbonyl)-4,4-dimethylpyrrolidinyl (1S)-1-(oxo{[(1R)-1-phenylethyl]amino}acetyl)pentylcarbamate (10 mg, 14%) was obtained as a yellow glass that contained ethyl acetate and acetic acid (0.07 eq. and 0.34 eq. respectively, based on integration of signals in the $^1$H NMR spectrum) in two steps from (3S)-4,4-dimethylpyrrolidinyl (1S)-1-(1-hydroxy-2-oxo-2-{[(1R)-1-phenylethyl]amino}ethyl)pentylcarbamate (1.0 mL, 120 mM in dichloromethane, 0.12 mmol) and 1H-indole-2-carboxylic acid (21 mg, 0.13 mmol) following the procedure outlined in example 21. $^1$H NMR (300 MHz, DMSO-d$_6$, Temp=100° C.) δ 11.21 (br s, 1H), 8.72-8.66 (m, 1H), 7.62 (d J=8 Hz, 1H), 7.46 (d J=9 Hz, 1H), 7.34-7.16 (m, 7H), 7.06-7.01 (m, 1H), 6.92 (s, 1H), 5.00-4.90 (m, 1H), 4.83-4.76 (m, 2H), 4.18-4.02 (m, 1H), 3.70-3.50 (m, 3H), 1.72-1.59 (m, 1H), 1.57-1.43 (m, 1H), 1.40 (d, J=7 Hz, 3H), 1.33-1.17 (m, 4H), 1.09 (s, 3H), 1.07 (s, 3H), 0.81-0.77 (m, 3H). ES-LCMS m/z 547 (M+H) HRMS C$_{31}$H$_{38}$N$_4$O$_5$ m/z 547.2920 (M+H)$_{Cal.}$ 547.2922 (M+H)$_{Obs.}$.

Example 33

(3S)-4,4-Dimethyl-1-(3-pyridinylacetyl)pyrrolidinyl 1-(oxo{[(1R)-1-phenylethyl]amino}acetyl)pentylcarbamate

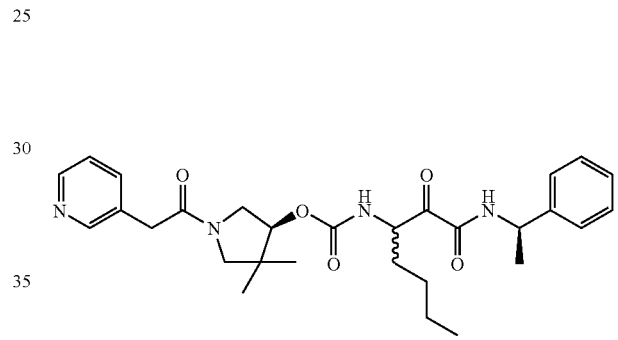

(3S)-4,4-Dimethyl-1-(3-pyridinylacetyl)pyrrolidinyl 1-(oxo{[(1R)-1-phenylethyl]amino}acetyl)pentylcarbamate (31 mg, 47%) was obtained as a colorless gum that contained ethyl acetate (0.35 eq. based on integration of signals in the $^1$H NMR spectrum) in two steps from (3S)-4,4-dimethylpyrrolidinyl (1S)-1-(1-hydroxy-2-oxo-2-{[(1R)-1-phenylethyl]amino}ethyl)pentylcarbamate (1.0 mL, 120 mM in dichloromethane, 0.12 mmol) and 3-pyridinylacetic acid hydrochloride (23 mg, 0.13 mmol) following the procedure outlined in example 21, except that 3-(morpholino)propylpolystyrenesulfonamide (50 mg, 2.03 mmol/g, 0.10 mmol) was added to the acid prior to the addition of the 1-hydroxybenzotriazole solution. A solution of 30% acetone in dichloromethane was used as eluent in the final chromatographic purification. $^1$H NMR (300 MHz, DMSO-d$_6$, Temp=100° C.) δ 8.76-8.68 (m, H); 8.42 (br s, 2H); 7.61 (m, 1H); 7.37-7.15 (m, 7H); 5.02-4.91 (m, 1H); 4.86-4.63 (m, 2H); 4.01-3.91 (m) and 3.78-3.66 (m) total 3H, 3.50-3.10 (m, 3H); 1.79-1.61 (m, 1H); 1.56-1.44 (m, 1H); 1.44 (d, J=7 Hz, 3H); 1.38-1.15 (m, 4H); 1.02 (s) 1.00 (s), and 0.98 (s) total 3H, 0.90-0.78 (m, 3H). ES-LCMS m/z 523 (M+H) HRMS C$_{29}$H$_{38}$N$_4$O$_5$ m/z 523.2920 (M+H)$_{Cal.}$ 523.2924 (M+H)$_{Obs.}$.

Example 34

(3S)-4,4-Dimethyl-1-(1H-1,2,4-triazol-3-ylcarbonyl)pyrrolidinyl (1S)-1-(oxo{[(1R)-1-phenylethyl]amino}acetyl)pentylcarbamate

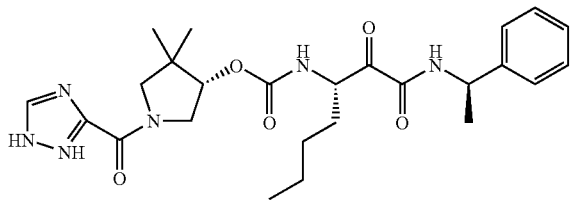

(3S)-4,4-Dimethyl-1-(1H-1,2,4-triazol-3-ylcarbonyl)pyrrolidinyl (1S)-1-(oxo{[(1R)-1-phenylethyl]amino}acetyl)pentylcarbamate (20 mg, 30%) was obtained in two steps from (3S)-4,4-dimethylpyrrolidinyl (1S)-1-(1-hydroxy-2-oxo-2-{[(1R)-1-phenylethyl]amino}ethyl)pentylcarbamate (1.0 mL, 120 mM in dichloromethane, 0.12 mmol) and 1H-1,2,4-triazole-3-carboxylic acid (0.014 g, 0.13 mmol) following the procedure outlined in example 21. $^1$H NMR (300 MHz, DMSO-$d_6$, Temp=100° C.) δ 8.71 (m, 1H), 7.36-7.18 (m, 7H), 4.96 (qnt, J=8 Hz, 1H), 4.83-4.39 (m, 2H), 4.22 (m, 1H), 3.91 (m, 1H), 3.67 (m, 1H), 3.47 (m, 1H), 3.35 (m, 1H), 1.64 (m, 1H), 1.48 (m, 1H), 1.43 (d, J=7 Hz, 3H), 1.20 (m, 4H), 1.03 (m, 6H), 0.79 (m, 3H). ES-LCMS m/z 499 (M+H) HRMS $C_{25}H_{34}N_6O_5$ m/z 521.2488 (M+Na)$_{Cal.}$ 521.2501 (M+Na)$_{Obs.}$.

Example 35

(3S)-4,4-Dimethyl-1-[(3-methyl-5-isoxazolyl)acetyl]pyrrolidinyl (1S)-1-(oxo{[(1R)-1-phenylethyl]amino}acetyl)pentylcarbamate

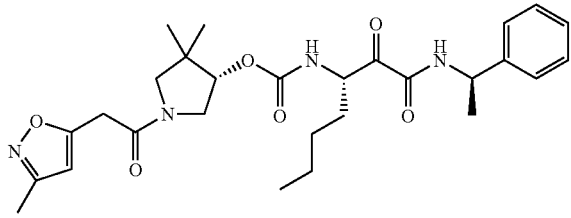

(3S)-4,4-Dimethyl-1-[(3-methyl-5-isoxazolyl)acetyl]pyrrolidinyl (1S)-1-(oxo{[(1R)-1-phenylethyl]amino}acetyl)pentylcarbamate (18 mg, 26%) was obtained in two steps from (3S)-4,4-dimethylpyrrolidinyl (1S)-1-(1-hydroxy-2-oxo-2-{[(1R)-1-phenylethyl]amino}ethyl)pentylcarbamate (1.0 mL, 120 mM in dichloromethane, 0.12 mmol) and (3-methyl-5-isoxazolyl)acetic acid (0.017 g, 0.13 mmol) following the procedure outlined in example 21. $^1$H NMR (300 MHz, DMSO-$d_6$, Temp=100° C.) δ 8.72 (m, 1H), 7.38-7.18 (m, 6H), 3.16 (s, 1H), 4.97 (qnt, J=8 Hz, 1H), 4.85-4.60 (m, 2H), 3.93 (m, 1H), 3.79 (s, 2H), 3.55-3.20 (m, 3H), 2.19 (s, 3H), 1.70 (m, 1H), 1.50 (m, 1H), 1.44 (d, J=7 Hz, 3H), 1.27 (m, 4H), 1.02 (s, 6H), 0.82 (t, J=7 Hz, 3H); ES-LCMS m/z 549 (M+H) HRMS $C_{28}H_{38}N_4O_6$ m/z 549.2689 (M+Na)$_{Cal.}$ 549.2697 (M+H)$_{Obs.}$.

Example 36

(3S)-1-(1H-Indazol-3-ylcarbonyl)-4,4-dimethylpyrrolidinyl (1S)-1-(oxo {[(1R)-1-phenylethyl]amino}acetyl)pentylcarbamate

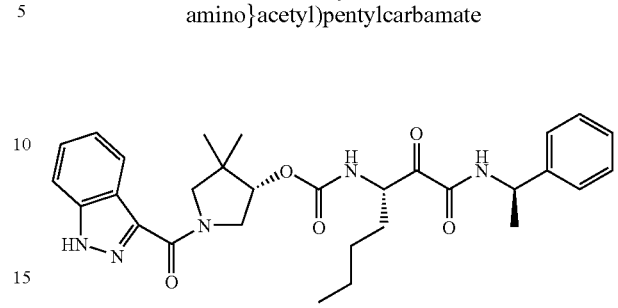

(3S)-1-(1H-Indazol-3-ylcarbonyl)-4,4-dimethylpyrrolidinyl (1S)-1-(oxo{[(1R)-1-phenylethyl]amino}acetyl)pentylcarbamate (25 mg, 35%) was obtained in two steps from (3S)-4,4-dimethylpyrrolidinyl (1S)-1-(1-hydroxy-2-oxo-2-{[(1R)-1-phenylethyl]amino}ethyl)pentylcarbamate (1.0 mL, 120 mM in dichloromethane, 0.12 mmol) and 1H-indazole-3-carboxylic acid (0.019 g, 0.13 mmol) following the procedure outlined in example 21. $^1$H NMR (300 MHz, DMSO-$d_6$, Temp=100° C.) δ 13.27 (s, 1H), 8.68 (m, 1H), 8.15 (d, J=8 Hz, 1H), 7.58 (d, J=8 Hz, 1H), 7.39 (t, J=7 Hz, 1H), 7.33-7.16 (m, 6H), 4.94 (m, 1H), 4.77 (m, 2H), 4.32 (m, 1H), 3.96 (m, 1H), 3.76 (m, 1H), 3.50 (m, 2H), 1.65 (m, 1H), 1.48 (m, 1H), 1.41 (d, J=7 Hz, 3H), 1.25 (m, 4H), 1.07 (m, 6H), 0.78 (m, 3H); ES-LCMS m/z 570 (M+Na) HRMS $C_{30}H_{37}N_5O_5$ m/z 548.2873 (M+H)$_{Cal.}$ 548.2867 (M+H)$_{Obs.}$.

Example 37

(3S)-4,4-Dimethyl-1-{[2-(4-methyl-1,2,3-thiadiazol-5-yl)-1,3-thiazol-4-yl]carbonyl}pyrrolidinyl (1S)-1-(oxo{[(1R)-1-phenylethyl]amino}acetyl)pentylcarbamate

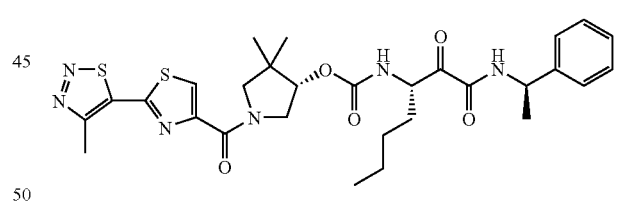

(3S)-4,4-Dimethyl-1-{[2-(4-methyl-1,2,3-thiadiazol-5-yl)-1,3-thiazol-4-yl]carbonyl}pyrrolidinyl (1S)-1-(oxo{[(1R)-1-phenylethyl]amino}acetyl)pentylcarbamate (25 mg, 35%) was obtained in two steps from (3S)-4,4-dimethylpyrrolidinyl (1S)-1-(1-hydroxy-2-oxo-2-{[(1R)-1-phenylethyl]amino}ethyl)pentylcarbamate (1.0 mL, 120 mM in dichloromethane, 0.12 mmol) and 2-(4methyl-1,2,3-thiadiazol-5-yl)-1,3-thiazole-4-carboxylic acid (0.027 g, 0.13 mmol) following the procedure outlined in example 21. $^1$H NMR (300 MHz, DMSO-$d_6$, Temp=100° C.) δ 8.69 (m, 1H), 8.48 (s, 1H), 7.37-7.15 (m, 6H), 4.95 (m, 1H), 4.77 (m, 2H), 4.22 (m, 1H), 4.10-3.60 (m, 3H), 3.47 (m, 2H), 2.95 (s, 3H) 1.65 (m, 1H), 1.50 (m, 1H), 1.42 (d, J=7 Hz, 3H), 1.25 (m, 4H), 1.06 (m, 6H), 0.78 (m, 3H). ES-LCMS m/z 635 (M+Na) HRMS $C_{36}H_{43}N_3O_6$ m/z 635.2086 (M+H)$_{Cal.}$ 635.2106 (M+H)$_{Obs.}$.

Example 38

(3S)-4,4-Dimethyl-1-{[2-(2-pyrazinyl)-1,3-thiazol-4-yl]acetyl-}pyrrolidinyl (1S)-1-(oxo{[(1R)-1-phenylethyl]amino}acetyl)pentylcarbamate

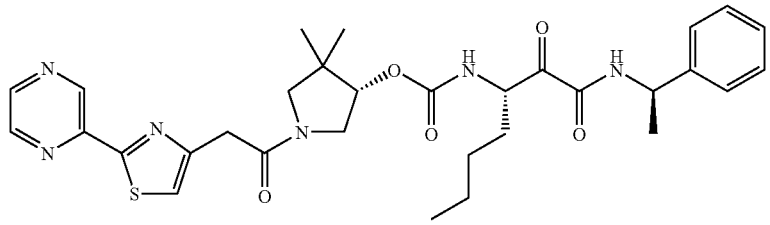

(3S)-4,4-Dimethyl-1-{[2-(2-pyrazinyl)-1,3-thiazol-4-yl]acetyl}pyrrolidinyl (1S)-1-(oxo{[(1R)-1-phenylethyl]amino}acetyl)pentylcarbamate (17 mg, 21%) was obtained in two steps from (3S)-4,4-dimethylpyrrolidinyl (1S)-1-(1-hydroxy-2-oxo-2-{[(1R)-1-phenylethyl]amino}ethyl)pentylcarbamate (1.0 mL, 120 mM in dichloromethane, 0.12 mmol) and [2-(2-pyrazinyl)-1,3-thiazol-4-yl]acetic acid (0.027 g, 0.13 mmol) following the procedure outlined in example 21. $^1$H NMR (300 MHz, DMSO-d$_6$, Temp=100° C.) δ 9.24 (s, 1H), 8.67 (m, 3H), 7.61 (s, 1H), 7.35-7.10 (m, 6H), 4.97 (qnt, J=7 Hz, 1H), 4.83-4.65 (m, 2H), 4.06 (m, 1H), 3.86 (s, 2H), 3.80-3.20 (m, 3H), 1.65 (m, 1H), 1.50 (m, 1H), 1.44 (d, J=7 Hz, 3H), 1.26 (m, 4H), 1.03 (m, 6H), 0.80 (t, J=7 Hz, 3H). ES-LCMS m/z 629 (M+Na) HRMS C$_{31}$H$_{38}$N$_6$O$_5$S$_1$ m/z 607.2703 (M+H)$_{Cal.}$ 607.2723 (M+H)$_{Obs.}$.

Example 39

(3S)-1-[(4-Fluorophenyl)acetyl]-4,4-dimethylpyrrolidinyl (1S)-1-(oxo{[(1R)-1-phenylethyl]amino}acetyl)pentylcarbamate

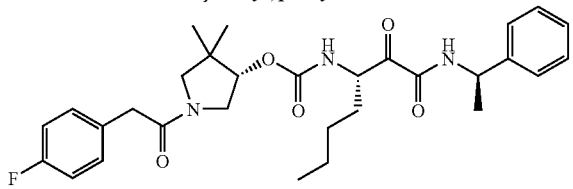

(3S)-1-[(4-Fluorophenyl)acetyl]-4,4-dimethylpyrrolidinyl (1S)-1-(oxo{[(1R)-1-phenylethyl]amino}acetyl)pentylcarbamate (16 mg, 22%) was obtained in two steps from (3S)-4,4-dimethylpyrrolidinyl (1S)-1-(1-hydroxy-2-oxo-2-{[(1R)-1-phenylethyl]amino}ethyl)pentylcarbamate (1.0 mL, 120 mM in dichloromethane, 0.12 mmol) and (4-fluorophenyl)acetic acid (0.018 g, 0.13 mmol) following the procedure outlined in example 21. $^1$H NMR (300 MHz, DMSO-d$_6$, Temp=100° C.) δ 8.70 (m, 1H); 7.35-7.18 (m, 8H); 7.07 (t, J=9 Hz, 2H); 4.97 (qnt, J=8 Hz, 1H); 4.82-4.60 (m, 2H); 3.87 (m) and 3.66 (m) total 1H, 3.58 (s, 2H); 3.45-3.10 (m, 3H); 1.64 (m, 1H); 1.50 (m, 1H); 1.44 (d, J=7 Hz, 3H); 1.26 (m, 4H); 0.99 (d, J=6 Hz, 6H); 0.81 (t, J=7 Hz, 3H). Cl-LCMS m/z 540 (M+H) HRMS C$_{30}$H$_{38}$N$_3$O$_5$ m/z 540.2874 (M+H)$_{Cal.}$ 540.2874 (M+H)$_{Obs.}$.

Example 40

[1,1'-biphenyl]-4-ylmethyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate

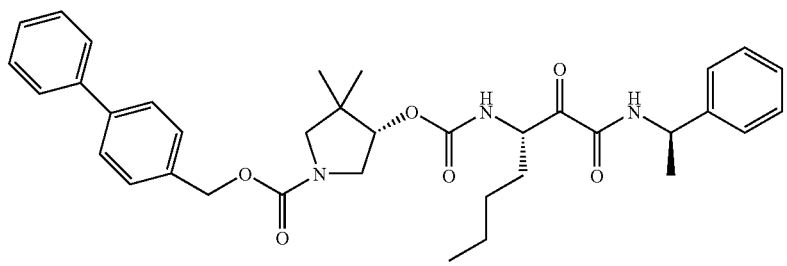

To a solution of 0.14 mL (0.27 mmol) of 1.93M phosgene in toluene in 1 mL of dichloromethane was added 25 mg (0.14 mmol) of 4-biphenylmethanol, and the reaction mixture was stirred at room temperature for 18 h. For 10 min a stream of nitrogen was passed through the reaction mixture, which was then added to a solution of 50 mg (0.12 mmol) of (3S)-4,4-dimethylpyrrolidinyl (1S)-1-(1-hydroxy-2-oxo-2-{[(1R)-1-phenylethyl]amino}ethyl)pentylcarbamate and 0.038 mL (0.27 mmol) of triethylamine in 2 mL of dichloromethane. The resulting reaction mixture was stirred for 3 h before 25 mg of tris-(2-aminoethyl)amine polystyrene was added. The resulting mixture was then shaken for 2 h. Dowex 50W×4 (H$^+$) resin (1.0 g) was added and the mixture was shaken for 1 h. The solids were filtered off and the filtrate was concentrated under reduced pressure. The residue was dissolved in 2 mL of dichloromethane before 19 mg (0.23 mmol) of sodium bicarbonate and 97 mg (0.23 mmol) of Dess-Martin periodinane were added. The reaction mixture was stirred for 20 min and then subjected directly to column chromatography on silica gel. Elution with 0.5:9.5 acetone:dichloromethane afforded 60 mg (79%) of [1,1'-biphenyl]-4-ylmethyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate. $^1$H NMR (300 MHz, DMSO-d$_6$, Temp=80° C.) δ 8.87 (d, J=7 Hz, 1H), 7.68 (d, J=8 Hz, 3H), 7.47 (d, J=8 Hz, 3H), 7.41-7.20 (m, 9H), 5.15 (s, 2H), 4.99 (qnt, J=7 Hz, 1H), 4.80 (m, 1H), 4.70 (s, 1H), 3.76 (m, 1H), 3.24 (m, 3), 1.67 (m, 1H), 1.51 (m, 1H), 1.46 (d, J=7 Hz, 3H), 1.27 (m, 4H), 1.05 (s, 6H), 0.83 (t, J=7 Hz, 3H). ES-LCMS m/z 614 (M+H) HRMS $C_{36}H_{43}N_3O_6$ m/z 668.3312 (M+Na+MeOH)$_{Cal.}$ 668.3312 (M+Na+MeOH)$_{Obs.}$.

Example 41

Tetrahydro-2-furanylmethyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate

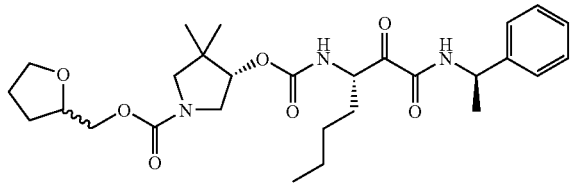

Tetrahydro-2-furanylmethyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate (16 mg, 22%) was obtained in two steps from 50 mg (0.12 mmol) of (3S)-4,4-dimethylpyrrolidinyl (1S)-1-(1-hydroxy-2-oxo-2-{[(1R)-1-phenylethyl]amino}ethyl)pentylcarbamate and 14 mg (0.14 mmol) of tetrahydrofurfuryl alcohol following the procedure outlined in example 40. $^1$H NMR (300 MHz, DMSO-d$_6$, Temp=100° C.) δ 8.76 (m, 1H), 7.42-7.20 (m, 6H), 5.01 (qnt, J=7 Hz, 1H), 4.81 (m, 1H), 4.69 (d, J=3 Hz, 1H), 4.01 (m, 3H), 3.83-3.64 (m, 3H), 3.32-3.15 (m, 3H), 2.00-1.80 (m, 3H), 1.75-1.58 (m, 3H), 1.48 (d, J=7 Hz, 3H), 1.30 (m, 4H), 1.04 (s, 6H), 0.85 (t, J=7 Hz, 3H). ES-LCMS m/z 532 (M+H) HRMS $C_{28}H_{41}N_3O_7$ m/z 532.3023 (M+H)$_{Cal.}$ 532.3023 (M+H)$_{Obs.}$.

Example 42

3-Thienylmethyl (4S)-3,3-dimethyl-4-[({[(1S)-1-(oxo {[(1R)-1-phenylethyl]amino}acetyl)pentyl]amino}carbonyl)oxy]-1-pyrrolidinecarboxylate

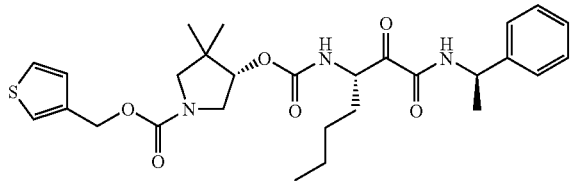

3-Thienylmethyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate (35 mg, 52%) was obtained in two steps from 50 mg (0.12 mmol) of (3S)-4,4-dimethylpyrrolidinyl (1S)-1-(1-hydroxy-2-oxo-2-{[(1R)-1-phenylethyl]amino}ethyl)pentylcarbamate and 16 mg (0.14 mmol) of 3-thienylmethanol following the procedure outlined in example 40. $^1$H NMR (300 MHz, DMSO-d$_6$) δ 9.15 (d, J=9 Hz, 1H), 7.65 (m, 1H), 7.50 (m, 1H), 7.34-7.19 (m, 5H), 7.10 (m, 1H), 5.03 (s, 2H), 4.94 (qnt, J=7 Hz, 1H), 4.73 (m, 1H), 3.71 (m, 1H), 3.17 (m, 3H), 1.60 (m, 1H), 1.45-1.13 (m, 8H), 0.97 (s, 6H), 0.77 (m, 3H). ES-LCMS m/z 544 (M+H) HRMS $C_{28}H_{37}N_3O_6S_1$ m/z 566.2301 (M+Na)$_{Cal.}$ 566.2300 (M+Na)$_{Obs.}$.

Example 43

(3S)-Tetrahydro-3-furanyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate

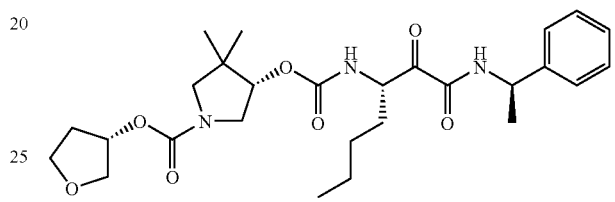

(3S)-Tetrahydro-3-furanyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate (35 mg, 55%) was obtained in two steps from 50 mg (0.12 mmol) of (3S)-4,4-dimethylpyrrolidinyl (1S)-1-(1-hydroxy-2-oxo-2-{[(1R)-1-phenylethyl]amino}ethyl)pentylcarbamate and 12 mg (0.14 mmol) of (3S)-tetrahydro-3-furanol following the procedure outlined in example 40. $^1$H NMR (300 MHz, DMSO-d$_6$, Temp=100° C.) δ 9.15 (d, J=8 Hz, 1H), 7.66 (m, 1H), 7.35-7.17 (m, 5H), 5.09 (m, 1H), 4.96 (qnt, J=7 Hz, 1H), 4.74 (m, 1H), 4.64 (m, 1H), 3.80-3.61 (m, 5H), 3.25-3.02 (m, 3H), 2.07 (m, 1H), 1.87 (m, 1H), 1.60 (m, 1H), 1.40 (d, J=7 Hz, 3H), 1.24 (m, 5H), 0.96 (s, 6H), 0.78 (m, 3H). ES-LCMS m/z 518 (M+H) HRMS $C_{27}H_{39}N_3O_7$ m/z 518.2866 (M+H)$_{Cal.}$ 518.2863 (M+H)$_{Obs.}$.

Example 44

Benzyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate

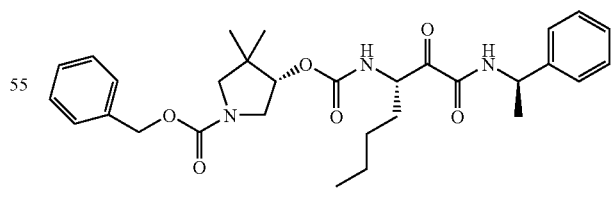

Benzyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate (27 mg, 41%) was obtained in two steps from 50 mg (0.12 mmol) of (3S)-4,4 dimethylpyrrolidinyl (1S)-1-(1-hydroxy-2-oxo-2-{[(1R)-1-phenylethyl]amino}ethyl)pentylcarbamate and 25 mg (0.15 mmol) of benzyloxychloroformate following the procedure outlined in example 40. ¹H NMR (300 MHz, DMSO-d$_6$) δ 9.12 (d, J=8 Hz, 1H), 7.62 (m, 1H), 7.38-7.14 (m, 10H), 5.00 (s, 2H), 4.90 (m, 1H), 4.69 (m, 1H), 4.62 (d, J=3 Hz, 1H), 3.68 (m, 1H), 3.25-3.05 (m, 3H), 1.55 (m, 1H), 1.36 (m, 4H), 1.20 (m, 4H), 0.94 (m, 6H), 0.73 (m, 3H). ES-LCMS m/z 538 (M+H) HRMS C$_{30}$H$_{39}$N$_3$O$_6$ m/z 538.2917 (M+H)$_{Cal.}$ 538.2935 (M+H)$_{Obs.}$.

Example 45

2-Phenylethyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate

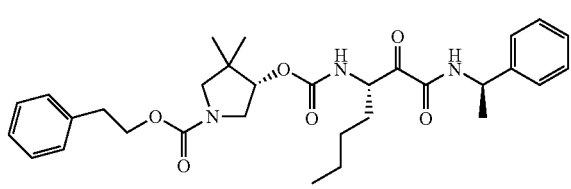

2-Phenylethyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate (12 mg, 17%) was obtained in two steps from 50 mg (0.12 mmol) of (3S)-4,4-dimethylpyrrolidinyl (1S)-1-(1-hydroxy-2-oxo-2-{[(1R)-1-phenylethyl]amino}ethyl)pentylcarbamate and 18 mg (0.14 mmol) of 2-phenylethanol following the procedure outlined in example 40. ¹H NMR (300 MHz, DMSO-d$_6$, Temp=100° C.) δ 8.74 (m, 1H), 7.38-7.20 (m, 11H), 5.02 (qnt, J=8 Hz, 1H), 4.80 (m, 1H), 4.67 (m, 1H), 4.23 (t, J=7 Hz, 2H), 3.67 (m, 1H), 3.25-2.90 (m, overlapping water peak 5H), 1.67 (m, 1H), 1.53 (m, 1H), 1.48 (d, J=7 Hz, 3H), 1.29 (m, 4H), 1.01 (s, 6H), 0.84 (t, J=7 Hz, 3H). Cl-LCMS m/z 552 (M+H); HRMS C$_{31}$H$_{41}$N$_3$O$_6$ m/z 574.2893 (M+Na)$_{Cal.}$ 574.2897 (M+H)$_{Obs.}$.

Example 46

(1-Phenyl-1H-1,2,3-triazol-4-yl)methyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate (1-Phenyl-1H-1,2,3-triazol-4-yl)methyl-(4S)-3,3-dimethyl-4-[({[(1S)-1-(oxo{[(1R)-1-phenylethyl]amino}acetyl)pentyl]amino}carbonyl)oxy]-1-pyrrolidinecarboxylate (20 mg, 27%) was obtained in two steps from 50 mg (0.12 mmol) of (3S)-4,4-dimethylpyrrolidinyl (1S)-1-(1-hydroxy-2-oxo-2-{[(1R)-1-phenylethyl]amino}ethyl)pentylcarbamate and 24 mg (0.14 mmol) of (1-phenyl-1H-1,2,3-triazol-4-yl) methanol following the procedure outlined in example 40 except that Dowex 50W×4(H⁺) resin was not utilized. ¹H NMR (400 MHz, DMSO-d$_6$) δ 9.11 (d, J=7 Hz, 1H), 8.79 (s, 1H), 7.85 (m, 2H), 7.57 (m, 3H), 7.44 (m, 1H), 7.28-7.15 (m, 5H), 5.14 (s, 2H), 4.90 (m, 1H), 4.68 (m, 1H), 4.62 (s, 1H), 3.68 (m, 1H), 3.40-3.06 (m, 3H), 1.53 (m, 1H), 1.35 (m, 4H), 1.18 (m, 4H), 0.94 (m, 6H), 0.73 (m, 3H). ES-LCMS m/z 605 (M+H) HRMS C$_{32}$H$_{40}$N$_6$O$_6$ m/z 605.3087 (M+H)$_{Cal.}$ 605.3083 (M+H)$_{Obs.}$.

Example 47

2-(2-Oxo-1-pyrrolidinyl)ethyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate

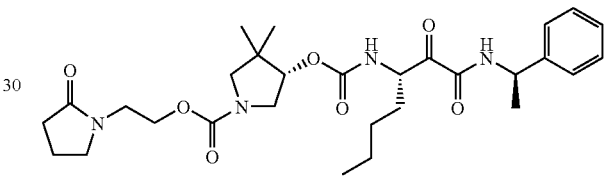

2-(2-Oxo-1-pyrrolidinyl)ethyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate (30 mg, 44%) was obtained in two steps from 50 mg (0.12 mmol) of (3S)-4,4-dimethylpyrrolidinyl (1S)-1-(1-hydroxy-2-oxo-2-{[(1R)-1-phenylethyl]amino}ethyl)pentylcarbamate and 18 mg (0.14 mmol) of 1-(2-hydroxyethyl)-2-pyrrolidinone following the procedure outlined in example 40 except that Dowex 50W×4(H⁺) resin was not utilized. ¹H NMR (400 MHz, DMSO-d$_6$) δ 9.12 (d, J=8 Hz, 1H), 7.60 (m, 1H), 7.30-7.14 (m, 5H), 4.90 (qnt, J=7 Hz, 1H), 4.70 (m, 1H), 4.60 (d, J=4 Hz, 1H), 4.09-3.95 (m, 2H), 3.62 (m, 1H), 3.25 (m, overlapping water peak 4H), 3.20-2.95 (m, 3H), 2.13 (m, 2H), 1.85 (m, 2H), 1.55 (m, 1H), 1.36 (d, J=7 Hz, 3H), 1.34 (m, 1H), 1.19 (m, 4H), 0.93 (s, 6H), 0.74 (m, 3H). ES-LCMS m/z 559 (M+H) HRMS C$_{29}$H$_{42}$N$_4$O$_7$ m/z 559.3132 (M+H)$_{Cal.}$ 559.3151 (M+H)$_{Obs.}$.

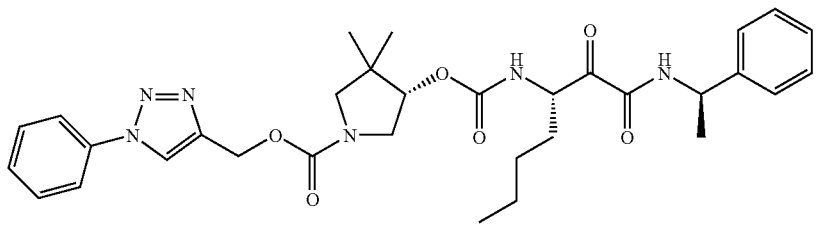

Example 48

Tetrahydro-2H-pyran-2-ylmethyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate

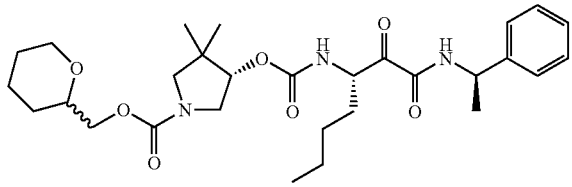

Tetrahydro-2H-pyran-2-ylmethyl (4S)-3,3-dimethyl-4-[({[(1S)-1-(oxo {[(1R)-1-phenylethyl]amino}acetyl)pentyl]amino}carbonyl)oxy]-1-pyrrolidinecarboxylate (12 mg, 24%) was obtained in two steps from 50 mg (0.12 mmol) of (3S)-4,4-dimethylpyrrolidinyl (1S)-1-(1-hydroxy-2-oxo-2-{[(1R)-1-phenylethyl]amino}ethyl)pentylcarbamate and 17 mg (0.14 mmol) of tetrahydro-2H-pyran-2-ylmethanol following the procedure outlined in example 40. $^1$H NMR (300 MHz, DMSO-$d_6$) δ 9.20 (d, J=8 Hz, 1H), 7.70 (m, 1H), 7.37-7.20 (m, 5H), 4.99 (m, 1H), 4.78 (m, 1H), 4.68 (m, 1H), 3.97-3.81 (m, 2H), 3.71 (m, 1H), 3.25 under water peak (m, 3H), 3.20 (m, 3H), 1.79 (m, 1H), 1.50 (m, 10H), 1.26 (m, 4H), 1.02 (m, 6H), 0.83 (m, 3H). ES-LCMS m/z 546 (M+H) HRMS $C_{29}H_{43}N_3O_7$ m/z 546.3179 (M+H)$_{Cal.}$ 546.3169 (M+H)$_{Obs.}$.

Example 49

Tetrahydro-3-furanylmethyl (4S)-3,3-dimethyl-4-[({[(1S)-1-(oxo {[(1R)-1-phenylethyl]amino}acetyl)pentyl]amino}carbonyl)oxy]-1-pyrrolidinecarboxylate

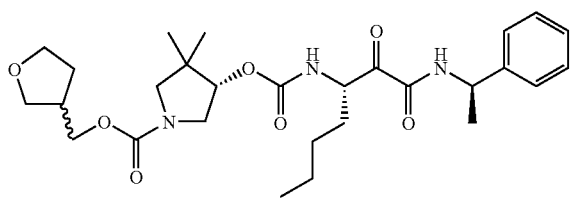

Tetrahydro-3-furanylmethyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate (8 mg, 12%) was obtained in two steps from 50 mg (0.12 mmol) of (3S)-4,4-dimethylpyrrolidinyl (1S)-1-(1-hydroxy-2-oxo-2-{[(1R)-1-phenylethyl]amino}ethyl)pentylcarbamate and 15 mg (0.14 mmol) of tetrahydro-3-furanylmethanol following the procedure outlined in example 40. $^1$H NMR (300 MHz, DMSO-$d_6$) δ 9.17 (d, J=9 Hz, 1H), 7.66 (m, 1H), 7.35-7.20 (m, 5H), 4.96 (qnt, J=8 Hz, 1H), 4.75 (m, 1H), 4.66 (m, 1H), 3.93 (m, 2H), 3.67 (m, 5H), 3.25 (m, overlapping water peak 3H), 1.92 (m, 2H), 1.57 (m, 3H), 1.41 (d, J=7 Hz, 3H), 1.23 (m, 4H), 0.99 (s, 6H), 0.82 (m, 3H). Cl-LCMS m/z 532 (M+H).

Example 50

[3-Methyl-5-(5-methyl-isoxazol-3-yl)-4-isoxazolyl]methyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate

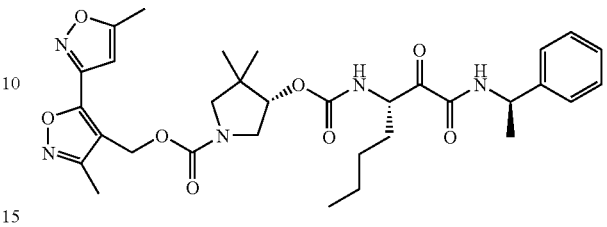

To a solution of 26 mg (0.14 mmol) of [3-methyl-5-(5-methyl-3-isoxazolyl)-4-isoxazolyl]methanol in 1 mL of tetrahydrofuran was added 0.28 mL of phosgene (1.93M in toluene, 0.54 mmol), and the reaction mixture was stirred at room temperature for 18 h. A stream of nitrogen was passed through the solution for 15 minutes before a solution of 50.0 mg (0.12 mmol) of (3S)-4,4-dimethylpyrrolidinyl (1S)-1-(1-hydroxy-2-oxo-2-{[(1R)-1-phenylethyl]amino}ethyl)pentylcarbamate and 0.076 mL (0.54 mmol) of triethylamine in 2 mL of tetrahydrofuran was added. The reaction mixture was shaken for 18 h and then filtered. Dowex 50W×4(H$^+$) resin was added to the filtrate, and the mixture was shaken for 1 h. Solids were filtered off, and the filtrate was concentrated under a stream of nitrogen. The residue was dissolved in 2 mL of dichloromethane, and 50.0 mg (0.59 mmol) of sodium bicarbonate and 100 mg (0.23 mmol) of Dess-Martin periodinane were added. The reaction mixture was stirred for 30 minutes before being washed with 2 mL of saturated aqueous sodium thiosulfate. The organic phase was concentrated, and the residue was purified by silica gel column, eluting with 1.5:8.5 acetone:dichloromethane to afford 15 mg (18%) of [3-methyl-5-(5-methyl-isoxazol-3-yl)-4-isoxazolyl]methyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate. $^1$H NMR (300 MHz, DMSO-$d_6$, Temp=80° C.) δ 9.34 (d, J=8 Hz, 1H), 7.81 (t, J=7 Hz, 1H), 7.52-7.36 (m, 5H), 7.00 (d, J=4 Hz, 1H), 5.35 (s, 2H), 5.13 (m, 1H), 4.91 (m, 1H), 4.82 (m, 1H), 3.68 (m, 1H), 3.50-3.15 (m, 3H), 2.68 (m, 6H), 1.77 (m, 1H), 1.65-1.30 (m, 8H), 1.40 (m, 6H), 0.96 (m, 3H). ES-LCMS m/z 624 (M+H) HRMS $C_{32}H_{41}N_5O_8$ m/z 646.2853 (M+Na)$_{Cal.}$ 646.2853 (M+H)$_{Obs.}$.

Example 51

2-(4-Methyl-1,3-thiazol-5-yl)ethyl (4S)-3,3-dimethyl-4-[({[(1S)-1-(oxo {[(1R)-1-phenylethyl]amino}acetyl)pentyl]amino}carbonyl)oxy]-1-pyrrolidinecarboxylate

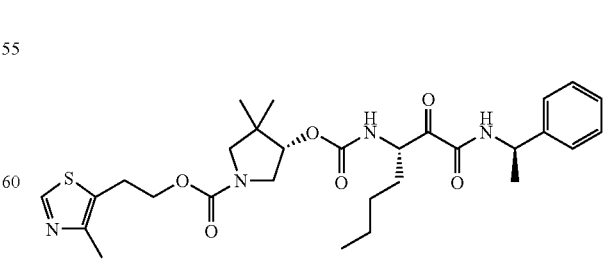

2-(4-Methyl-1,3-thiazol-5-yl)ethyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate (8 mg, 11%)

was obtained in two steps from 50.0 mg (0.12 mmol) of (3S)-4,4-dimethylpyrrolidinyl (1S)-1-(1-hydroxy-2-oxo-2-{[(1R)-1-phenylethyl]amino}ethyl)pentylcarbamate and 26 mg (0.14 mmol) of 2-(4-methyl-1,3-thiazol-5-yl)ethanol following the procedure outlined in example 50. $^1$H NMR (300 MHz, DMSO-$d_6$) δ 9.35 (d, J=8 Hz, 1H), 9.01 (d, J=7 Hz, 1H), 7.83 (t, J=7 Hz, 1H), 7.52-7.36 (m, 5H), 5.14 (qnt, J=8 Hz, 1H), 4.93 (m, 1H), 4.83 (m, 1H), 4.30 (m, 2H), 3.85 (m, 1H), 3.50-3.20 (m, 5H), 2.67 (s, 3H), 1.77 (m, 1H), 1.65-1.30 (m, 8H), 1.16 (m, 6H), 0.97 (m, 3H). ES-LCMS m/z 573 (M+H) HRMS $C_{29}H_{40}N_4O_6S_1$ m/z 573.2747 (M+H)$_{Cal.}$ 573.2731 (M+Na)$_{Obs.}$.

Example 52

(5-methyl-3-isoxazolyl)methyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate

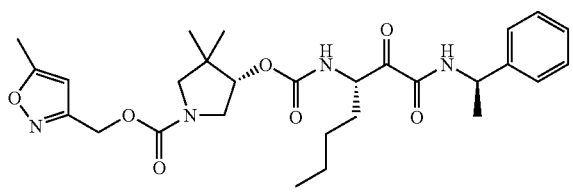

(5-Methyl-3-isoxazolyl)methyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate (42 mg, 57%) was obtained in two steps from 50.0 mg (0.12 mmol) of (3S)-4,4-dimethylpyrrolidinyl (1S)-1-(1-hydroxy-2-oxo-2-{[(1R)-1-phenylethyl]amino}ethyl)pentylcarbamate and 15 mg (0.14 mmol) of (5-methyl-3-isoxazolyl)methanol following the procedure outlined in example 50. $^1$H NMR (300 MHz, DMSO-$d_6$) δ 9.35 (d, J=8 Hz, 1H), 7.84 (dd, J=7 Hz, J=5 Hz, 1H), 7.52-7.35 (m, 5H), 6.43 (s, 1H), 5.23 (s, 1H), 5.13 (m, 1H), 4.92 (m, 1H), 4.85 (d, J=4 Hz, 1H), 3.91 (m, 1H), 3.50-3.25 (m, 3H), 2.67 (s, 3H), 1.78 (m, 1H), 1.65-1.30 (m, 8H), 1.17 (s, 6H), 0.96 (t, J=7 Hz, 3H). ES-LCMS m/z 543 (M+H) HRMS $C_{28}H_{38}N_4O_7$ m/z 565.2638 (M+H)$_{Cal.}$ 565.2638 (M+Na)$_{Obs.}$.

Example 53

[3-(2,6-Dichlorophenyl)-5-methyl-4-isoxazolyl]methyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate

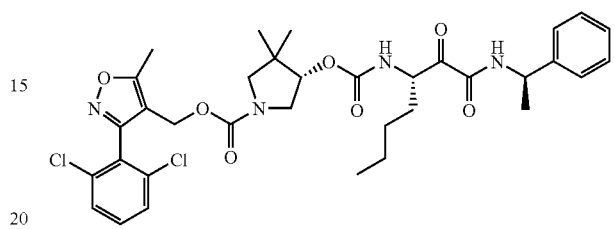

[3-(2,6-Dichlorophenyl)-5-methyl-4-isoxazolyl]methyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate (59 mg, 70%) was obtained in two steps from 50.0 mg (0.12 mmol) of (3S)-4,4-dimethylpyrrolidinyl (1S)-1-(1-hydroxy-2-oxo-2-{[(1R)-1-phenylethyl]amino}ethyl)pentylcarbamate and 35 mg (0.14 mmol) of [3-(2,6-dichlorophenyl)-5-methyl-4-isoxazolyl]methanol following the procedure outlined in example 50. $^1$H NMR (300 MHz, DMSO-$d_6$) δ 9.34 (d, J=8 Hz, 1H), 7.86-7.73 (m, 4H), 7.51-7.36 (m, 5H), 5.12 (qnt, J=7 Hz, 1H), 4.94 (m, 3H), 4.74 (t, J=5 Hz, 1H), 3.77 (m, 1H), 3.30-3.00 (m, 3H), 2.72 (s, 3H), 1.78 (m, 1H), 1.62-1.30 (m, 8H), 1.10 (m, 6H), 0.96 (m, 3H). ES-LCMS m/z 709 (M+Na) HRMS $C_{34}H_{40}N_4O_7Cl_2$ m/z 701.2172 (M+H)$_{Cal.}$ 701.2173 (M+Na)$_{Obs.}$.

Example 54

(2-Methyl[1,1'-biphenyl]-3-yl)methyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate

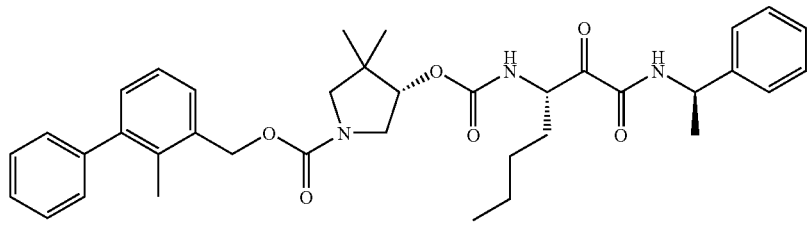

(2-Methyl[1,1'-biphenyl]-3-yl)methyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate (42 mg, 55%) was obtained in two steps from 50.0 mg (0.12 mmol) of (3S)-4,4-dimethylpyrrolidinyl (1S)-1-(1-hydroxy-2-oxo-2-{

[(1R)-1-phenylethyl]amino}ethyl)pentylcarbamate and 27 mg (0.14 mmol) of (2-methyl[1,1'-biphenyl]-3-yl)methanol following the procedure outlined in example 50. $^1$H NMR (300 MHz, DMSO-d$_6$) δ 9.16 (d, J=8 Hz, 1H), 7.65 (t, J=7 Hz, 1H), 7.47-7.12 (m, 13H), 5.12 (s, 2H), 4.94 (m, 1H), 4.73 (m, 1H), 4.66 (m, 1H), 3.74 (m, 1H), 3.50-3.05 (m, 3H), 2.15 (s, 1H), 1.57 (m, 1H), 1.43-1.10 (m, 8H), 0.99 (s, 6H), 0.77 (t, J=7 Hz, 3H). ES-LCMS m/z 650 (M+Na) HRMS C$_{37}$H$_{45}$N$_3$O$_6$ m/z 650.3206 (M+Na)$_{Cal.}$ 650.3207 (M+Na)$_{Obs.}$.

Example 55

[5-(2-Thienyl)-1,2,4-oxadiazol-3-yl]methyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate

Example 56

(3R)-Tetrahydro-3-furanyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate

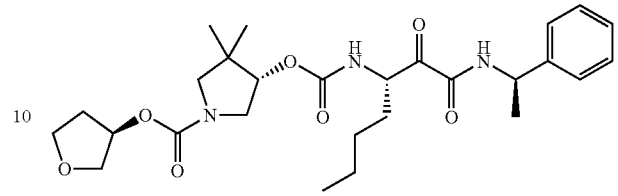

(3R)-Tetrahydro-3-furanyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate (28 mg, 44%) was obtained in two steps from 50.0 mg (0.12 mmol) of (3S)-4,4-dimethylpyrrolidinyl (1S)-1-(1-hydroxy-2-oxo-2-{

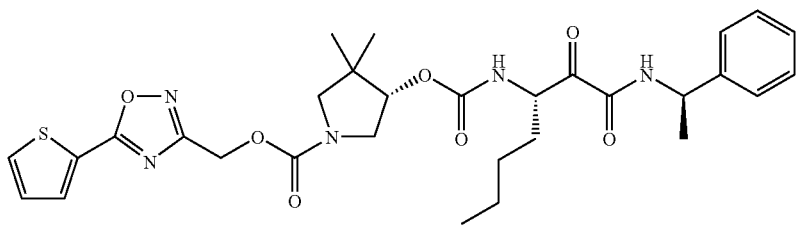

[5-(2-Thienyl)-1,2,4-oxadiazol-3-yl]methyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate (40 mg, 51%) was obtained in two steps from 50.0 mg (0.12 mmol) of (3S)-4,4-dimethylpyrrolidinyl (1S)-1-(1-hydroxy-2-oxo-2-{[(1R)-1-phenylethyl]amino}ethyl)pentylcarbamate and 25 mg (0.14 mmol) of [5-(2-thienyl)-1,2,4-oxadiazol-3-yl]methanol following the procedure outlined in example 50 except that the [5-(2-thienyl)-1,2,4-oxadiazol-3-yl]methanol solution was cooled to 0° C. before phosgene was added, and then let warm to room temperature. $^1$H NMR (300 MHz, DMSO-d$_6$) δ 9.17 (d, J=8 Hz, 1H), 8.10 (d, J=5 Hz, 1H), 8.04 (s, 1H), 7.68 (t, J=6 Hz, 1H), 7.40-7.15 (m, 6H), 5.25 (s, 2H), 4.96 (m, 1H), 4.80-4.67 (m, 2H), 3.75 (m, 1H), 3.50-3.10 (m, 3H), 1.60 (m, 1H), 1.41 (d, J=6 Hz, 3H), 1.24 (m, 5H), 1.01 (s, 6H), 0.78 (m, 3H). ES-LCMS m/z 612 (M+H) HRMS C$_{30}$H$_{37}$N$_5$O$_7$S$_1$ m/z 634.2311 (M+Na)$_{Cal.}$ 634.2317 (M+Na)$_{Obs.}$.

[(1R)-1-phenylethyl]amino}ethyl)pentylcarbamate and 12 mg (0.14 mmol) of (3R)-tetrahydro-3-furanol following the procedure outlined in example 50 except that the (3R)-tetrahydro-3-furanol solution was cooled to 0° C. before phosgene was added, and then let warm to room temperature. $^1$H NMR (300 MHz, DMSO-d$_6$) δ 9.17 (d, J=9 Hz, 1H), 7.66 (m, 1H), 7.37-7.19 (m, 5H), 5.11 (m, 1H), 4.96 (qnt, J=8 Hz, 1H), 4.75 (m, 1H), 4.66 (d, J=4 Hz, 1H), 3.81-3.60 (m, 5H), 3.25-3.02 (m, 3H), 2.15 (m, 1H), 1.88 (m, 1H), 1.66 (m, 1H), 1.42 (d, J=7 Hz, 3H), 1.21 (m, 5H), 0.99 (s, 6H), 0.80 (t, J=7 Hz, 3H). ES-LCMS m/z 518 (M+H) HRMS C$_{27}$H$_{39}$N$_3$O$_7$ m/z 540.2686 (M+Na)$_{Cal.}$ 540.2665 (M+Na)$_{Obs.}$.

Example 57

[1,1'-Biphenyl]-4-yl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate

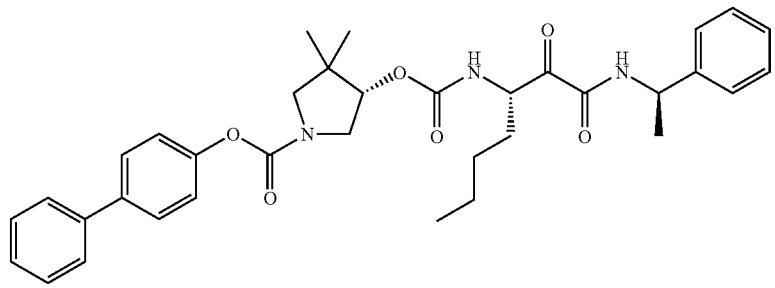

To a solution of 0.28 mL of phosgene (1.93M in toluene, 0.54 mmol) in 1 mL of dichloromethane was added 23 mg (0.14 mmol) of 4-phenylphenol. The solution was cooled in an ice 1 mL (0.14 mol) of N,N-dimethylaniline was added dropwise. The reaction mixture was allowed to warm to room temperature and was stirred for 18 h. A stream of nitrogen was then passed through the reaction mixture for 10 minutes before a solution of 50.0 mg (0.12 mmol) of (3S)-4,4-dimethylpyrrolidinyl (1S)-1-(1-hydroxy-2-oxo-2-{[(1R)-1-phenylethyl]amino}ethyl)pentylcarbamate and 0.038 mL (0.27 mmol) of triethylamine in 2 mL of tetrahydrofuran was added. The reaction mixture was shaken for 1.5 h before 50.0 mg of tris-(2-aminoethyl)amine polystyrene and 1.0 g of Dowex 50W×4(H+) resin were added. The mixture was shaken for 2.5 h. The solids were filtered off and the filtrate was concentrated under a stream of nitrogen. The residue was dissolved in 1 mL of dichloromethane, and 21 mg (0.25 mmol) of sodium bicarbonate and 100 mg (0.25 mmol) of Dess-Martin periodinane were added. The reaction mixture was stirred for 30 minutes before being washed with 2 mL of saturated aqueous sodium thiosulfate. The organic phase was concentrated, and the residue was purified by silica gel chromatography eluting with 1.5:8.5 acetone:dichloromethane to afford 15 mg (18%) of [1,1'-biphenyl]-4-yl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate. $^1$H NMR (300 MHz, DMSO-d$_6$, Temp=80° C.) δ 39.17 (d, J=8 Hz, 1H); 7.75-7.62 (m, 5H); 7.45 (t, J=8 Hz, 2H); 7.34-7.19 (m, 8H); 4.96 (qnt, J=7 Hz, 1H); 4.74 (m, 1H); 3.97 (m) and 3.80 (m) total 1H, 3.55-3.17 (m, 3H); 1.61 (m, 1H); 1.41 (d, J=7 Hz, 3H); 1.27 (m, 5H); 1.06 (m, 6H); 0.80 (m, 3H). ES-LCMS m/z 600 (M+H) HRMS C$_{35}$H$_{41}$N$_3$O$_6$ m/z 622.2893 (M+Na)$_{Cal.}$ 622.2889 (M+Na)$_{Obs.}$.

Example 58

4-Phenoxyphenyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate 4-Phenoxyphenyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate (42 mg, 55%) was obtained in two steps from 50.0 mg (0.12 mmol) of (3S)-4,4-dimethylpyrrolidinyl (1S)-1-(1-hydroxy-2-oxo-2-{[(1R)-1-phenylethyl]amino}ethyl)pentylcarbamate and 25 mg (0.14 mmol) of 4-phenoxyphenol following the procedure outlined in example 57. $^1$H NMR (300 MHz, DMSO-d$_6$) δ 9.17 (d, J=9 Hz, 1H), 7.71 (m, 1H), 7.38 (t, J=8 Hz, 2H), 7.32-7.20 (m, 5H); 7.13 (d, J=9 Hz, 3H), 6.99 (d, J=9 Hz, 4H), 4.95 (m, 1H), 7.73 (m, 2H), 3.93-3.75 (m, 1H), 3.45-3.15 (m, 3H), 1.59 (m, 1H), 1.40 (d, J=6 Hz, 3H), 1.24 (m, 5H), 1.04 (m, 6H), 0.79 (t, J=7 Hz, 3H). Cl-LCMS m/z 638 (M+Na) HRMS C$_{35}$H$_{41}$N$_3$O$_7$ m/z 638.2842 (M+Na)$_{Cal.}$ 638.2821 (M+Na)$_{Obs.}$.

Example 59

3-Phenoxyphenyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate

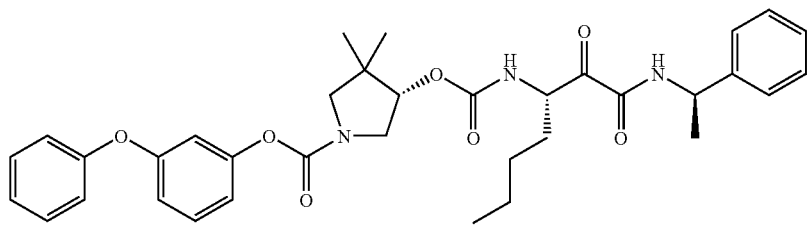

3-Phenoxyphenyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate (20 mg, 26%) was obtained in two steps from 50.0 mg (0.12 mmol) of (3S)-4,4-dimethylpyrrolidinyl (1S)-1-(1-hydroxy-2-oxo-2-{[(1R)-1-phenylethyl]amino}ethyl)pentylcarbamate and 25 mg (0.14 mmol) of 3-phenoxyphenol following the procedure outlined in example 57. $^1$H NMR (300 MHz, DMSO-d$_6$) δ 9.16 (d, J=8 Hz, 1H), 7.69 (m, 1H), 7.43-7.12 (m, 9H), 7.03 (m, 2H); 6.91-6.75 (m, 3H); 4.99 (m, 1H); 4.71 (m, 2H); 3.90 (m) and 3.75 (m) total 1H, 3.45-3.15 (m, 3H); 1.60 (m, 1H); 1.40 (d, J=6 Hz, 3H); 1.23 (m, 5H); 1.02 (m, 6H); 0.78 (m, 3H). ES-LCMS m/z 638 (M+Na) HRMS C$_{35}$H$_{41}$N$_3$O$_7$ m/z 638.2842 (M+Na)$_{Cal.}$ 638.2859 (M+Na)$_{Obs.}$.

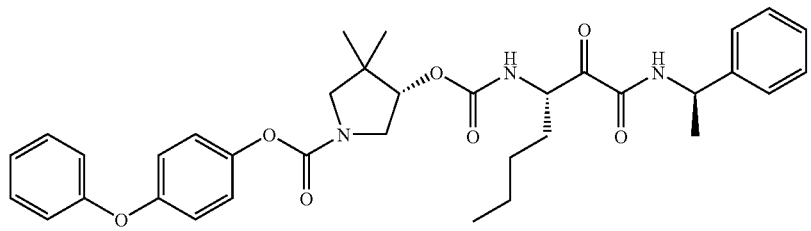

Example 60

2-Naphthyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate

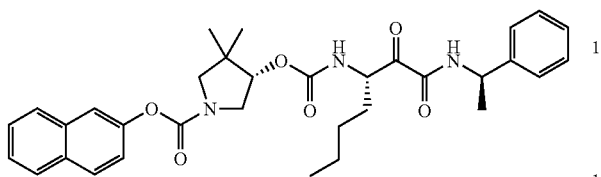

2-Naphthyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate (18 mg, 25%) was obtained in two steps from 50.0 mg (0.12 mmol) of (3S)-4,4-dimethylpyrrolidinyl (1S)-1-(1-hydroxy-2-oxo-2-{[(1R)-1-phenylethyl]amino}ethyl)pentylcarbamate and 25 mg (0.14 mmol) of 2-naphthol following the procedure outlined in example 57. $^1$H NMR (300 MHz, DMSO-$d_6$) δ 9.18 (d, J=8 Hz, 1H); 7.95-7.85 (m, 3H); 7.77-7.65 (m, 2H); 7.50 (qnt, J=6 Hz, 2H); 7.34-7.18 (m, 6H); 4.94 (m, 1H); 4.76 (m, 2H); 4.00 (m) and 3.81 (m) total 1H; 3.45-3.15 (m, 1H); 1.61 (m, 1H); 1.43-1.15 (m, 8H); 1.08 (m, 6H); 0.79 (t, J=7 Hz, 3H). ES-LCMS m/z 574 (M+H). HRMS $C_{33}H_{39}N_3O_6$ m/z 596.2737 (M+H)$_{Cal.}$ 596.2757 (M+Na)$_{Obs.}$.

Example 61

4-(1,2,3-Thiadiazol-4-yl)phenyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate

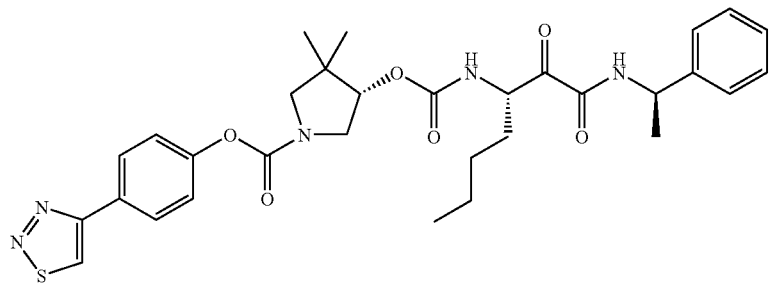

3-(1,2,3-Thiadiazol-4-yl)phenyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate (4 mg, 5%) was obtained in two steps from 50.0 mg (0.12 mmol) of (3S)-4,4-dimethylpyrrolidinyl (1S)-1-(1-hydroxy-2-oxo-2-{[(1R)-1-phenylethyl]amino}ethyl)pentylcarbamate and 24 mg (0.14 mmol) of 4-(1,2,3-thiadiazol-4-yl)phenol following the procedure outlined in example 57 except no Dowex 50W× 4(H$^+$) resin was utilized. $^1$H NMR (300 MHz, DMSO-$d_6$) δ 9.87 (d, J=4 Hz, 1H); 9.36 (d, J=8 Hz, 1H); 8.20 (d, J=7 Hz, 1H); 8.11 (s, 1H); 7.91 (t, J=8 Hz, 1H); 7.74 (t, J=8 Hz, 1H); 7.52-7.35 (m, 6H); 5.15 (m, 1H); 4.93 (m, 1H); 4.19 (m) and 4.00 (m) total 1H, 3.88-3.38 (m, 3H); 1.80 (m, 1H); 1.65-1.20 (m, 14H); 0.97 (t, J=7 Hz, 3H). ES-LCMS m/z 630 (M+Na).

Example 62

Phenyl 3,3-dimethyl-4-[({[(1S)-1-(oxo{[(1R)-1-phenylethyl]amino}acetyl)pentyl]amino}carbonyl)oxy]-1-pyrrolidinecarboxylate

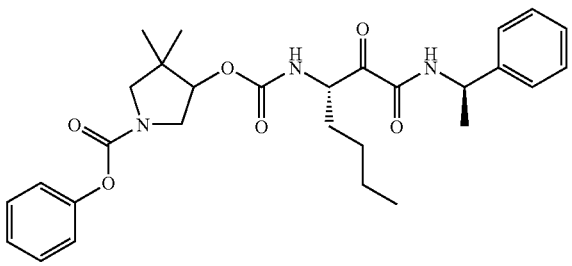

To a 0° C. solution of 28 mg (0.30 mmol) of phenol in 1 mL of dichloromethane was added a solution of 0.32 mL of phosgene (1.93 M in toluene, 0.63 mmol) in 2 mL of dichloromethane. To the resulting solution was added dropwise 0.024 mL (0.30 mmol) of pyridine, and the reaction mixture was allowed to warm to room temperature. After 18 h, a stream of nitrogen was passed through the mixture for 15 minutes, before it was added to a solution of 110 mg (0.27 mmol) of (3S)-4,4-dimethylpyrrolidinyl (1S)-1-(1-hydroxy-2-oxo-2-{[(1R)-1-phenylethyl]amino}ethyl)pentylcarbamate and 0.048 mL (0.6 mmol) of pyridine in 1 mL of dichloromethane. The mixture was stirred for 4 h, and was then concentrated under reduced pressure. The residue was taken up in 4 mL of dichloromethane, and 22 mg (0.26 mmol) of sodium bicarbonate and 95 mg (0.26 mmol) of Dess-Martin periodinane were added to the solution. The reaction mixture was stirred for 20 minutes before being applied directly to a silica gel column. Elution with 1:9 acetone:dichloromethane afforded 80 mg (73%) of phenyl 3,3-dimethyl-4-[({[(1S)-1-(oxo{[(1R)-1-phenylethyl]amino}acetyl)pentyl]amino}carbonyl)oxy]-1-pyrrolidinecarboxylate as a white foam. $^1$H NMR (300 MHz, DMSO-$d_6$) δ 8.89 (d, J=8 Hz, 1H), 7.44-7.13 (m, 11H), 4.99 (qnt, J=7 Hz, 1H), 4.88-4.72 (m, 2H), 4.03-3.75 (m, 1H), 3.60-3.20 (m, 3H), 1.75-1.20 (m, 9H), 1.10 (d, J=5 Hz, 1H), 0.85 (t, J=7 Hz, 3H). ES-LCMS m/z 524 (M+H) HRMS $C_{29}H_{37}N_3O_6$ m/z 546.2580 (M+Na)$^+$ 546.2587 (M+Na)⁺_Obs. Anal. calcd. for $C_{29}H_{37}N_3O_6 \cdot 0.1H_2O$: C, 66.29; H, 7.14; N, 8.00. Found: C, 65.94; H, 7.16; N, 7.91.

Example 63

(3S)-1-(Anilinocarbonyl)-4,4-dimethylpyrrolidinyl (1S)-1-(oxo{[(1R)-1-phenylethyl]amino}acetyl)pentylcarbamate

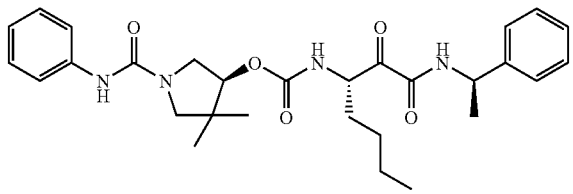

Example 63a

Preparation of (3S)-1-(anilinocarbonyl)-4,4-dimethylpyrrolidinyl (1S)-1-(1-hydroxy-2-oxo-2-{[(1R)-1-phenylethyl]amino}ethyl)pentylcarbamate

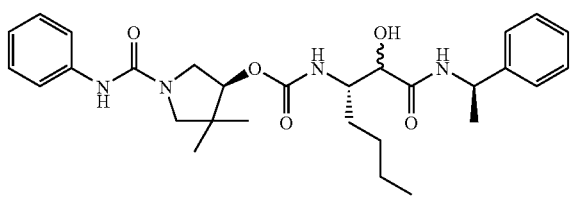

To a solution of (3S)-4,4-dimethylpyrrolidinyl (1S)-1-(1-hydroxy-2-oxo-2-{[(1R)-1-phenylethyl]amino}ethyl)pentylcarbamate (0.10 g, 0.24 mmol) in anhydrous acetonitrile (2 mL) was added phenyl isocyanate (0.033 g, 0.03 mL, 0.27 mmol), and the mixture was stirred at ambient temperature for 1.5 h. Solvent was evaporated and the residue was purified by chromatography (silica gel, hexanes/ethyl acetate, 2:3) to provide the title compound as a diastereomeric mixture (0.087 g, solid foam, 78%). ¹H NMR (DMSO-d₆): δ 8.09 (s, 1H), 8.01 (d, J=9 Hz, 1H), 7.45 (d, J=8 Hz, 2H), 7.30-7.15 (m, 7H), 6.9-6.8 (m, 2H), 5.65 (d, J=6 Hz, 1H), 4.88 (sextuplet, J=7 Hz, 1H), 4.65 (d, J=4 Hz, 1H), 3.89 (br s, 1H), 3.8-3.7 (m, 2H), 3.1-3.2 (m, 2H), 1.34 (d, J=7 Hz, 3H), 1.3-1.0 (m, 13H), 0.7 (m, 3H). ES-LCMS $C_{29}H_{40}N_4O_5$ m/z 525.26 (M+H).

Example 63b

Preparation of (3S)-1-(anilinocarbonyl)-4,4-dimethylpyrrolidinyl (1S)-1-(oxo{[(1R)-1-phenylethyl]amino}acetyl)pentylcarbamate

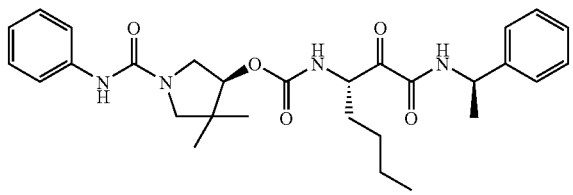

To a solution of (3S)-1-(anilinocarbonyl)-4,4-dimethylpyrrolidinyl (1S)-1-(1-hydroxy-2-oxo-2-{[(1R)-1-phenyl-ethyl]amino}ethyl)pentylcarbamate (0.085 g, 0.162 mmol) in anhydrous dichloromethane (3 mL) was added Dess-Martin periodinane (0.085g, 0.2 mmol). After 20 min at ambient temperature, the mixture was diluted with dichloromethane and washed with saturated sodium bicarbonate/water containing 5% sodium thiosulfate. The organic phase was dried (sodium sulfate), concentrated and purified by chromatography (silica gel, dichloromethane/methanol, 97:3) to provide the title compound as a solid foam (0.045 g, 53%). ¹H NMR (DMSO-d₆): 9.15(d, J=8 Hz, 1H), 8.1 (s, 1H), 7.65 (d, J=7 Hz, 1H), 7.45 (d, J=8 Hz, 2H), 7.3-7.1 (m, 7H), 6.87 (t, J=7 Hz, 1H), 5.0-4.8 (m, 1H), 4.75-4.60 (m, 2H), 3.8-3.7 (m, 1H). 3.20-3.15 (m, 3H), 1.6 (br s, 1H), 1.38 (d, J=7 Hz, 3H), 1.30-0.95 (m, 11H), 0.8 (m, 3H). ES-LCMS m/z 523.19 (M+H). Anal. calcd. for $C_{29}H_{38}N_4O_5 \cdot 0.5H_2O$: C, 65.52; H, 7.39; N, 10.54. Found: C, 65.40; H, 7.30; N, 10.39.

Example 64

(3S)-1-[(Benzylamino)carbonyl]-4,4-dimethylpyrrolidinyl (1S)-1-(oxo{[(1R)-1-phenylethyl]amino}acetyl)pentylcarbamate)

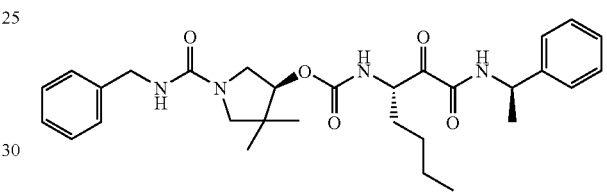

(3S)-1-[(Benzylamino)carbonyl]-4,4-dimethylpyrrolidinyl (1S)-1-(oxo{[(1R)-1-phenylethyl]amino}acetyl)pentylcarbamate (0.065 g, 65%) was obtained as a solid foam from (3S)-4,4-dimethylpyrrolidinyl (1S)-1-(1-hydroxy-2-oxo-2-{[(1R)-1-phenylethyl]amino}ethyl)pentylcarbamate (0.08 g, 0.19 mmol) and benzylisocyanate (0.027 g, 0.2 mmol) followed by oxidation with Dess-Martin periodinane (0.084 g, 0.2 mmol) according to the procedures outlined in examples 63a and 63b, respectively. ¹H NMR (DMSO-d₆): δ 9.14 (d, J=8 Hz, 1H), 7.61 (d, J=7 Hz, 1H), 7.30-7.15 (m, 10H), 6.69 (t, J=6 Hz, 1H), 5.0-4.9 (m, 1H), 4.8-4.7 (m, 1H), 4.65-4.60 (m, 1H), 4.16 (d, J=6 Hz, 2H), 3.61 (dd, J=12 Hz, 5 Hz, 1H), 3.15-3.00 (m, 3H), 1.6 (br s, 1H), 1.4 (d, 3H), 1.35-1.15 (m, 5H), 0.95 (2s, 6H), 0.8 (m, 3H). ES-LCMS m/z 537.2 (M+H). Anal. calcd. for $C_{30}H_{40}N_4O_5 \cdot 0.66H_2O$: C, 65.69; H, 7.59; N, 10.21. Found: C, 65.59; H, 7.44; N, 9.93.

Example 65

(3S)-4,4-Dimethyl-1-{[(2-phenylethyl)amino]carbonyl}pyrrolidinyl (1S)-1-(oxo{[(1R)-1-phenylethyl]amino}acetyl)pentylcarbamate

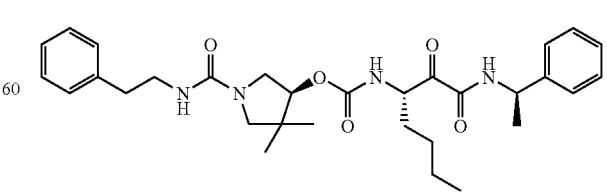

(3S)-4,4-Dimethyl-1-{[(2-phenylethyl)amino]carbonyl}pyrrolidinyl (1S)-1-(oxo{[(1R)-1-phenylethyl]

amino}acetyl)pentylcarbamate (0.107 g, 66%) was obtained as a solid foam from (3S)-4,4-dimethylpyrrolidinyl (1S)-1-(1-hydroxy-2-oxo-2-{[(1R)-1-phenylethyl]amino}ethyl)pentylcarbamate (0.12 g, 0.29 mmol) and phenethylisocyanate (0.045 g, 0.29 mmol) followed by oxidation with Dess-Martin periodinane (0.125 g, 0.29 mmol) according to the procedures outlined in examples 63a and 63b, respectively. $^1$H NMR (DMSO-$d_6$): δ 9.14 (d, J=8 Hz, 1H), 7.61 (d, J=7 Hz, 1H), 7.3-7.1 (m, 10H), 6.2-6.15 (m, 1H), 5.0-4.9 (m, 1H), 4.8-4.7 (m, 1H), 4.65-4.60 (m, 1H), 3.55 (dd, J=12 Hz, 5 Hz, 1H), 3.2-2.9 (m, 5H), 2.66 (t, J=8 Hz, 2H), 1.6 (br s, 1H), 1.37 (d, J=7 Hz, 3H), 1.30-1.15 (m, 5H), 0.94 (2s, 6H), 0.8 (m, 3H). ES-LCMS m/z 551.19 (M+H). Anal. calcd. for $C_{31}H_{42}N_4O_5 \cdot 1 H_2O$: C, 65.47; H, 7.80; N, 9.85. Found: C, 65.28; H, 7.47; N, 9.54.

Example 66

(3S)-4,4-Dimethyl-1-(3-pyridinylcarbonyl)pyrrolidinyl (1S)-1-(oxo{[(1R)-1-phenylethyl]amino}acetyl)pentylcarbamate

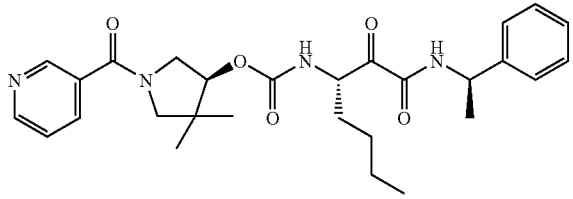

(3S)-4,4-Dimethyl-1-(3-pyridinylcarbonyl)pyrrolidinyl (1S)-1-(oxo{[(1R)-1-phenylethyl]amino}acetyl)pentylcarbamate (0.077 g, 51%) was obtained as a solid foam from (3S)-4,4-dimethylpyrrolidinyl (1S)-1-(1-hydroxy-2-oxo-2-{[(1R)-1-phenylethyl]amino}ethyl)pentylcarbamate (0.12 g, 0.29 mmol) and nicotinoyl chloride (0.039 g, 0.22 mmol) followed by oxidation with Dess-Martin periodinane (0.125 g, 0.29 mmol) according to the procedures outlined in examples 63a and 63b, respectively. $^1$H NMR (DMSO-$d_6$): δ 9.2-9.1 (m, 1H), 8.7-8.6 (m, 2H), 8.0-7.2 (m, 8H), 5.0-4.9 (m, 1H), 4.78 (br s, 1H), 4.65 (br s, 1H), 4.0-3.8 (m, 1H), 3.43.15 (m, 3H), 1.6-1.5 (m, 1H), 1.4-0.7 (m, 17H). ES-LCMS $C_{28}H_{36}N_4O_5$ m/z 509.18 (M+H).

Example 67

(3S)-1-{[(3,5-Dimethyl-4-isoxazolyl)amino]carbonyl}-4,4-dimethylpyrrolidinyl (1S)-1-(oxo{[(1R)-1-phenylethyl]amino}acetyl)pentylcarbamate

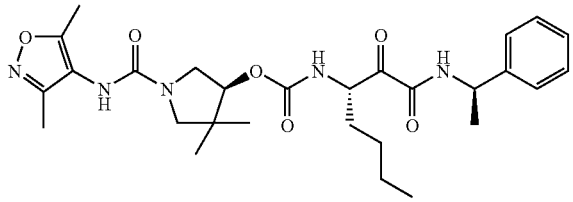

(3S)-1-{[(3,5-Dimethyl-4-isoxazolyl)amino]carbonyl}-4,4-dimethylpyrrolidinyl (1S)-1-(oxo{[(1R)-1-phenylethyl]amino}acetyl)pentylcarbamate (0.118 g, 74%) was obtained as a solid foam from (3S)-4,4-dimethylpyrrolidinyl (1S)-1-(1-hydroxy-2-oxo-2-{[(1R)-1-phenylethyl]amino}ethyl)pentylcarbamate (0.120 g, 0.290 mmol) and 3,5-dimethyl-4-isoxazolylisocyanate (0.041 g, 0.30 mmol) followed by oxidation with Dess-Martin periodinane (0.125 g, 0.290 mmol) according to the procedures outlined in examples 63a and 63b, respectively. $^1$H NMR (DMSO-$d_6$): S 9.15 (d, J=8 Hz, 1H), 7.65 (d, J=8 Hz, 1H), 7.58 (s, 1H), 7.30-7.18 (m, 5H), 5.0-4.9 (m, 1H), 4.8-4.7 (m, 1H), 4.65 (br s, 1H), 3.8-3.7 (m 1H), 3.3-3.0 (m, 3H), 2.18 (s, 3H), 2.01 (s, 3H), 1.6-1.5 (m, 1H), 1.38 (d, J=7 Hz, 3H), 1.3-1.1 (m, 5H), 0.98 (s, 6H), 0.8 (m, 3H). ES-LCMS $C_{28}H_{39}N_5O_6$ m/z 542.15 (M+H).

Example 68

(3S)-1-[(Cyclohexylamino)carbonyl]-4,4-dimethylpyrrolidinyl (1S)-1-(oxo{[(1R)-1-phenylethyl]amino}acetyl)pentylcarbamate

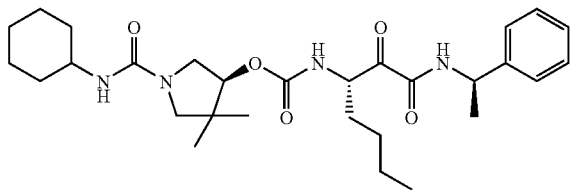

(3S)-1-[(Cyclohexylamino)carbonyl]-4,4-dimethylpyrrolidinyl (1S)-1-(oxo{[(1R)-1-phenylethyl]amino}acetyl)pentylcarbamate (0.125 g, 96%) was obtained as a solid foam from (3S)-4,4-dimethylpyrrolidinyl (1S)-1-(1-hydroxy-2-oxo-2-{[(1R)-1-phenylethyl]amino}ethyl)pentylcarbamate (0.10 g, 0.24 mmol) and cyclohexylisocyanate (0.031 g, 0.24 mmol) followed by oxidation with Dess-Martin periodinane (0.111 g, 0.260 mmol) according to the procedures outlined in examples 63a and 63b, respectively. $^1$H NMR (DMSO-$d_6$): δ 9.14 (d, J=8 Hz, 1H), 7.61 (d, J=8 Hz, 1H), 7.30-7.18 (m, 6H), 5.71 (d, J=8 Hz, 1H), 5.0-4.9 (m, 1H), 4.8-4.7 (m, 1H), 4.58 (d, J=4 Hz, 1H), 3.54 (dd, J=12 Hz, 5 Hz, 1H), 3.17 (d, J=12 Hz, 1H), 3.10-2.95 (m, 2H), 1.7-1.5 (m, 5H), 1.37 (d, J=7 Hz, 3H), 1.3-1.0 (m, 11H), 0.98 (2s, 6H), 0.8 (m, 3H). ES-LCMS m/z 529.20 (M+H). Anal. calcd. for $C_{29}H_{44}N_4O_5 \cdot 0.61 H_2O$: C, 64.54; H, 8.45; N, 10.38. Found: C, 64.44; H, 8.21; N, 9.84.

Example 69

Preparation of (3S)-1-[(4-Cyanoanilino)carbonyl]-4,4-dimethylpyrrolidinyl (1S)-1-(oxo{[(1R)-1-phenylethyl]amino}acetyl)pentylcarbamate

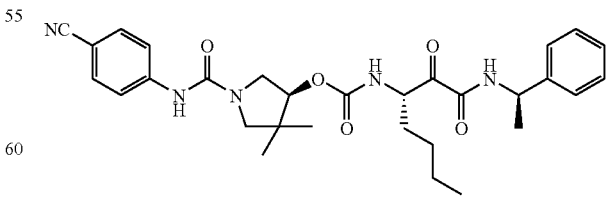

(3S)-1-[(4-Cyanoanilino)carbonyl]-4,4-dimethylpyrrolidinyl (1S)-1-(oxo{[(1R)-1-phenylethyl]amino}acetyl)pentylcarbamate (0.070 g, 70%) was obtained as a solid foam from (3S)-4,4-dimethylpyrrolidinyl (1S)-1-(1-hydroxy-2- oxo-2-{[(1R)-1-phenylethyl]amino}ethyl)pentylcarbamate (0.074 g, 0.18 mmol) and 4-cyanophenylisocyanate (0.027 g, 0.18 mmol) followed by oxidation with Dess-Martin periodinane (0.080 g, 0.18 mmol) according to the procedures outlined in examples 63a and 63b, respectively. ¹H NMR (DMSO-d₆): δ 9.15 (d, J=8 Hz, 1H), 8.6 (s, 1H), 7.8-7.6 (m, 5H), 7.30-7.15 (m, 5H), 5.0-4.9 (m, 1H), 4.8-4.6 (m, 2H), 3.8-3.7 (m, 1H), 3.4-3.2 (m, 3H), 1.6 (br s, 1H), 1.38 (d, J=7 Hz, 3H), 1.3-1.1 (m, 5H), 1.00, 0.99 (2s, 6H), 0.78 (m, 3H). ES-LCMS m/z 548.11 (M+H). Anal. calcd. for $C_{30}H_{37}N_5O_5 \cdot 0.36H_2O$: C, 65.02; H, 6.86; N, 12.64. Found: C, 65.03; H, 6.75; N, 12.72.

Example 70

(3S)-4,4-Dimethyl-1-{[4-(trifluoromethyl)anilino]carbonyl}pyrrolidinyl (1S)-1-(oxo {[(1R)-1-phenylethyl]amino}acetyl)pentylcarbamate

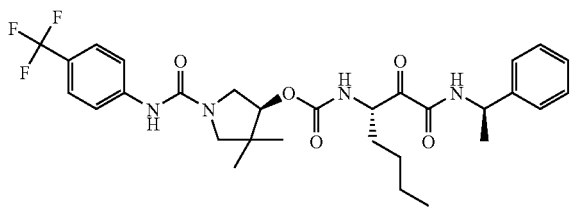

(3S)-4,4-Dimethyl-1-{[4-(trifluoromethyl)anilino]carbonyl}pyrrolidinyl (1S)-1-(oxo{[(1R)-1-phenylethyl]amino}acetyl)pentylcarbamate (0.050 g, 47%) was obtained as a solid foam from (3S)-4,4-dimethylpyrrolidinyl (1S)-1-(1-hydroxy-2-oxo-2-{[(1R)-1-phenylethyl]amino}ethyl)pentylcarbamate (0.074 g, 0.18 mmol) and α,α,α-trifluoro-p-tolylisocyanate (0.034 g, 0.18 mmol) followed by oxidation with Dess-Martin periodinane (0.080 g, 0.18 mmol) according to the procedures outlined in examples 63a and 63b, respectively. ¹H NMR (DMSO-d₆): δ 9.14 (d, J=8 Hz, 1H), 8.51 (s, 1H), 7.8-7.6 (m, 3H), 7.53 (d, J=9 Hz, 2H), 7.35-7.15 (m, 5H), 5.0-4.9 (m, 1H), 4.8-4.6 (m, 2H), 3.8-3.7 (m, 1H), 3.4-3.1 (m, 3H), 1.6 (br s, 1H), 1.38 (d, J=7 Hz, 3H), 1.3-1.1 (m, 5H), 1.0, 0.98 (2s, 6H), 0.78 (m, 3H). ES-LCMS m/z 591.1 (M+H). Anal. calcd. for $C_{30}H_{37}F_3N_4O_5 \cdot 0.3H_2O$: C, 60.45; H, 6.36; N, 9.40. Found: C, 60.46; H, 6.25; N, 9.26.

Example 71

(3S)-4,4-dimethyl-1-{[4-(trifluoromethyl)anilino]carbonyl}pyrrolidinyl (1S)-1-[oxo(1H-pyrazol-5-ylamino)acetyl]pentylcarbamate

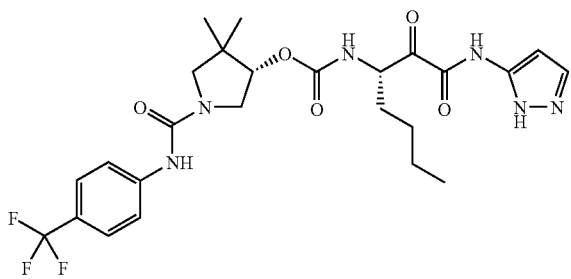

Example 71a

Preparation of (3S)-4,4-dimethyl-3-pyrrolidinol hydrochloride

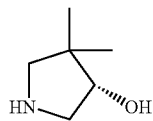

A solution of 6.34 g (41.7 mmol) of (3S)-1-benzyl-4,4-dimethyl-3-pyrrolidinol in 250 mL of ethanol and 50 mL of 1N hydrochloric acid was stirred under hydrogen (40 psi) for 18 h in the presence of 300 mg of 10% Pd/C, after which the amount of 10% Pd/C was doubled and 2 mL of concentrated hydrochloric acid were added. The mixture was stirred for an additional 72 h under hydrogen (40 psi), before the 10% Pd/C was filtered off over celite. The filtrate was concentrated and several portions of toluene were distilled from the residue, which was then dried under high vacuum to afford 4.74 g (quantitative yield) of (3S)-4,4-dimethyl-3-pyrrolidinol hydrochloride. ¹H NMR (300 MHz, DMSO-d₆) δ 9.46 (m, 2H), 5.43 (br s, 1H), 3.75 (m, 1H), 3.36 (m, 1H), 2.88 (m, 3H), 0.98 (s, 3H), 0.94 (s, 3H).

Example 71b

Preparation of (4S)-4-hydroxy-3,3-dimethyl-N-[4-(trifluoromethyl)phenyl]-1-pyrrolidinecarboxamide

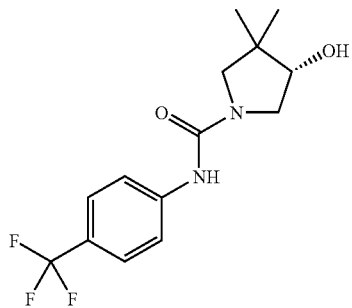

To 200 mg (1.3 mmol) of (3S)-4,4-dimethyl-3-pyrrolidinol hydrochloride and 0.25 mL (1.3 mmol) of N,N-diisopropylethylamine in 4 mL of dichloromethane was added dropwise 0.19 mL (1.3 mmol) of 1-isocyanato-4-(trifluoromethyl)benzene. The reaction mixture was stirred at room temperature for 18 h. It was then diluted with ethyl acetate, and the resulting solution was washed with 1 N hydrochloric acid and brine, dried over magnesium sulfate, and concentrated under reduced pressure to afford 390 mg (quantitative yield) of (4S)-4-hydroxy-3,3-dimethyl-N-[4-(trifluoromethyl)phenyl]-1-pyrrolidinecarboxamide. ¹H NMR (300 MHz, DMSO-d₆) δ 8.45 (s, 1H), 7.73 (d, J=9 Hz, 2H), 7.54 (d, J=9

Hz, 2H), 5.08 (s, 1H), 3.74-3.55 (m, 2H), 3.27-3.09 (m, 3H), 0.97 (s, 3H), 0.95 (s, 3H). Cl-LCMS m/z 303 (M+H).

Example 71c

Preparation of tert-butyl (1S)-1-{[methoxy(methyl)amino]carbonyl}pentylcarbamate

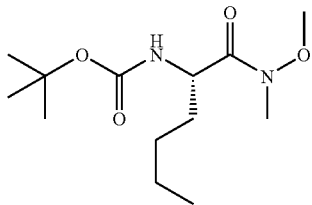

To a stirred solution of (2S)-2-[(tert-butoxycarbonyl)amino]hexanoic acid (27.8 g, 120.0 mmol) in dichloromethane (150 mL) at −40° C. was added a solution of 1-methylpiperidine (18.4 mL, 151.5 mmol) in dichloromethane (40 mL) over 20 min. Ethyl chloroformate (13.9 mL, 145.4 mmol) in dichloromethane (40 mL) was then added over 30 min and the reaction mixture was stirred at −40° C. for 2.5 h. A solution of N,O-dimethylhydroxylamine hydrochloride (14.2 g, 145.4 mmol) and 1-methylpiperidine (18.4 mL, 151.5 mmol) in dichloromethane (90 mL) was added over 45 min, and the reaction mixture was allowed to slowly warm to ambient temperature. It was stirred for 18 h, and then washed with water (100 mL), 1% hydrochloric acid (2×100 mL), and saturated aqueous sodium bicarbonate (100 mL). The organic layer was then dried with magnesium sulfate and concentrated in vacuo to afford the desired title compound (35.0 g, 106%) as a thick oil. $^1$H NMR (400 MHz, DMSO-$d_6$): δ 6.94 (d, J=8 Hz, 1H), 4.35-4.25 (m, 1H), 3.68 (s, 3H), 3.05 (s, 3H), 1.52-1.36 (m, 2H), 1.32 (s, 9H), 1.30-1.14 (m, 4H), 0.80 (t, J=6 Hz, 3H).

Example 71d

Preparation of tert-butyl (1S)-1-formylpentylcarbamate

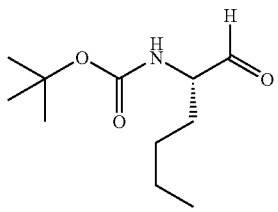

To a stirred solution of bis(2-methoxyethoxy)aluminum hydride (54.0 mL, 65% by weight in toluene, 180.0 mmol) in toluene (100 mL) at −20° C. was added a solution of tert-butyl (1S)-1-{[methoxy(methyl)amino]carbonyl}pentylcarbamate (35.0 g, 120.0 mmol) in toluene (100 mL) over 30 min. After 2 h at −20° C., 3M sodium chloride (300 mL) was added dropwise, and the layers were separated. The toluene portion was washed with 1N hydrochloric acid (2×100 mL), 0.1N sodium hydroxide (2×50 mL), and brine (50 mL), dried over magnesium sulfate, and concentrated to 200 mL. The aldehyde was used immediately in solution. An aliquot of the solution was removed and concentrated, and the aldehyde was analyzed immediately. $^1$H NMR (400 MHz, DMSO-$d_6$): δ 9.39 (s, 1H), 7.23 (d, J=7 Hz, 1H), 3.75 (m, 1H), 1.70-1.08 (m, 6H), 1.36 (s, 9H), 0.81 (t, J=6 Hz, 3H).

Example 71e

Preparation of tert-butyl (1S)-1-[cyano(hydroxy)methyl]pentylcarbamate

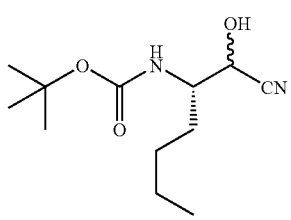

To a stirred solution of tert-butyl (1S)-1-formylpentylcarbamate in toluene was added water (50 mL), acetone cyanohydrin (16.4 mL, 180.0 mmol), potassium cyanide (250 mg) and tetrabutylammonium iodide (300 mg). The mixture was stirred at ambient temperature for 20 h, and then the layers were separated. The organic layer was washed with water (5×60 mL), dried with magnesium sulfate and concentrated in vacuo to afford the title compound (26.7 g, 92%) as a thick oil. The $^1$H NMR spectrum showed an approximately equal mixture of diastereomers. $^1$H NMR (400 MHz, DMSO-$d_6$): δ 6.91,6.83 (2d, J=8 Hz, J=9 Hz, 1H), 6.54, 6.47 (2d, J=7 Hz, J=6 Hz, 1H), 4.44, 4.17 (2t, J=5 Hz, J=8 Hz, 1H), 3.60-3.50 (m, 1H), 1.65-1.10 (m, 6H), 1.34 (s, 9H), 0.80 (t, J=6 Hz, 3H).

Example 71f

Preparation of (3S)-3-amino-2-hydroxyheptanoic acid hydrochloride

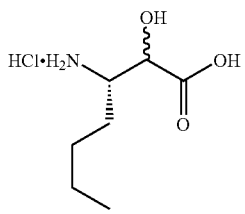

A mixture of tert-butyl (1S)-1-[cyano(hydroxy)methyl]pentylcarbamate (26.7 g, 110.0 mmol) and concentrated hydrochloric acid (200 mL) was stirred at 110° C. for 6 h and then allowed to stand at ambient temperature for 18 h. The reaction mixture was concentrated in vacuo, toluene (200 mL) was added, and the solution was concentrated again to afford the crude title compound (25.6 g, quantitative crude yield) as a white paste. The $^1$H NMR spectrum showed this material to be an approximately equal mixture of diastereomers containing ammonium chloride. The material was used without further purification. $^1$H NMR (400 MHz, DMSO-$d_6$): δ 8.25, 8.02 (2br s, 3H), 4.38,4.05 (2d, J=5 Hz, J=7 Hz, 1H), 3.35-3.10 (m, 1H), 1.70-1.10(m, 6H), 0.80 (2t, J=6 Hz, 3H).

Example 71g

Preparation of (3S)-3-[(tert-butoxycarbonyl)amino]-2-hydroxyheptanoic acid

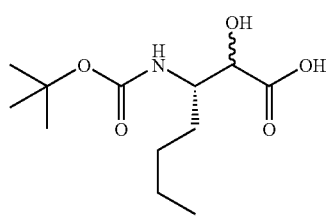

To a stirred solution of (3S)-3-amino-2-hydroxyheptanoic acid hydrochloride (25.6 g crude, 110.0 mmol) in 1N sodium hydroxide (300 mL) was added a solution of di-tert-butyldicarbonate (26.4 g, 121.2 mmol) in tetrahydrofuran (75 mL) over 30 min. After stirring at ambient temperature for 20 h, the reaction mixture was diluted with ether (100 mL) and the layers were separated. The aqueous layer was cooled in an ice bath, acidified to pH 2 with concentrated hydrochloric acid, and extracted with dichloromethane (2×150 mL). The dichloromethane layer was washed with brine (100 mL), dried with magnesium sulfate, and concentrated in vacuo to afford the title compound (21.7 g, 75% over 2 steps) as a thick paste. $^1$H NMR (400 MHz, DMSO-$d_6$): δ 12.40 (broad, 1H), 6.45, 6.15 (2d, J=9 Hz, J=10 Hz, 1H), 5.20, 4.98 (2br, 1H), 3.89 (2d, J=12 Hz, J=10 Hz, 1H), 3.73-3.60 (m, 1H), 1.46-1.08 (m, 6H), 1.32, 1.31 (2s, 9H), 0.80 (t, J=6 Hz, 3H).

Example 71h

Preparation of tert-butyl (1S)-1-[1-hydroxy-2-oxo-2-(7H-pyrazol-5-ylamino)ethyl]pentylcarbamate

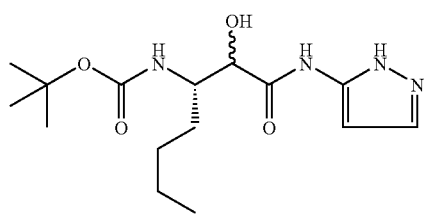

To a stirred solution of (3S)-3-[(tert-butoxycarbonyl)amino]-2-hydroxyheptanoic acid (5.0 g, 19.1 mmol) and 1-methylpiperidine (3.5 mL, 28.7 mmol) in dichloromethane (40 mL) at –40° C. was added a solution of ethyl chloroformate (2.0 mL, 21.0 mmoL) in dichloromethane (20 mL) over 20 minutes. The reaction mixture was stirred at –40° C. for 10 min and then allowed to warm to 5° C. over 30 min. N,N$^1$-Carbonyldiimidazole (3.4 g, 21.0 mmol) was added. After 1 h, 3-aminopyrazole (4.5 g, 54.2 mmol) was added, and the reaction mixture was allowed to warm to ambient temperature. It was diluted with toluene (60 mL), and dichloromethane was distilled off as the temperature was slowly increased to 110° C. The mixture was stirred for 20 h at that temperature. The toluene was then removed in vacuo, and the residue was taken up in ether (150 mL). The solution was washed with water (3×50 mL), and concentrated in vacuo. The resulting foam was dissolved in methanol (75 mL), and 10% aqueous potassium carbonate (15 mL) was added. The reaction mixture was stirred at ambient temperature for 48 h. The methanol was removed in vacuo and ether (150 mL) was added. The ether layer was washed with water (3×50 mL), dried with magnesium sulfate, and concentrated in vacuo to afford the title compound (4.8 g, 77%) as an off-white solid. $^1$H NMR (400 MHz, DMSO-$d_6$): δ 12.29 (br s, 1H), 9.73, 9.50 (2br s, 1H), 7.54 (s, 1H), 6.45 (s, 1H), 6.42, 6.15 (2d, J=7 Hz, J=9 Hz, 1H), 5.87, 5.57 (2br s, 1H), 3.98 (m, 1H), 3.77-3.72 (m, 1H), 1.47-1.09 (m, 6H), 1.31, 1.25 (2s, 9H), 0.81, 0.76 (2t, J=6 Hz, 3H); ES-LCMS m/z 327 (M+H).

Example 71i

Preparation of (3S)-4,4-dimethyl-1-{[4-(trifluoromethyl)anilino]carbonyl}pyrrolidinyl (1S)-1-[1-hydroxy-2-oxo-2-(1H-pyrazol-5-ylamino)ethyl]pentylcarbamate

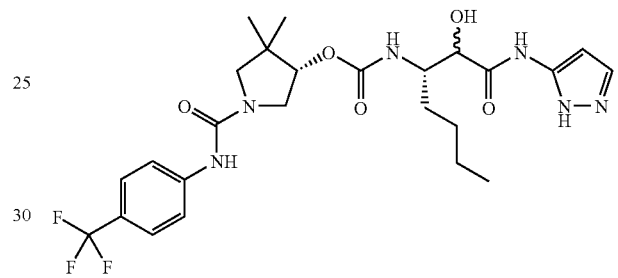

To a 0° C. suspension of 390 mg (1.3 mmol) of (4S)-4-hydroxy-3,3-dimethyl-N-[4-(trifluoromethyl)phenyl]-1-pyrrolidinecarboxamide in 4 mL of dichloromethane was added 260 mg (1.3 mmol) of 4-nitrophenyl chloroformate. Pyridine 0.11 mL (1.3 mmol) was added dropwise, and the reaction mixture was let warm to room temperature. The reaction mixture was stirred for 18 h, and then concentrated to afford the carbonate as an oil. In a separate flask, 5 mL of 4M hydrochloric acid in dioxane was added to a suspension of 480 mg (1.3 mmol) of tert-butyl (1S)-1-[(1R)-1-hydroxy-2-oxo-2-(1H-pyrazol-5-ylamino)ethyl]pentylcarbamate &tert-butyl (1S)-1-[(1S)-1-hydroxy-2-oxo-2-(1H-pyrazol-5-ylamino)ethyl]pentylcarbamate in 1 mL of dioxane. The reaction mixture was stirred for 1 h, and concentrated under reduced pressure. The residue was dissolved in 8 mL of N,N-dimetehylformamide, and 0.69 mL (4.0 mmol) of N,N-diisopropylethylamine was added, followed by the carbonate. The reaction mixture was stirred for 18 h, and then diluted with ethyl acetate. The resulting solution was washed with 1M aqueous sodium hydroxide and brine, dried over magnesium sulfate, and concentrated under reduced pressure. The residue was purified by silica gel chromatography to afford 240 mg (33%) of (3S)-4,4-dimethyl-1-{[4(trifluoromethyl)anilino]carbonyl}pyrrolidinyl (1S)-1-[1-hydroxy-2-oxo-2-(1H-pyrazol-5-ylamino)ethyl]pentylcarbamate. $^1$H NMR (300 MHz, DMSO-$d_6$) δ 12.30 (m, 1H); 9.74 (m) and 9.52 (m) total 1H, 8.52 (d, J=8 Hz, 1H); 7.72 (m, 2H); 7.55 (m, 3H); 7.03 (d, J=9 Hz) and 6.77 (d, J=9 Hz) total 1H, 6.45 (m, 1H); 5.94 (m) and 5.59 (m) total 1H, 4.67 (m, 1H); 4.02 (m, 1H); 3.83 (m, 2H); 3.44-3.05 (m, 3H); 1.60-0.75 (m, 15H). Cl-LCMS m/z 555 (M+H).

Example 71j

Preparation of (3S)-4,4-dimethyl-1-{[4-(trifluoromethyl)anilino]carbonyl}pyrrolidinyl (1S)-1-[oxo(1H-pyrazol-5-ylamino)acetyl]pentylcarbamate

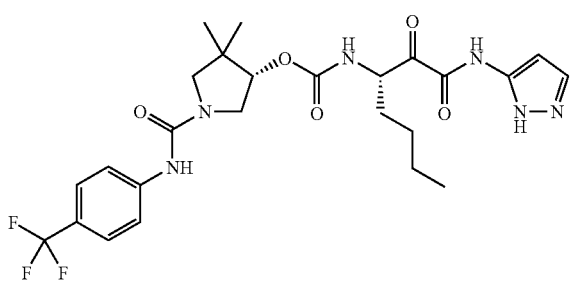

To a solution of 220 mg (0.40 mmol) of (3S)-4,4-dimethyl-1-{[4-(trifluoromethyl)anilino]carbonyl}pyrrolidinyl (1S)-1-[1-hydroxy-2-oxo-2-(1H-pyrazol-5-ylamino)ethyl]pentylcarbamate in 4 mL of dichloromethane was added 210 mg (0.49 mmol) of Dess-Martin periodinane. The reaction mixture was stirred for 30 minutes at room temperature and then filtered through a celite plug. The filtrate was concentrated, and the residue was purified by silica gel chromatography eluting with 3:7 acetone:dichloromethane to afford 110 mg (50%) of (3S)-4,4-dimethyl-1-{[4-(trifluoromethyl)anilino]carbonyl}pyrrolidinyl (1S)-1-[oxo(1H-pyrazol-5-ylamino)acetyl]pentylcarbamate. $^1$H NMR (400 MHz, DMSO-$d_6$) δ 12.54 (m, 1H), 10.89 (br s, 1H), 8.55 (s, 1H), 7.77-7.45 (m, 6H), 6.51 (s, 1H), 4.85 (m, 1H), 4.72 (m, 1H), 3.80 (m, 1H), 3.47-3.10 (m, 3H), 1.72 (m, 1H), 1.55-1.18 (m, 5H), 1.03 (m, 6H), 0.83 (t, J=7 Hz, 3H). Cl-LCMS m/z 553 (M+H) HRMS $C_{25}H_{31}N_6O_5F_3$ m/z 553.2386 (M+)$_{Cal.}$ 553.2408 (M+H)$_{Obs.}$.

Example 72

(3S)-1-[(5-Fluoro-2-methylanilino)carbonyl]-4,4-dimethylpyrrolidinyl (1S)-1-(oxo{[(1R)-1-phenylethyl]amino}acetyl)pentylcarbamate

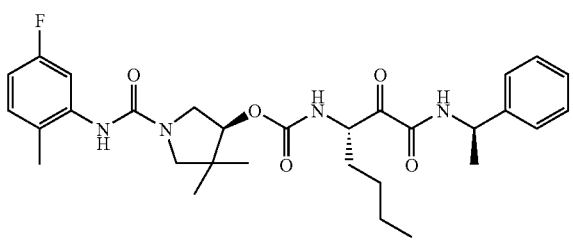

(3S)-1-[(5-Fluoro-2-methylanilino)carbonyl]-4,4-dimethylpyrrolidinyl (1S)-1-(oxo{[(1R)-1-phenylethyl]amino}acetyl)pentylcarbamate (0.050 g, 50%) was obtained as a solid foam from (3S)-4,4-dimethylpyrrolidinyl (1S)-1-(1-hydroxy-2-oxo-2-{[(1R)-1-phenylethyl]amino}ethyl)pentylcarbamate (0.074 g, 0.18 mmol) and 5-fluoro-2-methylphenylisocyanate (0.027 g, 0.18 mmol) followed by oxidation with Dess-Martin periodinane (0.080 g, 0.18 mmol) according to the procedures outlined in examples 63a and 63b, respectively. $^1$H NMR (DMSO-$d_6$): δ 9.14 (d, J=8 Hz, 1H), 7.65 (d, J=7 Hz, 1H), 7.51 (s, 1H), 7.4-7.2 (m, 6H), 7.13 (t, J=8 Hz, 1H), 6.77 (td, J=8 Hz, 3 Hz, 1H), 4.9-5.0 (m, 1H), 4.85-4.60 (m, 2H), 3.8-3.7 (m, 1H), 3.4-3.1 (m, 3H), 2.12 (s, 3H), 1.6 (br s, 1H), 1.38 (d, J=7 Hz, 3H), 1.3-1.1 (m, 5H), 1.00, 0.99 (2s, 6H), 0.78 (m, 3H). ES-LCMS m/z 555.2 (M+H). Anal. calcd. for $C_{30}H_{39}FN_4O_5 \cdot 0.35H_2O$: C, 64.23; H, 7.13; N, 9.99. Found: C, 64.24; H, 7.06; N, 10.12.

Example 73

(3S)-4,4-Dimethyl-1-(4-morpholinylcarbonyl)pyrrolidinyl (1S)-1-(oxo{[(1R)-1-phenylethyl]amino}acetyl)pentylcarbamate

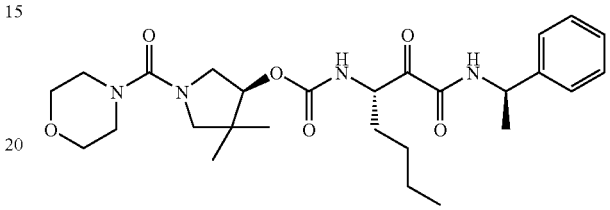

To a solution of (3S)-4,4-dimethylpyrrolidinyl (1S)-1-(1-hydroxy-2-oxo-2-{[(1R)-1-phenylethyl]amino}ethyl)pentylcarbamate (0.074 g, 0.18 mmol) and triethylamine (0.036 g, 0.05 mL, 0.36 mmol) in anhydrous dichloromethane (2.5 mL) at 0° C. was added morpholine 4-carbonyl chloride (0.027 g, 0.021 mL, 0.18 mmol), and the mixture was stirred at 0° C. for 1 h. The mixture was diluted with dichloromethane and washed with saturated sodium bicarbonate/water, dried (sodium sulfate), and concentrated. The residue was dissolved in dichloromethane (3 mL) and Dess-Martin periodinane (0.076 g, 0.18 mmol) was added. After 1 h at ambient temperature, dichloromethane was added and the mixture was stirred with saturated sodium bicarbonate/water containing 5% sodium thiosulfate. The organic phase was dried (sodium sulfate), concentrated and purified by chromatography (silica gel, hexanes/ethyl acetate, 2:3) to provide the title compound as a solid foam (0.061 g, 60%). $^1$H NMR (DMSO-$d_6$): δ 9.14 (d, J=8 Hz, 1H), 7.61 (d, J=7 Hz, 1H), 7.35-7.15 (m, 5H), 5.0-4.9 (m, 1H), 4.8-4.7 (m, 1H), 4.61 (d, J=4 Hz, 1H), 3.8 (dd, J=12 Hz, 5 Hz, 1H), 3.6-3.5 (m, 4H), 3.2-3.0 (m, 7H), 1.6 (br s, 1H), 1.37 (d, J=7 Hz, 3H), 1.3-1.1 (m, 5H), 0.94, 0.90 (2s, 6H), 0.78 (m, 3H). ES-LCMS m/z 517.2 (M+H). Anal. calcd. for $C_{27}H_{40}N_4O_6 \cdot 0.19H_2O$: C, 62.36; H, 7.83; N, 10.77. Found: C, 62.35; H, 7.77; N, 10.55.

Example 74

(3S)-4,4-Dimethyl-1-(1-pyrrolidinylcarbonyl)pyrrolidinyl (1S)-1-(oxo{[(1R)-1-phenylethyl]amino}acetyl)pentylcarbamate

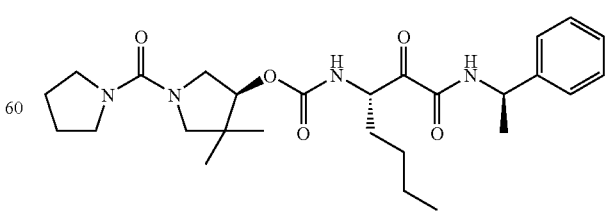

(3S)-4,4-Dimethyl-1-(1-pyrrolidinylcarbonyl)pyrrolidinyl (1S)-1-(oxo{[(1R)-1-phenylethyl]amino}acetyl)pentylcarbamate (0.057 g, 66%) was obtained as a solid foam from (3S)-4,4-dimethylpyrrolidinyl (1S)-1-(1-hydroxy-2-oxo-2-{[(1R)-1-phenylethyl]amino}ethyl)pentylcarbamate (0.070 g, 0.17 mmol) and pyrrolidine carbonyl chloride (0.023 g, 0.17 mmol) followed by oxidation with Dess-Martin periodinane (0.080 g, 0.18 mmol) according to the procedure described in example 73. $^1$H NMR (DMSO-d$_6$): δ 9.14 (d, J=8 Hz, 1H), 7.6 (d, J=7 Hz, 1H), 7.35-7.15 (m, 5H), 5.0-4.9 (m, 1H), 4.85-4.75 (m, 1H), 4.6 (d, J=4 Hz, 1H), 3.73 (dd, J=12, 5 Hz, 1H), 3.4-3.0 (m, 7H), 1.8-1.6 (m, 4H), 1.55 (br s, 1H), 1.37 (d, J=7 Hz, 3H), 1.35-1.15 (m, 5H), 0.94, 0.92 (2s, 6H), 0.8 (m, 3H). ES-LCMS C$_{27}$H$_{40}$N$_4$O$_5$ m/z 501.21 (M+H).

Example 75

(3S)-1-[(Benzoylamino)carbonyl]-4,4-dimethylpyrrolidinyl (1S)-1-(oxo{[(1R)-1-phenylethyl]amino}acetyl)pentylcarbamate

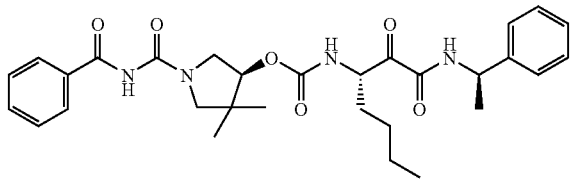

(3S)-1-[(Benzoylamino)carbonyl]-4,4-dimethylpyrrolidinyl (1)-1-(oxo{[(1R)-1-phenylethyl]amino}acetyl)pentylcarbamate (0.060 g, 63%) was obtained as a solid foam from (3S)-4,4-dimethylpyrrolidinyl (1S)-1-(1-hydroxy-2-oxo-2-{[(1R)-1-phenylethyl]amino}ethyl)pentylcarbamate (0.071 g, 0.17 mmol) and benzoylisocyanate (90% pure, 0.029 g, 0.17 mmol) followed by oxidation with Dess-Martin periodinane (0.074 g, 0.17 mmol) according to the procedures outlined in examples 63a and 63b, respectively. $^1$H NMR (DMSO-d$_6$): δ 10.17, 10.12 (2s, 1H), 9.13 (br s, 1H), 7.8 (br s, 2H), 7.7 (br s, 1H), 7.60-7.55 (m, 1H), 7.5-7.4 (m, 2H), 7.3-7.2 (m, 4H), 7.19-7.14 (m, 1H), 5.0-4.9 (m, 1H), 4.8-4.6 (m, 2H), 3.9-3.8 (m, 1H), 3.43.2 (m, 3H), 1.6 (br s, 1H), 1.4-1.1 (m, 8H), 1.0, 0.97 (2s, 6H), 0.8-0.7 (m, 3H). ES-LCMS m/z 551.11 (M+H). Anal. calcd. for C$_{30}$H$_{38}$N$_4$O$_6$.0.23H$_2$O: C, 64.95; H, 6.99; N, 10.10. Found: C, 64.94; H, 6.96; N, 9.95.

Example 76

(3S)-4,4-Dimethyl-1-({[(4-methylphenyl)sulfonyl]amino}carbonyl)pyrrolidinyl (1S)-1-(oxo{[(1R)-1-phenylethyl]amino}acetyl)pentylcarbamate

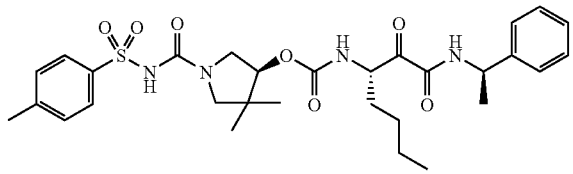

(3S)-4,4-Dimethyl-1-({[(4methylphenyl)sulfonyl]amino}carbonyl)pyrrolidinyl (1S)-1-(oxo{[(1R)-1-phenylethyl]amino}acetyl)pentylcarbamate (0.056 g, 54%) was obtained as a solid foam from (3S)-4,4-dimethylpyrrolidinyl (1S)-1-(1-hydroxy-2-oxo-2-{[(1R)-1-phenylethyl]amino}ethyl)pentylcarbamate (0.071 g, 0.17 mmol) and p-toluenesulfonylisocyanate (0.034 g, 0.17 mmol) followed by oxidation with Dess-Martin periodinane (0.074 g, 0.17 mmol) according to the procedures outlined in examples 63a and 63b, respectively. $^1$H NMR (DMSO-d$_6$): δ 10.63 (s, 1H), 9.18 (br s, 1H), 7.74 (d, J=8 Hz, 2H), 7.62 (br s, 1H), 7.34 (d, J=8 Hz, 2H), 7.3-7.2 (m, 5H), 5.0-4.9 (m, 1H), 4.8-4.5 (m, 2H), 3.8-3.7 (m, 1H), 3.2-2.9 (m, 3H), 2.34 (s, 3H), 1.6-1.5 (m, 1H), 1.37 (d, J=7 Hz, 3H), 1.3-1.1 (m, 5H), 0.92 (s, 6H), 0.8-0.7 (m, 3H). ES-LCMS C$_{30}$H$_{40}$N$_4$O$_7$S m/z 601.09 (M+H).

Example 77

(3S)-4,4-Dimethyl-1-(phenylsulfonyl)pyrrolidinyl (1S)-1-(oxo{[(1R)-1-phenylethyl]amino}acetyl)pentylcarbamate

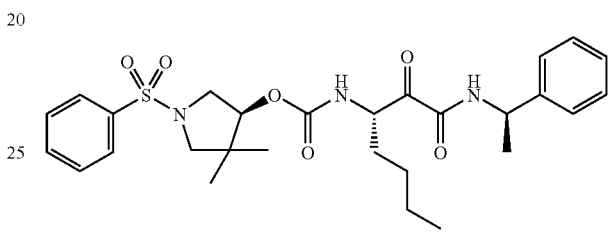

(3S)-4,4-Dimethyl-1-(phenylsulfonyl)pyrrolidinyl (1S)-1-(oxo{[(1R)-1-phenylethyl]amino}acetyl)pentylcarbamate (0.087 g, 81%) was obtained as a solid foam from (3S)-4,4-dimethylpyrrolidinyl (1S)-1-(1-hydroxy-2-oxo-2-{[(1R)-1-phenylethyl]amino}ethyl)pentylcarbamate (0.080 g, 0.20 mmol) and benzenesulfonyl chloride (0.037 g, 0.21 mmol) followed by oxidation with Dess-Martin periodinane (0.089 g, 0.21 mmol) according to the procedure described in example 73. $^1$H NMR (DMSO-d$_6$): δ 9.12 (d, J=8 Hz, 1H), 7.8-7.5 (m, 6H), 7.3-7.1 (m, 5H), 5.0-4.9 (m, 1H), 4.7-4.6 (m, 1H), 4.5 (d, J=3 Hz, 1H), 3.5 (dd, J=12 Hz, 5 Hz, 1H), 3.12 (d, J=10 Hz, 1H), 3.05 (d, J=10 Hz, 1H), 3.0 (d, J=10 Hz, 1H), 1.6 (br s, 1H), 1.36 (d J=7 Hz, 3H), 1.40-1.15 (m, 5H), 0.83 (s, 3H), 0.77 (m, 3H), 0.62 (s, 3H). ES-LCMS m/z 544.11 (M+H). Anal. calcd. for C$_{28}$H$_{37}$N$_3$O$_6$S: C, 61.86; H, 6.86; N. 7.73. Found: C, 61.58; H, 6.87; N, 7.62.

Example 78

(3S)-1-(Benzylsulfonyl)-4,4-dimethylpyrrolidinyl (1S)-1-(oxo{[(1R)-1-phenylethyl]amino}acetyl)pentylcarbamate

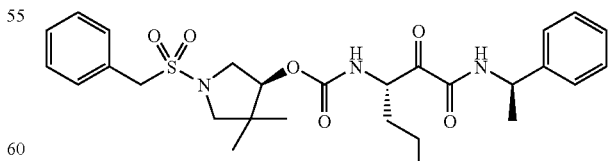

(3S)-1-(Benzylsulfonyl)-4,4-dimethylpyrrolidinyl (1S)-1-(oxo{[(1R)-1-phenylethyl]amino}acetyl)pentylcarbamate (0.053 g, 55%) was obtained as a solid foam from (3S)-4,4-dimethylpyrrolidinyl (1S)-1-(1-hydroxy-2-oxo-2-{[(1R)-1- phenylethyl]amino}ethyl)pentylcarbamate (0.070 g, 0.17 mmol) and α-toluenesulfonyl chloride (0.035 g, 0.18 mmol) followed by oxidation with Dess-Martin periodinane (0.068 g. 0.16 mmol) according to the procedure described in example 73. $^1$H NMR (DMSO-d$_6$): δ 9.14 (d, J=8 Hz, 1H), 7.67 (d, J=7 Hz, 1H), 7.4-7.1 (m, 10H), 5.0-4.9 (m, 1H), 4.8-4.7 (m, 1H), 4.58(d, J=3 Hz, 1H), 4.42(d, J=13 Hz, 1H), 4.34(d, J=13 Hz, 1H), 3.6 (dd, J=12 Hz, 5 Hz, 1H), 3.14 (d, J=11 Hz, 1H), 3.05 (d, J=9 Hz, 1H), 3.02 (d, J=9 Hz, 1H), 1.6 (br s, 1H), 1.37 (d, J=7 Hz, 3H), 1.3-1.1 (m, 5H), 0.95 (s, 6H), 0.78 (m, 3H). ES-LCMS m/z 558.13 (M+H). Anal. calcd. for C$_{29}$H$_{39}$N$_3$O$_6$S: C, 62.46; H, 7.05; N, 7.53. Found: C, 62.25; H, 7.04; N, 7.37.

Example 79

(3S)-1-(1,3-Benzodioxol-5-ylsulfonyl)-4,4-dimethylpyrrolidinyl (1S)-1-(oxo{[(1R)-1-phenylethyl]amino}acetyl)pentylcarbamate

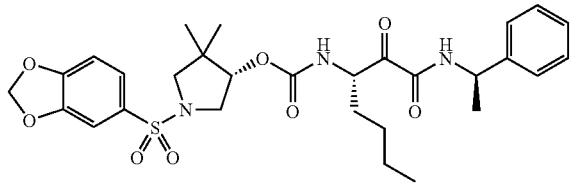

(3S)-1-(1,3-Benzodioxol-5-ylsulfonyl)-4,4-dimethylpyrrolidinyl (1S)-1-(oxo{[(1R)-1-phenylethyl]amino}acetyl)pentylcarbamate (66 mg, 57%) was obtained as a white foam in two steps from (3S)-4,4-dimethylpyrrolidinyl 2-hydroxy-3-oxo-3-{[(1R)-1-phenylethyl]amino}propylcarbamate (80 mg, 0.20 mmol) and 1,3-benzodioxole-5-sulfonyl chloride (46 mg, 0.21 mmol) following the procedure outlined in example 73. $^1$H NMR (400 MHz, DMSO-d$_6$): δ 9.12 (d, J=8 Hz, 1H), 7.54 (d, J=7 Hz, 1H), 7.31-7.06 (m, 8H), 6.13 (d, 2H), 4.94-4.89 (m, 1H), 4.69-4.64 (m, 1H), 4.51-4.50 (m, 1H), 3.53-3.46 (m, 1H), 3.11-2.96 (m, 3H), 1.70-1.11 (m, 6H), 1.36 (d, J=7 Hz, 3H), 0.85 (s, 3H), 0.76 (t, J=7 Hz, 3H), 0.67 (s, 3H). ES-LCMS C$_{29}$H$_{37}$N$_3$O$_8$S$_1$ m/z 588 (M+H).

Example 80

(3S)-1-(2,3-Dihydro-1,4-benzodioxin-6-ylsulfonyl)-4,4-dimethylpyrrolidinyl (1S)-1-(oxo{[(1R)-1-phenylethyl]amino}acetyl)pentylcarbamate

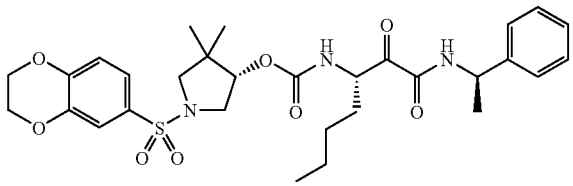

(3S)-1-(2,3-Dihydro-1,4-benzodioxin-6-ylsulfonyl)-4,4-dimethylpyrrolidinyl (1S)-1-(oxo{[(1R)-1-phenylethyl]amino}acetyl)pentylcarbamate (78 mg, 66%) was obtained as a white foam in two steps from (3S)-4,4-dimethylpyrrolidinyl 2-hydroxy-3-oxo-3-{[(1R)-1-phenylethyl]amino}propylcarbamate (80.0 mg, 0.20 mmol) and 2,3-dihydro-1,4-benzodioxine-6-sulfonyl chloride (49 mg, 0.21 mmol) following the procedure outlined in example 73. $^1$H NMR (400 MHz, DMSO-d$_6$): δ 9.12 (d, J=8 Hz, 1H), 7.54 (d, J=7 Hz, 1H), 7.29-7.01 (m, 8H), 4.93-4.89 (m, 1H), 4.69-4.65 (m, 1H), 4.51-4.50 (m, 1H), 4.28-4.26 (m, 4H), 3.51-3.47 (m, 1H), 3.10-2.96 (m, 3H), 1.70-1.13 (m, 6H), 1.36 (d, J=7 Hz, 3H), 0.84 (s, 3H), 0.76 (t, J=7 Hz, 3H), 0.67 (s, 3H). ES-LCMS C$_{30}$H$_{39}$N$_3$O$_8$S$_1$ m/z 602 (M+H).

Example 81

(3S)-1-(1,3-Benzothiazol-2-yl)-4,4-dimethylpyrrolidinyl (1S)-1-[oxo(1H-pyrazol-5-ylamino)acetyl]pentylcarbamate

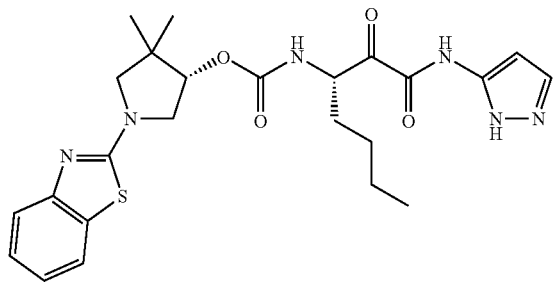

Example 81a

Preparation of (3S)-1-(1,3-benzothiazol-2-yl)-4,4-dimethyl-3-pyrrolidinol

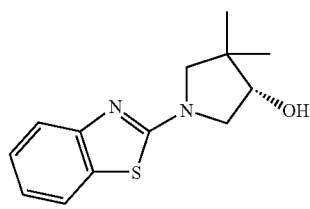

To a slurry of 600 mg (4 mmol) of (3S)-4,4-dimethyl-3-pyrrolidinol hydrochloride and 670 mg (4 mmol) of 2-chlorobenzthiazole was added a solution of 1.0 g (12 mmol) of sodium bicarbonate in water. The reaction mixture was stirred at 80° C. overnight, diluted with water, and extracted with ethyl acetate. The extract was dried over magnesium sulfate and concentrated under reduced pressure to afford 950 mg (96%) of (3S)-1-(1,3-benzothiazol-2-yl)-4,4-dimethyl-3-pyrrolidinol. $^1$H NMR (300 MHz, DMSO-d$_6$) δ 7.72 (d, J=8 Hz, 1H), 7.41 (d, J=8 Hz, 1H), 7.23 (t, J=7 Hz, 1H), 7.00 (t, J=7 Hz, 1H), 5.23 (d, J=5 Hz, 1H), 3.84 (m, 1H), 3.77 (m, 1H), 3.38-3.21 (m, 3H) 1.02 (s 3H), 1.00 (s, 3H). Cl-LCMS m/z 249 (M+H).

Example 81b

Preparation of (3S)-1-(1,3-benzothiazol-2-yl)-4,4-dimethylpyrrolidinyl (1S)-1-[1-hydroxy-2-oxo-2-(1H-pyrazol-5-ylamino)ethyl]pentylcarbamate

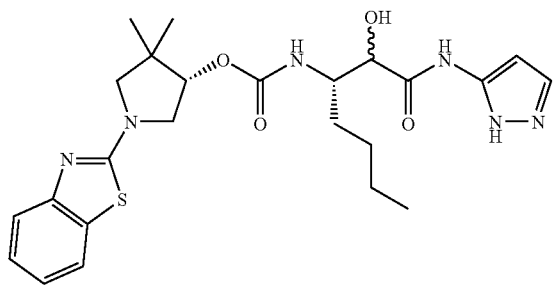

(3S)-1-(1,3-Benzothiazol-2-yl)-4,4-dimethylpyrrolidinyl (1S)-1-[1-hydroxy-2-oxo-2-(1H-pyrazol-5-ylamino)ethyl]pentylcarbamate (95 mg, 20%) was obtained from (3S)-1-(1,3-benzothiazol-2-yl)-4,4-dimethyl-3-pyrrolidinol (230 mg, 0.93 mmol) following the procedure outlined in example 71i. $^1$H NMR (400 MHz, DMSO-$d_6$) δ 12.33 (m, 1H); 9.74 (m) and 9.55 (m) total 1H, 7.75 (d, J=7 Hz, 1H); 7.58 (s, 1H); 7.44 (m, 1H); 7.25 (t, J=8 Hz, 1H); 7.04 (t, J=8 Hz, 1H); 6.47 (m, 1H); 5.94 (m) and 5.59 (m) total 1H, 4.80 (m, 1H); 4.06-3.85 (m, 4H); 3.40 (m overlapping water peak 3H) 1.55-0.75 (m, 15H). Cl-LCMS m/z 501 (M+H).

Example 81c

Preparation of (3S)-1-(1,3-benzothiazol-2-yl)-4,4-dimethylpyrrolidinyl (1S)-1-[oxo(1H-pyrazol-5-ylamino)acetyl]pentylcarbamate

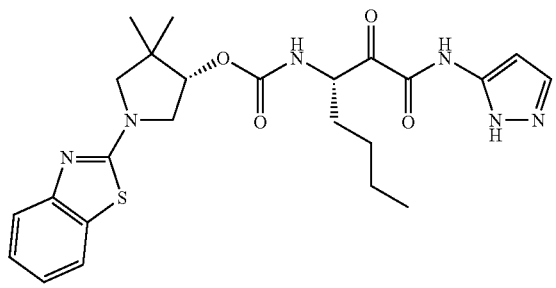

(3S)-1-(1,3-Benzothiazol-2-yl)-4,4-dimethylpyrrolidinyl (1S)-1-[oxo(1H-pyrazol-5-ylamino)acetyl]pentylcarbamate (60 mg, 67%) was obtained from (3S)-1-(1,3-benzothiazol-2-yl)-4,4-dimethylpyrrolidinyl (1S)-1-[1-hydroxy-2-oxo-2-(1H-pyrazol-5-ylamino)ethyl]pentylcarbamate (90 mg, 0.18 mmol) following the procedure outlined in example 71j. $^1$H NMR (300 MHz, DMSO-$d_6$) δ 12.48 (m, 1H), 10.89 (s, 1H), 7.76 (t, J=7 Hz, 2H), 7.65 (s, 1H), 7.44 (d, J=8 Hz, 1H), 7.25 (t, J=8 Hz, 1H), 7.03 (t, J=8 Hz, 1H), 6.51 (s, 1H), 4.85 (m, 2H), 3.96 (m, 1H), 3.50-3.20 (m, 3H), 1.71 (m, 1H), 1.53-1.20 (m, 5H), 1.09 (s, 3H), 1.07 (s, 3H), 0.83 (t, J=7 Hz, 3H). ES-LCMS m/z 499 (M+H) HRMS $C_{24}H_{30}N_6O_4S_1$ m/z 499.2128 (M+)$_{Cal}$. 499.2141 (M+H)$_{Obs}$.

Example 82

(3S)-4,4-Dimethyl-1-[5-(trifluoromethyl)-1,3,4-thiadiazol-2-yl]pyrrolidinyl-(1S)-1-[oxo(1H-pyrazol-5-ylamino)acetyl]pentylcarbamate

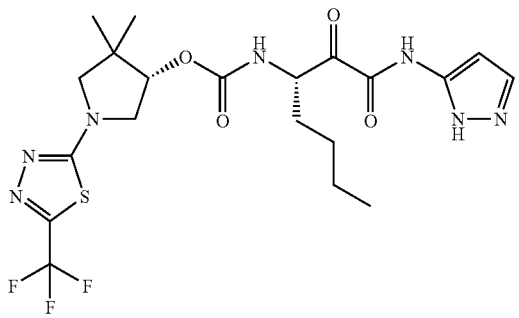

Example 82a

Preparation of (3S)-4,4-dimethyl-1-[5-(trifluoromethyl)-1,3,4-thiadiazol-2-yl]-3-pyrrolidinol

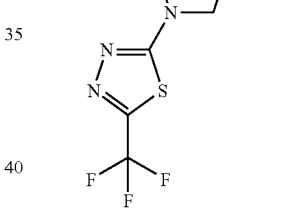

To 3 mL of 48% aqueous HBr was added 1.0 g (5.9 mmol) of 5-(trifluoromethyl)-1,3,4-thiadiazol-2-amine with stirring. The mixture was cooled in a salt ice-water bath, and 2.27 mL (44 mmol) of bromine was added slowly dropwise. The salt ice-water bath was replaced with an ice-water bath and a solution of 1.05 g (15 mmol) of sodium nitrite in 1.5 mL of water was added slowly dropwise. The reaction mixture was stirred for 1 h and then let warm to room temperature. The mixture was neutralized with 5M aqueous sodium hydroxide, and the resulting precipitate was filtered off. The filtrate was extracted with chloroform, and the extract was dried over magnesium sulfate before being concentrated to afford 750 mg (54%) of 2-bromo-5-(trifluoromethyl)-1,3,4-thiadiazole, 330 mg (1.4 mmol) of which was added to a solution of 240 mg (1.6 mmol) of (3S)-4,4-dimethyl-3-pyrrolidinol hydrochloride and 0.73 mL (4.2 mmol) of N,N-diisopropylethylamine in 5 mL of isopropanol. The reaction mixture was heated at reflux for 2 h, and then concentrated. The residue was purified by silica gel chromatography eluting with 0.3:9.7 methanol dichloromethane to afford 328 mg (88%) of (3S)-4,4-dimethyl-1-[5-(trifluoromethyl)-1,3,4-thiadiazol-2-yl]-3-pyrrolidinol. $^1$H NMR (300 MHz, DMSO-$d_6$) δ 5.31 (d, J=5 Hz, 1H), 3.89-3.76 (m, 2H), 3.40-3.22 (m, 3H), 1.02 (s, 3H), 1.00 (s, 3H). Cl-LCMS m/z 268 (M+H).

Example 82b

Preparation of (3S)-4,4-dimethyl-1-[5-(trifluoromethyl)-1,3,4-thiadiazol-2-yl]pyrrolidinyl (1S)-1-[1-hydroxy-2-oxo-2-(1H-pyrazol-5-ylamino)ethyl]pentylcarbamate

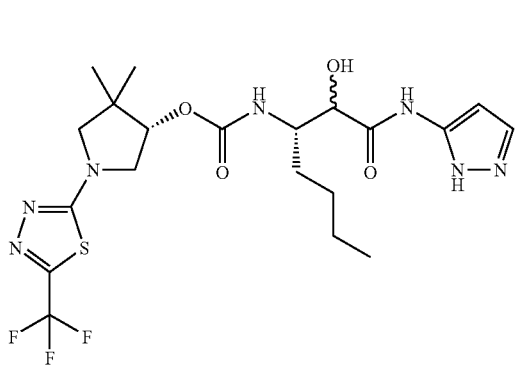

(3S)-4,4-Dimethyl-1-[5-(trifluoromethyl)-1,3,4-thiadiazol-2-yl]pyrrolidinyl (1S)-1-[1-hydroxy-2-oxo-2-(1H-pyrazol-5-ylamino)ethyl]pentylcarbamate (30 mg, 21%) was obtained from (3S)-4,4-dimethyl-1-[5-(trifluoromethyl)-1,3,4-thiadiazol-2-yl]-3-pyrrolidinol (330 mg, 1.2 mmol) following the procedure outlined in example 71i. Cl-LCMS m/z 520 (M+H).

Example 82c

Preparation of (3S)-1-(1,3-benzothiazol-2-yl)-4,4-dimethylpyrrolidinyl (1S)-1-[oxo(1H-pyrazol-5-ylamino)acetyl]pentylcarbamate

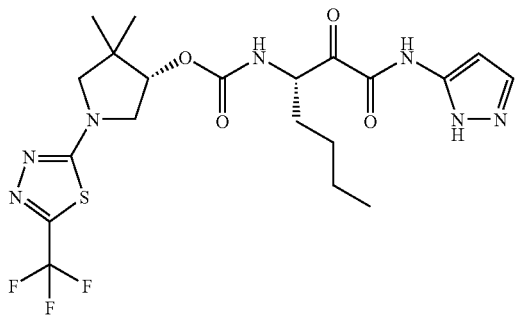

(3S)-1-(1,3-Benzothiazol-2-yl)-4,4-dimethylpyrrolidinyl (1S)-1-[oxo(1H-pyrazol-5-ylamino)acetyl]pentylcarbamate (25 mg, 84%) was obtained from (3S)-4,4-dimethyl-1-[5-(trifluoromethyl)-1,3,4-thiadiazol-2-yl]pyrrolidinyl (1S)-1-[1-hydroxy-2-oxo-2-(1H-pyrazol-5-ylamino)ethyl]pentylcarbamate (30 mg, 0.058 mmol) following the procedure outlined in example 71j. $^1$H NMR (300 MHz, DMSO-d$_6$, Temp=100° C.) δ 10.41 (m, 1H), 7.57 (s, 1H), 7.42 (m, 1H), 6.46 (m, 1H), 4.87 (m, 2H), 3.99 (m, 1H), 3.51-3.38 (m, 3H), 1.81 (m, 1H), 1.56 (m, 1H), 1.32 (m, 4H), 1.10 (m, 6H), 0.85 (m, 3H). Cl-LCMS m/z 518 (M+H) HRMS C$_{20}$H$_{26}$N$_7$O$_4$S$_1$F$_3$ m/z 518.1797 (M+H)$_{Cal.}$ 518.1805 (M+H)$_{Obs.}$.

Example 83

(3S)-4,4-Dimethyltetrahydro-3-furanyl 1-(oxo{[(1R)-1-phenylethyl]amino}acetyl)pentylcarbamate

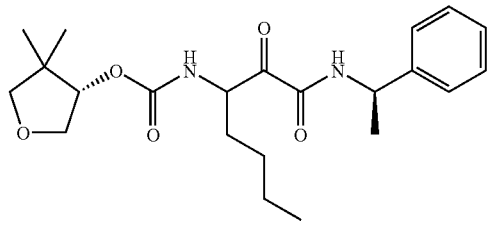

Example 83a

Preparation of 2-[(4S)-2,2-diethyl-1,3-dioxolan-4-yl]-2-methylpropyl 4-methylbenzenesulfonate

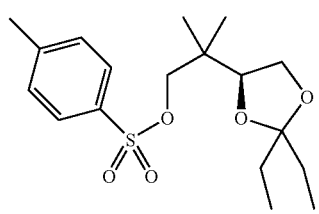

To a solution of 670 mg (5.0 mmol) of (2S)-3,3-dimethyl-1,2,4-butanetriol in 10 mL of tetrahydrofuran and 5 mL of 3-pentanone was added 40 mg of p-toluensulfonic acid, and the reaction mixture was heated at 70° C. overnight. It was concentrated and the residue was purified by silica gel chromatography eluting with 3:7 ether:hexanes to afford 880 mg of a liquid. The liquid was dissolved in 5 mL of pyridine and cooled to 0° C. before 1.6 g (8.7 mmol) of p-toluenesulfonyl chloride was added. The reaction mixture was allowed to warm to room temperature, and was stirred for 5 hours before being left to stand at 4° C. for 72 h. It was then diluted with water, and extracted with ether. The extracts were washed with saturated sodium bicarbonate and brine, and concentrated under reduced pressure. The residue was purified by silica gel chromatography eluting with 2.5:7.5 ether:dichloromethane to afford 930 mg (52%) of 2-[(4S)-2,2-diethyl-1,3-dioxolan-4-yl]-2-methylpropyl 4-methylbenzenesulfonate. $^1$H NMR (300 MHz, CDCl$_3$) δ 7.61 (dd, J=13 Hz, J=8 Hz, 4H), 3.81-3.97 (m, 4H), 3.65 (t, J=7 Hz, 1H), 2.49 (s, 3H), 1.65-1.53 (m, 4H), 0.93 (d, J=7 Hz, 6H), 0.87 (dt, J=7 Hz, J=2 Hz, 6H). Cl-GCMS m/z 357 (M+H).

Example 83b

Preparation of (3S)-tetrahydro-3-furanol

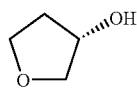

A solution of 540 mg (1.5 mmol) of 2-[(4S)-2,2-diethyl-1,3-dioxolan-4-yl]-2-methylpropyl 4-methylbenzenesulfonate in 2 mL of 1N hydrochloric acid and 4 mL of tetrahydrofuran was stirred at room temperature for 5 d. Solid sodium chloride was added to the reaction mixture, which was then extracted with ethyl acetate. The combined ethyl acetate layers were dried over magnesium sulfate and concentrated. The residue was purified by silica gel chromatography eluting with 1:1 ethyl acetate:hexanes to afford 120 mg (69%) of (3S)-tetrahydro-3-furanol. $^1$H NMR (400 MHz, DMSO-$d_6$) δ 4.83 (m, 1H), 3.89 (dd, J=9 Hz, J=5 Hz, 1H), 3.62 (dd, J=5 Hz, J=3 Hz), 3.38 (dd, J=9 Hz, J=3 Hz, 1H), 3.36 (1/2Abq, J=8 Hz, 1H), 3.28 (1/2Abq, J=8 Hz, 1H), 0.88 (s, 3H), 0.85 (s, 3H).

Example 83c

Preparation of (3S)-4,4-dimethyltetrahydro-3-furanyl 1-(1hydroxy-2-oxo-2-{[(1R)-1-phenylethyl]amino}ethyl)pentylcarbamate

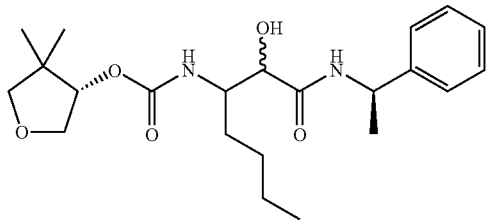

(3S)-4,4-dimethyltetrahydro-3-furanyl 1-(1-hydroxy-2-oxo-2-{[(1R)-1-phenylethyl]amino}ethyl)pentylcarbamate was prepared in 47% yield from 3-(3S)-tetrahydro-3-furanol and 3-amino-2-hydroxy-N-[(1R)-1-phenylethyl]heptanamide following the procedure outlined in example 3c. $^1$H NMR (300 MHz, CDCl$_3$) δ 7.40-7.31 (m, 5H), 6.97 (d, J=7 Hz, 1H), 5.40 (d, J=9 Hz, 1H), 5.15 (qnt, J=14 Hz, 1H), 4.74 (d, J=3 Hz, 1H), 4.24-4.17 (m, 2H), 3.87 (m, 1H), 3.73 (dd, J=11 Hz, J=2 Hz, 1H), 3.55 (s, 2H), 1.64 (m, 5H), 1.53 (d, J=7 Hz, 3H), 1.33 (m, 4H), 1.09 (s, 3H), 0.98-0.89 (m, 3H). ES-LCMS m/z 407 (M+H).

Example 83d

Preparation of (3S)-4,4-dimethyltetrahydro-3-furanyl 1-(oxo{[(1R)-1-phenylethyl]amino}acetyl)pentylcarbamate

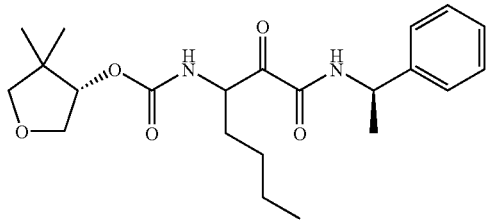

(3S)-4,4-Dimethyltetrahydro-3-furanyl 1-(oxo{[(1R)-1-phenylethyl]amino}acetyl)pentylcarbamate was prepared in 53% yield from (3S)-4,4-dimethyltetrahydro-3-furanyl 1-(1-hydroxy-2-oxo-2-{[(1R)-1-phenylethyl]amino}ethyl)pentylcarbamate following the procedure outlined in example 3d. $^1$H NMR (300 MHz, DMSO-$d_6$) δ 9.20 (m, 1H), 7.68 (d, J=7 Hz, 1H), 7.39-7.21 (m, 5H), 4.99 (qnt, J=7 Hz, 1H), 4.78 (m, 1H), 4.68 (m, 1H), 4.10 (m, 1H), 3.59 (m, 1H), 1.38 (m, 2H), 1.80-1.18 (m, 9H), 1.04-0.79 (m, 9H). ES-LCMS m/z 405 (M.

Biological Data

The compounds of the present invention elicit important and measurable pharmacological responses. Each of the compounds exemplified in the Examples section bind with high affinity (IC$_{50}$<10 μM) to the cathepsin K enzyme, as described by the cathepsin K assay recited below.

All assays for cathepsin K were carried out with human and rat recombinant enzyme. Assays for cathepsins S & V were also carried out with human recombinant enzyme. Assays for human cathepsins B, H, and L were carried out with enzyme, purchased from Athens Research and Technology, Inc., prepared from human liver tissue. Standard assay conditions for the determination of kinetic constants used a fluorogenic peptide substrate, typically (5S,8S)-13-amino-5-benzyl-13-imino-3-methylene-N-(4-methyl-2-oxo-2H-chromen-7-yl)-6-oxo-1-phenyl-2-oxa-4,7,12triazatridecane-8-carboxamide (Cbz-Phe-Arg-AMC), and were determined in 100 mM sodium acetate at pH 5.5 containing 10 mM dithiothreitol and 120 mM sodium chloride. A stock substrate solution of Cbz-Phe-Arg-AMC was prepared at a concentration of 50 mM in dimethyl sulfoxide. This substrate was diluted into the assay for a final substrate concentration of 10 μM in the rat cathepsin K, human cathepsin K, and human cathepsin B assays; a final substrate concentration of 5 μM in the human cathepsin L assay; and a final substrate concentration of 2 μM in the human cathepsin V assay.

A stock substrate solution of benzyl (1S)-1-{[((1S)-1-{[((1S)-4-{[amino(imino)methyl]amino}-1-{[(4-methyl-2-oxo-2H-chromen-7-yl)amino]carbonyl}-butyl)amino]carbonyl}-2-methylpropyl)amino]carbonyl}-2-methylpropylcarbamate (Cbz-Val-Val-Arg-AMC) was prepared at a concentration of 10 mM in dimethyl sulfoxide. This substrate was diluted into the assay for a final substrate concentration of 10 μM in the human cathepsin S assay.

A stock substrate solution of (2S)-2-amino-5-{[amino(imino)methyl]amino}-N-(2-naphthyl)pentanamide hydrochloride (L-Arg-β-naphthalamide-HCl) was prepared at a concentration of 10 mM in dimethyl sulfoxide. This substrate was diluted into the assay for a final substrate concentration of 50 μM in the cathepsin H assay.

All assays contained 10% dimethyl sulfoxide. Independent experiments found that this level of dimethyl sulfoxide had no effect on kinetic enzymatic constants. All assays were conducted at 30° C. Product fluorescence (excitation at 360 nm; emission at 440 nm, (except cathepsin H which used excitation at 340 nm; emission at 420 nm)) was monitored with a PerSeptive Biosystems Cytofluor II fluorescence plate reader. Product progress curves were generated over 2.3 h monitoring the formation of 7-amino-4-methylcoumarin product (or β-naphthalamide for cathepsin H).

Human and rat Cathepsin K:

Scale-Up and Fermentation: The method of O'Reilly et al. (1994) was used for baculovirus expression with the following details. Two liters of *Spodoptera frugiperda* (Sf-9) cells (ATCC) were grown in Grace's Supplemented medium (Life Technologies) supplemented with 2 g/L glucose, 10% fetal bovine serum (HyClone) and 0.1% pluronic F-68 (Life Technologies). Cells were grown in a 6 L shake flask at 150 RPM at 28° C. for 24 h to a density of 106 cells/mL, and then infected at a multiplicity of infection (MOI) of 0.1. The cells continued to grow for 72 h post-infection, before the virus was harvested by centrifugation at 1400×g for 30 min. Virus was titered as described (Summers and Smith, 1987).

One and one-half liters of *Trichoplusia ni* (*T. ni*) High Five (™) cells [JRH Biosciences, Woodland, Calif. (adapted to suspension and serum-free medium)] grown in Excell 405 ™ medium (JRH Biosciences) with 50 ug/mL gentamicin (Life Technologies) were added to a 15 L stirred tank reactor (Quark Enterprises, Inc) at a density of ~0.5×106 cells/mL. The cells were grown for 24 h at 28° C., 50 RPM, and 50% dissolved oxygen. Cells were then infected at a density of ~106 cells/mL with an MOI of 1 and grown for 48 h post-infection. Media were separated from cells at a rate of 1 L/min using the Centritech 100 ™ continuous-flow centrifuge (DuPont) operating at 200×g.

Protein Purification: Media (human and rat) were filtered through a Whatman 3 filter, and then loaded onto a 25 mL. Poros HS II (26 mm×47 mm) cation exchange column equilibrated in 25 mM sodium acetate at pH 5.5 (equilibration buffer). The column was washed until the absorbance reached the baseline value, and then the protein was eluted with a linear gradient from 0-2 M sodium chloride in the equilibration buffer. Column fractions were analyzed by SDS-PAGE, N-terminal sequencing, and mass spectrometry. Fractions containing the proform of cathepsin K were pooled and frozen at −80° C. The proform was concentrated in an Amicon Centriprep 10 and fractionated with a Superdex 75 column (26 mm×600 mm, Pharmacia) equilibrated in 400 mM sodium chloride, 25 mM sodium acetate at pH 5.5.

Cathepsin K Activation: The proform of cathepsin K was converted to mature cathepsin K by brief exposure to pH 4 in the presence of 5 mM L-cysteine. Typically, 5 mM L-cysteine was added to 10 mL of approximately 1 mg/mL procathepsin K. One mL of this solution was diluted ten-fold into 450 mM sodium acetate at pH 4.0 containing 5 mM L-cysteine. This solution was reacted at 23° C. for 2 min before neutralization with 2 mL, 1.8 M sodium acetate at pH 6.0. The neutralized sample was added to the remaining 9 mL of procathepsin K. The mixture was incubated at 4° C. for 2-3 days. The activated cathepsin K was chromatographed on a Poros HS II column as described above.

Inhibition Studies

Potential inhibitors were evaluated using the progress curve method. Assays were carried out in the presence of variable concentrations of test compound. Reactions were initiated by addition of buffered solutions of inhibitor and substrate to enzyme. Data analysis was conducted according to one of two procedures depending on the appearance of the progress curves in the presence of inhibitors. For those compounds whose progress curves were linear, the enzymatic activity (RATE) was plotted against the concentration of test compound, including inhibitor concentration of zero ([I]=0), and the $IC_{50}$ determined from a fit of equation 1 to the data, $$\text{RATE} = V_{max}/(1+([I]/IC50)) \quad (1)$$

where $V_{max}$ is the best fit estimate of the maximal enzymatic activity. $K_i$ values were calculated from $IC_{50}$ values using equation 2 assuming a competitive model.

$$K_i = IC_{50} * \left[1 - \frac{S}{(S+K_m)}\right] \quad (2)$$

For those compounds whose progress curves showed downward curvature characteristic of time-dependent inhibition, the data from individual sets was analyzed using the computer program DynaFit (Kuzmic, P. *Anal. Biochem.* 1996, 237. 260-273) to give Ki values according to the following kinetic mechanism:

TABLE 1

| = Inhibition of Cathepsin K ($IC_{50}$ in nM) Cathepsin Inhibitory Activity | |
|---|---|
| Example | h Cat K $IC_{50}$ |
| 1 | +++ |
| 2 | +++ |
| 3 | +++ |
| 4 | ++ |
| 5 | ++ |
| 6 | +++ |
| 6 | ++ |
| 7 | ++ |
| 8 | ++ |
| 9 | ++ |
| 10 | ++ |
| 11 | +++ |
| 12 | +++ |
| 13 | ++ |
| 14 | +++ |
| 15 | +++ |
| 16 | +++ |
| 17 | +++ |
| 18 | +++ |
| 19 | ++ |
| 20 | +++ |
| 21 | +++ |
| 22 | +++ |
| 23 | ++ |
| 24 | ++ |
| 25 | ++ |
| 26 | ++ |
| 27 | ++ |
| 28 | ++ |
| 29 | ++ |
| 30 | ++ |
| 31 | ++ |
| 32 | ++ |
| 33 | ++ |
| 34 | ++ |
| 35 | +++ |
| 36 | +++ |
| 37 | ++ |
| 38 | ++ |
| 39 | ++ |
| 40 | +++ |
| 41 | +++ |
| 42 | ++ |
| 43 | ++ |
| 44 | ++ |
| 45 | ++ |
| 46 | +++ |
| 47 | ++ |
| 48 | + |
| 49 | ++ |
| 50 | ++ |
| 51 | +++ |
| 52 | ++ |
| 53 | +++ |
| 54 | ++ |
| 55 | ++ |
| 56 | ++ |
| 57 | +++ |
| 58 | ++ |
| 59 | ++ |
| 60 | ++ |
| 61 | ++ |
| 62 | ++ |
| 63 | +++ |
| 64 | +++ |
| 65 | +++ |
| 66 | ++ |
| 67 | ++ |
| 68 | ++ |

TABLE 1-continued

= Inhibition of Cathepsin K ($IC_{50}$ in nM)
Cathepsin Inhibitory Activity

| Example | h Cat K $IC_{50}$ |
|---|---|
| 69 | ++ |
| 70 | +++ |
| 71 | ++++ |
| 72 | +++ |
| 73 | ++ |
| 74 | ++ |
| 75 | ++ |
| 76 | + |
| 77 | +++ |
| 78 | ++ |
| 79 | ++ |
| 80 | ++ |
| 81 | ++++ |
| 82 | ++++ |
| 83 | ++ |

+ Inhibitors (1,000-100 nM)
++ Potent inhibitors (100-10 nM)
+++ More potent inhibitors (10-1 nM)
++++ Most potent inhibitors (1-0.1 nM)

TABLE 2

Inhibition of Cathepsins B, H, K, L, S, and V ($IC_{50}$ in nM)

| Example | h Cat B $IC_{50}$ | h Cat H $IC_{50}$ | h Cat K $IC_{50}$ | r Cat K $IC_{50}$ | h Cat L $IC_{50}$ | h Cat S $IC_{50}$ | h Cat V $IC_{50}$ |
|---|---|---|---|---|---|---|---|
| 71 | + | + | ++++ | ++ | + | +++ | ++ |
| 82 | + | + | ++++ | ++ | + | ++ | ++ |

+ Inhibitors (1,000-100 nM)
++ Potent inhibitors (100-10 nM)
+++ More potent inhibitors (10-1 nM)
++++ Most potent inhibitors (1-0.1 nM)

We claim:

1. A compound of Formula (I):

(I)

or a salt or solvate thereof wherein
A is the group defined by $(Q^4)_p$-$(Q^3)_n$-$(Q^2)_m$-$(Q^1)$-, wherein
  $Q^1$ is heterocyclyl or heterocyclylene,
  $Q^2$ is OC(O), C(O), N(H)C(O), C(O)N(H)C(O), S(O)$_2$N(H)C(O), S(O)$_2$, or N(H)S(O)$_2$ and m is 0 or 1,
  $Q^3$ is $C_1$-$C_6$ alkyl, $C_1$-$C_6$ haloalkyl, $C_3$-$C_7$ cycloalkyl, aralkyl, aralkylene, aryl, arylene, heteroaryl, heteroarylene, heterocyclyl, or heterocyclylene, and n is 0 or 1, and
  $Q^4$ is $C_1$-$C_6$ alkyl, $C_1$-$C_6$ haloalkyl, aryl, aryloxy, heteroaryl, halo, or cyano, and p is 0, 1, or 2;
D is O or S;
R is hydrogen or —N($R^1$)—$R^2$—$R^3$;
$R^1$ is hydrogen or $C_1$-$C_6$ alkyl;
$R^2$ is C(O), C(O)O, C(O)N(H), SO$_2$, or SO$_2$N(H);
$R^3$ is hydrogen or $C_1$-$C_6$ alkyl;
Z is the group defined by —(X)$_t$—(X$^1$), wherein
  X is C(R')(R"), wherein R' is hydrogen or $C_1$-$C_6$ alkyl, R" is hydrogen or $C_1$-$C_6$ alkyl, and t is 0, 1, or 2; and
  $X^1$ is aryl, heteroaryl, or heterocyclyl.

2. A compound of Formula (II):

II or a salt or solvate thereof wherein
A' is the group defined by $(Q^4)_p$-$(Q^3)_n$-$(Q^2)_m$, wherein
  $Q^2$ is OC(O), C(O), N(H)C(O), C(O)N(H)C(O), S(O)$_2$N(H)C(O), S(O)$_2$, or N(H)S(O)$_2$ and m is 0 or 1,
  $Q^3$ is $C_1$-$C_6$ alkyl, $C_1$-$C_6$ haloalkyl, $C_3$-$C_7$ cycloalkyl, aralkyl, aralkylene, aryl, arylene, heteroaryl, heteroarylene, heterocyclyl, or heterocyclylene, and n is 0 or 1, and
  $Q^4$ is $C_1$-$C_6$ alkyl, $C_1$-$C_6$ haloalkyl, aryl, aryloxy, heteroaryl, halo, or cyano, and p is 0, 1, or 2;
$R^a$ is hydrogen or oxo;
$R^b$ is hydrogen or $C_1$-$C_6$ alkyl;
$R^c$ is hydrogen or $C_1$-$C_6$ alkyl;
R is hydrogen or —N($R^1$)—$R^2$—$R^3$;
$R^1$ is hydrogen or $C_1$-$C_6$ alkyl;
$R^2$ is C(O), C(O)O, C(O)N(H), SO$_2$, or SO$_2$N(H);
$R^3$ is hydrogen or $C_1$-$C_6$ alkyl;
Z is the group defined by —(X)$_t$—(X$^1$), wherein
  X is C(R')(R"), wherein R' is hydrogen or $C_1$-$C_6$ alkyl, R" is hydrogen or $C_1$-$C_6$ alkyl, and t is 0, 1, or 2; and
  $X^1$ is aryl, heteroaryl, or heterocyclyl.

3. A compound as claimed in claim 1, wherein m is 0, n is 0, and p is 0 and A is ($Q^1$)-.

4. A compound as claimed in claim 1, wherein n is 0, p is 0 and A is ($Q^2$)$_m$-($Q^1$)-.

5. A compound as claimed in claim 1, wherein p is 0 and A is ($Q^3$)$_n$-($Q^2$)$_m$-($Q^1$)-.

6. A compound as claimed in claim 1, wherein m is 0, n is 1, p is 0, 1, or 2, and A is ($Q^4$)$_p$-($Q^3$)-($Q^1$)-.

7. A compound as claimed in claim 1, wherein $Q^1$ is heterocyclyl.

8. A compound as claimed in claim 1, wherein $Q^1$ is heterocyclylene.

9. A compound as claimed in claim 1, wherein $Q^1$ is selected from the group

-continued

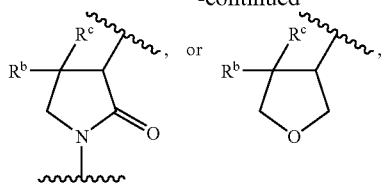

wherein $R^b$ is hydrogen or $C_1$-$C_6$ alkyl and $R^c$ is hydrogen or $C_1$-$C_6$ alkyl.

10. A compound as claimed in claim 1, wherein $Q^1$ is selected from the group

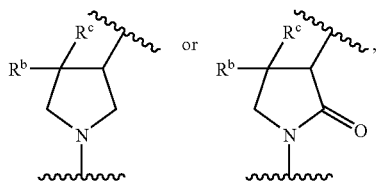

wherein $R^b$ is hydrogen or $C_1$-$C_6$ alkyl and $R^c$ is hydrogen or $C_1$-$C_6$ alkyl.

11. A compound as claimed in claim 1, wherein $Q^1$ is

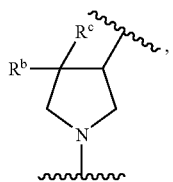

wherein $R^b$ is hydrogen or $C_1$-$C_6$ alkyl and $R^c$ is hydrogen or $C_1$-$C_6$ alkyl.

12. A compound as claimed in claim 1, wherein $Q^1$ is selected from the group

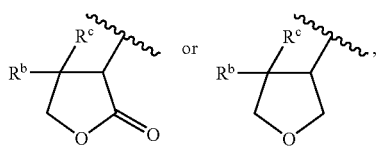

wherein $R^b$ is hydrogen or $C_1$-$C_6$ alkyl and $R^c$ is hydrogen or $C_1$-$C_6$ alkyl.

13. A compound as claimed in claim 1, wherein $Q^1$ is selected from the group

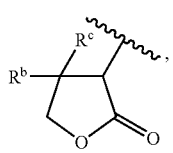

wherein $R^b$ is hydrogen or $C_1$-$C_6$ alkyl and $R^c$ is hydrogen or $C_1$-$C_6$ alkyl.

14. A compound as claimed in claim 1 wherein m is 1 and $Q^2$ is OC(O), C(O), N(H)C(O), S(O)$_2$, or N(H)S(O)$_2$.

15. A compound as claimed in claim 1 wherein m is 1 and $Q^2$ is OC(O) or C(O).

16. A compound as claimed in claim 1 wherein m is 1 and $Q^2$ is C(O).

17. A compound as claimed in claim 1 wherein m is 1 and $Q^2$ is N(H)C(O).

18. A compound as claimed in claim 1, wherein m is 1 and $Q^2$ is S(O)$_2$.

19. A compound as claimed in claim 1 wherein n is 1 and $Q^3$ is aryl or arylene, heteroaryl or heterarylene, heterocyclyl or heterocyclylene, or aralkyl or aralkylene.

20. A compound as claimed in claim 1 wherein, $Q^3$ is aryl or arylene.

21. A compound as claimed in claim 1 wherein $Q^3$ is selected from the group

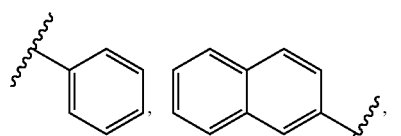

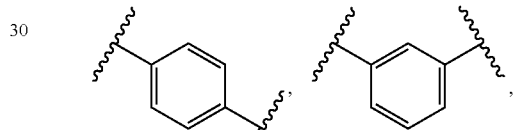

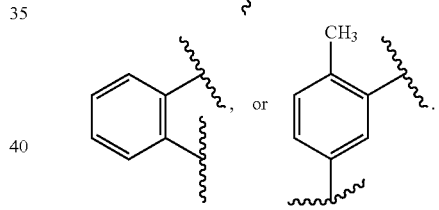

22. A compound as claimed in claim 1 wherein $Q^3$ is

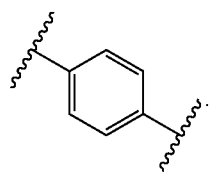

23. A compound as claimed in claim 1 wherein $Q^3$ is aralkyl or aralkylene.

24. A compound as claimed in claim 1 wherein $Q^3$ is selected from the group

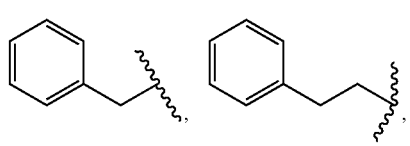

-continued
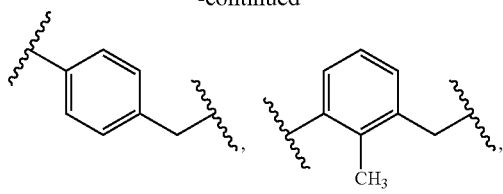
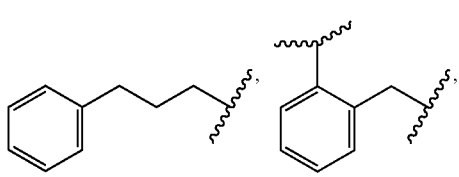
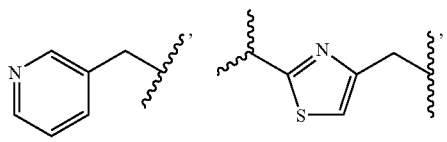
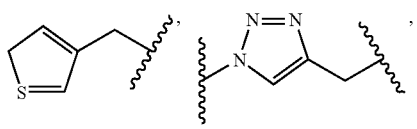
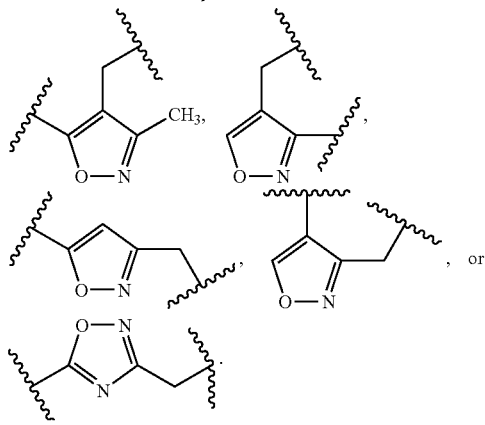
25. A compound as claimed in claim 1 wherein $Q^3$ is selected from the group
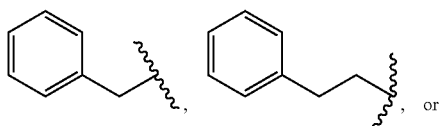
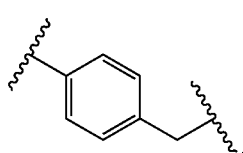
26. A compound as claimed in claim 2, wherein $Q^3$ is selected from the group
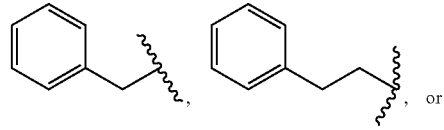
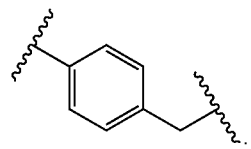
27. A compound as claimed in claim 1 wherein $Q^3$ is heteroaryl or heteroarylene.
28. A compound as claimed in claim 1 wherein $Q^3$ is selected from the group
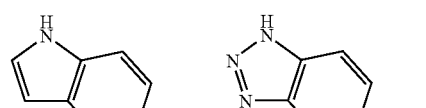
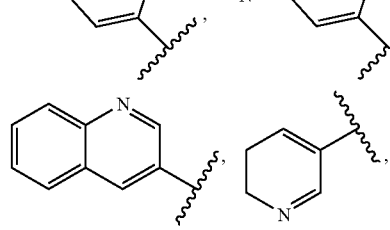
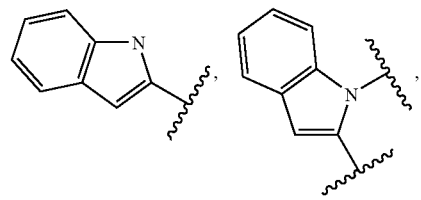
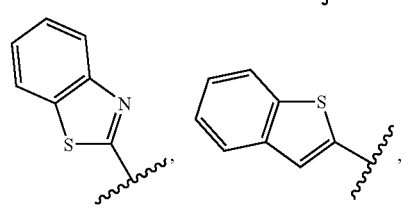
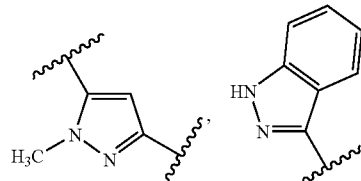
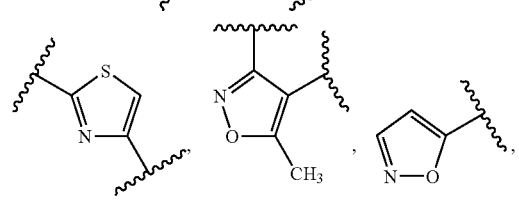

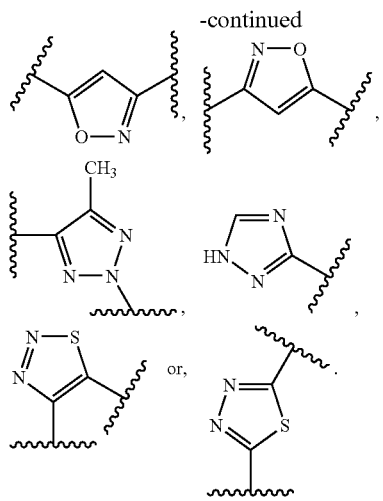

29. A compound as claimed in claim 1 wherein Q³ is heterocyclyl or heterocyclylene.

30. A compound as claimed in claim 1 wherein Q³ is selected from the group

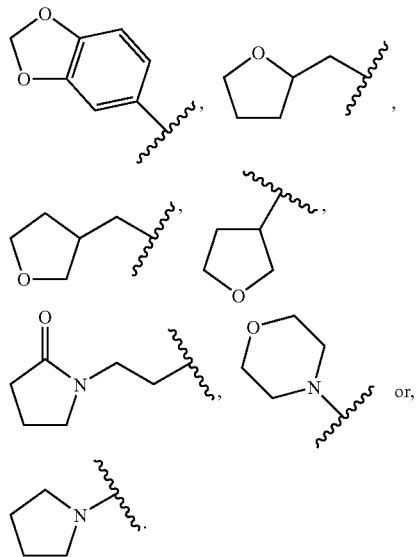

31. A compound as claimed in claim 1 wherein Q⁴ is methyl, tert-butyl, —CF₃, phenyl, phenoxy, isoxazolyl, thiadiazolyl, thienyl, pyrazinyl, fluoro, chloro, cyano, and p is 1 or 2.

32. A compound as claimed in claim 1 wherein Q⁴ is methyl, tert-butyl, —CF₃, phenyl, phenoxy, and fluoro and p is 1 or 2.

33. A compound as claimed in claim 1 wherein Q⁴ is methyl, and p is 1.

34. A compound as claimed in claim 1 wherein D is O.

35. A compound as claimed in claim 1 wherein R is hydrogen.

36. A compound as recited in claim 1 wherein m is 0 and Z is —(X¹).

37. A compound as claimed in claim 1 wherein X is CHR", R" is hydrogen and m is 0, 1, or 2.

38. A compound as claimed in claim 1 wherein X is CHR", R" is —CH₃ and m is 1.

39. A compound as claimed in claim 1 wherein X¹ is aryl.

40. A compound as claimed in claim 1 wherein X¹ is

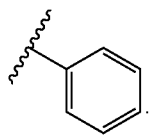

41. A compound as claimed in claim 1 wherein X¹ is heteroaryl or heterocyclyl.

42. A compound as claimed in claim 1 wherein X¹ is

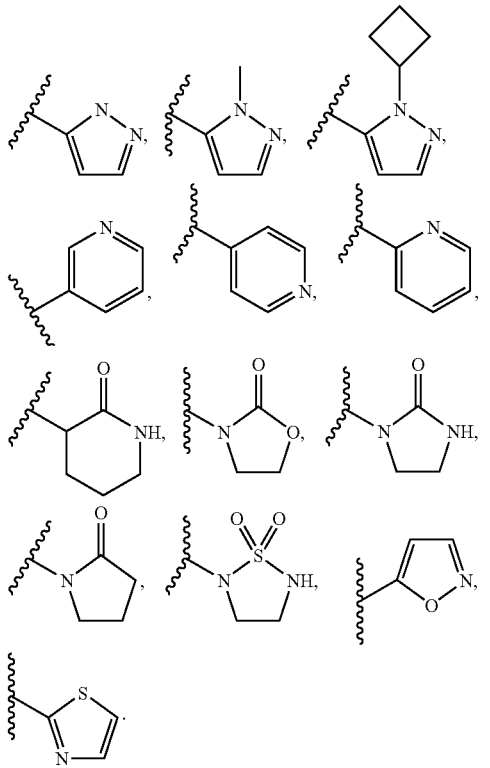

43. A compound as claimed in claim 1, selected from the group consisting of:

(3S)-4,4-dimethyl-2-oxotetrahydro-3-furanyl (1S)-1-(oxo{[(1R)-1-phenylethyl]amino}acetyl)pentylcarbamate;

(3S)-4,4-dimethyl-2-oxotetrahydro-3-furanyl (1S)-5-{[(methylamino) carbonyl]amino}-1-(oxo{[(1R)-1-phenylethyl]amino}acetyl)pentylcarbamate;

(4S)-4-ethyl-4-methyl-2-oxotetrahydro-3-furanyl (1S)-1-(oxo{[(1R)-1-phenylethyl]amino}acetyl)pentylcarbamate;

1-benzyl-4,4-dimethyl-2-oxo-3-pyrrolidinyl (1S)-1-(oxo{[(1R)-1-phenylethyl]amino}acetyl)pentylcarbamate;

benzyl 4,4-dimethyl-2-oxo-3-[({[(1S)-1-(oxo{[(1R)-1-phenylethyl]amino}acetyl)pentyl]amino}carbonyl)oxy]-1-pyrrolidinecarboxylate;

3S)-4,4-dimethyl-2-oxopyrrolidinyl (1S)-1-(1-hydroxy-2-oxo-2-{[(1R)-1-phenylethyl]amino}ethyl)pentylcarbamate;

(3R)-4,4-dimethyl-2-oxopyrrolidinyl (1S)-1-(1-hydroxy-2-oxo-2-{[(1R)-1-phenylethyl]amino}ethyl)pentylcarbamate;

1,4,4-trimethyl-2-oxo-3-pyrrolidinyl (1S)-1-(oxo{[(1R)-1-phenylethyl]amino}acetyl)pentylcarbamate;

(3S)-1-benzyl-4,4-dimethylpyrrolidinyl 1-(oxo{[(1R)-1-phenylethyl]amino}acetyl)pentylcarbamate;

(3S)-1-benzoyl-4,4-dimethylpyrrolidinyl (1S)-1-(oxo{[(1R)-1-phenylethyl]amino}acetyl)pentylcarbamate;

(3S)-1-acetyl-4,4-dimethylpyrrolidinyl (1S)-1-(oxo{[(1R)-1-phenylethyl]amino}acetyl)pentylcarbamate;

(3S)-4,4-dimethyl-1-(phenylacetyl)pyrrolidinyl (1S)-1-(oxo{[(1R)-1-phenylethyl]amino}acetyl)pentylcarbamate;

(3S)-1-(5-isoxazolylcarbonyl)-4,4-dimethylpyrrolidinyl (1S)-1-(oxo{[(1R)-1-phenylethyl]amino}acetyl)pentylcarbamate;

(3S)-4,4-dimethyl-1-[(4-methyl-1,2,3-thiadiazol-5-yl)carbonyl]pyrrolidinyl (1S)-1-(oxo{[(1R)-1-phenylethyl]amino}acetyl)pentylcarbamate;

(3S)-1-[(3-tert-butyl-1-methyl-1H-pyrazol-5-yl)carbonyl]-4,4-dimethylpyrrolidinyl (1S)-1-(oxo{[(1R)-1-phenylethyl]amino}acetyl)pentylcarbamate;

(3S)-4,4-dimethyl-1-[(5-methyl-2-phenyl-2H-1,2,3-triazol-4-yl)carbonyl]pyrrolidinyl (1S)-1-(oxo{[(1R)-1-phenylethyl]amino}acetyl)pentylcarbamate;

(3S)-1-(1,3-benzodioxol-5-ylcarbonyl)-4,4-dimethylpyrrolidinyl (1S)-1-(oxo{[(1R)-1-phenylethyl]amino}acetyl)pentylcarbamate;

(3S)-1-(1-benzothien-2-ylcarbonyl)-4,4-dimethylpyrrolidinyl (1S)-1-(oxo{[(1R)-1-phenylethyl]amino}acetyl)pentylcarbamate;

(3S)-4,4-dimethyl-1-(2-naphthoyl)pyrrolidinyl (1S)-1-(oxo{[(1R)-1-phenylethyl]amino}acetyl)pentylcarbamate;

(3S)-4,4-dimethyl-1-[(5-methyl-3-isoxazolyl)carbonyl]pyrrolidinyl (1S)-1-(oxo{[(1R)-1-phenylethyl]amino}acetyl)pentylcarbamate;

(3S)-1-([1,1'-biphenyl]-4-ylcarbonyl)-4,4-dimethylpyrrolidinyl (1S)-1-(oxo{[(1R)-1-phenylethyl]amino}acetyl)pentylcarbamate;

(3S)-1-(1H-indol-5-ylcarbonyl)-4,4-dimethylpyrrolidinyl (1S)-1-(oxo{[(1R)-1-phenylethyl]amino}acetyl)pentylcarbamate;

(3S)-1-(1H-1,2,3-benzotriazol-5-ylcarbonyl)-4,4-dimethylpyrrolidinyl (1S)-1-(oxo{[(1R)-1-phenylethyl]amino}acetyl)pentylcarbamate;

(3S)-4,4-dimethyl-1-[(3-phenoxyphenyl)acetyl]pyrrolidinyl (1S)-1-(oxo{[(1R)-1-phenylethyl]amino}acetyl)pentylcarbamate;

(3S)-4,4-dimethyl-1-(4-phenylbutanoyl)pyrrolidinyl (1S)-1-(oxo{[(1R)-1-phenylethyl]amino}acetyl)pentylcarbamate;

(3S)-1-[(4-tert-butylphenyl)acetyl]-4,4-dimethylpyrrolidinyl (1S)-1-(oxo{[(1R)-1-phenylethyl]amino}acetyl)pentylcarbamate;

(3S)-4,4-dimethyl-1-{[2-(4-pyridinyl)-1,3-thiazol-4-yl]carbonyl}pyrrolidinyl (1S) -1-(oxo{[(1R)-1-phenylethyl]amino}acetyl)pentylcarbamate;

(3S)-4,4-dimethyl-1-[(5-methyl-3-phenyl-4-isoxazolyl)carbonyl]pyrrolidinyl (1S)-1-(oxo{[(1R)-1-phenylethyl]amino}acetyl)pentylcarbamate;

(3S)-4,4-dimethyl-1-[(1-methyl-1H-indol-2-yl)carbonyl]pyrrolidinyl (1S)-1-(oxo{[(1R)-1-phenylethyl]amino}acetyl)pentylcarbamate;

(3S)-4,4-dimethyl-1-(3-quinolinylcarbonyl)pyrrolidinyl 1-(oxo{[(1R)-1-phenylethyl]amino}acetyl)pentylcarbamate;

(3S)-1-([1,1'-biphenyl]-4-ylacetyl)-4,4-dimethylpyrrolidinyl (1S)-1-(oxo{[(1R)-1-phenylethyl]amino}acetyl)pentylcarbamate;

(3S)-4,4-dimethyl-1-[(2-phenoxyphenyl)acetyl]pyrrolidinyl (1S)-1-(oxo{[(1R)-1-phenylethyl]amino}acetyl)pentylcarbamate;

(3S)-1-(1H-indol-2-ylcarbonyl)-4,4-dimethylpyrrolidinyl (1S)-1-[(1R)-1-phenylethyl]amino}acetyl)pentylcarbamate;

(3S)-4,4-dimethyl-1-(3-pyridinylacetyl)pyrrolidinyl 1-(oxo{[(1R)-1-phenylethyl]amino}acetyl)pentylcarbamate;

(3S)-4,4-dimethyl-1-(1H-1,2,4-triazol-3-ylcarbonyl)pyrrolidinyl (1S)-1-(oxo{[(1R)-1-phenylethyl]amino}acetyl)pentylcarbamate;

(3S)-4,4-dimethyl-1-[(3-methyl-5-isoxazolyl)acetyl]pyrrolidinyl (1S)-1-(oxo{[(1R)-1-phenylethyl]amino}acetyl)pentylcarbamate;

(3S)-1-(1H-indazol-3-ylcarbonyl)-4,4-dimethylpyrrolidinyl (1S)-1-(oxo{[(1R)-1-phenylethyl]amino}acetyl)pentylcarbamate;

(3S)-4,4-dimethyl-1-{[2-(4-methyl-1,2,3-thiadiazol-5-yl)-1,3-thiazol-4-yl]carbonyl}pyrrolidinyl (1S)-1-(oxo{[(1R)-1-phenylethyl]amino}acetyl)pentylcarbamate;

(3S)-4,4-dimethyl-1-{[2-(2-pyrazinyl)-1,3-thiazol-4-yl]acetyl}pyrrolidinyl (1S)-1-(oxo{[(1R)-1-phenylethyl]amino}acetyl)pentylcarbamate;

(3S)-1-[(4-fluorophenyl)acetyl]-4,4-dimethylpyrrolidinyl (1S)-1-(oxo{[(1R)-1-phenylethyl]amino}acetyl)pentylcarbamate;

[1,1'-biphenyl]-4-ylmethyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

tetrahydro-2-furanylmethyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

3-thienylmethyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

(3S)-tetrahydro-3-furanyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

benzyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

2-phenylethyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

(1-phenyl-1H-1,2,3-triazol-4-yl)methyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

2-(2-oxo-1-pyrrolidinyl)ethyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

tetrahydro-2H-pyran-2-ylmethyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

tetrahydro-3-furanylmethyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

[3-methyl-5-(5-methyl-isoxazol-3-yl)-4-isoxazolyl]methyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

2-(4-methyl-1,3-thiazol-5-yl)ethyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

(5-methyl-3-isoxazolyl)methyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

[3-(2,6-dichlorophenyl)-5-methyl-4-isoxazolyl]methyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

(2-methyl[1,1'-biphenyl]-3-yl)methyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

[5-(2-thienyl)-1,2,4-oxadiazol-3-yl]methyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

(3R)-tetrahydro-3-furanyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

[1,1'-biphenyl]-4-yl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

4-phenoxyphenyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

3-phenoxyphenyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

2-naphthyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

4-(1,2,3-thiadiazol-4-yl)phenyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate;

phenyl 3,3-dimethyl-4-[({[(1S)-1-(oxo{[(1R)-1-phenylethyl]amino}acetyl)pentyl]amino}carbonyl)oxy]-1-pyrrolidinecarboxylate;

(3S)-1-(anilinocarbonyl)-4,4-dimethylpyrrolidinyl (1S)-1-(oxo{[(1R)-1-phenylethyl]amino}acetyl)pentylcarbamate;

(3S)-1-[(benzylamino)carbonyl-44-dimethylpyrrolidinyl (1S)-1-(oxo{[(1r)-1-phenylethyl]amino}acetyl)pentylcarbamate;)

(3S)-4,4-dimethyl-1-{[(2-phenylethyl)amino]carbonyl}pyrrolidinyl (1S)-1-(oxo{[(1R)-1-phenylethyl]amino}acetyl)pentylcarbamate;

(3S)-4,4-dimethyl-1-(3-pyridinylcarbonyl)pyrrolidinyl (1S)-1-(oxo{[(1R)-1-phenylethyl]amino}acetyl)pentylcarbamate;

(3S)-1-{[(3,5-dimethyl-4-isoxazolyl)amino]carbonyl}-4,4-dimethylpyrrolidinyl (1S)-1-(oxo{[(1R)-1-phenylethyl]amino}acetyl)pentylcarbamate;

(3S)-1-[(cyclohexylamino)carbonyl]-4,4-dimethylpyrrolidinyl (1S)-1-(oxo{[(1R)-1-phenylethyl]amino}acetyl)pentylcarbamate;

(3S)-1-[(4-cyanoanilino)carbonyl]-4,4-dimethylpyrrolidinyl (1S)-1-(oxo{[(1R)-1-phenylethyl]amino}acetyl)pentylcarbamate;

(3S)-4,4-dimethyl-1-{[4-(trifluoromethyl)anilino]carbonyl}pyrrolidinyl (1S)-1-(oxo{[(1R)-1-phenylethyl]amino}acetyl)pentylcarbamate;

(3S)-4,4-dimethyl-1-{[4-(trifluoromethyl)anilino]carbonyl}pyrrolidinyl (1S)-1-[oxo(1H-pyrazol-5-ylamino)acetyl]pentylcarbamate;

(3S)-1-[(5-fluoro-2-methylanilino)carbonyl]-4,4-dimethylpyrrolidinyl (1S)-1-(oxo{[(1R)-1-phenylethyl]amino}acetyl)pentylcarbamate;

(3S)-4,4-dimethyl-1-(4-morpholinylcarbonyl)pyrrolidinyl (1S)-1-(oxo{[(1R)-1-phenylethyl]amino}acetyl)pentylcarbamate;

(3S)-4,4-dimethyl-1-(1-pyrrolidinylcarbonyl)pyrrolidinyl (1S)-1-(oxo{[(1R)-1-phenylethyl]amino}acetyl)pentylcarbamate;

(3S)-1-[(benzoylamino)carbonyl]-4,4-dimethylpyrrolidinyl (1S)-1-(oxo{[(1R)-1-phenylethyl]amino}acetyl)pentylcarbamate;

(3S)-4,4-dimethyl-1-({[(4-methylphenyl)sulfonyl]amino}carbonyl)pyrrolidinyl (1S)-1-(oxo{[(1R)-1-phenylethyl]amino}acetyl)pentylcarbamate;

(3S)-4,4-dimethyl-1-(phenylsulfonyl)pyrrolidinyl (1S)-1-(oxo{[(1R)-1-phenylethyl]amino}acetyl)pentylcarbamate;

(3S)-1-(benzylsulfonyl)-4,4-dimethylpyrrolidinyl (1S)-1-(oxo{[(1R)-1-phenylethyl]amino}acetyl)pentylcarbamate;

(3S)-1-(1,3-benzodioxol-5-ylsulfonyl)-4,4-dimethylpyrrolidinyl (1S)-1-(oxo{[(1R)-1-phenylethyl]amino}acetyl)pentylcarbamate;

(3S)-1-(2,3-dihydro-1,4-benzodioxin-6-ylsulfonyl)-4,4-dimethylpyrrolidinyl (1S)-1-(oxo{[(1R)-1-phenylethyl]amino}acetyl)pentylcarbamate;

(3S)-1-(1,3-benzothiazol-2-yl)-4,4-dimethylpyrrolidinyl (1S)-1-[oxo(1H-pyrazol-5-ylamino)acetyl]pentylcarbamate;

(3S)-4,4-dimethyl-1-[5-(trifluoromethyl)-1,3,4-thiadiazol-2-yl]pyrrolidinyl (1S)-1-[oxo(1H-pyrazol-5-ylamino)acetyl]pentylcarbamate; and (3S)-4,4-dimethyltetrahydro-3-furanyl 1-(oxo{[(1R)-1-phenylethyl]amino}acetyl)pentylcarbamate;

or a salt or solvate thereof.

44. A pharmaceutical composition comprising a therapeutically effective amount of a compound as claimed in claim 1, or a salt or solvate thereof and one or more of pharmaceutically acceptable carriers, diluents and excipients.

45. A method of treating osteoporosis, comprising: administering to said mammal a therapeutically effective amount of a compound as claimed in claim 1, or a salt or solvate thereof.

46. A method of treating osteoporosis, comprising: administering to said mammal therapeutically effective amounts of (i) a compound as claimed in claim 1, or a salt or solvate thereof and (ii) at least one bone building agent.

\* \* \* \* \*

UNITED STATES PATENT AND TRADEMARK OFFICE
CERTIFICATE OF CORRECTION

PATENT NO. : 7,402,606 B2
APPLICATION NO. : 10/510469
DATED : July 22, 2008
INVENTOR(S) : Barrett et al.

It is certified that error appears in the above-identified patent and that said Letters Patent is hereby corrected as shown below:

On the Title page:

Please correct the first inventor's residence as follows:

(75)   Inventors:   -- David Gene Barrett, Norderstedt (DE); --

Please correct the first sentence of the Abstract as follows:

Title page, item

(57)   ABSTRACT

-- Heterocycle substituted ketoamide derivatives of Formula (I), wherein the substitutes A, D, A and R are defined as in claim 1, which are useful as cathepsin K inhibitors are described herein. --

In the Claims:

Claim 2 (Column 122, Line 22) should read as follows:

-- A' is the group defined by $(Q^4)_p$-$(Q^3)_n$-$(Q^2)_m$-, wherein --

UNITED STATES PATENT AND TRADEMARK OFFICE
CERTIFICATE OF CORRECTION

PATENT NO. : 7,402,606 B2
APPLICATION NO. : 10/510469
DATED : July 22, 2008
INVENTOR(S) : Barrett et al.

It is certified that error appears in the above-identified patent and that said Letters Patent is hereby corrected as shown below:

Claim 43 (Column 130, Lines 10-12) should read as follows:

-- (3S)-1-(1H-indol-2-ylcarbonyl)-4,4-dimethylpyrrolidinyl phenylethyl]amino}acetyl)pentylcarbamate;
(1S)-1-(oxo{[(1R)-1-phenylethyl]amino}acetyl)pentylcarbamate; --

Claim 43 (Column 130, Lines 41-43) should read as follows:

-- 3-thienylmethyl (4S)-3,3-dimethyl-4-[({[(1S)-1-(oxo{[(1R)-1-phenylethyl]amino}acetyl)pentyl]amino}carbonyl)oxy]-1-pyrrolidinecarboxylate; --

Claim 43 (Column 131, Lines 46-48) should read as follows:

-- (3S)-1-[(benzoylamino)carbonyl]-4,4-dimethylpyrrolidinyl (1S)-1-(oxo{[(1R)-1-phenylethyl]amino}acetyl)pentylcarbamate; --

Signed and Sealed this

Eighth Day of December, 2009

David J. Kappos
*Director of the United States Patent and Trademark Office*